US012806247B2

(12) United States Patent
Rudolph et al.

(10) Patent No.: US 12,806,247 B2
(45) **Date of Patent: *Nov. 24, 2026**

(54) USE OF IFN-LAMBDA MRNA FOR TREATING VIRAL INFECTIONS

(71) Applicant: ethris GmbH, Planegg (DE)

(72) Inventors: Carsten Rudolph, Krailling (DE); Christian Plank, Wessling (DE); Thomas Langenickel, Bingen (CH); Anna Macht, Munich (DE); Kristin Lohmer, Vierkirchen (DE)

(73) Assignee: ethris GmbH, Planegg (DE)

( * ) Notice: Subject to any disclaimer, the term of this patent is extended or adjusted under 35 U.S.C. 154(b) by 613 days.

This patent is subject to a terminal disclaimer.

(21) Appl. No.: 18/035,249

(22) PCT Filed: Nov. 4, 2021

(86) PCT No.: PCT/EP2021/080658

§ 371 (c)(1),
(2) Date: May 3, 2023

(87) PCT Pub. No.: WO2022/096582

PCT Pub. Date: May 12, 2022

(65) Prior Publication Data

US 2024/0181011 A1 Jun. 6, 2024

(30) Foreign Application Priority Data

Nov. 4, 2020 (EP) .................................... 20205674

(51) Int. Cl.

| | |
|---|---|
| ***A61K 38/21*** | (2006.01) |
| ***A61K 48/00*** | (2006.01) |
| ***A61P 31/14*** | (2006.01) |
| ***C07K 14/555*** | (2006.01) |

(52) U.S. Cl.

CPC ............ *A61K 38/21* (2013.01); *A61K 38/212* (2013.01); *A61K 38/215* (2013.01); *A61K 48/0075* (2013.01); *A61P 31/14* (2018.01); *C07K 14/555* (2013.01)

(58) Field of Classification Search

CPC .............................. A61K 38/21; C07K 14/555
See application file for complete search history.

(56) References Cited

U.S. PATENT DOCUMENTS

| | | | | |
|---|---|---|---|---|
| 7,569,216 B2 | | 8/2009 | Davies et al. | |
| 8,273,342 B2 | | 9/2012 | Davies et al. | |
| 9,089,535 B2 | * | 7/2015 | Davies | A61M 16/14 |
| 9,107,931 B2 | | 8/2015 | Zelphati et al. | |
| 2007/0134763 A1 | | 6/2007 | Davies et al. | |
| 2012/0195936 A1 | | 8/2012 | Rudolph et al. | |
| 2020/0147176 A1 | | 5/2020 | Gieseke et al. | |
| 2021/0095272 A1 | | 4/2021 | Rudolph et al. | |

FOREIGN PATENT DOCUMENTS

| | | | |
|---|---|---|---|
| EP | 1003711 | B1 | 7/2001 |
| EP | 3 542 825 | A1 | 9/2019 |
| EP | 3013964 | B1 | 6/2020 |
| EP | 2285772 | B1 | 7/2022 |
| JP | 2013/500704 | A | 1/2012 |
| JP | 2009-514794 | A | 3/2013 |
| WO | WO 2005/087253 | A2 | 9/2005 |
| WO | 2007/029041 | A2 | 3/2007 |
| WO | WO 2011/012316 | A2 | 2/2011 |
| WO | WO 2014/207231 | A1 | 12/2014 |
| WO | WO 2016/075154 | A1 | 5/2016 |
| WO | 2016/170176 | A1 | 10/2016 |
| WO | WO 2017/167910 | A1 | 10/2017 |
| WO | WO 2020/165158 | A1 | 8/2020 |
| WO | WO 2020/165352 | A1 | 8/2020 |

OTHER PUBLICATIONS

Baptista et al. mRNA, a Revolution in Biomedicine. Pharmaceutics 2021, 13, 2090 (Year: 2021).*
Hermant et al. Interferon-λ in the Context of Viral Infections: Production, Response and Therapeutic Implications. J Innate Immun 2014;6:563-574 (Year: 2014).*
Punta et al. The Rough Guide to In Silico Function Prediction, or How to use Sequence and Structure Information to Predict Protein Function. PLoS Comput Biol 4(10): e1000160, 2008 (Year: 2008).*
Whisstock et al. Prediction of proteinfunction fromprotein sequence and structure. Quarterly Reviews in Biophysics. 36(3):307-340, 2007 (Year: 2007).*
Burgess et al. Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue. J. Cell Biol. 111:2129-2138, 1990 (Year: 1990).*
Song et al. A Single Amino Acid Change (Asp 533Ala53) Converts Survivin from Anti-apoptotic to Pro-apoptotic. Molecular Biology of the Cell, 15:1287-1296, Mar. 2004 (Year: 2004).*
Defeo-Jones et al. Substitution of Lysine for Arginine at Position 42 of Human Transforming Growth Factor-a Eliminates Biological Activity without Changing Internal Disulfide Bonds. Molecular and Cellular Biology, Sep. 1989, p. 4083-4086 (Year: 1989).*
Bork. Powers and Pitfalls in Sequence Analysis: The 70% Hurdle. Genome Research, 2000; 10:398-400 (Year: 2000).*
Uchida, "Vaccines and Therapeutics Using Messenger RNA," *Kyoto Prefectural University of Medicine Journal* 103(7): 441-449 (2021)(w/ English language machine translation).
Uchida et al., "In Vivo Messenger RNA Introduction into the Central Nervous System Using PolyPlex Nanomicelle," *PLoS One* 8(2):e56220, 9 pages, Feb. 13, 2013.
Uchida et al., "mRNA as a Tool for Gene Transfection in 3D Cell Culture for Future Regenerative Therapy," *Micromachines* 11(4):426, 10 pages, Apr. 18, 2020.

(Continued)

*Primary Examiner* — Vanessa L. Ford
*Assistant Examiner* — Sandra Carter
(74) *Attorney, Agent, or Firm* — Klarquist Sparkman, LLP; Susan Alpert Siegel; Gregory K. Scott

(57) ABSTRACT

The present invention relates to pharmaceutical compositions comprising an mRNA encoding an IFN-λ polypeptide for use in treating a viral-induced disorder, preferably a viral-induced respiratory disorder, such as COVID-19.

34 Claims, 67 Drawing Sheets

Specification includes a Sequence Listing.

(56) References Cited

OTHER PUBLICATIONS

International Search Report from International Application No. PCT/EP2021/080658; date mailed: Mar. 7, 2022.
Anderson et al., "Stability of mRNA/cationic lipid lipoplexes in human and rat cerebrospinal fluid: Methods and evidence for nonviral mRNA gene delivery to the central nervous system," *Human Gene Therapy* 14:191-202 (Feb. 10, 2003).
Anderson et al., "The effect of different lipid components on the in vitro stability and release kinetics of liposome formulations," *Drug Delivery* 11(1):33-39, Jan. 2004.
Cantara et al., "The RNA modification database, RNAMDB: 2011 update," *Nucleic Acids Research* 39(Issue suppl. 1):D195-D201, e-Pub Nov. 10, 2010.
Carell et al., "Structure and Function of Noncanonical Nucleobases," *Angewandte Chemie International Edition* 51(29):7110-7131, Jun. 28, 2012.
Da Rocha Matos et al., "Antiviral potential of human IFN-α subtypes against influenza A H3N2 infection in human lung explants reveals subtype-specific activities," *Emerging Microbes & Infections* 8(1):1763-1776, e-Pub Dec. 11, 2019.
Davidson et al., "IFNλ is a potent anti-influenza therapeutic without the inflammatory side effects of IFNα treatment," *EMBO Molecular Medicine* 8(9):1099-1112, e-Pub Aug. 12, 2016.
Díaz et al., "Structure of the Human Type-1 Interferon Gene Cluster Determined from a YAC Clone Contig," *Genomics* 22:540-552, May 6, 1994.
Dinnon III et al., "A mouse-adapted model of SARS-CoV-2 to test COVID-19 countermeasures," *Nature* 586:560-566, e-Pub Aug. 27, 2020.
Galani et al., "Interferon-λ Mediates Non-redundant Front-Line Antiviral Protection against Influenza Virus Infection without Compromising Host Fitness," *Immunity* 46(5):875-890, May 16, 2017.
Helm and Alfonzo, "Post-transcriptional RNA modifications: Playing metabolic games in a cell's chemical legoland," *Chemistry & Biology* 21(2):174-185, Feb. 20, 2014.
Hoffmann et al., "SARS-CoV-2 Cell Entry Depends on ACE2 and TMPRSS2 and is Blocked by a Clinically Proven Protease Inhibitor," *Cell* 181:271-280, E-pub Mar. 5, 2020.
Humlicek et al., "Paracellular permeability restricts airway epithelial responses to selectively allow activation by mediators at the basolateral surface," *The Journal of Immunology* 178(10):6395-6403, May 15, 2007.
Jarzębińska et al., "A Single Methylene Group in Oligoalkylamine-Based Cationic Polymers and Lipids Promotes Enhanced mRNA Delivery," *Angewandte Chemie International Edition* 55(33):9591-9595, Jul. 4, 2016, with supporting information (31 pages total).
Kim et al., "The Superiority of IFN-λ as a Therapeutic Candidate to Control Acute Influenza Viral Lung Infection ," *American Journal of Respiratory Cell and Molecular Biology* 56(2):202-212, Feb. 1, 2017.
Kormann et al., "Expression of therapeutic proteins after delivery of chemically modified mRNA in mice," *Nature Biotechnology* ; 29(2):154-157,e-Pub Jan. 9, 2011.
Lazear et al., "Interferon-λ: immune functions at barrier surfaces and beyond," *Immunity* 43(1):15-28, Jul. 21, 2015.
Liang et al., "Mechanical properties and stability measurement of cholesterol-containing liposome on mica by atomic force microscopy," *Journal of Colloid and Interface Science* 278(1):53-62, Oct. 1, 2004.
Ma, "Animal Models of Disease," *Modern Drug Discovery* 7(6), 6 pages, Jun. 2004.
Milla et al., "PEGylation of proteins and liposomes: a powerful and flexible strategy to improve the drug delivery," *Current Drug Metabolism* 13(1):105-119, Jan. 2012.
Muir et al., "A randomized phase 2b study of peginterferon lambda-la for the treatment of chronic HCV infection," *Journal of Hepatology* 61(6):1238-1246, e-Pub Jul. 24, 2014.
Tavernier et al., "mRNA as gene therapeutic: How to control protein expression," Journal of Controlled Release, 150(3):238-247, e-Pub Oct. 21, 2010.
Yamamoto et al., "Current prospects for mRNA gene delivery," *European Journal of Pharmaceutics and Biopharmaceutics* 71(3):484-489, e-Pub Oct. 10, 2008.
Zhang et al., "An improved, chemically modified RNA encoding BMP-2 enhances osteogenesis in vitro and in vivo," *Tissue Engineering Part A* 25(1-2):131-144, E-pub Sep. 25, 2018.

* cited by examiner

| Group | Animal ID | Study Day 1 | 2 | 3 | 4 | 5 | 6 |
|---|---|---|---|---|---|---|---|
| | | Percentual body weight change [%] relative to study day 1 | | | | | |
| hIFNλ1 mRNA 0.1 µg | 1.1 | 0.0 | -0.5 | 1.0 | 0.0 | 1.0 | 3.1 |
| | 1.2 | 0.0 | 0.6 | 1.1 | -0.6 | -3.4 | -1.1 |
| | 1.3 | 0.0 | -0.5 | 3.1 | 2.1 | 0.5 | 1.0 |
| | 1.4 | 0.0 | 0.0 | -0.5 | 0.5 | 2.1 | 1.6 |
| | 1.5 | 0.0 | 2.5 | 5.0 | 5.0 | 5.9 | 4.5 |
| | 1.6 | 0.0 | 0.6 | 4.4 | 3.9 | 3.9 | 2.2 |
| hIFNλ1 mRNA 0.3 µg | 2.1 | 0.0 | -1.5 | -1.0 | -1.9 | 1.5 | 3.4 |
| | 2.2 | 0.0 | -1.5 | -2.5 | -3.9 | -2.5 | 1.5 |
| | 2.3 | 0.0 | -0.9 | -1.9 | -5.1 | -3.7 | -2.3 |
| | 2.4 | 0.0 | -1.0 | -0.5 | -1.0 | -1.5 | -1.5 |
| | 2.5 | 0.0 | 0.5 | 2.7 | 2.2 | -0.5 | -1.1 |
| | 2.6 | 0.0 | 2.5 | 4.5 | 3.0 | 1.5 | 3.0 |
| hIFNλ1 mRNA 1 µg | 3.1 | 0.0 | 0.0 | 4.0 | 3.5 | 4.5 | 4.5 |
| | 3.2 | 0.0 | 0.0 | 0.5 | 1.6 | 2.1 | 0.5 |
| | 3.3 | 0.0 | 0.5 | 0.5 | 0.0 | -0.5 | -0.9 |
| | 3.4 | 0.0 | -1.0 | 2.6 | 2.6 | 1.6 | 1.6 |
| | 3.5 | 0.0 | -0.5 | -1.0 | -1.5 | -1.0 | 1.0 |
| | 3.6 | 0.0 | 0.5 | 2.7 | 2.2 | 1.6 | 6.5 |
| Stop mRNA | 4.1 | 0.0 | -0.6 | -2.8 | -2.8 | -4.0 | 0.0 |
| | 4.2 | 0.0 | -0.5 | -0.5 | -1.1 | -1.6 | 4.3 |
| | 4.3 | 0.0 | 1.0 | 2.6 | 3.6 | 2.1 | 1.6 |
| | 4.4 | 0.0 | -0.5 | -1.6 | -1.1 | 0.0 | 0.0 |
| | 4.5 | 0.0 | 2.5 | 6.5 | 6.0 | 5.5 | 6.0 |
| | 4.6 | 0.0 | 1.0 | 3.5 | 0.5 | -1.5 | 1.0 |
| Vehicle | 5.1 | 0.0 | 1.7 | 5.0 | 4.5 | 2.2 | 2.2 |
| | 5.2 | 0.0 | -1.9 | -5.6 | -6.5 | -6.5 | -5.1 |
| | 5.3 | 0.0 | -0.5 | -0.5 | -0.5 | -1.0 | 2.0 |
| | 5.4 | 0.0 | 1.0 | 2.5 | 4.1 | 0.5 | 2.0 |
| | 5.5 | 0.0 | -0.5 | 0.0 | -1.5 | -0.5 | 0.0 |
| | 5.6 | 0.0 | -0.6 | -1.1 | -1.7 | -1.1 | -0.6 |

Figure 25

SEQUENCE LISTING

```
<160> NUMBER OF SEQ ID NOS: 36

<210> SEQ ID NO 1
<211> LENGTH: 603
<212> TYPE: RNA
<213> ORGANISM: Homo sapiens
<220> FEATURE:
<223> OTHER INFORMATION: IFN Lambda 1
<220> FEATURE:
<221> NAME/KEY: CDS
<222> LOCATION: 1..603
<223> OTHER INFORMATION: /transl_table=1

<400> SEQUENCE: 1

aug gcu gcu gcu ugg aca gug gug cug guc aca cug gug cug gga cuu       48
Met Ala Ala Ala Trp Thr Val Val Leu Val Thr Leu Val Leu Gly Leu
1               5                   10                  15

gcu gug gcu gga ccu gug ccu acc agc aag ccu acc aca aca ggc aag       96
Ala Val Ala Gly Pro Val Pro Thr Ser Lys Pro Thr Thr Thr Gly Lys
            20                  25                  30

ggc ugc cac auc ggc aga uuc aag agc cug ucu ccu caa gag cug gcc      144
Gly Cys His Ile Gly Arg Phe Lys Ser Leu Ser Pro Gln Glu Leu Ala
        35                  40                  45

ucc uuc aag aaa gcc agg gac gcc cug gaa gag agc cug aag cug aag      192
Ser Phe Lys Lys Ala Arg Asp Ala Leu Glu Glu Ser Leu Lys Leu Lys
    50                  55                  60

aac ugg ucc ugc agc agc ccu gug uuc ccc ggc aau ugg gau cug aga      240
Asn Trp Ser Cys Ser Ser Pro Val Phe Pro Gly Asn Trp Asp Leu Arg
65                  70                  75                  80

cug cug caa gug cgc gag agg ccu guu gcu cug gaa gcu gaa cug gcc      288
Leu Leu Gln Val Arg Glu Arg Pro Val Ala Leu Glu Ala Glu Leu Ala
                85                  90                  95

cug aca cug aag gug cug gaa gcc gcu gcu gga ccc gca cug gaa gau      336
Leu Thr Leu Lys Val Leu Glu Ala Ala Ala Gly Pro Ala Leu Glu Asp
            100                 105                 110

guu cug gau cag ccu cug cac acc cug cac cac auu cug agu cag cug      384
Val Leu Asp Gln Pro Leu His Thr Leu His His Ile Leu Ser Gln Leu
        115                 120                 125
```

```
cag gcc ugu auc cag ccu cag ccu aca gcu ggc ccu aga ccu aga ggc      432
Gln Ala Cys Ile Gln Pro Gln Pro Thr Ala Gly Pro Arg Pro Arg Gly
    130                 135                 140

aga cug cac cac ugg cug cac aga cug caa gag gcc ccu aag aaa gag      480
Arg Leu His His Trp Leu His Arg Leu Gln Glu Ala Pro Lys Lys Glu
145                 150                 155                 160

agc gcc ggc ugu cug gaa gcc agc gug acc uuc aac cug uuc aga cug      528
Ser Ala Gly Cys Leu Glu Ala Ser Val Thr Phe Asn Leu Phe Arg Leu
                165                 170                 175

cug acc cgg gac cug aaa uac gug gcc gau ggc aau cug ugc cug cgg      576
Leu Thr Arg Asp Leu Lys Tyr Val Ala Asp Gly Asn Leu Cys Leu Arg
            180                 185                 190

aca ucu aca cac ccc gag agc aca uga                                  603
Thr Ser Thr His Pro Glu Ser Thr
        195                 200


<210> SEQ ID NO 2
<211> LENGTH: 200
<212> TYPE: PRT
<213> ORGANISM: Homo sapiens
<220> FEATURE:
<223> OTHER INFORMATION: [CDS]:1..603 from SEQ ID NO 1

<400> SEQUENCE: 2

Met Ala Ala Ala Trp Thr Val Val Leu Val Thr Leu Val Leu Gly Leu
1               5                   10                  15

Ala Val Ala Gly Pro Val Pro Thr Ser Lys Pro Thr Thr Thr Gly Lys
            20                  25                  30

Gly Cys His Ile Gly Arg Phe Lys Ser Leu Ser Pro Gln Glu Leu Ala
        35                  40                  45

Ser Phe Lys Lys Ala Arg Asp Ala Leu Glu Glu Ser Leu Lys Leu Lys
    50                  55                  60

Asn Trp Ser Cys Ser Ser Pro Val Phe Pro Gly Asn Trp Asp Leu Arg
65                  70                  75                  80

Leu Leu Gln Val Arg Glu Arg Pro Val Ala Leu Glu Ala Glu Leu Ala
                85                  90                  95

Leu Thr Leu Lys Val Leu Glu Ala Ala Ala Gly Pro Ala Leu Glu Asp
            100                 105                 110

Val Leu Asp Gln Pro Leu His Thr Leu His His Ile Leu Ser Gln Leu
        115                 120                 125

Gln Ala Cys Ile Gln Pro Gln Pro Thr Ala Gly Pro Arg Pro Arg Gly
    130                 135                 140

Arg Leu His His Trp Leu His Arg Leu Gln Glu Ala Pro Lys Lys Glu
145                 150                 155                 160

Ser Ala Gly Cys Leu Glu Ala Ser Val Thr Phe Asn Leu Phe Arg Leu
                165                 170                 175

Leu Thr Arg Asp Leu Lys Tyr Val Ala Asp Gly Asn Leu Cys Leu Arg
            180                 185                 190

Thr Ser Thr His Pro Glu Ser Thr
        195                 200


<210> SEQ ID NO 3
<211> LENGTH: 603
<212> TYPE: RNA
<213> ORGANISM: Homo sapiens
<220> FEATURE:
<223> OTHER INFORMATION: IFN Lambda 2
<220> FEATURE:
<221> NAME/KEY: CDS
```

```
<222> LOCATION: 1..603
<223> OTHER INFORMATION: /transl_table=1

<400> SEQUENCE: 3

aug aag cug gac aug acc ggc gau ugc acc ccu gug cug guu cug aug       48
Met Lys Leu Asp Met Thr Gly Asp Cys Thr Pro Val Leu Val Leu Met
1               5                   10                  15

gcu gcc gug cug aca gug aca ggu gcu gug ccu gug gcu aga cug cau       96
Ala Ala Val Leu Thr Val Thr Gly Ala Val Pro Val Ala Arg Leu His
            20                  25                  30

ggc gca cug ccu gau gcc aga ggc ugu cac auu gcc cag uuc aag agc      144
Gly Ala Leu Pro Asp Ala Arg Gly Cys His Ile Ala Gln Phe Lys Ser
        35                  40                  45

cug ucu ccu caa gag cug cag gcc uuc aag aga gcc aag gac gcc cug      192
Leu Ser Pro Gln Glu Leu Gln Ala Phe Lys Arg Ala Lys Asp Ala Leu
    50                  55                  60

gaa gag agc cug cug cug aag gau ugc cgg ugc cac agc aga cug uuc      240
Glu Glu Ser Leu Leu Leu Lys Asp Cys Arg Cys His Ser Arg Leu Phe
65                  70                  75                  80

ccc aga acc ugg gac cug aga cag cug caa gug cgc gaa aga ccc aug      288
Pro Arg Thr Trp Asp Leu Arg Gln Leu Gln Val Arg Glu Arg Pro Met
                85                  90                  95

gcu cug gaa gcc gaa cug gcc cug aca cug aaa gug cug gaa gcc acc      336
Ala Leu Glu Ala Glu Leu Ala Leu Thr Leu Lys Val Leu Glu Ala Thr
            100                 105                 110

gcc gac acc gau ccu gcu cug gug gau guu cug gac cag ccu cug cac      384
Ala Asp Thr Asp Pro Ala Leu Val Asp Val Leu Asp Gln Pro Leu His
        115                 120                 125

acc cug cac cac auc cug agc cag uuc agg gcc ugu auc cag ccu cag      432
Thr Leu His His Ile Leu Ser Gln Phe Arg Ala Cys Ile Gln Pro Gln
    130                 135                 140

ccu aca gcu ggc ccu aga acc aga ggc aga cug cac cac ugg cug uac      480
Pro Thr Ala Gly Pro Arg Thr Arg Gly Arg Leu His His Trp Leu Tyr
145                 150                 155                 160

aga cug caa gag gcc ccu aag aaa gag agc ccc ggc ugu cug gaa gcu      528
Arg Leu Gln Glu Ala Pro Lys Lys Glu Ser Pro Gly Cys Leu Glu Ala
                165                 170                 175

agc gug acc uuc aac cug uuc cgg cug cug acc agg gac cug aau ugu      576
Ser Val Thr Phe Asn Leu Phe Arg Leu Leu Thr Arg Asp Leu Asn Cys
            180                 185                 190

gug gcu agc ggc gac cug ugc gug uga                                  603
Val Ala Ser Gly Asp Leu Cys Val
        195                 200


<210> SEQ ID NO 4
<211> LENGTH: 200
<212> TYPE: PRT
<213> ORGANISM: Homo sapiens
<220> FEATURE:
<223> OTHER INFORMATION: [CDS]:1..603 from SEQ ID NO 3

<400> SEQUENCE: 4

Met Lys Leu Asp Met Thr Gly Asp Cys Thr Pro Val Leu Val Leu Met
1               5                   10                  15

Ala Ala Val Leu Thr Val Thr Gly Ala Val Pro Val Ala Arg Leu His
            20                  25                  30

Gly Ala Leu Pro Asp Ala Arg Gly Cys His Ile Ala Gln Phe Lys Ser
        35                  40                  45

Leu Ser Pro Gln Glu Leu Gln Ala Phe Lys Arg Ala Lys Asp Ala Leu
    50                  55                  60
```

-continued

```
Glu Glu Ser Leu Leu Leu Lys Asp Cys Arg Cys His Ser Arg Leu Phe
65                  70                  75                  80

Pro Arg Thr Trp Asp Leu Arg Gln Leu Gln Val Arg Glu Arg Pro Met
                85                  90                  95

Ala Leu Glu Ala Glu Leu Ala Leu Thr Leu Lys Val Leu Glu Ala Thr
            100                 105                 110

Ala Asp Thr Asp Pro Ala Leu Val Asp Val Leu Asp Gln Pro Leu His
        115                 120                 125

Thr Leu His His Ile Leu Ser Gln Phe Arg Ala Cys Ile Gln Pro Gln
    130                 135                 140

Pro Thr Ala Gly Pro Arg Thr Arg Gly Arg Leu His His Trp Leu Tyr
145                 150                 155                 160

Arg Leu Gln Glu Ala Pro Lys Lys Glu Ser Pro Gly Cys Leu Glu Ala
                165                 170                 175

Ser Val Thr Phe Asn Leu Phe Arg Leu Leu Thr Arg Asp Leu Asn Cys
            180                 185                 190

Val Ala Ser Gly Asp Leu Cys Val
        195                 200


<210> SEQ ID NO 5
<211> LENGTH: 591
<212> TYPE: RNA
<213> ORGANISM: Homo sapiens
<220> FEATURE:
<223> OTHER INFORMATION: IFN Lambda 3
<220> FEATURE:
<221> NAME/KEY: CDS
<222> LOCATION: 1..591
<223> OTHER INFORMATION: /transl_table=1

<400> SEQUENCE: 5

aug aca ggc gau ugc aug ccu gug cug gug cug aug gcu gcc gug cug       48
Met Thr Gly Asp Cys Met Pro Val Leu Val Leu Met Ala Ala Val Leu
1               5                   10                  15

aca guu aca ggu gcu gug ccu gug gcc aga cug aga ggu gca cug ccu       96
Thr Val Thr Gly Ala Val Pro Val Ala Arg Leu Arg Gly Ala Leu Pro
            20                  25                  30

gau gcc aga ggc ugu cac auu gcc cag uuc aag agc cug ucu ccu caa      144
Asp Ala Arg Gly Cys His Ile Ala Gln Phe Lys Ser Leu Ser Pro Gln
        35                  40                  45

gag cug cag gcc uuc aag aga gcc aag gac gcc cug gaa gag agc cug      192
Glu Leu Gln Ala Phe Lys Arg Ala Lys Asp Ala Leu Glu Glu Ser Leu
    50                  55                  60

cug cug aag gac ugc aag ugc aga agc cgg cug uuc ccc aga acc ugg      240
Leu Leu Lys Asp Cys Lys Cys Arg Ser Arg Leu Phe Pro Arg Thr Trp
65                  70                  75                  80

gau cug aga cag cug caa guc cgc gaa aga ccc gug gcu cug gaa gcu      288
Asp Leu Arg Gln Leu Gln Val Arg Glu Arg Pro Val Ala Leu Glu Ala
                85                  90                  95

gaa cug gcc cug aca cug aag gug cug gaa gcc acc gcc gau acc gau      336
Glu Leu Ala Leu Thr Leu Lys Val Leu Glu Ala Thr Ala Asp Thr Asp
            100                 105                 110

ccu gcu cug gga gau gug cug gac cag ccu cug cac aca cug cac cac      384
Pro Ala Leu Gly Asp Val Leu Asp Gln Pro Leu His Thr Leu His His
        115                 120                 125

auc cug agc cag cug agg gcc ugu auu cag ccc caa ccu aca gcu ggc      432
Ile Leu Ser Gln Leu Arg Ala Cys Ile Gln Pro Gln Pro Thr Ala Gly
    130                 135                 140
```

-continued

```
ccu cgg aca aga ggc aga cug cac cau ugg cug cac cgg cug caa gag      480
Pro Arg Thr Arg Gly Arg Leu His His Trp Leu His Arg Leu Gln Glu
145                 150                 155                 160

gcc ccu aag aaa gag ucu ccu ggc ugc cug gaa gcc ucc gug acc uuc      528
Ala Pro Lys Lys Glu Ser Pro Gly Cys Leu Glu Ala Ser Val Thr Phe
                165                 170                 175

aac cug uuc aga cug cug acc cgg gac cug aau ugu gug gcc ucu ggc      576
Asn Leu Phe Arg Leu Leu Thr Arg Asp Leu Asn Cys Val Ala Ser Gly
            180                 185                 190

gau cug ugc gug uga                                                  591
Asp Leu Cys Val
        195


<210> SEQ ID NO 6
<211> LENGTH: 196
<212> TYPE: PRT
<213> ORGANISM: Homo sapiens
<220> FEATURE:
<223> OTHER INFORMATION: [CDS]:1..591 from SEQ ID NO 5

<400> SEQUENCE: 6

Met Thr Gly Asp Cys Met Pro Val Leu Val Leu Met Ala Ala Val Leu
1               5                   10                  15

Thr Val Thr Gly Ala Val Pro Val Ala Arg Leu Arg Gly Ala Leu Pro
            20                  25                  30

Asp Ala Arg Gly Cys His Ile Ala Gln Phe Lys Ser Leu Ser Pro Gln
        35                  40                  45

Glu Leu Gln Ala Phe Lys Arg Ala Lys Asp Ala Leu Glu Glu Ser Leu
    50                  55                  60

Leu Leu Lys Asp Cys Lys Cys Arg Ser Arg Leu Phe Pro Arg Thr Trp
65                  70                  75                  80

Asp Leu Arg Gln Leu Gln Val Arg Glu Arg Pro Val Ala Leu Glu Ala
                85                  90                  95

Glu Leu Ala Leu Thr Leu Lys Val Leu Glu Ala Thr Ala Asp Thr Asp
            100                 105                 110

Pro Ala Leu Gly Asp Val Leu Asp Gln Pro Leu His Thr Leu His His
        115                 120                 125

Ile Leu Ser Gln Leu Arg Ala Cys Ile Gln Pro Gln Pro Thr Ala Gly
    130                 135                 140

Pro Arg Thr Arg Gly Arg Leu His His Trp Leu His Arg Leu Gln Glu
145                 150                 155                 160

Ala Pro Lys Lys Glu Ser Pro Gly Cys Leu Glu Ala Ser Val Thr Phe
                165                 170                 175

Asn Leu Phe Arg Leu Leu Thr Arg Asp Leu Asn Cys Val Ala Ser Gly
            180                 185                 190

Asp Leu Cys Val
        195


<210> SEQ ID NO 7
<211> LENGTH: 13
<212> TYPE: DNA
<213> ORGANISM: Artificial Sequence
<220> FEATURE:
<223> OTHER INFORMATION: primer

<400> SEQUENCE: 7

gggagacgcc acc                                                        13
```

-continued

<210> SEQ ID NO 8
<211> LENGTH: 17
<212> TYPE: DNA
<213> ORGANISM: Artificial Sequence
<220> FEATURE:
<223> OTHER INFORMATION: primer

<400> SEQUENCE: 8
taatacgact cactata 17

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
taatacgact cactataggg agacgccacc 30

<210> SEQ ID NO 10
<211> LENGTH: 637
<212> TYPE: DNA
<213> ORGANISM: Homo sapiens
<220> FEATURE:
<223> OTHER INFORMATION: DNA construct IFN Lambda 1

<400> SEQUENCE: 10
taatacgact cactataggg agacgccacc atggctgctg cttggacagt ggtgctggtc 60
acactggtgc tgggacttgc tgtggctgga cctgtgccta ccagcaagcc taccacaaca 120
ggcaagggct gccacatcgg cagattcaag agcctgtctc ctcaagagct ggcctccttc 180
aagaaagcca gggacgccct ggaagagagc ctgaagctga agaactggtc ctgcagcagc 240
cctgtgttcc ccggcaattg ggatctgaga ctgctgcaag tgcgcgagag gcctgttgct 300
ctggaagctg aactggccct gacactgaag gtgctggaag ccgctgctgg acccgcactg 360
gaagatgttc tggatcagcc tctgcacacc ctgcaccaca ttctgagtca gctgcaggcc 420
tgtatccagc ctcagcctac agctggccct agacctagag gcagactgca ccactggctg 480
cacagactgc aagaggcccc taagaaagag agcgccggct gtctggaagc cagcgtgacc 540
ttcaacctgt tcagactgct gacccgggac ctgaaatacg tggccgatgg caatctgtgc 600
ctgcggacat ctacacaccc cgagagcaca tgattcg 637

<210> SEQ ID NO 11
<211> LENGTH: 637
<212> TYPE: DNA
<213> ORGANISM: Homo sapiens
<220> FEATURE:
<223> OTHER INFORMATION: DNA construct IFN Lambda 2

<400> SEQUENCE: 11
taatacgact cactataggg agacgccacc atgaagctgg acatgaccgg cgattgcacc 60
cctgtgctgg ttctgatggc tgccgtgctg acagtgacag gtgctgtgcc tgtggctaga 120
ctgcatggcg cactgcctga tgccagaggc tgtcacattg cccagttcaa gagcctgtct 180
cctcaagagc tgcaggcctt caagagagcc aaggacgccc tggaagagag cctgctgctg 240
aaggattgcc ggtgccacag cagactgttc cccagaacct gggacctgag acagctgcaa 300
gtgcgcgaaa gacccatggc tctggaagcc gaactggccc tgacactgaa agtgctggaa 360
gccaccgccg acaccgatcc tgctctggtg gatgttctgg accagcctct gcacaccctg 420

-continued

```
caccacatcc tgagccagtt cagggcctgt atccagcctc agcctacagc tggccctaga    480

accagaggca gactgcacca ctggctgtac agactgcaag aggcccctaa gaaagagagc    540

cccggctgtc tggaagctag cgtgaccttc aacctgttcc ggctgctgac cagggacctg    600

aattgtgtgg ctagcggcga cctgtgcgtg tgattcg                              637
```

```
<210> SEQ ID NO 12
<211> LENGTH: 625
<212> TYPE: DNA
<213> ORGANISM: Homo sapiens
<220> FEATURE:
<223> OTHER INFORMATION: DNA construct IFN Lambda 3

<400> SEQUENCE: 12

taatacgact cactataggg agacgccacc atgacaggcg attgcatgcc tgtgctggtg     60

ctgatggctg ccgtgctgac agttacaggt gctgtgcctg tggccagact gagaggtgca    120

ctgcctgatg ccagaggctg tcacattgcc cagttcaaga gcctgtctcc tcaagagctg    180

caggccttca agagagccaa ggacgccctg gaagagagcc tgctgctgaa ggactgcaag    240

tgcagaagcc ggctgttccc cagaacctgg gatctgagac agctgcaagt ccgcgaaaga    300

cccgtggctc tggaagctga actggccctg acactgaagg tgctggaagc caccgccgat    360

accgatcctg ctctgggaga tgtgctggac cagcctctgc acacactgca ccacatcctg    420

agccagctga gggcctgtat tcagccccaa cctacagctg gccctcggac aagaggcaga    480

ctgcaccatt ggctgcaccg gctgcaagag gcccctaaga aagagtctcc tggctgcctg    540

gaagcctccg tgaccttcaa cctgttcaga ctgctgaccc gggacctgaa ttgtgtggcc    600

tctggcgatc tgtgcgtgtg attcg                                          625
```

```
<210> SEQ ID NO 13
<211> LENGTH: 620
<212> TYPE: RNA
<213> ORGANISM: Homo sapiens
<220> FEATURE:
<223> OTHER INFORMATION: mRNA construct for IFN Lambda 1

<400> SEQUENCE: 13

gggagacgcc accauggcug cugcuuggac aguggugcug gucacacugg ugcugggacu     60

ugcuguggcu ggaccugugc cuaccagcaa gccuaccaca acaggcaagg gcugccacau    120

cggcagauuc aagagccugu cuccucaaga gcuggccucc uucaagaaag ccagggacgc    180

ccuggaagag agccugaagc ugaagaacug guccugcagc agcccugugu uccccggcaa    240

uugggaucug agacugcugc aagugcgcga gaggccuguu gcucuggaag cugaacuggc    300

ccugacacug aaggugcugg aagccgcugc uggacccgca cuggaagaug uucuggauca    360

gccucugcac acccugcacc acauucugag ucagcugcag gccuguaucc agccucagcc    420

uacagcuggc ccuagaccua gaggcagacu gcaccacugg cugcacagac ugcaagaggc    480

cccuaagaaa gagagcgccg gcugucugga agccagcgug accuucaacc uguucagacu    540

gcugacccgg gaccugaaau acguggccga uggcaaucug ugccugcgga caucuacaca    600

ccccgagagc acaugauucg                                                620
```

```
<210> SEQ ID NO 14
<211> LENGTH: 620
<212> TYPE: RNA
<213> ORGANISM: Homo sapiens
<220> FEATURE:
<223> OTHER INFORMATION: mRNA construct for IFN Lambda 2
```

<400> SEQUENCE: 14
gggagacgcc accaugaagc uggacaugac cggcgauugc accccugugc ugguucugau 60
ggcugccgug cugacaguga caggugcugu gccuguggcu agacugcaug gcgcacugcc 120
ugaugccaga ggcugucaca uugcccaguu caagagccug ucuccucaag agcugcaggc 180
cuucaagaga gccaaggacg cccuggaaga gagccugcug cugaaggauu gccggugcca 240
cagcagacug uuccccagaa ccugggaccu gagacagcug caagugcgcg aaagacccau 300
ggcucuggaa gccgaacugg cccugacacu gaaagugcug gaagccaccg ccgacaccga 360
uccugcucug guggauguuc uggaccagcc ucugcacacc cugcaccaca uccugagcca 420
guucagggcc uguauccagc cucagccuac agcuggcccu agaaccagag gcagacugca 480
ccacuggcug uacagacugc aagaggcccc uaagaaagag agccccggcu gucuggaagc 540
uagcgugacc uucaaccugu uccggcugcu gaccagggac cugaauugug uggcuagcgg 600
cgaccugugc gugugauucg 620

<210> SEQ ID NO 15
<211> LENGTH: 597
<212> TYPE: RNA
<213> ORGANISM: Homo sapiens
<220> FEATURE:
<223> OTHER INFORMATION: mRNA construct for IFN Lambda 3

<400> SEQUENCE: 15
gggagacgcc accaugacag gcgauugcau gccugugcug gugcugaugg cugccgugcu 60
gacaguuaca ggugcugugc cuguggccag acugagaggu gcacugccug augccagagg 120
cugucacauu gcccaguuca agagccuguc uccucaagag cugcaggccu ucaagagagc 180
caaggacgcc cuggaagaga gccugcugcu gaaggacugc aagugcagaa gccggcuguu 240
ccccagaacc ugggaucuga gacagcugca aguccgcgaa agacccgugg cucuggaagc 300
ugaacuggcc cugacacuga aggugcugga agccaccgcc gauaccgauc cugcucuggg 360
agaugugcug gaccagccuc ugcacacacu gcaccacauc cugagccagc ugagggccug 420
uauucagccc caaccuacag cuggcccucg gacaagaggc agacugcacc auuggcugca 480
ccggcugcaa gaggccccua agaaagaguc uccuggcugc cuggaagccu ccgugaccuu 540
caaccuguuc agacugcuga cccgggaccu gaauugugug gccucuggcg aucugug 597

<210> SEQ ID NO 16
<211> LENGTH: 570
<212> TYPE: RNA
<213> ORGANISM: Homo sapiens
<220> FEATURE:
<223> OTHER INFORMATION: IFN alpha 16
<220> FEATURE:
<221> NAME/KEY: CDS
<222> LOCATION: 1..570
<223> OTHER INFORMATION: /transl_table=1

<400> SEQUENCE: 16

```
aug gcc cug agc uuc ucu cug cug aug gcu gug cug gug cug agc uac       48
Met Ala Leu Ser Phe Ser Leu Leu Met Ala Val Leu Val Leu Ser Tyr
1               5                   10                  15

aag agc auc ugc agc cug ggc ugc gac cug ccu cag aca cac ucu cug       96
Lys Ser Ile Cys Ser Leu Gly Cys Asp Leu Pro Gln Thr His Ser Leu
            20                  25                  30
```

-continued

```
gga aac aga cgg gcc cug auu cug cug gcc cag aug ggc aga auc ucc      144
Gly Asn Arg Arg Ala Leu Ile Leu Leu Ala Gln Met Gly Arg Ile Ser
        35                  40                  45

cac uuc agc ugc cug aag gac aga uac gac uuc ggc uuc ccu caa gag      192
His Phe Ser Cys Leu Lys Asp Arg Tyr Asp Phe Gly Phe Pro Gln Glu
    50                  55                  60

gug uuc gac ggc aac cag uuc cag aag gcc cag gcc auc ucu gcc uuc      240
Val Phe Asp Gly Asn Gln Phe Gln Lys Ala Gln Ala Ile Ser Ala Phe
65                  70                  75                  80

cac gag aug auc cag cag acc uuc aac cug uuc agc acc aag gau agc      288
His Glu Met Ile Gln Gln Thr Phe Asn Leu Phe Ser Thr Lys Asp Ser
                85                  90                  95

agc gcc gcc ugg gau gag aca cug cug gac aag uuc uac auc gag cug      336
Ser Ala Ala Trp Asp Glu Thr Leu Leu Asp Lys Phe Tyr Ile Glu Leu
            100                 105                 110

uuc cag cag cug aac gac cug gaa gcc ugc gug aca caa gaa gug ggc      384
Phe Gln Gln Leu Asn Asp Leu Glu Ala Cys Val Thr Gln Glu Val Gly
        115                 120                 125

guc gaa gag auc gcc cug aug aac gag gau agc auc cug gcc gug cgc      432
Val Glu Glu Ile Ala Leu Met Asn Glu Asp Ser Ile Leu Ala Val Arg
    130                 135                 140

aag uac uuc cag cgg auc acc cug uac cug aug ggc aag aag uac agc      480
Lys Tyr Phe Gln Arg Ile Thr Leu Tyr Leu Met Gly Lys Lys Tyr Ser
145                 150                 155                 160

ccu ugc gcc ugg gaa guc gug cgg gcc gaa auc aug aga agc uuc agc      528
Pro Cys Ala Trp Glu Val Val Arg Ala Glu Ile Met Arg Ser Phe Ser
                165                 170                 175

uuu agc acc aac cug cag aag ggc cug aga aga aag gac uga              570
Phe Ser Thr Asn Leu Gln Lys Gly Leu Arg Arg Lys Asp
            180                 185


<210> SEQ ID NO 17
<211> LENGTH: 189
<212> TYPE: PRT
<213> ORGANISM: Homo sapiens
<220> FEATURE:
<223> OTHER INFORMATION: [CDS]:1..570 from SEQ ID NO 16

<400> SEQUENCE: 17

Met Ala Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
            20                  25                  30

Gly Asn Arg Arg Ala Leu Ile Leu Leu Ala Gln Met Gly Arg Ile Ser
        35                  40                  45

His Phe Ser Cys Leu Lys Asp Arg Tyr Asp Phe Gly Phe Pro Gln Glu
    50                  55                  60

Val Phe Asp Gly Asn Gln Phe Gln Lys Ala Gln Ala Ile Ser Ala Phe
65                  70                  75                  80

His Glu Met Ile Gln Gln Thr Phe Asn Leu Phe Ser Thr Lys Asp Ser
                85                  90                  95

Ser Ala Ala Trp Asp Glu Thr Leu Leu Asp Lys Phe Tyr Ile Glu Leu
            100                 105                 110

Phe Gln Gln Leu Asn Asp Leu Glu Ala Cys Val Thr Gln Glu Val Gly
        115                 120                 125

Val Glu Glu Ile Ala Leu Met Asn Glu Asp Ser Ile Leu Ala Val Arg
    130                 135                 140
```

```
Lys Tyr Phe Gln Arg Ile Thr Leu Tyr Leu Met Gly Lys Lys Tyr Ser
145                 150                 155                 160

Pro Cys Ala Trp Glu Val Val Arg Ala Glu Ile Met Arg Ser Phe Ser
                165                 170                 175

Phe Ser Thr Asn Leu Gln Lys Gly Leu Arg Arg Lys Asp
            180                 185


<210> SEQ ID NO 18
<211> LENGTH: 564
<212> TYPE: RNA
<213> ORGANISM: Homo sapiens
<220> FEATURE:
<223> OTHER INFORMATION: IFN beta
<220> FEATURE:
<221> NAME/KEY: CDS
<222> LOCATION: 1..564
<223> OTHER INFORMATION: /transl_table=1

<400> SEQUENCE: 18

aug acc aac aag ugc cug cug cag auu gcc cug cug cug ugc uuc agc       48
Met Thr Asn Lys Cys Leu Leu Gln Ile Ala Leu Leu Leu Cys Phe Ser
1               5                   10                  15

aca aca gcc cug agc aug agc uac aac cug cug ggc uuc cug cag cgg       96
Thr Thr Ala Leu Ser Met Ser Tyr Asn Leu Leu Gly Phe Leu Gln Arg
            20                  25                  30

agc agc aac uuc cag ugc cag aaa cug cug ugg cag cug aac ggc cgg      144
Ser Ser Asn Phe Gln Cys Gln Lys Leu Leu Trp Gln Leu Asn Gly Arg
        35                  40                  45

cug gaa uac ugc cug aag gac cgg aug aac uuc gac auc ccc gag gaa      192
Leu Glu Tyr Cys Leu Lys Asp Arg Met Asn Phe Asp Ile Pro Glu Glu
    50                  55                  60

auc aag cag cug cag cag uuc cag aaa gag gac gcc gcu cug acc auc      240
Ile Lys Gln Leu Gln Gln Phe Gln Lys Glu Asp Ala Ala Leu Thr Ile
65                  70                  75                  80

uac gag aug cug cag aac auc uuc gcc auc uuc cgg cag gac agc agc      288
Tyr Glu Met Leu Gln Asn Ile Phe Ala Ile Phe Arg Gln Asp Ser Ser
                85                  90                  95

ucc aca ggc ugg aac gag aca auc gug gaa aau cug cug gcc aac gug      336
Ser Thr Gly Trp Asn Glu Thr Ile Val Glu Asn Leu Leu Ala Asn Val
            100                 105                 110

uac cac cag auc aac cac cug aaa acc gug cug gaa gag aag cug gaa      384
Tyr His Gln Ile Asn His Leu Lys Thr Val Leu Glu Glu Lys Leu Glu
        115                 120                 125

aaa gag gac uuc acc cgg ggc aag cug aug agc agc cug cac cug aag      432
Lys Glu Asp Phe Thr Arg Gly Lys Leu Met Ser Ser Leu His Leu Lys
    130                 135                 140

cgg uac uac ggc aga auc cug cac uac cug aag gcc aaa gag uac agc      480
Arg Tyr Tyr Gly Arg Ile Leu His Tyr Leu Lys Ala Lys Glu Tyr Ser
145                 150                 155                 160

cac ugc gcc ugg acc auc gug cgc gug gaa auc cug cgg aac uuc uac      528
His Cys Ala Trp Thr Ile Val Arg Val Glu Ile Leu Arg Asn Phe Tyr
                165                 170                 175

uuc auc aac cgg cug acc ggc uac cug aga aac uga                      564
Phe Ile Asn Arg Leu Thr Gly Tyr Leu Arg Asn
            180                 185


<210> SEQ ID NO 19
<211> LENGTH: 187
<212> TYPE: PRT
<213> ORGANISM: Homo sapiens
<220> FEATURE:
<223> OTHER INFORMATION: [CDS]:1..564 from SEQ ID NO 18
```

<400> SEQUENCE: 19

Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
            180                 185

<210> SEQ ID NO 20
<211> LENGTH: 501
<212> TYPE: RNA
<213> ORGANISM: Homo sapiens
<220> FEATURE:
<223> OTHER INFORMATION: IFN gamma
<220> FEATURE:
<221> NAME/KEY: CDS
<222> LOCATION: 1..501
<223> OTHER INFORMATION: /transl_table=1

<400> SEQUENCE: 20 aug aag uac acc agc uac auc cug gcc uuc cag cug ugc auc gug cug      48
Met Lys Tyr Thr Ser Tyr Ile Leu Ala Phe Gln Leu Cys Ile Val Leu
1               5                   10                  15 gga agc cug ggc ugc uac ugc cag gau ccu uac gug aaa gag gcc gag      96
Gly Ser Leu Gly Cys Tyr Cys Gln Asp Pro Tyr Val Lys Glu Ala Glu
            20                  25                  30 aac cug aag aag uac uuu aac gcc ggc cac agc gac gug gcc gac aau     144
Asn Leu Lys Lys Tyr Phe Asn Ala Gly His Ser Asp Val Ala Asp Asn
        35                  40                  45 gga aca cug uuc cug ggc auc cug aag aac ugg aaa gag gaa agc gac     192
Gly Thr Leu Phe Leu Gly Ile Leu Lys Asn Trp Lys Glu Glu Ser Asp
    50                  55                  60 cgg aag auc aug cag agc cag auc gug ucc uuc uac uuc aag cug uuc     240
Arg Lys Ile Met Gln Ser Gln Ile Val Ser Phe Tyr Phe Lys Leu Phe
65                  70                  75                  80 aag aac uuc aag gac gac cag agc auc cag aaa agc gug gaa acc auc     288
Lys Asn Phe Lys Asp Asp Gln Ser Ile Gln Lys Ser Val Glu Thr Ile
                85                  90                  95

```
aaa gaa gau aug aac guc aag uuc uuc aac ucc aac aag aag aag cgg      336
Lys Glu Asp Met Asn Val Lys Phe Phe Asn Ser Asn Lys Lys Lys Arg
            100                 105                 110

gac gac uuc gag aag cug acc aac uac agc gug acc gac cug aac gug      384
Asp Asp Phe Glu Lys Leu Thr Asn Tyr Ser Val Thr Asp Leu Asn Val
        115                 120                 125

cag aga aag gcc auc cac gag cug auc caa gug aug gcc gaa cug ucu      432
Gln Arg Lys Ala Ile His Glu Leu Ile Gln Val Met Ala Glu Leu Ser
    130                 135                 140

ccu gcc gcc aag acc gga aag cgg aag aga agc cag aug cug uuc aga      480
Pro Ala Ala Lys Thr Gly Lys Arg Lys Arg Ser Gln Met Leu Phe Arg
145                 150                 155                 160

ggc aga cgg gcc ucu cag uga                                          501
Gly Arg Arg Ala Ser Gln
                165


<210> SEQ ID NO 21
<211> LENGTH: 166
<212> TYPE: PRT
<213> ORGANISM: Homo sapiens
<220> FEATURE:
<223> OTHER INFORMATION: [CDS]:1..501 from SEQ ID NO 20

<400> SEQUENCE: 21

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165


<210> SEQ ID NO 22
<211> LENGTH: 604
<212> TYPE: DNA
<213> ORGANISM: Homo sapiens
<220> FEATURE:
<223> OTHER INFORMATION: DNA construct IFN alpha 16

<400> SEQUENCE: 22

taatacgact cactataggg agacgccacc atggccctga gcttctctct gctgatggct     60

gtgctggtgc tgagctacaa gagcatctgc agcctgggct gcgacctgcc tcagacacac    120

tctctgggaa acagacgggc cctgattctg ctggcccaga tgggcagaat ctcccacttc    180
```

agctgcctga aggacagata cgacttcggc ttccctcaag aggtgttcga cggcaaccag 240
ttccagaagg cccaggccat ctctgccttc cacgagatga tccagcagac cttcaacctg 300
ttcagcacca aggatagcag cgccgcctgg gatgagacac tgctggacaa gttctacatc 360
gagctgttcc agcagctgaa cgacctggaa gcctgcgtga cacaagaagt gggcgtcgaa 420
gagatcgccc tgatgaacga ggatagcatc ctggccgtgc gcaagtactt ccagcggatc 480
accctgtacc tgatgggcaa gaagtacagc ccttgcgcct gggaagtcgt gcgggccgaa 540
atcatgagaa gcttcagctt tagcaccaac ctgcagaagg gcctgagaag aaaggactga 600
ttcg 604

<210> SEQ ID NO 23
<211> LENGTH: 598
<212> TYPE: DNA
<213> ORGANISM: Homo sapiens
<220> FEATURE:
<223> OTHER INFORMATION: DNA construct IFN beta

<400> SEQUENCE: 23
taatacgact cactataggg agacgccacc atgaccaaca agtgcctgct gcagattgcc 60
ctgctgctgt gcttcagcac aacagccctg agcatgagct acaacctgct gggcttcctg 120
cagcggagca gcaacttcca gtgccagaaa ctgctgtggc agctgaacgg ccggctggaa 180
tactgcctga aggaccggat gaacttcgac atccccgagg aaatcaagca gctgcagcag 240
ttccagaaag aggacgccgc tctgaccatc tacgagatgc tgcagaacat cttcgccatc 300
ttccggcagg acagcagctc cacaggctgg aacgagacaa tcgtggaaaa tctgctggcc 360
aacgtgtacc accagatcaa ccacctgaaa accgtgctgg aagagaagct ggaaaaagag 420
gacttcaccc ggggcaagct gatgagcagc ctgcacctga agcggtacta cggcagaatc 480
ctgcactacc tgaaggccaa agagtacagc cactgcgcct ggaccatcgt gcgcgtggaa 540
atcctgcgga acttctactt catcaaccgg ctgaccggct acctgagaaa ctgattcg 598

<210> SEQ ID NO 24
<211> LENGTH: 535
<212> TYPE: DNA
<213> ORGANISM: Homo sapiens
<220> FEATURE:
<223> OTHER INFORMATION: DNA construct IFN gamma

<400> SEQUENCE: 24
taatacgact cactataggg agacgccacc atgaagtaca ccagctacat cctggccttc 60
cagctgtgca tcgtgctggg aagcctgggc tgctactgcc aggatcctta cgtgaaagag 120
gccgagaacc tgaagaagta ctttaacgcc ggccacagcg acgtggccga caatggaaca 180
ctgttcctgg gcatcctgaa gaactggaaa gaggaaagcg accggaagat catgcagagc 240
cagatcgtgt ccttctactt caagctgttc aagaacttca aggacgacca gagcatccag 300
aaaagcgtgg aaaccatcaa agaagatatg aacgtcaagt tcttcaactc caacaagaag 360
aagcgggacg acttcgagaa gctgaccaac tacagcgtga ccgacctgaa cgtgcagaga 420
aaggccatcc acgagctgat ccaagtgatg gccgaactgt ctcctgccgc caagaccgga 480
aagcggaaga gaagccagat gctgttcaga ggcagacggg cctctcagtg attcg 535

<210> SEQ ID NO 25
<211> LENGTH: 587
<212> TYPE: RNA

-continued

<213> ORGANISM: Homo sapiens
<220> FEATURE:
<223> OTHER INFORMATION: mRNA construct for IFN alpha 16

<400> SEQUENCE: 25
gggagacgcc accauggccc ugagcuucuc ucugcugaug gcugugcugg ugcugagcua 60
caagagcauc ugcagccugg gcugcgaccu gccucagaca cacucucugg gaaacagacg 120
ggcccugauu cugcuggccc agaugggcag aaucucccac uucagcugcc ugaaggacag 180
auacgacuuc ggcuucccuc aagagguguu cgacggcaac caguuccaga aggcccaggc 240
caucucugcc uuccacgaga ugauccagca gaccuucaac cuguucagca ccaaggauag 300
cagcgccgcc ugggaugaga cacugcugga caaguucuac aucgagcugu uccagcagcu 360
gaacgaccug gaagccugcg ugacacaaga agugggcguc gaagagaucg cccugaugaa 420
cgaggauagc auccuggccg ugcgcaagua cuuccagcgg aucacccugu accugauggg 480
caagaaguac agcccuugcg ccugggaagu cgugcgggcc gaaaucauga gaagcuucag 540
cuuuagcacc aaccugcaga agggccugag aagaaaggac ugauucg 587

<210> SEQ ID NO 26
<211> LENGTH: 581
<212> TYPE: RNA
<213> ORGANISM: Homo sapiens
<220> FEATURE:
<223> OTHER INFORMATION: mRNA construct for IFN beta

<400> SEQUENCE: 26
gggagacgcc accaugacca acaagugccu gcugcagauu gcccugcugc ugugcuucag 60
cacaacagcc cugagcauga gcuacaaccu gcugggcuuc cugcagcgga gcagcaacuu 120
ccagugccag aaacugcugu ggcagcugaa cggccggcug gaauacugcc ugaaggaccg 180
gaugaacuuc gacauccccg aggaaaucaa gcagcugcag caguuccaga aagaggacgc 240
cgcucugacc aucuacgaga ugcugcagaa caucuucgcc aucuuccggc aggacagcag 300
cuccacaggc uggaacgaga caaucgugga aaaucugcug gccaacgugu accaccagau 360
caaccaccug aaaaccgugc uggaagagaa gcuggaaaaa gaggacuuca cccggggcaa 420
gcugaugagc agccugcacc ugaagcggua cuacggcaga auccugcacu accugaaggc 480
caaagaguac agccacugcg ccuggaccau cgugcgcgug gaaauccugc ggaacuucua 540
cuucaucaac cggcugaccg gcuaccugag aaacugauuc g 581

<210> SEQ ID NO 27
<211> LENGTH: 518
<212> TYPE: RNA
<213> ORGANISM: Homo sapiens
<220> FEATURE:
<223> OTHER INFORMATION: mRNA construct for IFN gamma

<400> SEQUENCE: 27
gggagacgcc accaugaagu acaccagcua cauccuggcc uuccagcugu gcaucgugcu 60
gggaagccug ggcugcuacu gccaggaucc uuacgugaaa gaggccgaga accugaagaa 120
guacuuuaac gccggccaca gcgacguggc cgacaaugga acacuguucc ugggcauccu 180
gaagaacugg aaagaggaaa gcgaccggaa gaucaugcag agccagaucg uguccuucua 240
cuucaagcug uucaagaacu ucaaggacga ccagagcauc cagaaaagcg uggaaaccau 300
caaagaagau augaacguca aguucuucaa cuccaacaag aagaagcggg acgacuucga 360
gaagcugacc aacuacagcg ugaccgaccu gaacgugcag agaaaggcca uccacgagcu 420
gauccaagug auggccgaac ugucuccugc cgccaagacc ggaaagcgga agagaagcca 480
gaugcuguuc agaggcagac gggccucuca gugauucg 518

<210> SEQ ID NO 28
<211> LENGTH: 24
<212> TYPE: DNA
<213> ORGANISM: Artificial Sequence
<220> FEATURE:
<223> OTHER INFORMATION: M+24 F primer

<400> SEQUENCE: 28
agatgagtct tctaaccgag gtcg 24

<210> SEQ ID NO 29
<211> LENGTH: 24
<212> TYPE: DNA
<213> ORGANISM: Artificial Sequence
<220> FEATURE:
<223> OTHER INFORMATION: Rev-mod primer

<400> SEQUENCE: 29
tgcaaagaca ctttccagtc tctg 24

<210> SEQ ID NO 30
<211> LENGTH: 20
<212> TYPE: DNA
<213> ORGANISM: Artificial Sequence
<220> FEATURE:
<223> OTHER INFORMATION: M+64 probe

<400> SEQUENCE: 30
tcaggccccc tcaaagccga 20

<210> SEQ ID NO 31
<211> LENGTH: 20
<212> TYPE: DNA
<213> ORGANISM: Artificial Sequence
<220> FEATURE:
<223> OTHER INFORMATION: Fer_GAPDH FWD primer

<400> SEQUENCE: 31
caacggattt ggccgtattg 20

<210> SEQ ID NO 32
<211> LENGTH: 23
<212> TYPE: DNA
<213> ORGANISM: Artificial Sequence
<220> FEATURE:
<223> OTHER INFORMATION: Fer_GAPDH REV primer

<400> SEQUENCE: 32
ctggaacatg tagaccatgt agt 23

<210> SEQ ID NO 33
<211> LENGTH: 27
<212> TYPE: DNA
<213> ORGANISM: Artificial Sequence
<220> FEATURE:
<223> OTHER INFORMATION: Fer_GAPDH PRB probe

<400> SEQUENCE: 33
agggtcattg atggcgacaa tatccac 27

<210> SEQ ID NO 34

-continued

```
<211> LENGTH: 20
<212> TYPE: DNA
<213> ORGANISM: Artificial Sequence
<220> FEATURE:
<223> OTHER INFORMATION: SARS-CoV-2 N gene qPCR primer 1

<400> SEQUENCE: 34

aaattttggg gaccaggaac                                              20


<210> SEQ ID NO 35
<211> LENGTH: 20
<212> TYPE: DNA
<213> ORGANISM: Artificial Sequence
<220> FEATURE:
<223> OTHER INFORMATION: SARS-CoV-2 N gene qPCR primer 2

<400> SEQUENCE: 35

tggcacctgt gtaggtcaac                                              20


<210> SEQ ID NO 36
<211> LENGTH: 20
<212> TYPE: DNA
<213> ORGANISM: Artificial Sequence
<220> FEATURE:
<223> OTHER INFORMATION: SARS-CoV-2 N gene qPCR probe

<400> SEQUENCE: 36

atgtcgcgca ttggcatgga                                              20
```

USE OF IFN-LAMBDA MRNA FOR TREATING VIRAL INFECTIONS

RELATED APPLICATIONS

This application is a national stage filing under 37 U.S.C. 371 of International Application No. PCT/EP2021/080658, filed Nov. 4, 2021, which claims priority to European Application No. EP 20205674.3, filed Nov. 4, 2020. The entire teachings of said applications are incorporated herein by reference herein. International Application PCT/EP2021/080658 was published under PCT Article 21(2) in English.

The present invention relates to pharmaceutical compositions comprising an mRNA encoding an IFN-λ polypeptide for use in treating a viral-induced disorder, preferably a viral-induced respiratory disorder, such as influenza or COVID-19.

Interferons are a group of proteins which presently are classified into three different families, type I interferons, type II interferons and type III interferons.

Type I interferons are a family of closely related glycoproteins comprised of thirteen IFN-α subtypes as well as IFN-β, IFN-κ, IFN-ε and IFN-ω. In humans, the IFNα gene family is composed of 12 different subtypes encoded by 14 genes, including one pseudogene and two genes that encode identical proteins (Diaz et al., Genomics 22 (1994), 540-552), i.e. IFN-α1, IFN-α2, IFN-α8, IFN-α14, IFN-α17, IFN-α4, IFN-α5, IFN-α6, IFN-α7, IFN-α10, IFN-α16, IFN-α21 (da Rocha Matos et al., Emerg Microbes Infect. 8, (2019), 1763-1776). As regards IFN-α subtypes, it has been found that they reveal a spectrum of anti-viral, anti-proliferative and immunomodulatory responses. Type I interferons play an important role in the innate immune response to respiratory virus infection. The mechanism involves initial release of interferon-β which in turn stimulates the further release of interferon-β and of the interferon-αs in a cascade mediated via the type-1 interferon receptor.

There is one type II interferon, i.e. IFN-gamma, which binds a different receptor than type I interferons and has largely distinct functions from the type I IFNs.

Type III interferons are thee most recently discovered family of interferons. They are also referred to as interferon lambdas (IFNλs). The IFNλs are three closely related proteins which have been discovered in 2003. Interferon λ-1 is also known as IL-29, while Interferon λ-2 and λ-3 are also known as IL-28A and IL-28B, respectively. These interferons bind to a third receptor distinct from those of type I and type II interferons. These interferons have been shown to have anti-viral activity. It has been found that interferon λ is important in a wide variety of viral infections including HCV, HBV, influenza virus, rhinovirus, respiratory syncytial virus (RSV), lymphocytic choriomeningitis virus (LCMV), rotavirus, reovirus, norovirus and West Nile virus (WNV). Experimental in vivo approaches using IFNλ receptor knockout mice have highlighted the importance of IFNλ signaling in control of influenza A virus (IAV), SARS coronavirus, RSV and human metapneumovirus levels in the lung as well as norovirus, reovirus and rotavirus levels in the gastrointestinal tract. In vivo studies indicate that IFNλ shows, in comparison to IFNα/β, a reduced ISG response while it is much less inflammatory in vivo than IFNα/β. Interestingly, IFNλ retains many antiviral properties despite the less inflammatory response compared with type I IFNs. This has spurred development of IFNλ for clinical use as an alternative treatment to IFNα for HCV infection (Muir et al., J. Hepatol. 61 (2014), 1238-1246). More recent developments also indicate that IFNλ treatment could also be utilized to control respiratory viral infections. IFNλ2 and 3 was shown to control IAV pulmonary titers similarly to IFNα or IFN3 treatment (Davidson et al., EMBO Mol. Med. 8 (2016), 1099-1112; Kim et al, Am. J. Respir. Cell. Mol. Biol. 56 (2017), 202-212). Importantly, IFNλ treatment avoided excessive pulmonary inflammation associated with IFNα treatment (Kim et al., Am. J. Respir. Cell. Mol. Biol. 56 (2017), 202-212). Therapeutic applications of IFNλ so far concentrate on the administration of the recombinantly produced protein. However, the use of recombinantly produced protein requires the repeated administration of relatively high doses of protein since the protein is relatively quickly cleared from the system and can, thus, only act for a brief period of time. For example in Dinnon I I I et al. (Nature, doi.org/10.1038/s41586-020-2708-8 (2020)) 2 μg of peg-IFNλ1 is administered subcutaneously to mice. Similarly, Davidson et al. (EMBO Mol. Med. 8 (2016), 1099-1112) describe the administration of 2.6 μg/50 μl of IFNλ3 to B6.A2G-Mx mice for treating or preventing influenza infection. In Galani et al. (Immunity 46 (2017), 875-890), it was reported that mice were treated with 5 or 10 μg of recombinant mouse pegylated IFNλ2.

Therefore, there is a need to provide means and methods for an efficient way to deliver IFNλ in vivo to target tissues, i.e. in a manner which ensures that it is active for an extended period of time and can exert its effect for an extended period of time. This would allow to reduce the amount of IFNλ to be administered to a patient within a given period of time and would also allow to reduce the numbers of administrations to a patient.

The present invention addresses this need by providing the embodiments as recited in the claims.

Thus, the present invention relates to a pharmaceutical composition comprising an mRNA encoding an IFN-λ polypeptide for use in treating and/or preventing a viral-induced disorder.

The present invention is based on the finding that mRNA which codes for IFNλ allows for an extremely efficient and long-lasting activating effect on down-stream targets important for antiviral activity of IFN-λ when transfected into cells which serve as a model for alveolar epithelial cells. In particular, in an in vitro model using A-549 cells (a model for type Il-like pneumocytes/alveolar epithelial cells), even at extremely low doses of mRNA the downstream-targets IFIT3, ISG15, IFIT1 and OAS3 (which are indicative of the antiviral activity of IFNλ) are activated to high levels and for an extended period of time (more than 120 hours). These results could be confirmed in in vivo experiments in mice. Moreover, it has surprisingly been found that in A-549 cells which had previously been stably transfected so as to express the ACE2 receptor, the induction of the downstream targets is as high as in the case of A-549 cells which do not express the ACE2 receptor when mRNA encoding an IFN-λ polypeptide is used, while in the case of the administration of recombinant IFNλ protein the induction of downstream targets is much lower in ACE2 expressing A-549 cells when compared to A-549 cells which do not express the ACE2 receptor. This indicates that the administration of the recombinant IFNλ polypeptide does not lead to an efficient activation of downstream targets in cells which express the ACE2 receptor while the administration of mRNA encoding IFNλ allows for an efficient activation. Accordingly, the use of mRNA encoding IFNλ is particularly advantageous in cases where viral infections target ACE2 expressing cells, i.e. where the virus enters the cells via the ACE2 receptor.

Moreover, it could be shown in Air-Liquid Interface (ALI) cultures of different cell-types that unexpectedly mRNA encoding IFNλ is able to show an effect as regards activating downstream targets when applied to the apical side of the cells (facing the air) although the corresponding receptor is expected to be located on the basolateral side of the cells (facing the liquid culture medium). These results could be confirmed by in vivo experiments in mice in which the mRNA encoding IFNλ was directly applied to the lung. It is known that airway epithelia form mechanical barriers that separate the external environment from the internal milieu and that structural polarity of epithelia is critical for barrier integrity and is controlled by intricate cell-cell adhesive complexes that contain adherens and tight junctions (see, e.g., Humlicek et al., J. Immunol. 178 (2007), 6395-6403). Moreover, it is known that there is a polarity as regards the functionality of certain cytokines in the sense that only their basolateral location with regard to the airway epithelium leads to an effect since the corresponding receptors are obviously only present at the basolateral side of the cells. Accordingly, airway epithelial responses to certain cytokines could only be observed after application to the airway lumen if the barrier function of the epithelia was physically or pharmacologically disrupted previously (Humlicek et al., loc. cit.). Thus, it is surprising that the administration of IFNλ mRNA to the apical side of epithelial cells cultured in ALI cultures or applied directly to the lung of mice without disruption of the barrier function of the epithelia leads to an efficient activation of downstream targets of IFNλ (which is indicative for an antiviral effect).

In principle, in the context of the present invention, mRNA encoding an IFNλ polypeptide can be used for treating and/or preventing any possible viral-induced disorder. It has been shown that IFNλ exhibits antiviral activity against many viruses in vitro. In vivo the antiviral activity of IFNλ has in particular been observed for viruses that infect epithelial cells of the respiratory, gastrointestinal and urogenital tracts as well as the liver (see, e.g., Lazear et al., Immunity 43 (2015), 15-28; Table 1). Viral-induced diseases which can be treated or prevented according to the present invention include diseases caused by a virus belonging to the family of Pneumoviridae, Orthomyxoviridae, Adenoviridae, Arenaviridae, Paramyxoviridae, Flaviviridae, Retroviridae, Caliciviridae, Picornaviridae, Coronaviridae, Parvoviridae, Reoviridae, Herpesviridae or Hepadnaviridae.

Viruses belonging to the family of Pneumoviridae include Human Metapneumo virus.

Viruses belonging to the family of Orthomyxoviridae include Influenza virus.

Viruses belonging to the group of Adenoviridae include Adenovirus.

Viruses belonging to the family of Arenaviridae include Lymphocytic choriomeningitis virus.

Viruses belonging to the family of Paramyxoviridae include Respiratory syncytial virus.

Viruses belonging to the family of Flaviviridae include Dengue virus, Hepatitis C virus, Zika virus and West Nile virus.

Viruses belonging to the family of Retroviridae include Human immunodeficiency virus.

Viruses belonging to the family of Caliciviridae include norovirus.

Viruses belonging to the family of Picornaviridae include rhinovirus.

Viruses belonging to the family of Coronaviridae include SARS-CoV, SARS-CoV2, MERS and HCoV-NL63, -OC43, -229E and HKU1.

Viruses belonging to the family of Parvoviridae include bocavirus.

Viruses belonging to the family of Reoviridae include Reovirus and Rotavirus.

Viruses belonging to the family of Herpesviridae include Cytomegalovirus and Herpes simplex virus, such as Herpes simplex virus 1 and 2.

Viruses belonging to the family of Hepadnaviridae include Hepatitis B virus.

In a preferred embodiment, the viral-induced disorder is a viral-induced respiratory disorder. In this context, it is preferred that the virus which induces the respiratory disorder is selected from the group consisting of rhinovirus, influenza virus, parainfluenza virus, metapneumo virus, respiratory syncytial virus, adenovirus and corona virus.

In a particularly preferred embodiment, the virus is a virus which enters cells via the ACE2 receptor. ACE2 (Angiotensin-Converting-Enzyme 2) is an enzyme attached to the cell membranes of cells in the lungs, arteries, heart, kidney and intestines. It lowers blood pressure by catalyzing the hydrolysis of angiotensin II into angiotensin. ACE2 also serves as the entry point into cells for some coronaviruses, including SARS-CoV, SARS-CoV-2 and HCoV-NL63.

Thus, in a particularly preferred embodiment, the virus is a coronavirus and most preferably a virus selected from the group consisting of SARS-CoV, SARS-CoV-2 and HCoV-NL63.

Accordingly, in a particularly preferred embodiment, the viral-induced disease is SARS (caused by SARS-CoV), COVID-19 (caused by SARS-CoV-2) and mild to moderate upper respiratory tract infections, severe lower respiratory tract infection, croup and bronchiolitis (caused by HCoV-NL63).

The IFNλ protein encoded by the mRNA comprised in the pharmaceutical composition can be any possible IFNλ protein, in particular Interferon λ-1 (is also known as IL-29), Interferon λ-2 (also known as IL-28A) or Interferon λ-3 (IL-28B) or any combination thereof. In a preferred embodiment, the IFNλ protein is a human protein.

In one embodiment the IFNλ protein encoded by the mRNA comprised in the pharmaceutical composition is IFNλ-1, preferably IFNλ-1 comprising the amino acid sequence as shown in SEQ ID NO:2. In a more preferred embodiment the mRNA encoding IFNλ-1 comprises a coding region as shown in SEQ ID NO:1.

In one embodiment the IFNλ protein encoded by the mRNA comprised in the pharmaceutical composition is IFNλ-2, preferably IFNλ-2 comprising the amino acid sequence as shown in SEQ ID NO:4. In a more preferred embodiment the mRNA encoding IFNλ-2 comprises a coding region as shown in SEQ ID NO:3.

In one embodiment the IFNλ protein encoded by the mRNA comprised in the pharmaceutical composition is IFNλ-3, preferably IFNλ-3 comprising the amino acid sequence as shown in SEQ ID NO:6. In a more preferred embodiment the mRNA encoding IFNλ-3 comprises a coding region as shown in SEQ ID NO:5.

In some embodiments of the present invention the polyribonucleotide employed according to the present invention may contain unmodified and modified nucleotides. The term "unmodified nucleotide" used herein refers to A, C, G and U nucleotides. The term "modified nucleotide" used herein refers to any naturally occurring or non-naturally occurring isomers of A, C, G and U nucleotides as well as to any naturally occurring or naturally occurring analogs, alternative or modified nucleotide or isomer thereof having for example chemical modifications or substituted residues. Modified nucleotides can have a base modification and/or a sugar modification. Modified nucleotides can also have phosphate group modifications, e.g., with respect to the 5'-prime cap of an mRNA molecule. Modified nucleotides also include nucleotides that are synthesized post-transcriptionally by covalent modification of the nucleotides. Further, any suitable mixture of non-modified and modified nucleotides is possible. A non-limiting number of examples of modified nucleotides can be found in the literature (e.g. Cantara et al., Nucleic Acids Res, 2011, 39(Issue suppl_1): D195-D201; Helm and Alfonzo, Chem Biol, 2014, 21(2): 174-185; Carell et al., Angew Chem Int Ed Engl, 2012, 51(29):7110-31) and some preferable modified nucleotides are mentioned exemplarily in the following based on their respective nucleoside residue:

1-methyladenosine, 2-methylthio-N6-hydroxynorvalyl carbamoyladenosine, 2-methyladenosine, 2'-O-ribosylphosphate adenosine, N6-methyl-N6-threonylcarbamoyladenosine, N6-acetyladenosine, N6-glycinylcarbamoyladenosine, N6-isopentenyladenosine, N6-methyladenosine, N6-threonylcarbamoyladenosine, N6,N6-dimethyladenosine, N6-(cis-hydroxyisopentenyl)adenosine, N6-hydroxynorvalylcarbamoyladenosine, 1,2'-O-dimethyladenosine, N6,2'-O-dimethyladenosine, 2'-O-methyladenosine, N6,N6,2'-O-trimethyladenosine, 2-methylthio-N6-(cis-hydroxyisopentenyl)adenosine, 2-methylthio-N6-methyladenosine, 2-methylthio-N6-isopentenyladenosine, 2-methylthio-N6-threonyl carbamoyladenosine, N6-2-methylthio-N6-threonyl carbamoyladenosine, 2-methylthio-N6-(cis-hydroxyisopentenyl)adenosine, 7-methyladenosine, 2-methylthio-adenosine, 2-methoxy-adenosine, 2'-amino-2'-deoxyadenosine, 2'-azido-2'-deoxyadenosine, 2'-fluoro-2'-deoxyadenosine, 2-aminopurine, 2,6-diaminopurine, 7-deaza-adenosine, 7-deaza-8-aza-adenosine, 7-deaza-2-aminopurine, 7-deaza-8-aza-2-aminopurine, 7-deaza-2,6-diaminopurine, 7-deaza-8-aza-2,6-diaminopurine; 2-thiocytidine, 3-methylcytidine, N4-acetylcytidine, 5-formylcytidine, N4-methylcytidine, 5-methylcytidine, 5-hydroxymethylcytidine, 5-hydroxycytidine, lysidine, N4-acetyl-2'-O-methylcytidine, 5-formyl-2'-O-methylcytidine, 5,2'-O-dimethylcytidine, 2-O-methylcytidine, N4,2'-O-dimethylcytidine, N4,N4,2'-O-trimethylcytidine, isocytidine, pseudocytidine, pseudoisocytidine, 2-thio-cytidine, 2'-methyl-2'-deoxycytidine, 2'-amino-2'-deoxycytidine, 2'-fluoro-2'-deoxycytidine, 5-iodocytidine, 5-bromocytidine, 2'-azido-2'-deoxycytidine, 2'-amino-2'-deoxycytidine, 2'-fluor-2'-deoxycytidine, 5-aza-cytidine, 3-methyl-cytidine, 1-methyl-pseudoisocytidine, pyrrolo-cytidine, pyrrolo-pseudoisocytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, 2-methoxy-cytidine, 2-methoxy-5-methyl-cytidine, 4-methoxy-pseudoisocytidine, 4-methoxy-1-methyl-pseudoisocytidine, zebularine,5-aza-zebularine, 5-methyl-zebularine, 5-aza-2-thio-zebularine, 2-thio-zebularine; 1-methylguanosine, N2,7-dimethylguanosine, N2-methylguanosine, 2'-O-ribosylphosphate guanosine, 7-methylguanosine, hydroxywybutosine, 7-aminomethyl-7-deazaguanosine, 7-cyano-7-deazaguanosine, N2,N2-dimethylguanosine, N2,7,2'-O-trimethylguanosine, N2,2'-O-dimethylguanosine, 1,2'-O-dimethylguanosine, 2'-O-methylguanosine, N2,N2,2'-O-trimethylguanosine, N2,N2J-trimethylguanosine, Isoguanosine, 4-demethylwyosine, epoxyqueuosine, undermodified hydroxywybutosine, methylated undermodified hydroxywybutosine, isowyosine, peroxywybutosine, galactosyl-queuosine, mannosyl-queuosine, queuosine, archaeosine, wybutosine, methylwyosine, wyosine, 7-aminocarboxypropyldemethylwyosine, 7-aminocarboxypropylwyosine, 7-aminocarboxypropylwyosinemethylester, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, 8-oxo-guanosine, 7-methyl-8-oxo-guanosine, 1-methyl-6-thio-guanosine, N2-methyl-6-thio-guanosine, N2,N2-dimethyl-6-thio-guanosine, N1-methylguanosine, 2'-amino-3'-deoxyguanosine, 2'-azido-2'-deoxyguanosine, 2'-fluoro-2'-deoxyguanosine, 2-thiouridine, 3-(3-amino-3-carboxypropyl)uridine, 3-methyluridine, 4-thiouridine, 5-methyl-2-thiouridine, 5-methylaminomethyluridine, 5-carboxymethyluridine, 5-carboxymethylaminomethyluridine, 5-hydroxyuridine, 5-methyluridine, 5-taurinomethyluridine, 5-carbamoylmethyluridine, 5-(carboxyhydroxymethyl)uridine methyl ester, dihydrouridine, 5-methyldihydrouridine, 5-methylaminomethyl-2-thiouridine, 5-(carboxyhydroxymethyl)uridine, 5-(carboxyhydroxymethyl)-2'-O-methyluridine methyl ester, 5-(isopentenylaminomethyl)uridine, 5-(isopentenylaminomethyl)-2-thiouridine, 3,2'-O-dimethyluridine, 5-carboxymethylaminomethyl-2'-O-methyluridine, 5-carbamoylhydroxymethyluridine, 5-carbamoylmethyl-2'-O-methyluridine, 5-carbamoylmethyl-2-thiouridine, 5-methoxycarbonylmethyl-2'-O-methyluridine, 5-(isopentenylaminomethyl)-2'-O-methyluridine, 5,2'-O-dimethyluridine, 2'-O-methyluridine, 2'-O-methyl-2-thiorudine, 2-thio-2'-O-methyluridine, uridine 5-oxyacetic acid, 5-methoxycarbonylmethyluridine, uridine 5-oxyacetic acid methyl ester, 5-methoxyuridine, 5-aminomethyl-2-thiouridine, 5-carboxymethylaminomethyl-2-thiouridine, 5-methylaminomethyl-2-selenouridine, 5-methoxycarbonylmethyl-2-thiouridine, 5-taurinomethyl-2-thiouridine, pseudouridine, 1-methyl-3-(3-amino-3-carboxypropyl)pseudouridine, 1-methylpseudouridine, 3-methylpseudouridine, 2'-O-methylpseudouridine, 5-formyluridine, 5-aminomethyl-2-geranyluridine, 5-taurinomethyluridine, 5-iodouridine, 5-bromouridine, 2'-methyl-2'-deoxyuridine, 2'-amino-2'-deoxyuridine, 2'-azido-2'-deoxyuridine, 2'-fluoro-2'-deoxyuridine, inosine, 1-methylinosine, 1,2'-O-dimethylinosine, 2'-O-methylinosine, 5-aza-uridine, 2-thio-5-aza-uridine, 4-thio-pseudouridine, 2-thio-pseudouridine, 5-carboxymethyl-uridine, 1-carboxymethyl-pseudouridine, 5-propynyl-uridine, 1-propynyl-pseudouridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 1,2'-O-dimethyladenosine, 1,2'-O-dimethylguanosine, 1,2'-O-dimethylinosine, 2,8-dimethyladenosine, 2-methylthiomethylenethio-N6-isopentenyl-adenosine, 2-geranylthiouridine, 2-lysidine, 2-methylthio cyclic N6-threonylcarbamoyladenosine, 2-methylthio-N6-(cis-hydroxyisopentenyl)

adenosine, 2-methylthio-N6-hydroxynorvalylcarbamoyladenosine, 2-methylthio-N6-threonylcarbamoyladenosine, 2-selenouridine, 2-thio-2'-O-methyluridine, 2'-O-methyladenosine, 2'-O-methylcytidine, 2'-O-methylguanosine, 2'-O-methylinosine, 2'-O-methylpseudouridine, 2'-O-methyluridine, 2'-O-methyluridine 5-oxyacetic acid methyl ester, 2'-O-ribosyladenosinephosphate, 2'-O-ribosylguanosinephosphate, 3,2'-O-dimethyluridine, 3-(3-amino-3-carboxypropyl)-5,6-dihydrouridine, 3-(3-amino-3-carboxypropyl) pseudouridine, 5,2'-O-dimethylcytidine, 5,2'-0-dimethyluridine, 5-(carboxyhydroxymethyl)-2'-O-methyluridine methyl ester, 55-(isopentenylaminomethyl)-2'-O-methyluridine, 5-aminomethyl-2-geranylthiouridine, 5-aminomethyl-2-selenouridine, 5-aminomethyluridine, 5-carbamoylmethyl-2'-O-methyluridine, 5-carboxyhydroxymethyluridine, 5-carboxymethyl-2-thiouridine, 5-carboxymethylaminomethyl-2-geranylthiouridine, 5-carboxymethylaminomethyl-2-selenouridine, 5-carboxymethylaminomethyl-2'-O-methyluridine, 5-cyanomethyluridine, 5-formyl-2'-O-methylcytidine, 5-methoxycarbonylmethyl-2'-O-methyluridine, 5-methylaminomethyl-2-geranylthiouridine, 7-aminocarboxypropyl-demethylwyosine, 7-methylguanosine, 8-methyladenosine, N2,2'-O-dimethylguanosine, N2,7,2'-O-trimethylguanosine, N2,7-dimethylguanosine, N2,N2,2'-O-trimethylguanosine, N2,N2,7-trimethylguanosine, N2,N2,7-trimethylguanosine, N4,2'-O-dimethylcytidine, N4,N4,2'-O-trimethylcytidine, N4,N4-dimethylcytidine, N4-acetyl-2'-O-methylcytidine, N6,2'-O-dimethyladenosine, N6,N6,2'-O-trimethyladenosine, N6-formyladenosine, N6-hydroxymethyladenosine, agmatidine, 2-methylthio cyclic N6-threonylcarbamoyladenosine, glutamyl-queuosine, guanosine added to any nucleotide, guanylylated 5' end, hydroxy-N6-threonylcarbamoyladenosine; most preferably pseudo-uridine, N1-methyl-pseudo-uridine, 2'-fluoro-2'-deoxycytidine, 5-iodocytidine, 5-methylcytidine, 2-thiouridine, 5-iodouridine and/or 5-methyl-uridine.

Furthermore, the term "modified nucleotide" comprises nucleotides containing isotopes such as deuterium. The term "isotope" refers to an element having the same number of protons but different number of neutrons resulting in different mass numbers. Thus, isotopes of hydrogen for example are not limited to deuterium, but include also tritium. Furthermore, the polyribonucleotide can also contain isotopes of other elements including for example carbon, oxygen, nitrogen and phosphor. It is also possible that modified nucleotides are deuterated or contain another isotope of hydrogen or of oxygen, carbon, nitrogen or phosphor.

The total number of modified nucleotide types in the polyribonucleotide can be 0, 1, 2, 3, or 4. Hence, in some embodiments, at least one nucleotide of one nucleotide type, e.g. at least one U nucleotide, can be a modified nucleotide. In some embodiments, at least one nucleotide of in total two nucleotide types, e.g. at least one U nucleotide and at least one C nucleotide, can be a modified nucleotide. In some embodiments, at least one nucleotide of in total three nucleotide types, e.g. at least one G nucleotide, at least one U nucleotide and at least one C nucleotide, can be a modified nucleotide. In some embodiments, at least one nucleotide of all four nucleotide types can be a modified nucleotide. In all these embodiments one or more nucleotides per nucleotide type can be modified, the percentage of said modified nucleotides of per nucleotide type being 0%, 2.5%, 5%, 7.5%, 10%, 15%, 20%, 25%, 30%, 35%, 40%, 45%, 50%, 55%, 60%, 65%, 70%, 75%, 80%, 85%, 90% or 100%.

In some embodiments, the total percentage of modified nucleotides comprised in the mRNA molecules to be purified is 0%, 2.5%, 5%, 7.5%, 10%, 15%, 20%, 25%, 30%, 35%, 40%, 45%, 50%, 55%, 60%, 65%, 70%, 75%, 80%, 85%, 90% or 100%.

In a preferred embodiment the mRNA is an mRNA which contains a combination of modified and unmodified nucleotides. Preferably, it is an mRNA containing a combination of modified and unmodified nucleotides as described in WO2011/012316. The mRNA described therein is reported to show an increased stability and diminished immunogenicity. In a preferred embodiment, in such a modified mRNA 5 to 50% of the cytidine nucleotides and 5 to 50% of the uridine nucleotides are modified. The adenosine- and guanosine-containing nucleotides can be unmodified. The adenosine and guanosine nucleotides can be unmodified or partially modified, and they are preferably present in unmodified form. Preferably 10 to 35% of the cytidine and uridine nucleotides are modified and particularly preferably the content of the modified cytidine nucleotides lies in a range from 7.5 to 25% and the content of the modified uridine nucleotides in a range from 7.5 to 25%. It has been found that in fact a relatively low content, e.g. only 10% each, of modified cytidine and uridine nucleotides can achieve the desired properties. It is particularly preferred that the modified cytidine nucleotides are 5-methylcytidin residues and the modified uridine nucleotides are 2-thiouridin residues. Most preferably, the content of modified cytidine nucleotides and the content of the modified uridine nucleotides is 25%, respectively.

In certain embodiments of any of the foregoing, the percentage of analogs of a given nucleotide refers to input percentage (e.g., the percentage of analogs in a starting reaction, such as a starting in vitro transcription reaction). In certain embodiments of any of the foregoing, the percentage of analogs of a given nucleotide refers to output (e.g., the percentage in a synthesized or transcribed compound). Both options are equally contemplated.

The mRNA may be produced recombinantly in in vivo systems by methods known to a person skilled in the art.

Alternatively, the modified RNA, preferably the mRNA molecules of the present invention may be produced in an in vitro system using, for example, an in vitro transcription system which is known to the person skilled in the art. An in vitro transcription system capable of producing RNA, preferably mRNA requires an input mixture of modified and unmodified nucleoside triphosphates to produce modified mRNA molecules.

Furthermore, the modified RNA, preferably mRNA molecules may be chemically synthesized, e.g., by conventional chemical synthesis on an automated nucleotide sequence synthesizer using a solid-phase support and standard techniques or by chemical synthesis of the respective DNA sequences and subsequent in vitro or in vivo transcription of the same.

The coding region comprised in the mRNA and which encodes an IFNλ protein can be a partly or fully codon optimized sequence. Codon optimization refers to a technique which is applied to maximize protein expression by increasing the translational efficiency of the respective polyribonucleotide as in some cases codons exist that are preferentially used by some species for a given amino acid. Examples of codon optimized coding regions are the coding regions depicted in SEQ ID NO: 1, 3 and 5.

Further, said polyribonucleotide might comprise further modifications to adjust and/or extend the duration of action. Said polyribonucleotide might also contain an m7GpppG cap, an internal ribosome entry site (IRES) and/or a polyA tail at the 3' end and/or additional sequences for promoting translation.

In addition, the polyribonucleotide employed according to the present invention may also comprise further functional regions and/or 3' or 5' non-coding regions. The 3' and/or 5' non-coding regions can be sequences which naturally flank the encoded protein or artificial sequences which contribute to the stabilization and/or regulation of said polyribonucleotide. Suitable sequences may be identified and investigated by routine experiments. Further, said polyribonucleotide can also have further functional regions and may be combined with regulatory elements and target sequences of micro-RNAs for example for spatial and temporal control the activity of the desired polyribonucleotide comprising a sequence which encodes a protein, i.e. for example with respect to specific cells or cell types and/or developmental stages or specific time frames.

In one embodiment, the mRNA also contains a 5'- and/or 3'-UTR. In a particularly preferred embodiment, the UTR sequence is a 5'-UTR sequence as described in WO 2017/167910. Even more preferably, the mRNA contains a 5'-UTR sequence directly upstream of the start codon of the coding region which shows the following sequence: GGGAGACGCCACC (SEQ ID NO:7)

In a further preferred embodiment, the mRNA also contains a 3'-UTR, preferably a 3'-UTR of the sequence 5'-TTCG-3'.

In another preferred embodiment, the mRNA is transcribed from a DNA molecule as described in WO 2017/167910. More preferably, such a DNA molecule comprises one strand with the following elements:

(a) a coding region, including a start codon at its 5' end, coding for an IFNλ polypeptide; and
(b) directly upstream of said coding sequence the sequence GGGAGACGCCACC (SEQ ID NO:7) and upstream of this sequence a promoter which is recognized by a DNA-dependent RNA polymerase, preferably a promoter with the sequence TAATACGACTCACTATA (SEQ ID NO: 8) which is recognized by a T7 DNA-dependent RNA polymerase.

Thus, in such an embodiment the sequence upstream of the start codon of the coding region is TAATACGACTCACTATA GGGAGACGCCACC (SEQ ID NO:9)

In a particularly preferred embodiment, the mRNA is transcribed from a DNA molecule as shown in any one of SEQ ID NOs: 10 to 12. SEQ ID NO: 10 shows a DNA molecule for the transcription of an mRNA molecule which encodes IFNλ-1. SEQ ID NO: 11 shows a DNA molecule for the transcription of an mRNA molecule which encodes IFNλ-2. SEQ ID NO: 12 shows a DNA molecule for the transcription of an mRNA molecule which encodes IFN,-3.

The mRNA which codes for IFNλ can be combined with an mRNA which encodes another type of interferon, preferably with a type I interferon or a type II interferon. In a preferred embodiment the type I interferon is selected from the group consisting IFN-β, IFN-α1, IFN-α2, IFN-α8, IFN-α14, IFN-α17, IFN-α4, IFN-α5, IFN-α6, IFN-α7, IFN-α10, IFN-α16 and IFN-α21 or any combination thereof. In a particularly preferred embodiment the type I interferon is IFN-α16 or IFN-β. In another preferred embodiment the other type of interferon is a type II interferon, in particular IFNγ. For such an mRNA which encodes another interferon, the same applies in connection with the preferred embodiments (e.g. possible modifications, promoter sequences, UTRs etc.) as has been described above for the mRNA encoding IFNλ.

An exemplary RNA sequence encoding IFN-α16 is shown in SEQ ID NO: 16. The encoded protein is shown in SEQ ID NO: 17.

An exemplary RNA sequence encoding IFN-β is shown in SEQ ID NO: 18. The encoded protein is shown in SEQ ID NO: 19.

An exemplary RNA sequence encoding IFNγ is shown in SEQ ID NO: 20. The encoded protein is shown in SEQ ID NO: 21.

An exemplary DNA sequence which can be transcribed into an mRNA encoding IFN-α16 is shown in SEQ ID NO: 22.

An exemplary DNA sequence which can be transcribed into an mRNA encoding IFN-β is shown in SEQ ID NO: 23.

An exemplary DNA sequence which can be transcribed into an mRNA encoding IFNγ is shown in SEQ ID NO: 24.

An exemplary mRNA sequence encoding IFN-α16 is shown in SEQ ID NO: 25.

An exemplary mRNA sequence encoding IFN-β is shown in SEQ ID NO: 26.

An exemplary mRNA sequence encoding IFNγ is shown in SEQ ID NO: 27.

The mRNA which is to be administered in accordance with the present invention is in the form of a pharmaceutical composition. In accordance with this invention, the term “pharmaceutical composition” relates to a composition in for administration to a subject. Exemplary subjects include a mammal such as a dog, cat, pig, cow, sheep, horse, rodent, e.g., rat, mouse, and guinea pig, or a primate, e.g., gorilla, chimpanzee, and human. In a most preferable embodiment, the subject is a human.

Generally, the RNA is included in an effective amount in the pharmaceutical composition. The term “effective amount” refers to an amount sufficient to induce a detectable therapeutic response in the subject to which the pharmaceutical composition is to be administered.

The pharmaceutical composition can comprise a pharmaceutically acceptable carrier, i.e. chemical compounds, materials, ingredients, and/or compositions, which are, within the scope of sound medical judgment, suitable for use in contact with the tissues of human beings and animals without excessive toxicity, irritation, allergic response, or other problem or complication, commensurate with a reasonable benefit/risk ratio. Thus, a pharmaceutically acceptable carrier is an inactive substance formulated alongside the pharmaceutically active substance for facilitating its handling in view of dosage, adsorption, solubility or pharmacokinetic considerations. Examples of suitable pharmaceutical acceptable carriers are well known in the art and include phosphate buffered saline solutions, buffer, water, emulsions, such as oil/water emulsions, various types of wetting agents, and sterile solutions. In particularly, aqueous carriers include water, alcoholic/aqueous solutions, emulsions or suspensions, including saline and buffered media. Examples of non-aqueous solvents are propylene glycol, polyethylene glycol, vegetable oils such as olive oil, and organic esters such as ethyl oleate. Further examples of pharmaceutically acceptable carriers include but are not limited to saline, Ringer’s solution and dextrose solution, citrate, phosphate, and other organic acids; salt-forming counter-ions, e.g. sodium and potassium; low molecular-weight (>10 amino acid residues) polypeptides; proteins, e.g. serum albumin, or gelatine; hydrophilic polymers, e.g. polyvinylpyrrolidone; amino acids such as histidine, glutamine, lysine, asparagine, arginine, or glycine; carbohydrates including glucose, mannose, or dextrins; monosaccharides; disaccharides; other sugars, e.g. sucrose, mannitol, trehalose or sorbitol; chelating agents, e.g. EDTA; non-ionic surfactants, e.g., polyoxyethylene sorbitan monolaurate, available on the market with the commercial name Tween, propylene glycol, Pluronics or polyethylene glycol; antioxidants including methionine, ascorbic acid and tocopherol; and/or preservatives, e.g. octadecyldimethylbenzyl ammonium chloride; hexamethonium chloride; benzalkonium chloride, benzethonium chloride; phenol, butyl or benzyl alcohol; alkyl parabens, e.g. methyl or propyl paraben; catechol; resorcinol; cyclohexanol; 3-pentanol; and m-cresol). Suitable pharmaceutically acceptable carriers and their formulations are described in greater detail in Remington's Pharmaceutical Sciences, 17th ed., 1985, Mack Publishing Co. Furthermore, preservatives, stabilizers and other additives may also be present such as, for example, antimicrobials, anti-oxidants, chelating agents, and inert gases, nanosystems or liposomes, and the like.

The administration of the mRNA encoding an IFNλ protein for the treatment and/or prevention of a viral-induced disorder can be achieved by means and methods known to the person skilled in the art, in particular for ensuring that the mRNA reaches the intended target tissue/target cells. Possible routes are, e.g., intravenous, intramuscular, intradermal, subcutaneous and delivery into the respiratory system.

If the viral-induced disorder is a respiratory disorder, the administration into the respiratory system is preferred. Possibilities for delivery into the respiratory system include instillation and inhalation. Alternatively, for delivery of the mRNA into the lung, also an i.v. administration with formulations that have a tropism for the lung is possible.

In a preferred embodiment, the pharmaceutical composition comprising the mRNA encoding an IFN-λ polypeptide is administered to a patient via inhalation.

The mRNA can be inhaled in any form which is suitable for inhalation. In a preferred embodiment, the mRNA is present in the pharmaceutical composition in a form suitable for inhalation in the form of an aerosol. A particularly suitable way of administering the mRNA to the respiratory system of a patient is by nebulization.

In a preferred embodiment, the inhalation is bolus inhalation. This means that during inhalation only for a short amount of time the aerosol containing the active agent is mixed to the inhaled air. If the aerosol containing the active agent is mixed with the air at the beginning of the inhalation, the active agent reaches with the first part of the inhaled air the deeper parts of the lung. If at the end of inhalation the addition of the active agent is stopped, no active agent is deposited in the central region of the lung, i.e. the airways, at the end of the inhalation. By using bolus inhalation it is possible to better target the different regions of the lung, e.g. the periphery of the lung or the central region, as regards the deposition of the active agent, depending on the requirements of the underlying disease state.

The mRNA can advantageously be combined in the pharmaceutical composition with compounds which ease delivery of the mRNA to the target cells or the target tissue and/or which increase its stability. One possibility in this regard is the formation of the RNA into nanoparticles with suitable substances such as those described, e.g. in PCT/EP2020/053774.

Examples for preferred agents or reagents for delivering and/or introducing the RNA into a target cell or a target tissue are in this context liposomal transfection reagents (LTR'S).

One particular mode for delivering and/or introducing the mRNA into target cells or target tissue is transfection. Hence, the mRNA to be employed can be envisaged to be transfected (into (target) cells or tissue), to be delivered/administered via transfection and/or to be prepared for transfection. Means and methods for transfecting mRNA are well known in the art and are, for example, described in Tavernier (loc. cit.), Yamamoto (Eur J Pharm Biopharm. 71(3) (2009), 484-9) and Kormann (Nat Biotechnol. 29(2) (2011), 154-7). Particular modes of transfection are lipofection, magnetofection, magnetolipofection or complexation with polymers. Hence, the mRNA to be employed may be prepared for lipofection, prepared to be transfected by lipofection, delivered/introduced via lipofection and/or administered via lipofection.

Thus, the pharmaceutical composition may (further) comprise at least one lipid or liposomal transfection reagent or enhancer (LTR; liposomal transfection reagent). The mRNA to be employed may be comprised in, complexed with and/or delivered by the LTR. In particular, the mRNA to be employed may be comprised in and/or delivered by (respective) lipofection complexes comprising the mRNA and the LTR. The pharmaceutical composition may (further) comprise the lipofection complexes.

LTRs are known in the art and are, for example, distributed by OzBiosciences, Marseille, France. For example, such LTRs may be lipids or lipidoids, preferably cationic lipids or cationic lipidoids, like the lipidoids as disclosed in PCT/EP2014/063756 (e.g. C12-(2-3-2), the lipids as disclosed in EP2285772 (e.g. Dogtor) and the lipopolyamines as disclosed in EP1003711 (e. g. DREAMFECT™ and DREAMFECT GOLD™). A particular LTR may be selected from the group consisting of (i) C12-(2-3-2);

(ii) DREAMFECT™, preferably DREAMFECT GOLD™ (DF™/DF-GOLD™; OzBiosciences, Marseille, France);

(iii) Dogtor (OzBiosciences, Marseille, France); and (iv) LIPOFECTAMINE™ like, for example, LIPOFECTAMINE™ 2000 (Invitrogene, CA, USA).

In principle, Dogtor is a preferred, DREAMFECT™ is a more preferred and DF-GOLD™ and C12-(2-3-2) are even more preferred LTR(s).

LTRs like Dogtor are, for example, described in EP2285772. LTRs like DF™ or DF-GOLD™ are, for example, described in EP1003711. In principle, the oligomers, polymers or lipidoids as disclosed in PCT/EP2014/063756, the particular cationic lipids as disclosed in EP2285772 and the particular lipopolyamines as disclosed in EP1003711 are preferred LTRs. LTRs like C12-(2-3-2) and DF-GOLD™ are most preferred.

Non-limiting examples of lipofection complexes are DF-GOLD™/RNA lipoplexes and C12-(2-3-2)/RNA lipoplexes.

C12-(2-3-2) is a particularly preferred LTR having the structure shown in formula (V) (cf. Jarzębińska et al., Angew Chem Int Ed Engl., 2016; 55(33):9591-5):

formula (V)

C12-(2-3-2)

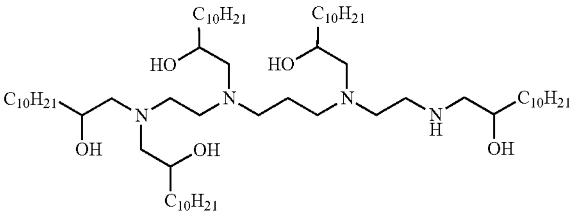

Hence, in preferred embodiments the pharmaceutical composition comprises an mRNA encoding IFNλ and further comprises a lipidoid having the structure shown in formula (V), preferably as shown in formula (VI).

A further particularly preferred LTR is a cationic lipidoid having formula (VII), herein also referred to as "dL_P" which can be synthesized via reaction of N,N'-Bis(2-aminoethyl)-1,3-propanediamine with N-Dodecylacrylamide using boric acid as catalyst. For the reaction, the mixture can be stirred at 100 °C under microwave irradiations.

Hence, in further preferred embodiments the pharmaceutical composition comprises an mRNA encoding IFNλ and further comprises a lipidoid having the structure shown in formula (VII).

formula (VII)

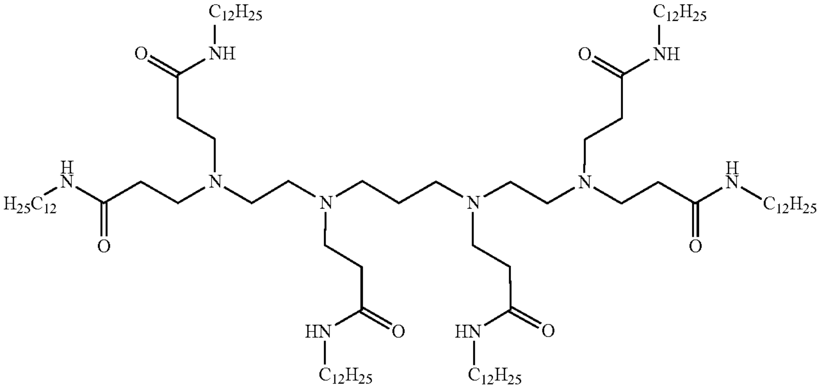

C12-(2-3-2) is preferably prepared as described e.g. in WO 2016/075154 A1, EP 3013964, and Jarzpbinska et al. (Angew Chem Int Ed Engl., 2016; 55(33):9591-5). The cationic lipidoid can be prepared by mixing N1-(2-aminoethyl)-N3-(2-((3,4-dimethoxybenzyl)amino)ethyl)propane-1,3-diamine (8.9 g, 1 eq., 28.67 mmol) with 1,2-Epoxydodecane (42.27, 8 eq., 229.4 mmol) and mixed for 24 h at 80 °C under constant shaking followed by purification and removal of the 3,4-dimethoxybenzyl protection group.

Different isomers, of C12-(2-3-2) can be used such as a racemate, an S-isomer, and/or an R-isomer. Preferably, C12-(2-3-2) is used as pure R-isomer and has the structure shown in formula (VI). For obtaining pure R-isomers of C12-(2-3-2) it can be prepared as described above for C12-(2-3-2) using the R-isomer of 1,2-Epxoydodecane for synthesis.

formula (VI)

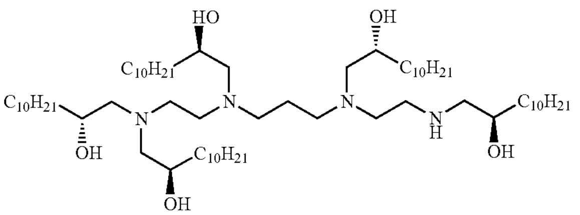

Furthermore, the pharmaceutical composition comprises a cationic lipidoid having formula (V), (VI) and/or (VII), preferably dL_P and/or C12-(2-3-2), more preferably dL_P and/or the R-isomer of C12-(2-3-2), comprised in a formulation as described in the following. In particular, the herein described agents and reagents for delivering and/or introducing the RNA into a target cell or a target tissue and the herein described LTRs may be combined with one or more (e.g. two, three or four) further lipid(s) (like, for example, cholesterol, DPPC, DOPE and/or PEG-lipids (e.g. DMPE-PEG, DMG-PEG2000)). These further lipids may support the desired function of the agents/reagents and LTRs (support and/or increase the delivering and/or introducing of RNA into the cell or tissue and improve transfection efficiency, respectively) and function as respective "helper lipids". Particular examples of such "helper lipids" are cholesterol, DPPC, DOPE and/or PEG-lipids (e.g. DMPE-PEG, DMG-PEG (e.g. DMG-PEG2000). The further lipids (e.g. "helper lipids") may also be part(s) of the herein disclosed complexes/particles. The skilled person is readily in the position to prepare complexes/particles in accordance with the invention. Examples of further lipids (e.g. "helper lipids") are also known in the art. The skilled person is readily in the position to choose suitable further lipids (e.g. "helper lipids") and ratios of the agents/reagents/LTRs and the further lipids (e.g. "helper lipids"). Such ratios may be molar ratios of 1-4: 1-5, 3-4: 4-6, about 4:about 5, about 4:about 5.3 of agents/reagents/LTRs:further lipid(s) (the more narrow ranges are preferred). For example, the agents/reagents/LTRs may be combined with three further lipids, like DPPC, cholesterol, and DMG-PEG2000, at a molar ratio of 8:5.3: 4.4:0.9, respectively, or, more particular, 8:5.29: 4.41:0.88, respectively.

Preferably, dL_P and/or C12-(2-3-2), more preferably dL_P and/or the R-isomer of C12-(2-3-2), is generated as described above and used with helper lipids DPPC and cholesterol and PEG-lipid DMG-PEG2000 at the molar ratios 8:5.29:4.41:0.88 for formulating lipoid particles.

A composition in which the R-isomer of C12-(2-3-2) (formula VI) is formulated with the lipids DPPC and cholesterol and PEG-lipid DMG-PEG2000 at the molar ratios 8:5.29:4.41:0.88 is also referred herein as "LF92". A composition in which the dL_P (formula VII) is formulated with the lipids DPPC and cholesterol and PEG-lipid DMG-PEG2000 at the molar ratios 8:5.29:4.41:0.88 is also referred herein as "LF111".

As also exemplarily described e.g. in WO 2016/075154 A1, EP 3013964, and Zhang et al. (TERMIS, 2019, Tissue Engineering: Part A, Vol. 25, Numbers 1 and 2), dL_P and/or C12-(2-3-2) can be used as a non-viral vector, to make a stable lipoplex with mRNA molecules, based on electrostatic interaction between the positive amino groups of lipidoid and negative phosphate groups of mRNA molecules (Anderson, Human Gene Therapy 14, 2003, 191-202). To stabilize the lipoplex structure and reduce the leakage, dL_P and/or C12-(2-3-2), more preferably dL_P and/or the R-isomer of C12-(2-3-2), can be supplied with two helper lipids entitled 1,2-dipalmitoyl-sn-glycero-3-phosphocholine (DPPC) and cholesterol (Anderson, Drug Delivery 11, 2004, 33-39; Liang, Journal of Colliod and Interface Science 278, 2004, 53-62). At the end, 1,2-Dimyristoyl-sn-glycerol, methoxypolyethylene Glycol (DMG-PEG) 2 kD (DMG-PEG2000) is to be added to the lipid mix to provide a PEGylated liposome. It is already well known that PEGylation improves the physico-chemical characteristic of liposome formulation by increasing water solubility, protecting from enzymatic degradation, and limiting immunogenic and antigenic reactions (Milla, Current Drug Metabolism 13, 2012, 105-119). Final N/P ratios for entire ethanoic lipid mixture are to be 8:5.29: 4.41:0.88 standing for molar ratios of amino group of dL_P and/or C12-(2-3-2)/DPPC/cholesterol/DMG-PEG2000, respectively, to one phosphate group of mRNA molecule.

Hence, in preferred embodiments the pharmaceutical composition comprises an mRNA encoding IFNλ and further comprises dL_P and/or C12-(2-3-2), preferably dL_P and/or the R-isomer of C12-(2-3-2), formulated with DPPC, cholesterol, and DMG-PEG2000. Moreover, in particularly preferred embodiments the pharmaceutical composition comprises an mRNA encoding IFNλ and further comprises dL_P and/or C12-(2-3-2), preferably dL_P and/or the R-isomer of C12-(2-3-2), formulated with DPPC, cholesterol, and DMG-PEG2000 with final N/P ratios for entire ethanoic lipid mixture of 8:5.29:4.41:0.88 for molar ratios of amino group of dL_P and/or C12-(2-3-2)/DPPC/cholesterol/DMG-PEG2000, respectively, to one phosphate group of mRNA molecule.

R-isomers of C12-(2-3-2) formulated with DPPC, cholesterol, and DMG-PEG2000 as stated above are also referred to as LF92 formulation.

Hence, in particularly preferred embodiments of the pharmaceutical composition comprising an mRNA encoding IFNλ, said pharmaceutical composition further comprises an LF92 formulation.

dL_P formulated with DPPC, cholesterol, and DMG-PEG2000 as stated above are also referred to as LF111 formulation.

Hence, in another preferred embodiment of the pharmaceutical composition comprising an mRNA encoding IFNλ, said pharmaceutical composition further comprises an LF111 formulation.

When the pharmaceutical composition is administered via inhalation to a human patient, one dose to be inhaled by a patient contains preferably between 200 μg and 15 mg of mRNA encoding an IFN-λ polypeptide. As shown in the appended Examples, experiments in mice show that an induction of downstream targets of IFNλ (which is indicative of antiviral activity) can already be achieved with extremely low levels of IFNλ mRNA when administered via instillation into the lung. When extrapolated to human patients based on the weight of the lung, it can be expected that effective amounts of IFNλ mRNA will lie in the range of 200 μg to 15 mg per dose, preferably between 250 μg and 5 mg per dose, even more preferably 250 μg and 1 mg per dose, even more preferably between 250 μg and 750 μg per dose.

The number of doses to be administered to a subject depend on the actual purpose. In the case of an acute viral infection, the administration is preferably effected:

One dose once (e.g. in cases of a mild infection); or

One dose every two days over a period of 2, 4, 6, 8, 10 or 14 days; or

One dose daily over a period of time of 2, 3, 4, 5, 6, 7, 8, 9, or 10 days; or

Two doses daily over a period of time of 2, 3, 4, 5, 6, 7, 8, 9, or 10 days.

In the case of a prevention of a virus infection or of a virus-induced exacerbation of lung diseases such as asthma or COPD the administration is preferably effected:

One dose per week, preferably for 1, 2, 3, 4, 5, 6, 7, 8, 9, 10, 11 or 12 weeks, preferably for 1, 2, 3, 4, 5, 6 or 7 months.

The present invention also relates to an mRNA molecule comprising a sequence as shown in any one of SEQ ID Nos: 13 to 15, 25, 26 or 27.

SEQ ID Nos: 13 to 15, 25, 26 and 27 contain a codon optimized coding region for IFNλ-1, -2 and -3, of IFN a16, IFN3 and IFNγ, respectively. Moreover, each of these mRNAs contains directly upstream of the start codon the sequence GGGAGACGCCACC (SEQ ID NO:7) and as a 3'-UTR the sequence 5'-TTCG-3'.

Preferably, such an mRNA further comprises a poly-A tail, e.g. of about 200 nucleotides.

The present invention also relates to a DNA molecule comprising a sequence as shown in any one of SEQ ID NOs: 10 to 12 or 22 to 24. SEQ ID NO: 10 shows a DNA molecule for the transcription of an mRNA molecule which encodes IFNλ-1. SEQ ID NO: 11 shows a DNA molecule for the transcription of an mRNA molecule which encodes IFNλ-2. SEQ ID NO: 12 shows a DNA molecule for the transcription of an mRNA molecule which encodes IFNλ-3. SEQ ID NO: 22 shows a DNA molecule for the transcription of an mRNA molecule which encodes IFN a16. SEQ ID NO: 23 shows a DNA molecule for the transcription of an mRNA molecule which encodes IFNβ. SEQ ID NO: 24 shows a DNA molecule for the transcription of an mRNA molecule which encodes IFNγ.

FIG. 1 shows IFNλ1 concentration in supernatants of cells treated with rec. hIL-29. Supernatants of A-549 cells treated with doses of rec. hIL-29 as indicated in x-axis were collected and stored at −80 °C. At day of analysis, hIL-29 ELISA was performed according to kit protocol. TMB was incubated for 15 min. Delta O.D of 650 and 450 nm was used for analysis using GraphPad Prism V.8.

FIG. 2 shows IFNλ1 concentrations in supernatants of cells transfected with IFNλ mRNA. Supernatants of A-549 cells transfected with doses of mRNA coding for hIL-29, as indicated in x-axis, were collected and stored at −80 °C. At day of analysis, hIL-29 ELISA was performed according to kit protocol. TMB was incubated for 15 min. Delta O.D of 450 and 650 nm is used for analysis using GraphPad Prism V.8.

FIG. 3 shows target activation after treatment or transfection with high dose. A549 cells were transfected with 15 ng/well IFN-Lambda mRNA and stimulated with 2.9 ng/well human rec. hIL-29. As a control, A549 were transfected with 15 ng/well BMP2-Stop encoding mRNA. At different time points (6, 10, 24, 48, 72 and 120 h) cells for Real-Time PCR analysis are collected and lysed.

FIG. 4 shows target induction after treatment or transfection with mid dose. A549 cells were transfected with 4 ng/well IFN-Lambda mRNA and stimulated with 0.6 ng/well human rec. hIL-29. As a control, A549 were transfected with 4 ng/well BMP2-Stop encoding mRNA. At different time points (6, 10, 24, 48, 72 and 120 h) cells for Real-Time PCR analysis are collected and lysed.

FIG. 5 shows target activation after transfection or treatment with low dose. A549 cells were transfected with 2 ng/well IFN-Lambda mRNA and stimulated with 0.3 ng/well human rec. hIL-29. As a control, A549 were transfected with 2 ng/well BMP2-Stop encoding mRNA. At different time points (6, 10, 24, 48, 72 and 120 h) cells for Real-Time PCR analysis were collected and lysed.

FIG. 6 shows target activation after treatment or transfection with very low dose. A549 cells were transfected with 1 ng/well IFN-Lambda mRNA and stimulated with 0.1 ng/well human rec. hIL-29. As a control, A549 were transfected with 1 ng/well BMP2-Stop encoding mRNA. At different time points (6, 10, 24, 48, 72 and 120 h) cells for Real-Time PCR analysis were collected and lysed FIG. 7 shows the downstream target activation 6 hours post treatment with recombinant IFNλ1 or mRNA coding for IFNλ1 as assessed via qPCR for IFIT1, IFIT3, OAS3 and ISG15. Downstream target activation is plotted against measured IFNλ1 levels.

FIG. 8 shows:

(a) IFNλ1 downstream signaling in A-549 and A-549-ACE2 cells 48 hours after mRNA transfection with different doses. Similar induction patterns are observed for both cell lines.
(b) IFNλ1 downstream signaling in A-549 and A-549-ACE2 cells using recombinant protein after48 hours. In this case higher induction levels are observed in A-549 cells.
(c) IFNλ1 expression in A-549-ACE2 cells: Transfection of A549-ACE2 cells with mRNA coding for IFNλ1 resulted in dose-dependent production of IFNλ1 after 48 hours.

FIG. 9 shows the IFNλ1 expression in supernatants of transfected cells after transfection of submersed cells. Comparable expression levels are observed between HEK293, A-549 and FreeStyle 293-F cells. Lower levels were observed in 16HBE14o-cells, untreated wells showed background in ELISA. Peak expression was observed at 24 h post transfection and levels remained constant at least up to 48 h post transfection. In all cell lines except 16HBE14o-cells, transfection doses below 4 ng/well were sufficient to reach an effective antiviral IFNλ concentration of 0.3 ng/mL at 6 h post transfection.

FIG. 10 shows:

(a) IFNλ1 downstream signaling in submersed A-549 cells after transfection with IFN-Lambda mRNA. The indicated values are normalized to UT (untransfected). An upregulation of all target genes was observed and peak expression was at 24 h after transfection. A very strong target inducement was observed, even with low mRNA doses.
(b) IFNλ1 downstream signaling in submersed 16HBE14o-cells after transfection with IFN-Lambda mRNA. The indicated values are normalized to UT (untransfected). An upregulation of all target genes (lower for OAS3) was observed and peak expression was at 24 h after transfection. Overall, a weak target inducement was observed compared to A-549 cells.

FIG. 11 shows:

(a) ELISA results for the detection of IFNλ1 in ALI cultures after transfection with IFNλ1 mRNA. Values were measured 24 h post transfection. The total amount of IFNλ1 was measured in the in apical and basolateral compartment. The detection of IFNλ1 was as follows: A-549>16HBE14o->Epithelix human primary wt ALIs. Maximum basal yield in Epithelix ALIs is 500 fold lower compared to that of A-549 ALIs.
(b) Measurement of the downstream target activation in ALI cultures 24 hours after transfection with IFNλ1 mRNA. The highest downstream target activation was observed in A-549 ALI culture. The indicated values are normalized to UT (untransfected). The same activation pattern was observed for all cell lines: ISG15>IFIT1≥IFIT3>OAS3.
(c) The endogenous levels of downstream targets in untreated 16HBE and Epithelix primary human ALIs compared to A-549 ALIs. 16HBE14o- and Epithelix human primary ALIs have up to 40-fold higher basal endogenous levels of downstream targets than A-549 ALIs.

FIG. 12 shows:

(a) The quantification of IFNλ1 mRNA in lung homogenate of treated mice 5 and 24 hours after treatment. IFNλ1 mRNA is detected dose-dependently at 5 h post application with very low levels at 24 h post application.
(b) The results of an ELISA assay detecting IFNλ1 in lung homogenate and in BALF at 5 h and 24 h post application. IFNλ1 was measurable in lung homogenate and in BALF at 5 h post application. 24 h post application only low levels of IFNλ1 were detectable.
(c) IFNλ1 downstream activation in lung homogenate. The functionality of human IFNλ1 mRNA in mouse is demonstrated. The indicated values are normalized to UT (untreated) mouse. Target genes are highly induced 5 h post application and still upregulated at 24 h post application although less strongly. OAS3 is induced less strongly compared to other target genes but induction is higher at 24 h than 5 h.

FIG. 25 shows body weight during repeated administration of hIFNλ1 mRNA (see also Example 20).

Figure 1:
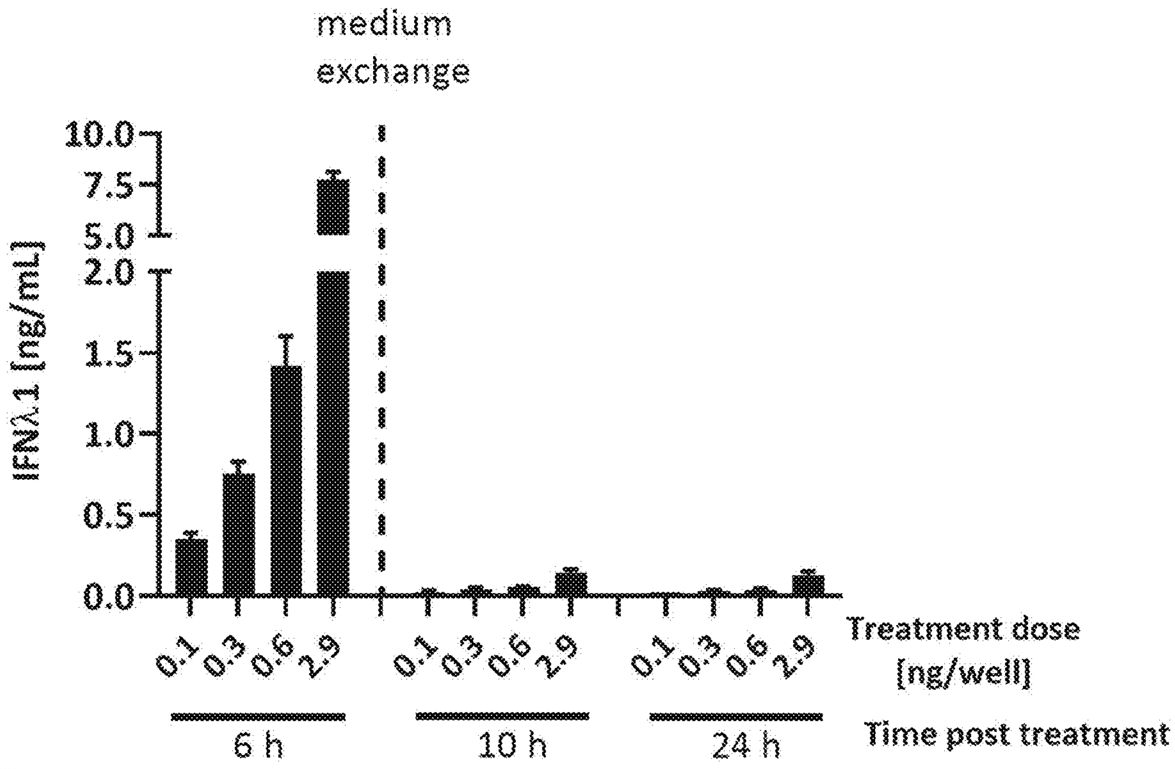

Other aspects and advantages of the invention will be described in the following examples, which are given for purposes of illustration and not by way of limitation. Each publication, patent, patent application or other document cited in this application is hereby incorporated by reference in its entirety.

EXAMPLES

Examples 1 and 2 described in the following aimed at assessing downstream target activation by IFNλ1 treatment with recombinant protein or mRNA coding for IFNλ1 in A-549 cells. For this purpose, A549 cells were incubated for 6 h with recombinant IFNλ1 or transfected with IFNλ1 coding mRNA and downstream activation was analyzed 6, 10, 24, 48, 72, 120 and 168 h post treatment via qPCR for IFIT1, IFIT3, OAS3 and ISG15. In addition, IFNλ1 levels were measured by hIL-29 ELISA in cell supernatant at all sampling time points.

Upon treatment of A-549 cells with recombinant IFNλ1, downstream target activation was observed at 6 h post treatment but declined rapidly at later time points after medium exchange. IFNλ1-ELISA revealed that about 30% of added protein was recovered in the supernatant at 6 h post treatment. Upon transfection of A-549 cells with mRNA coding for IFNλ1 and medium exchange 6 h post transfection, IFNλ1 was detectable in supernatants of these cells up to 168 h with a peak at 48 h. Downstream targets were highly induced also with low doses of transfected mRNA and remained upregulated up to 120 h post mRNA transfection The following abbreviations and definitions are used in the appended Examples:

| Abbreviation | Description |
|---|---|
| DMEM | Dulbecco's Modified Eagle Medium |
| ELISA | Enzyme linked immunosorbent assay |
| FBS | Fetal bovine serum |
| IFNλ1 | Interferon lambda 1 |
| PBS | Phosphate buffered saline |
| qPCR | Quantitative Polymerase Chain Reaction |
| IFIT1/3 | Interferon induced protein with tetratricopeptide repeat 1/3 |
| OAS3 | 2'-5'-oligoadenylate synthetase 3 |
| ISG15 | Interferon stimulated gene 15 |
| MX1 | MX dynamin like GTPase 1 |
| IL-6/8 | Interleukin 6/8 |
| MCP-1 | C-C motif chemokine ligand 2 |
| CXCL9/10/11 | C-X-C motif chemokine ligand 9/10/11 |
| CXCL10 | C-X-C motif chemokine ligand 10 |

In the appended Examples the following Materials and Methods were used.

1. Materials

| Material | Supplier | Cat no. |
|---|---|---|
| MEM with GLUTAMAX ™ | Gibco | 41090-028 |
| FBS, heat-inactivated | Thermo Fisher Scientific | 10500064 |
| Penicillin-Streptomycin 100× | Thermo Fisher Scientific | 15140122 |
| LIPOFECTAMINE ™ MESSENGERMAX ™ | Thermo Fisher Scientific | LMRNA008 |
| DPBS 1× without Ca and Mg | Thermo Fisher Scientific | Gibco 14190-250 |
| Human IL-29 ELISA Kit | Abcam | ab100568 |
| Recombinant hIL-29 | Abcam | ab155625 |

| TAQMAN ® Probes | Supplier | Cat no. |
|---|---|---|
| IFIT3 | Thermo Fisher Scientific | Hs01922752_s1 |
| IFIT1 | Thermo Fisher Scientific | Hs03027069_s1 |
| OAS3 | Thermo Fisher Scientific | Hs00196324_m1 |
| ISG15 | Thermo Fisher Scientific | Hs01921425_s1 |

| Device | Supplier | Cat no. or type |
|---|---|---|
| Countess Cell Counter | Thermo Fisher Scientific | C10281 |
| Countess Cell Counting chamber slides | Thermo Fisher Scientific | C10283 |
| 96-well cell culture plate | Corning | Costar 3599 |
| 96-well storage plate | Corning | Costar 3363 |
| Microplate shaker | Heidolph | Titramax |
| Microplate reader | Tecan | Tecan Infinite M200 Pro |
| LIGHT CYCLER ® 96 | Roche | Light Cycler ® 96 |

2. Methods

2.1 Cell Culture

A-549 cells were cultivated in MEM supplemented with 10% heat inactivated FBS and 1% P/S at 37 °C, in a humidified atmosphere with 5% $CO_2$. 24 h prior transfection 20.000 cells per well were seeded in 96-well plates in a total volume of 100 μL.

2.2 In Vitro Transcription

To generate templates for in vitro transcription, circular plasmids were linearized by restriction digestion with Bsp119I and further purified by chloroform ethanol precipitation.

mRNA was produced using a standard in vitro transcription mix (including indicated modified triphosphate nucleotides) containing T7 RNA polymerase, inorganic pyrophosphatase, and RNase inhibitor. Co-transcriptional capping was achieved by addition of an ARCA cap analogue. For in vitro transcription of chemically modified RNA, 25% of Cytidine-5'-Triphosphate were replaced by 5-Methylcytidine-5'-Triphosphate and 25% Uridine-5'-Triphosphate were replaced by 2-Thiouridine-5'-Triphosphate (Jena Biosciences), respectively (cf. e.g. SEQ ID NO: 1). Residual template DNA was digested using DNaseI. Subsequently mRNA was purified by a proprietary tangential flow filtration process (Verweis auf unser Patent).

Dephosphorylation of residual uncapped mRNA was carried out using a phosphatase (Quick cip) followed by purification via a proprietary tangential flow filtration process (Verweis auf unser Patent).

mRNA was further polyadenylated by using a poly(A) polymerase and purified again by a proprietary tangential flow filtration process (Verweis auf unser Patent). Finally, mRNA was filtrated using a 0.22 μm membrane. Critical quality attributes including poly(A) tail length, integrity, proportion of cap, incorporation of modified nucleotides were measured in a subsequent quality control of the mRNA.

2.3 Transfection mRNA coding for IFNλ1 (SEQ ID NO:13) (which was produced as described in section 2.2., above) was transfected using LIPOFECTAMINE™ MESSENGERMAX™ in a RNA to LIPOFECTAMINE™ ratio of 1:1.5 (w/v). For lipoplex formation mRNA was diluted in $dH_2O$. LIPOFECTAMINE™ MESSENGERMAX™ was diluted in serum free medium and was mixed by pipetting. After incubation of 10 min at RT, the RNA solution was added to the LIPOFECTAMINE™ MESSENGERMAX™ solution, mixed and incubated for another 5 min at RT. A dose titration ranging from 500 to 0.98 ng mRNA/well was performed. Afterwards, 25 μL of the Lipoplex solution for 15.6, 3.9, 1.95 and 0.98 ng mRNA/well was added to the respective wells.

2.4 Harvest 6, 10, 24, 48, 72, 120 and 168 h post transfection, supernatants were collected and stored in a fresh 96-well storage plate at −80 °C until ELISA. Prior ELISA the supernatants were centrifuged at 500×g for 2 min to pellet cell debris.

For qPCR, after collecting the supernatant, cells were washed with 150 μL D-PBS per well and frozen at −80 C.

2.5 IFNλ1 ELISA

Protocol for IFNλ ELISA was performed as established according to Kit protocol with the exception, that TMB incubation is shortened to 15 minutes.

Example 1: IFNλ1 Expression in Supernatants

Presence of IFNλ1 in supernatants of cells transfected with mRNA or treated with rec. hIL-29 were measured via hIL-29 ELISA. Treatment with recombinant hIL-29 was done in doses of 2.9, 0.6, 0.3 and 0.1 ng/well. The doses corresponded to 23, 5, 2.5 and 1 ng/mL in the supernatant. 6 h post treatment, concentrations between 0.3 and 8 ng/mL were quantified in supernatants by ELISA. 70% of the added protein was consumed by the cells or degraded (see FIG. 1).

Figure 2:
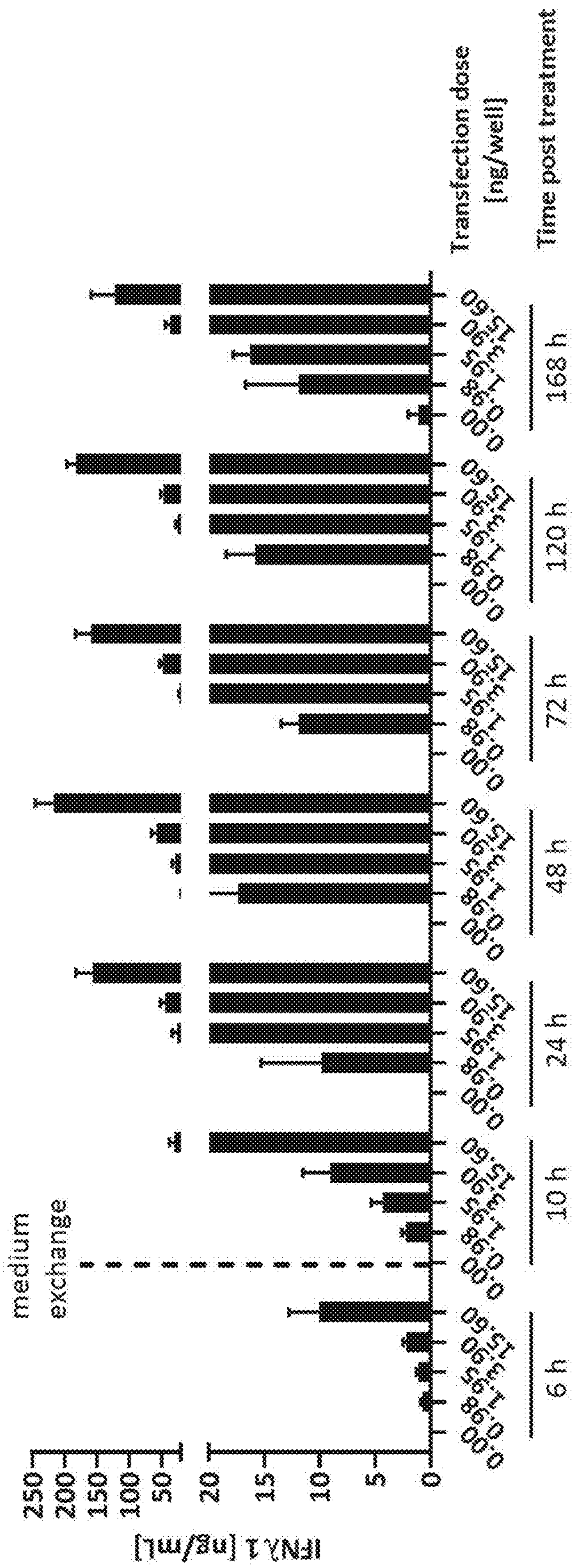
Figure 3:
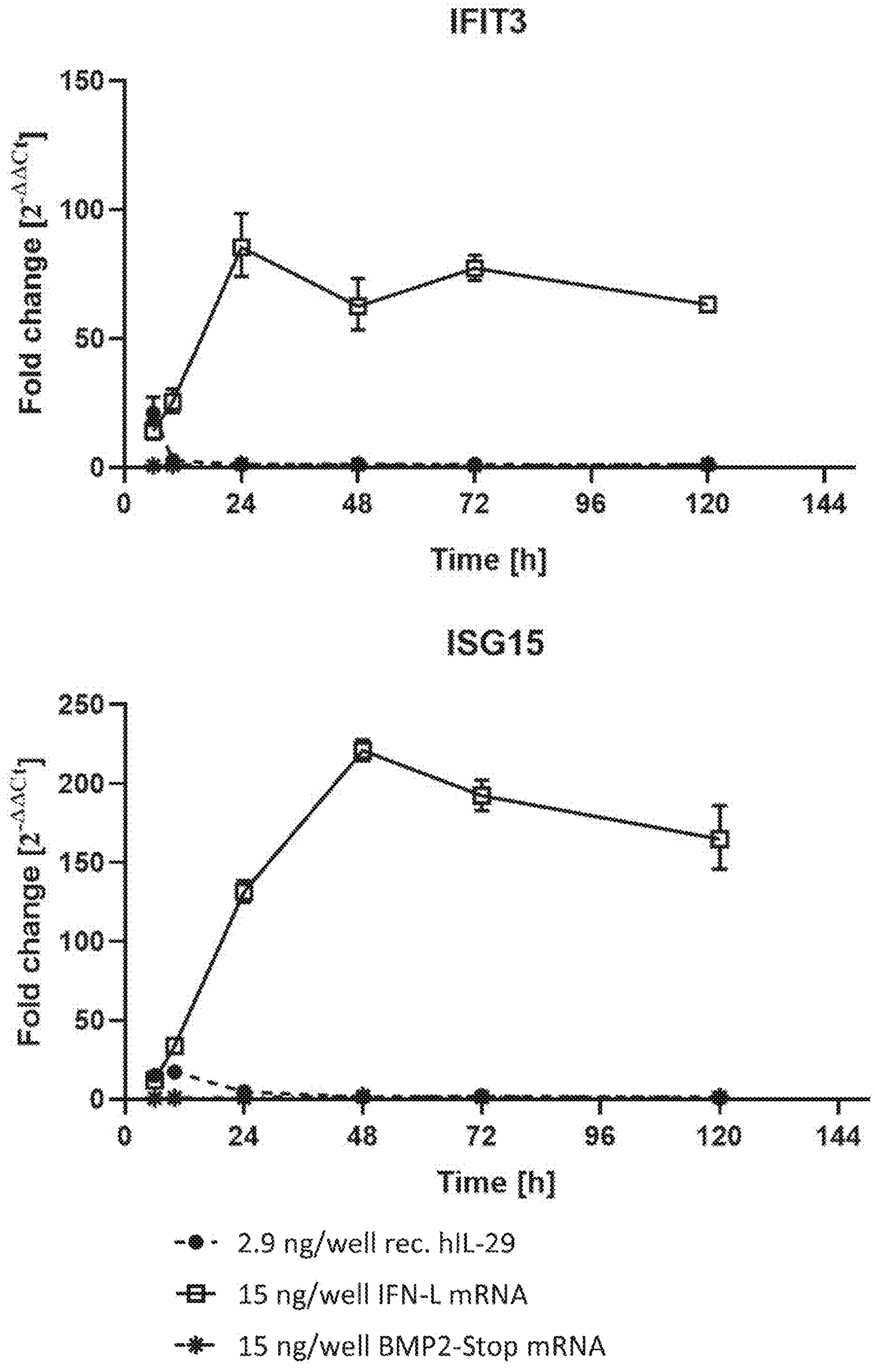
Figure 3:
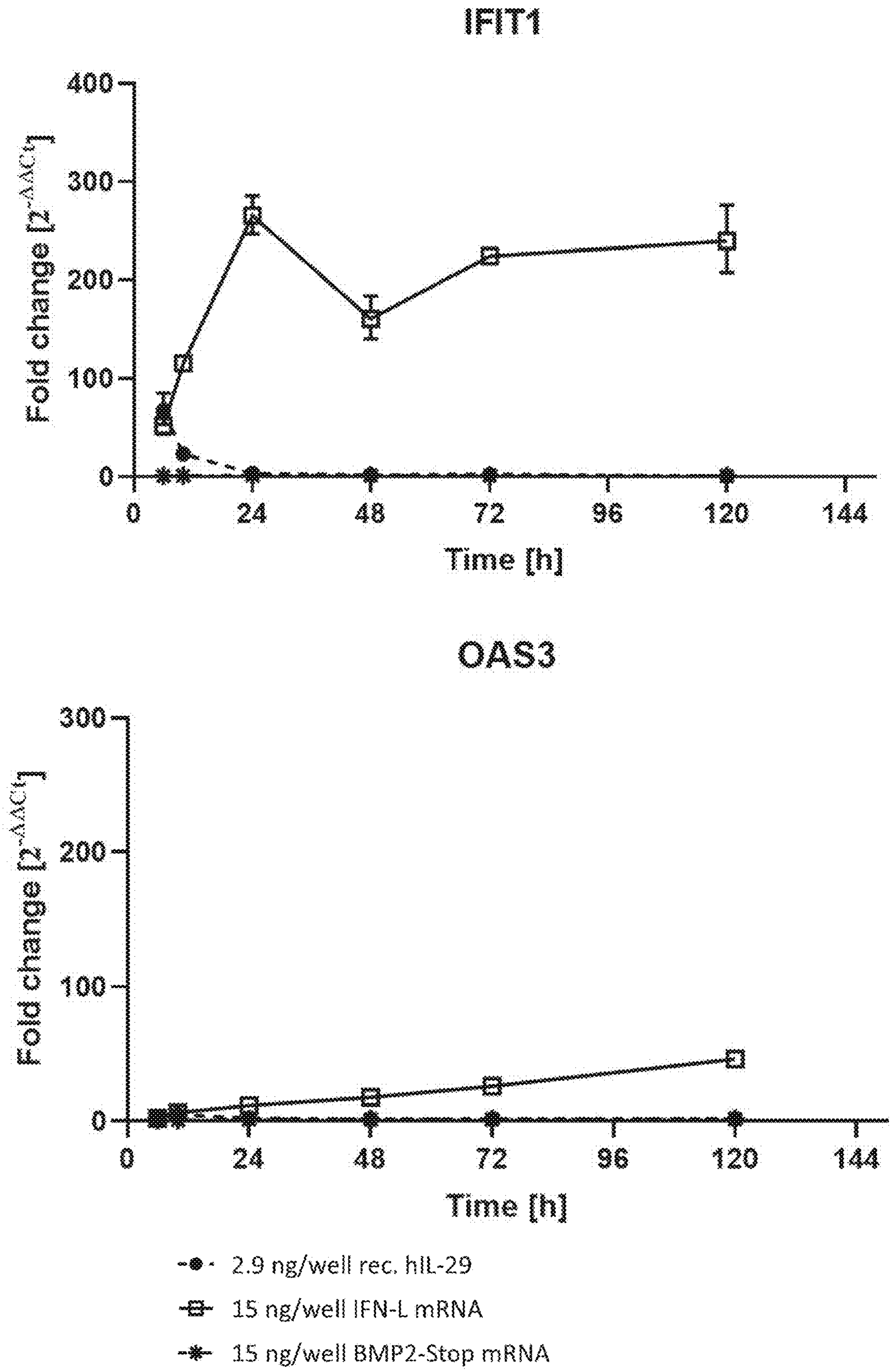
Figure 4:
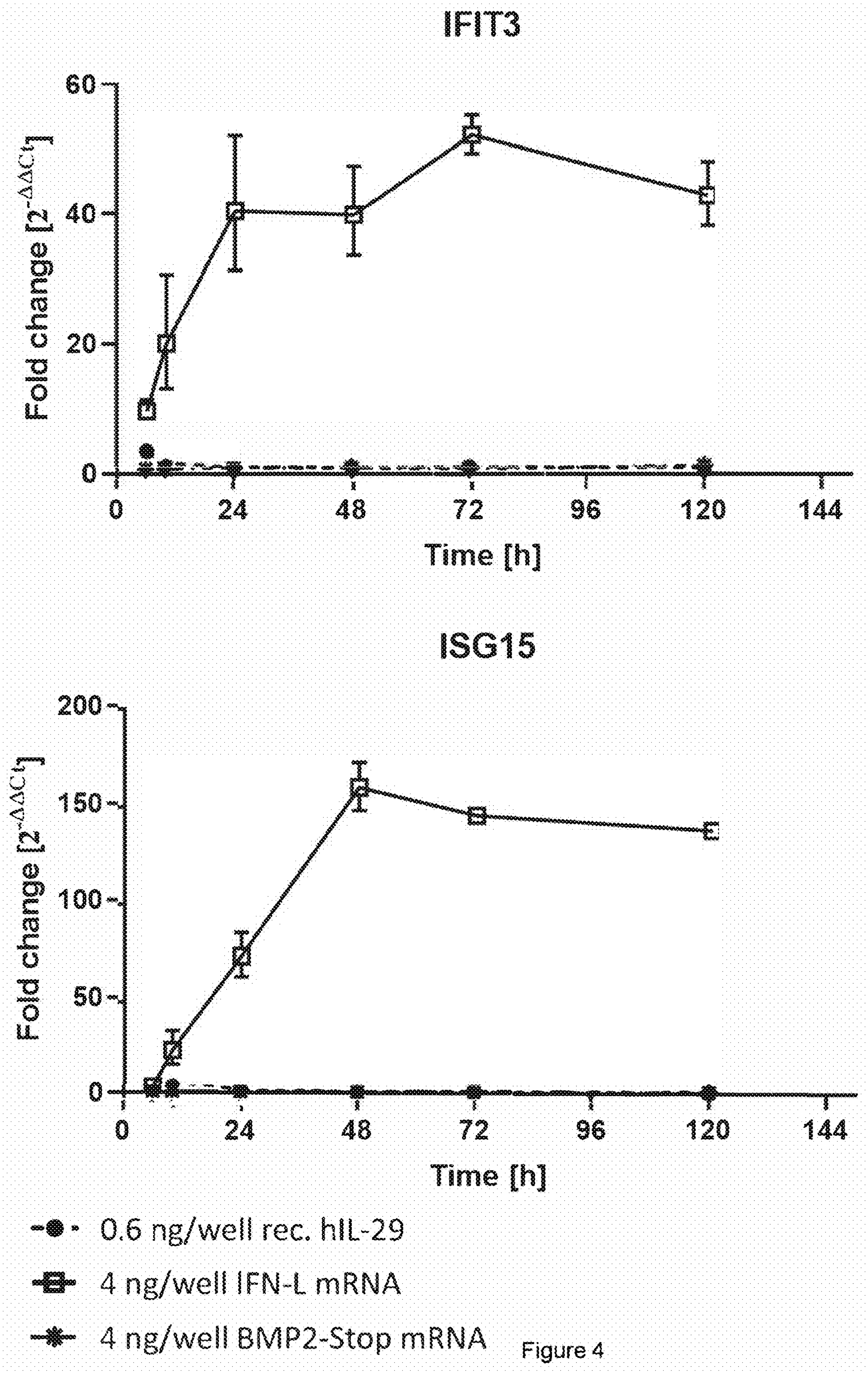
Figure 4:
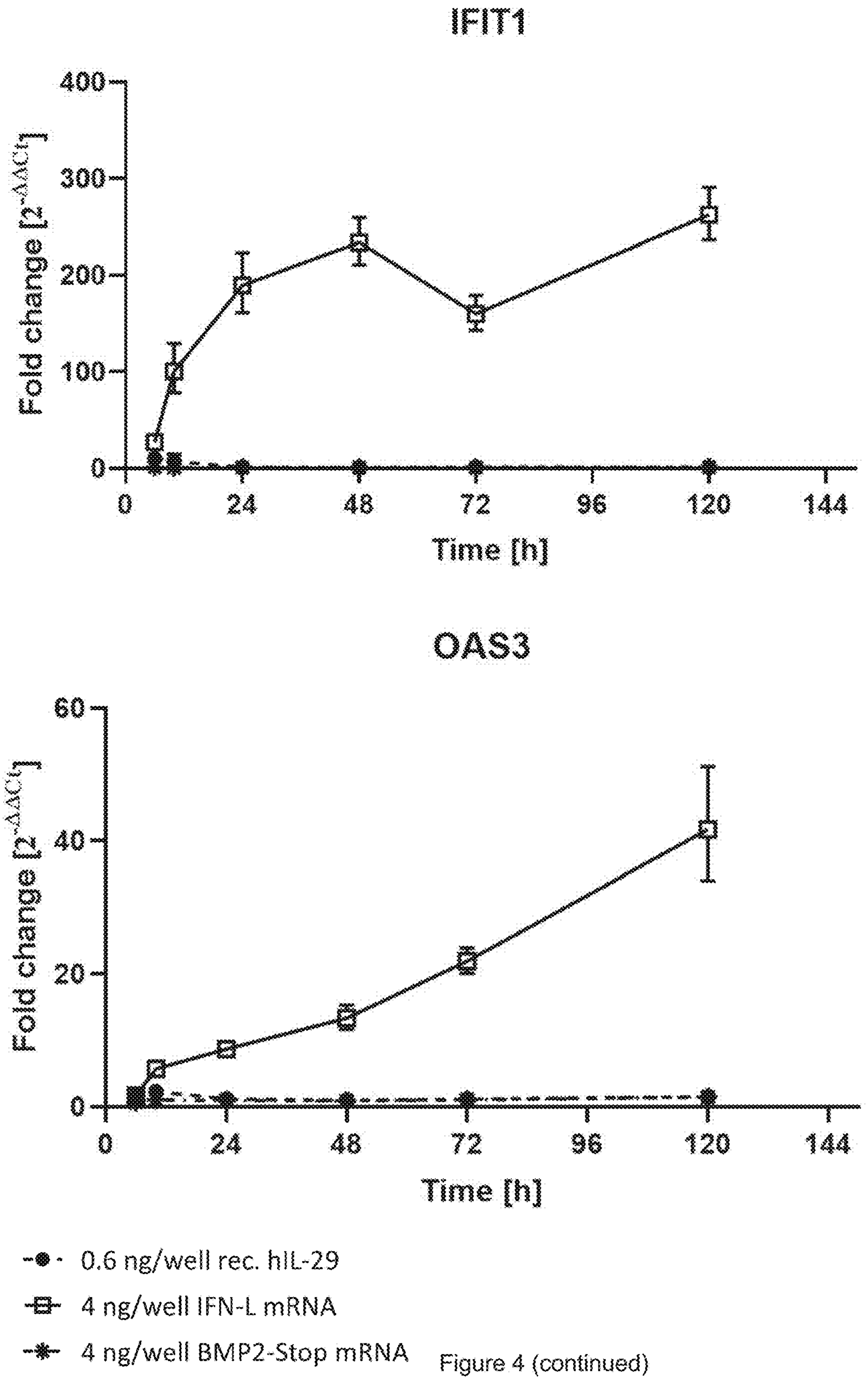
Figure 5:
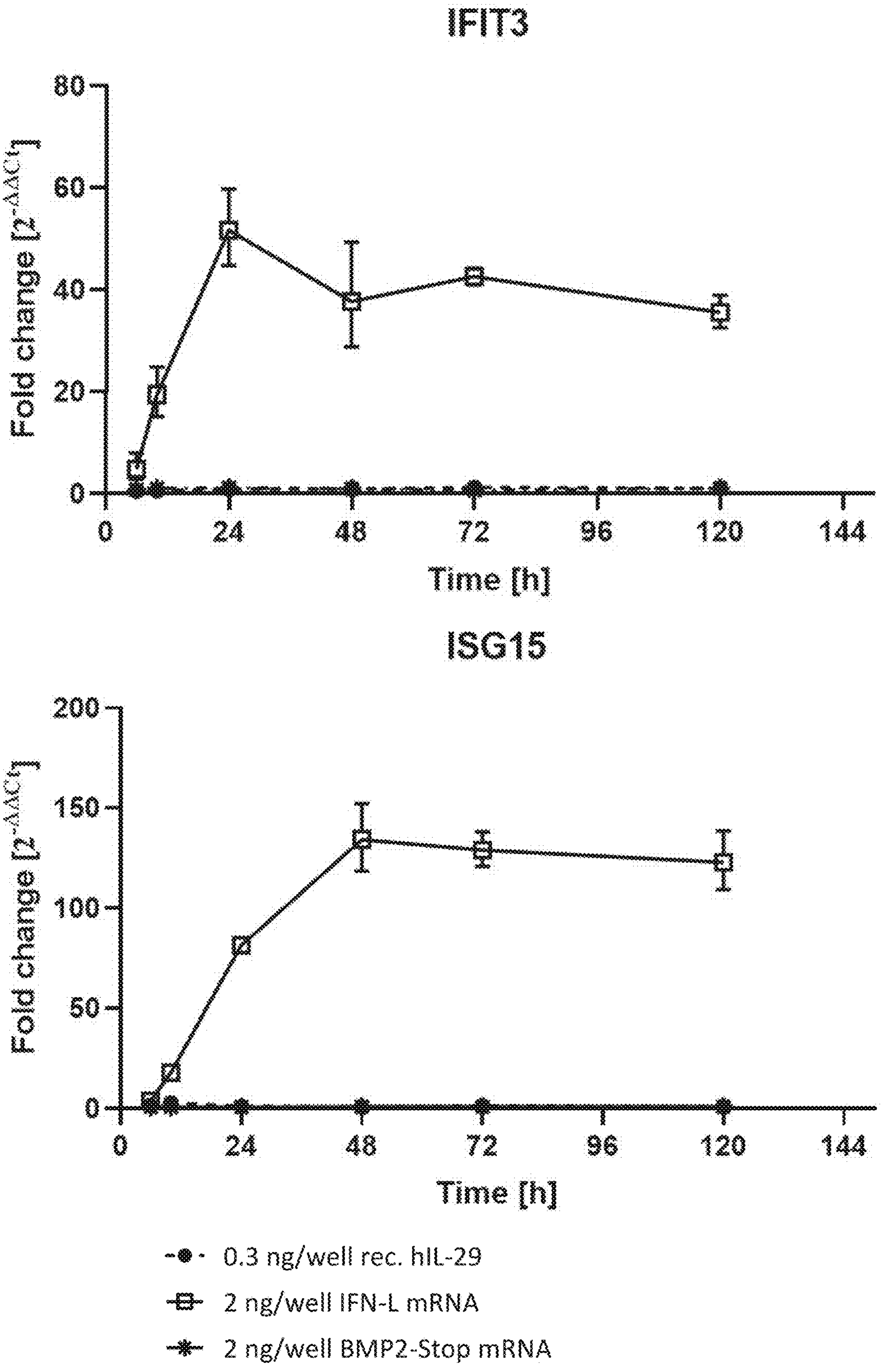
Figure 5:
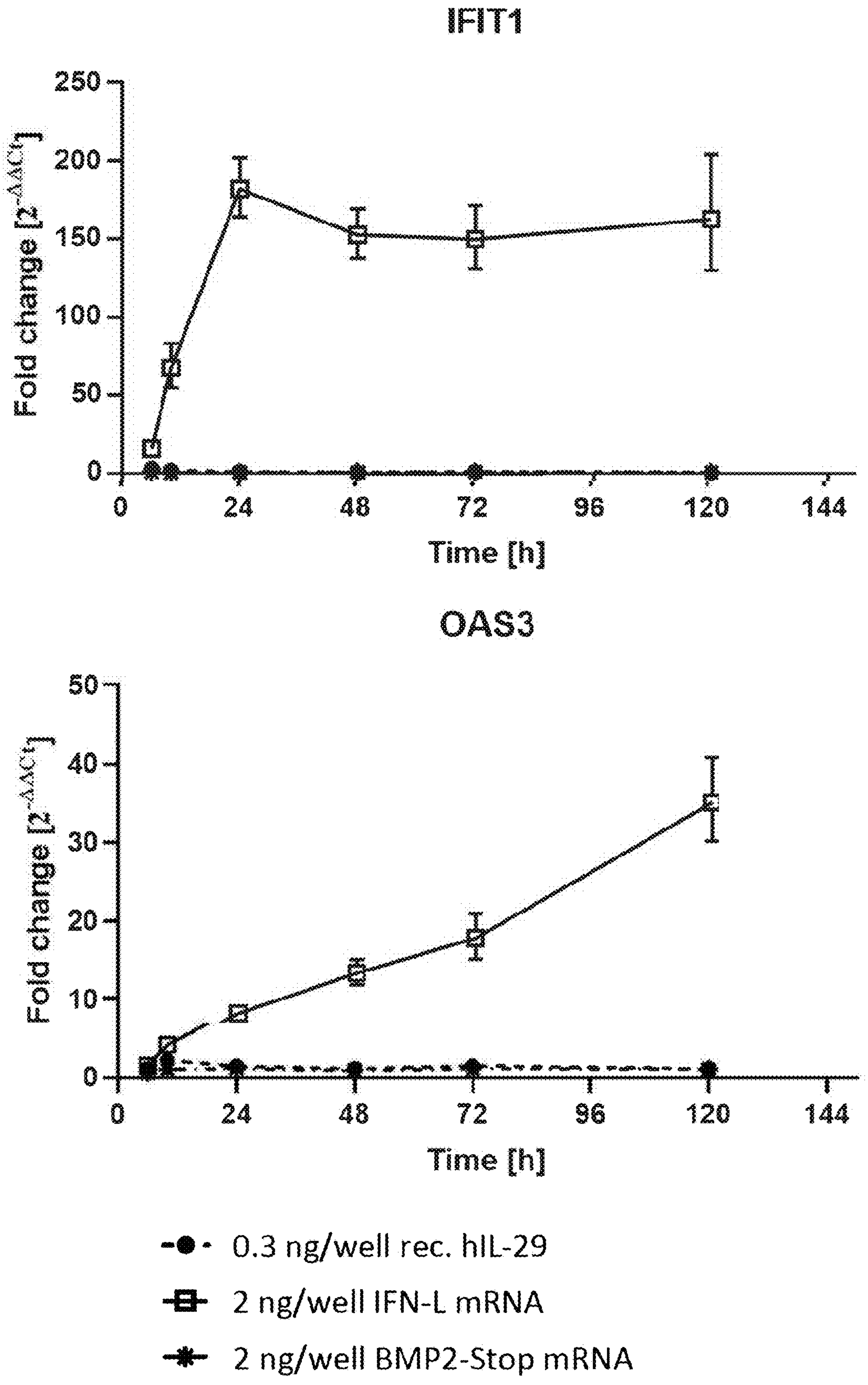
Figure 6:
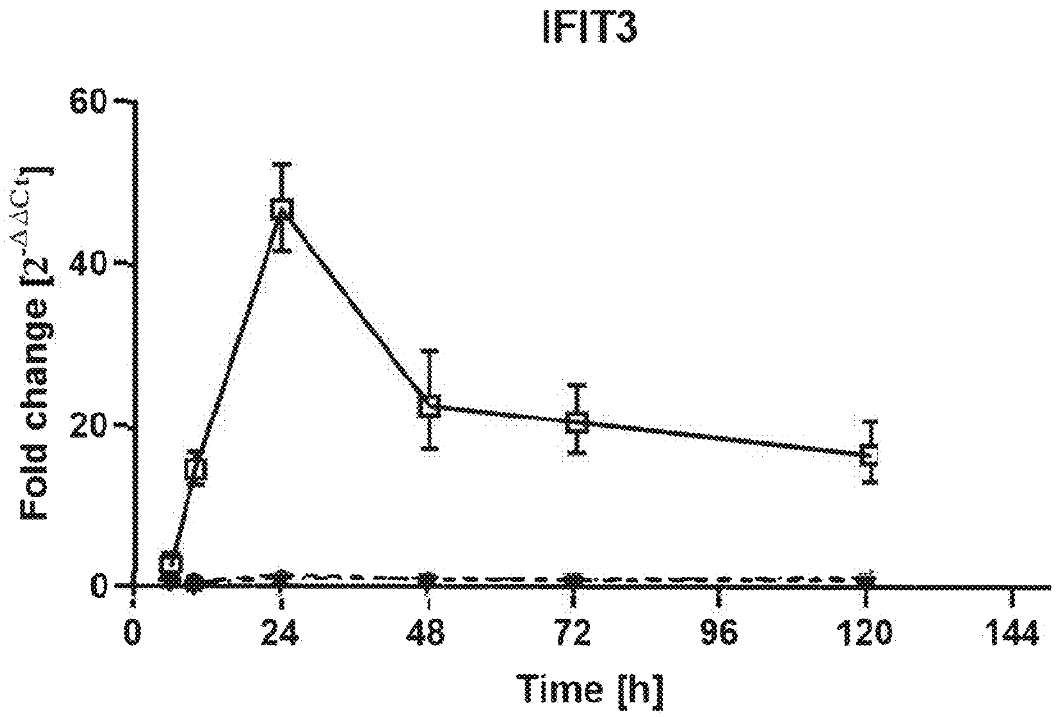
Figure 6:
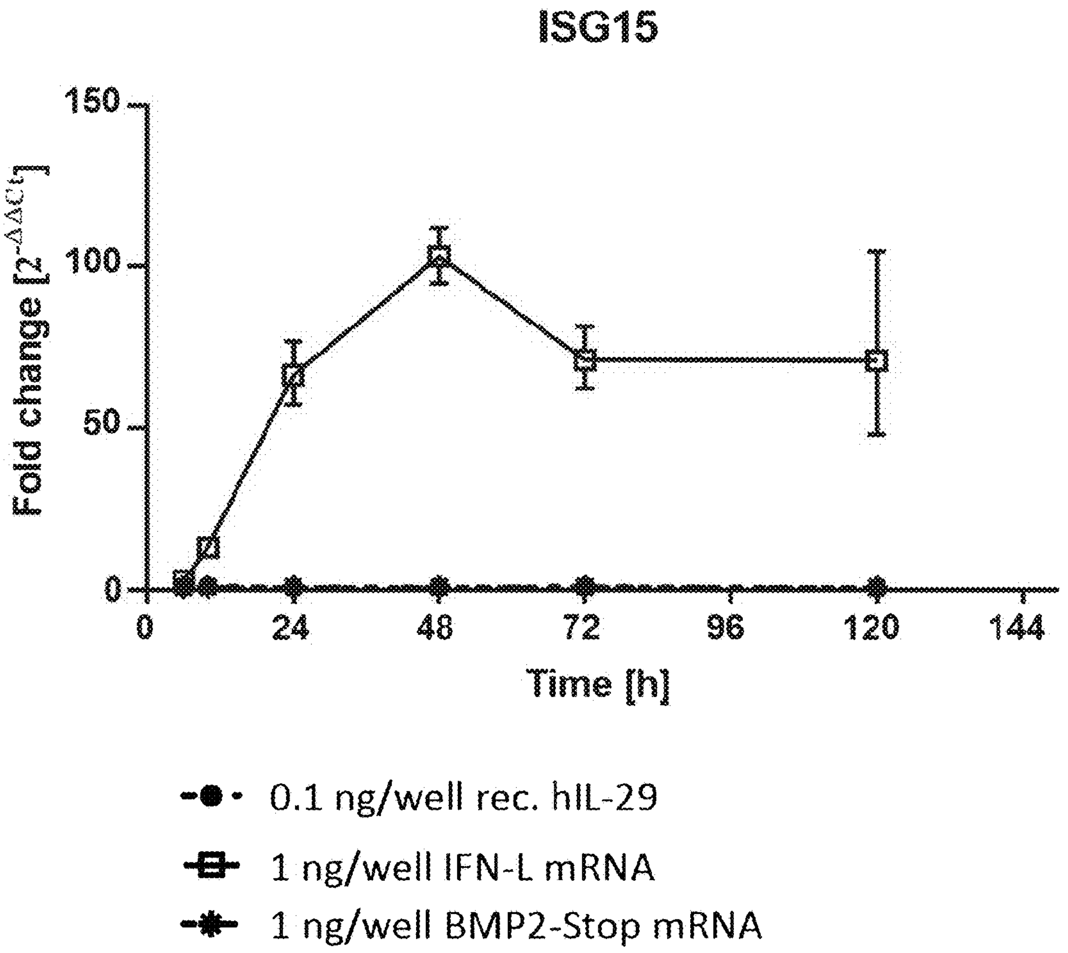
Figure 6:
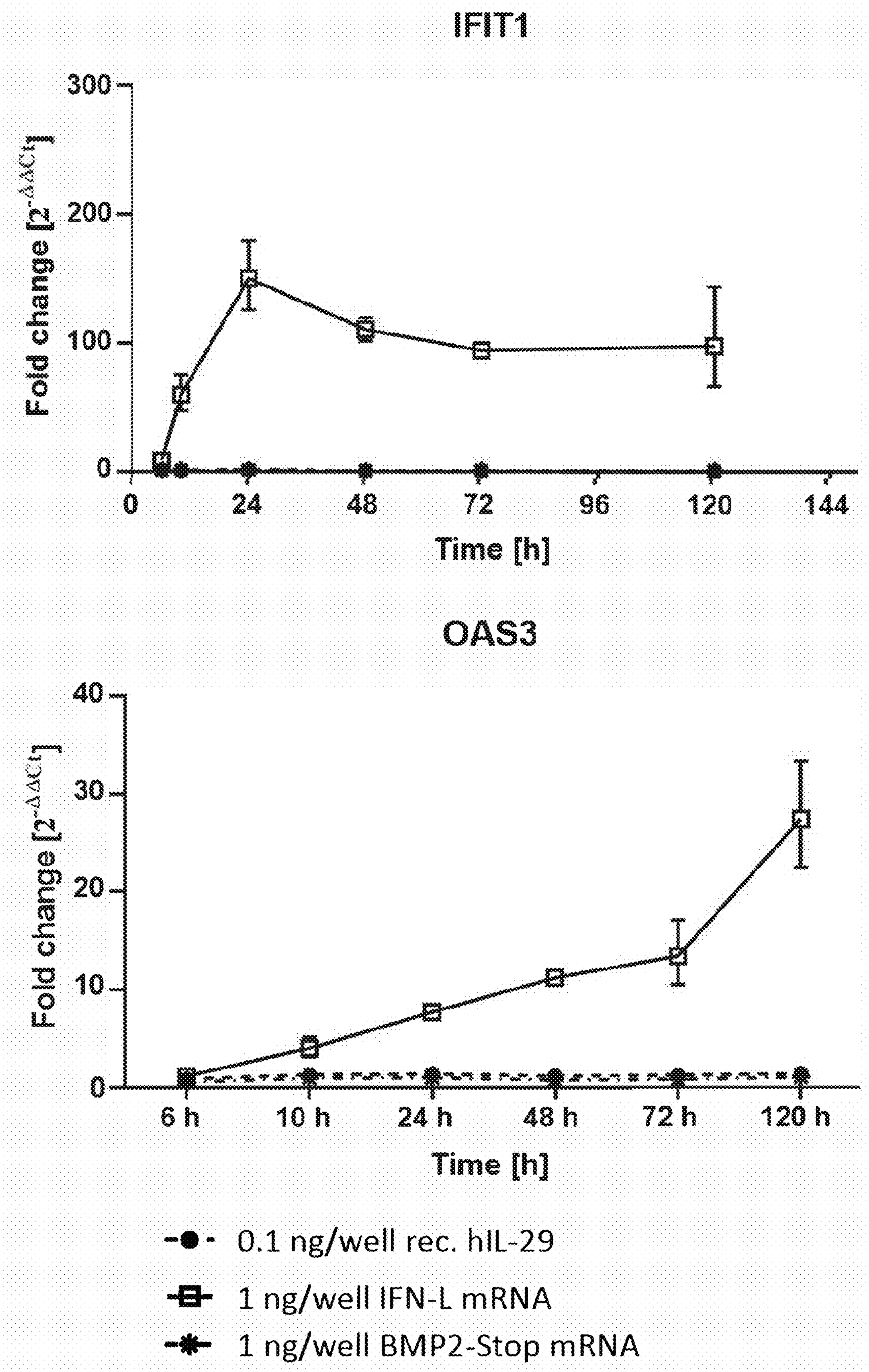

In supernatants of cells transfected with mRNA coding for IFNλ1, increasing concentrations of IFNλ1 were measurable for each dose up to 48 h. From 48 h to 168 h, IFNλ1 was still detectable with only a small decrease (see FIG. 2).

Example 2: Downstream Target Activation

Downstream target activation post treatment with recombinant IFNλ1 or mRNA coding for IFNλ1 was assessed via qPCR for IFIT1, IFIT3, OAS3 and ISG15.

For all doses of mRNA transfection, high induction for IFIT1, IFIT3 and ISG15 was observed. Peak induction was reached between 24 and 48 h depending on target and dose. Upon mRNA transfection, target genes remained upregulated up to 120 h. (see FIGS. 3 to 6). For OAS3 induction peak was reached at 120 h upon all transfection doses.

Treatment with recombinant protein showed comparable target induction to mRNA transfection at 6 h post treatment. At all later time points after medium was exchanged and the protein was no longer available for the cells, downstream activation declined rapidly (see FIGS. 3 to 6).

Figure 7:
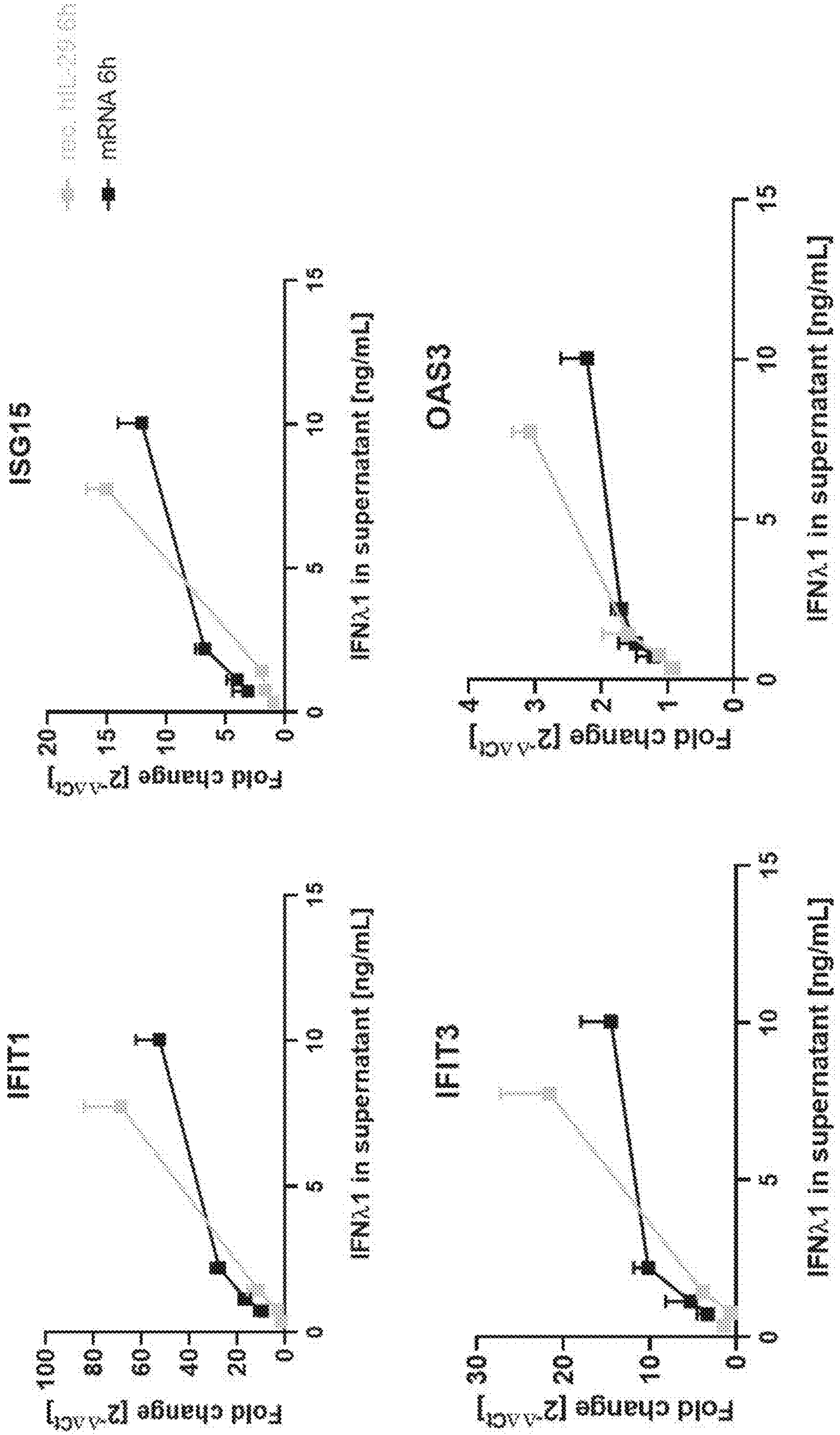
Figure 8A:
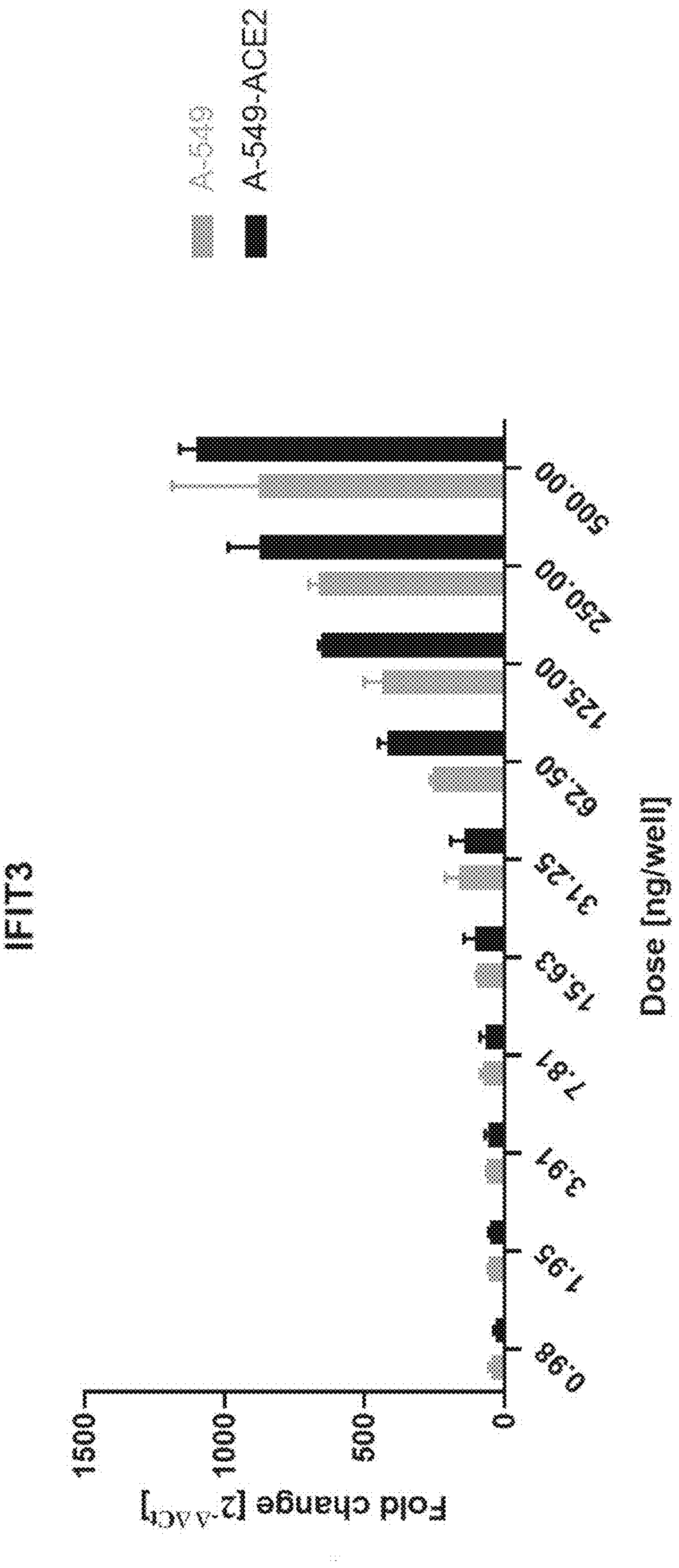
Figure 8A:
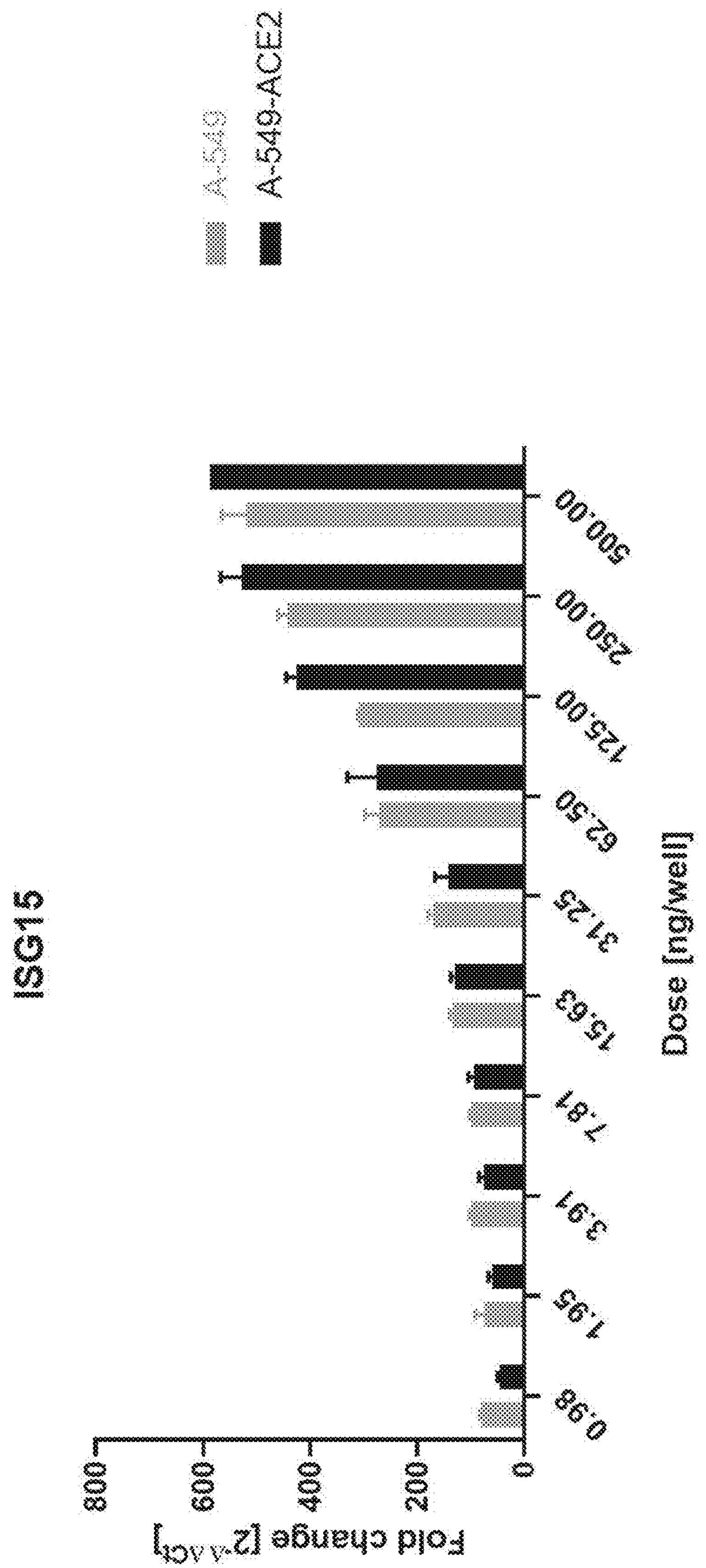
Figure 8A:
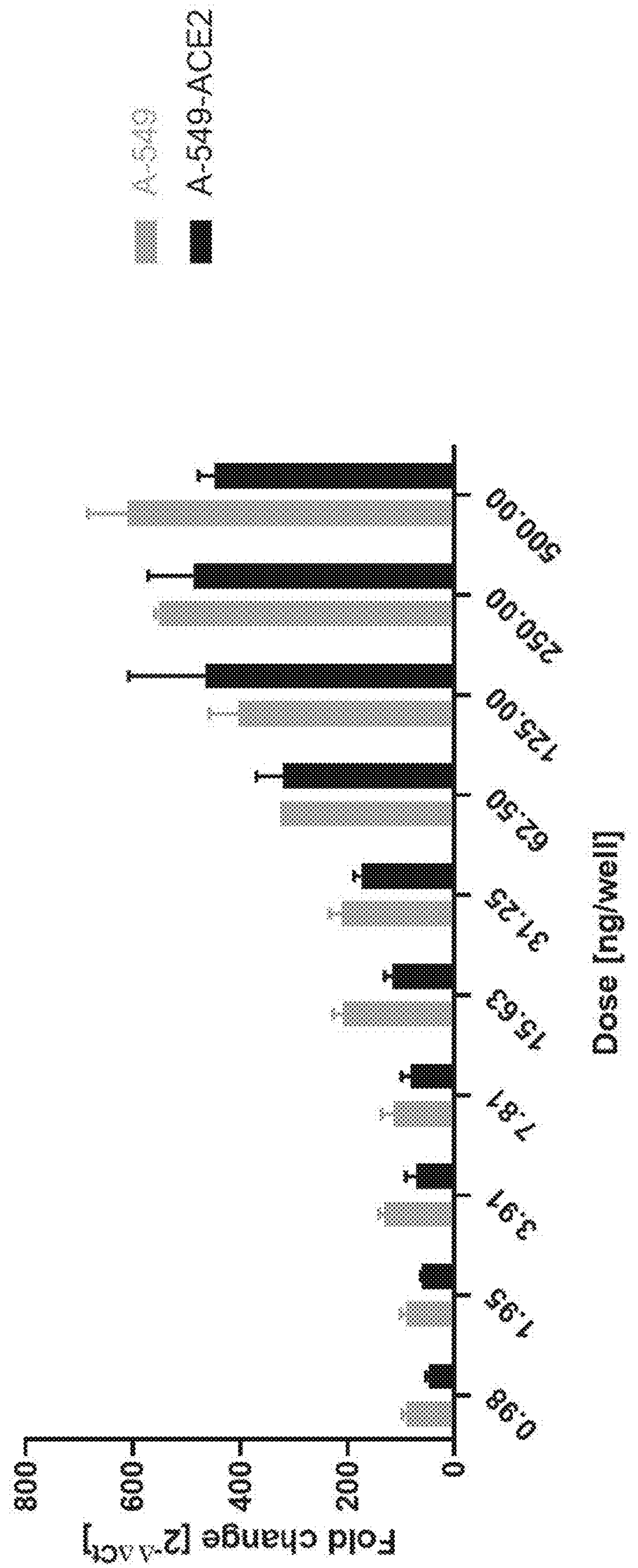
Figure 8A:
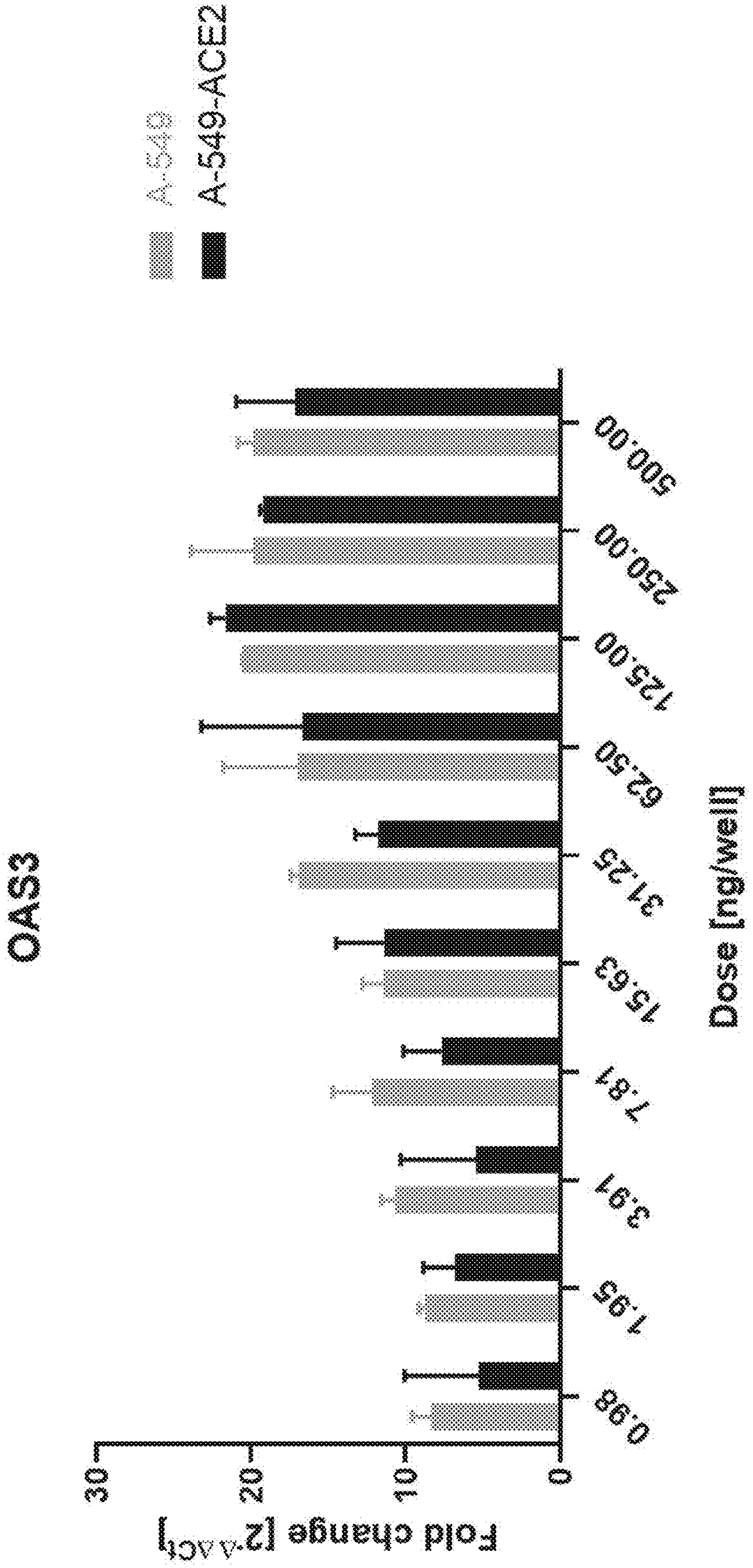
Figure 8B:
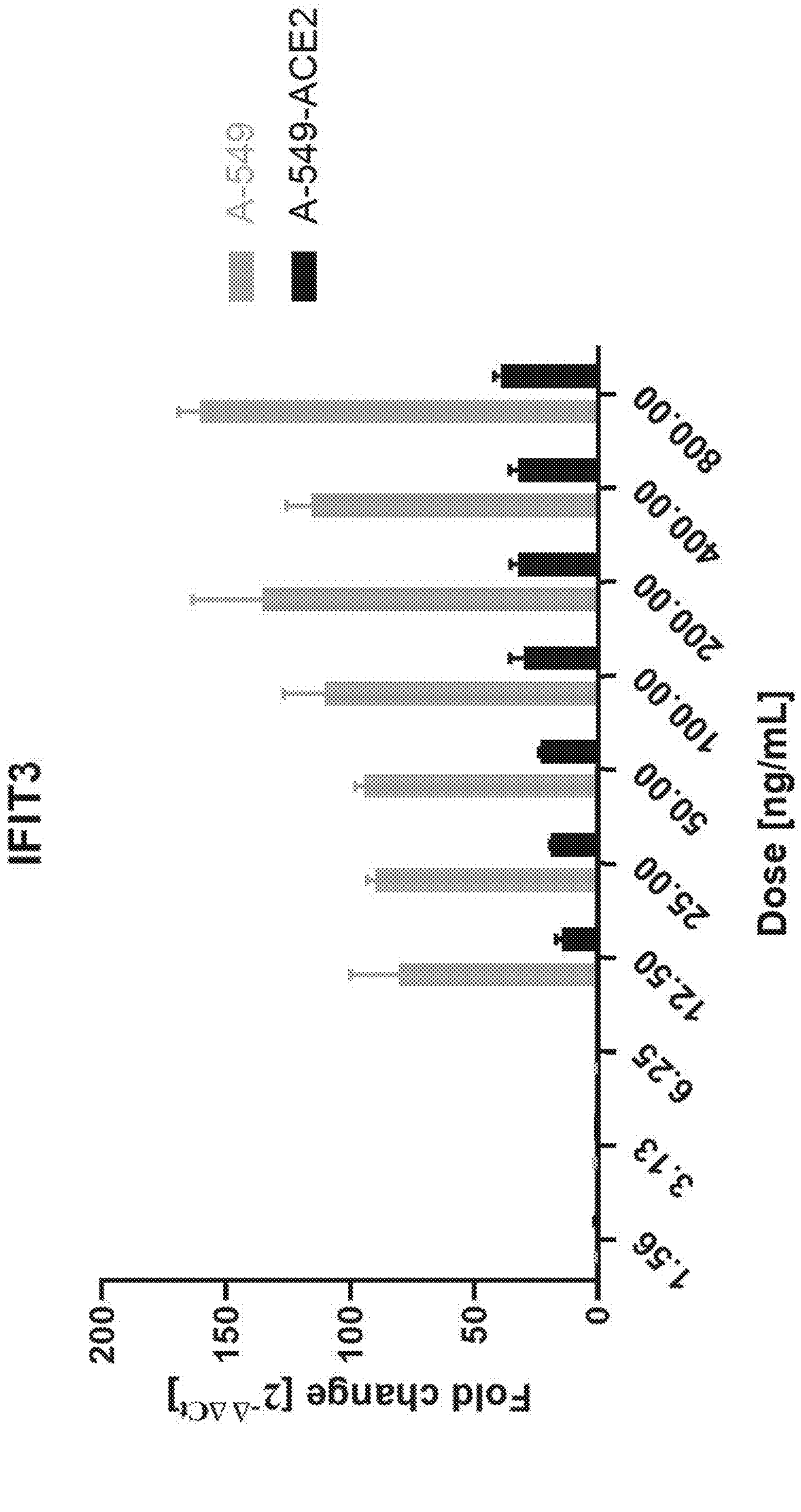
Figure 8B:
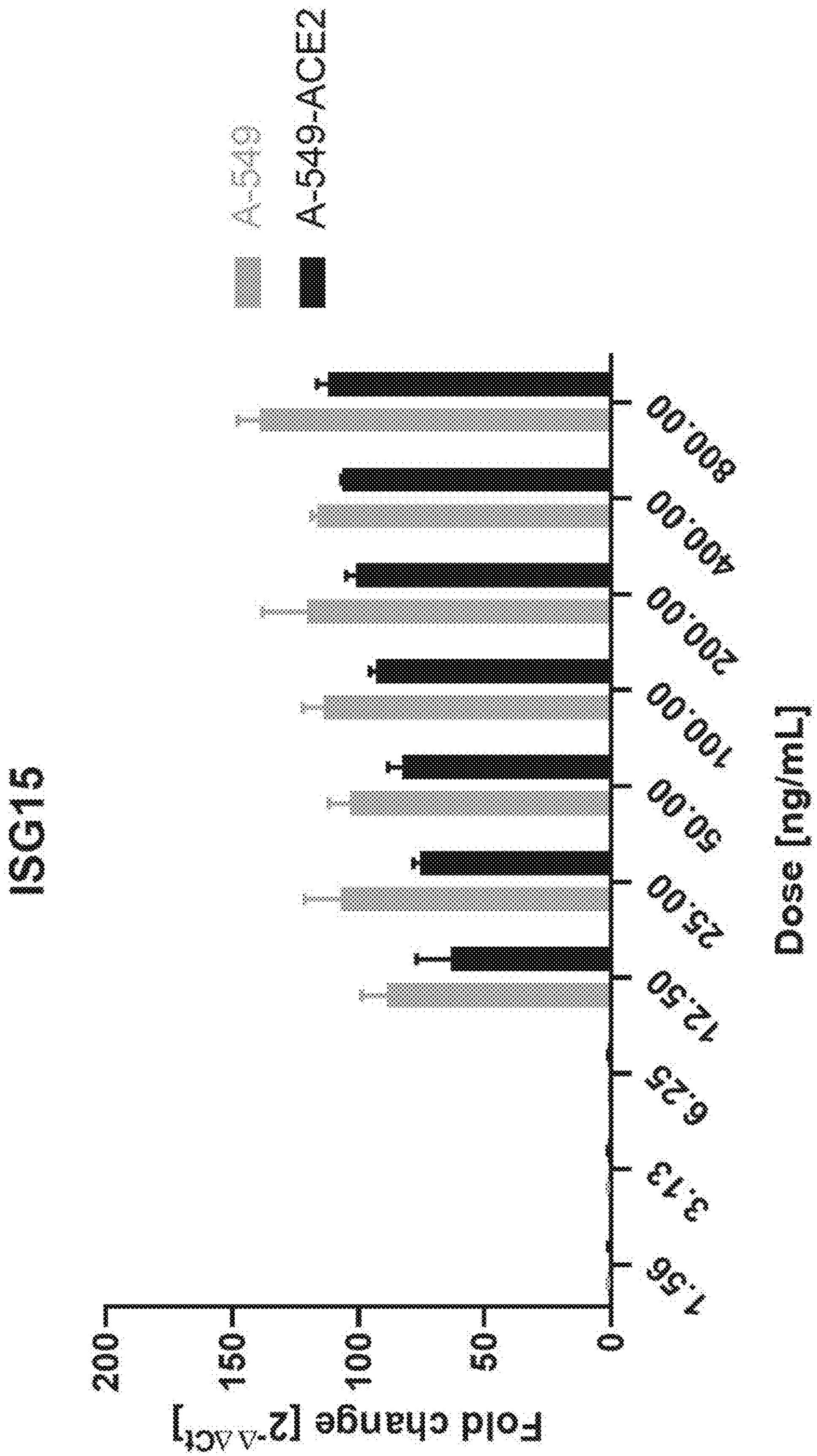
Figure 8B:
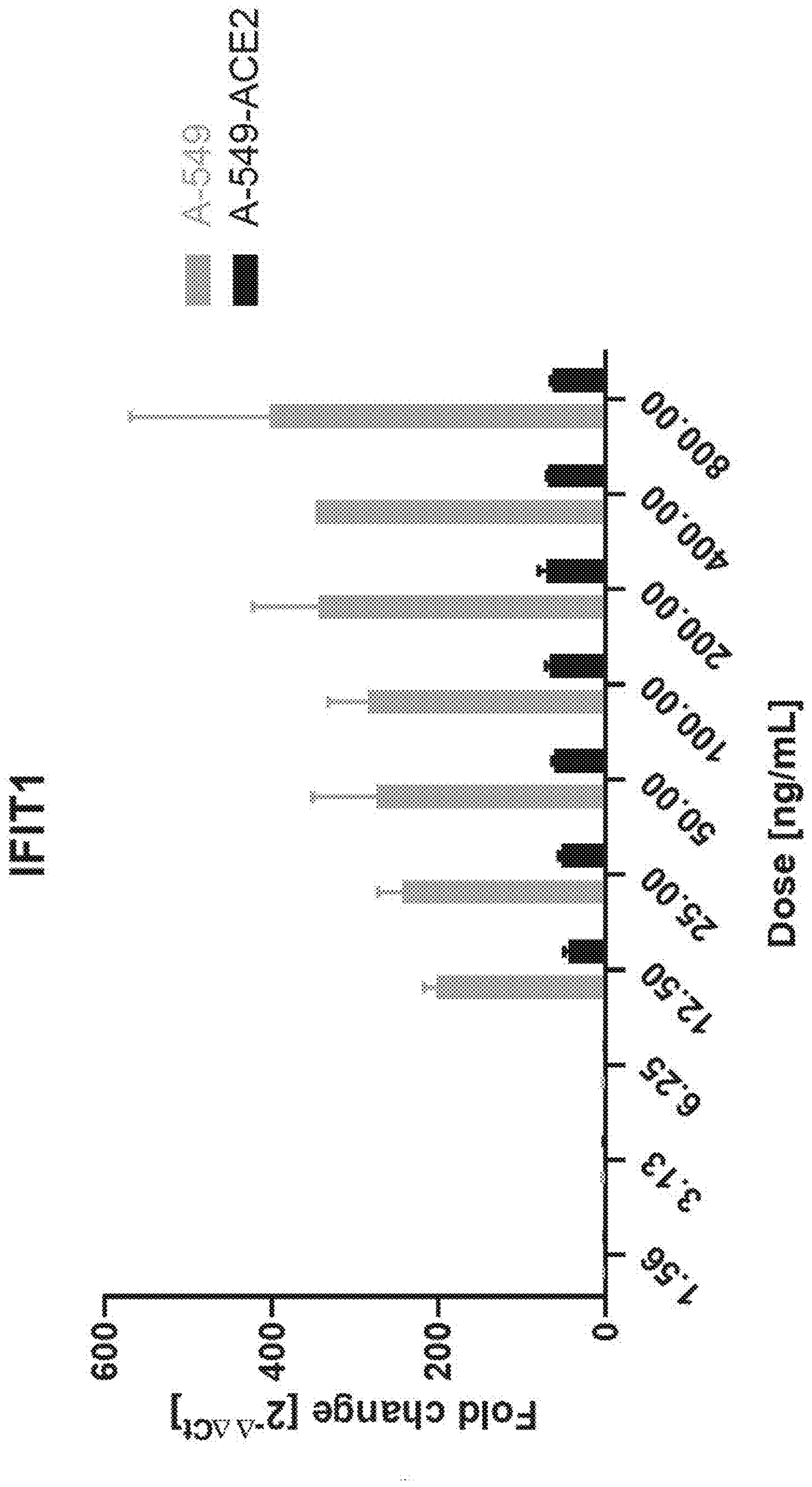
Figure 8B:
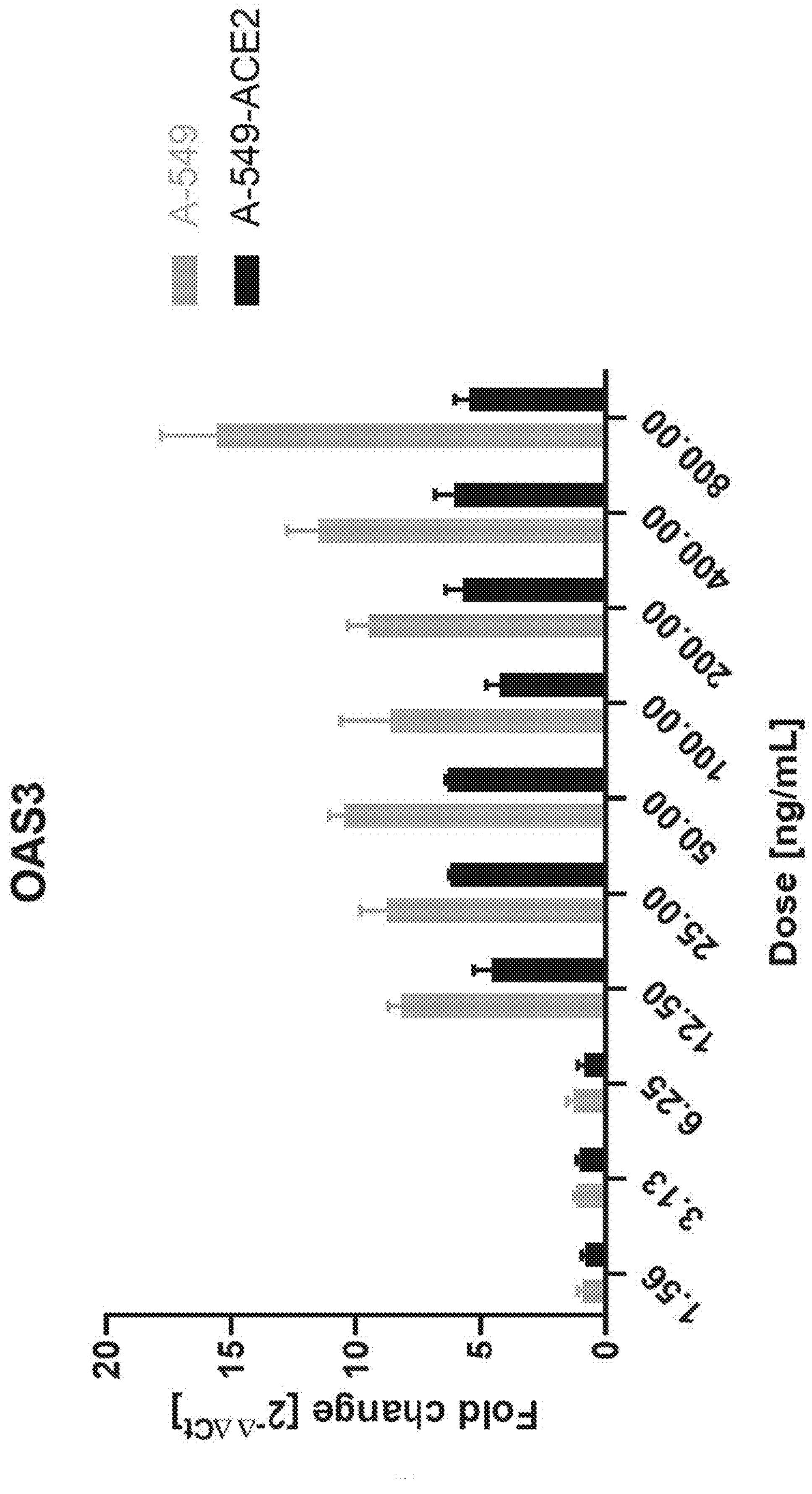
Figure 8C:
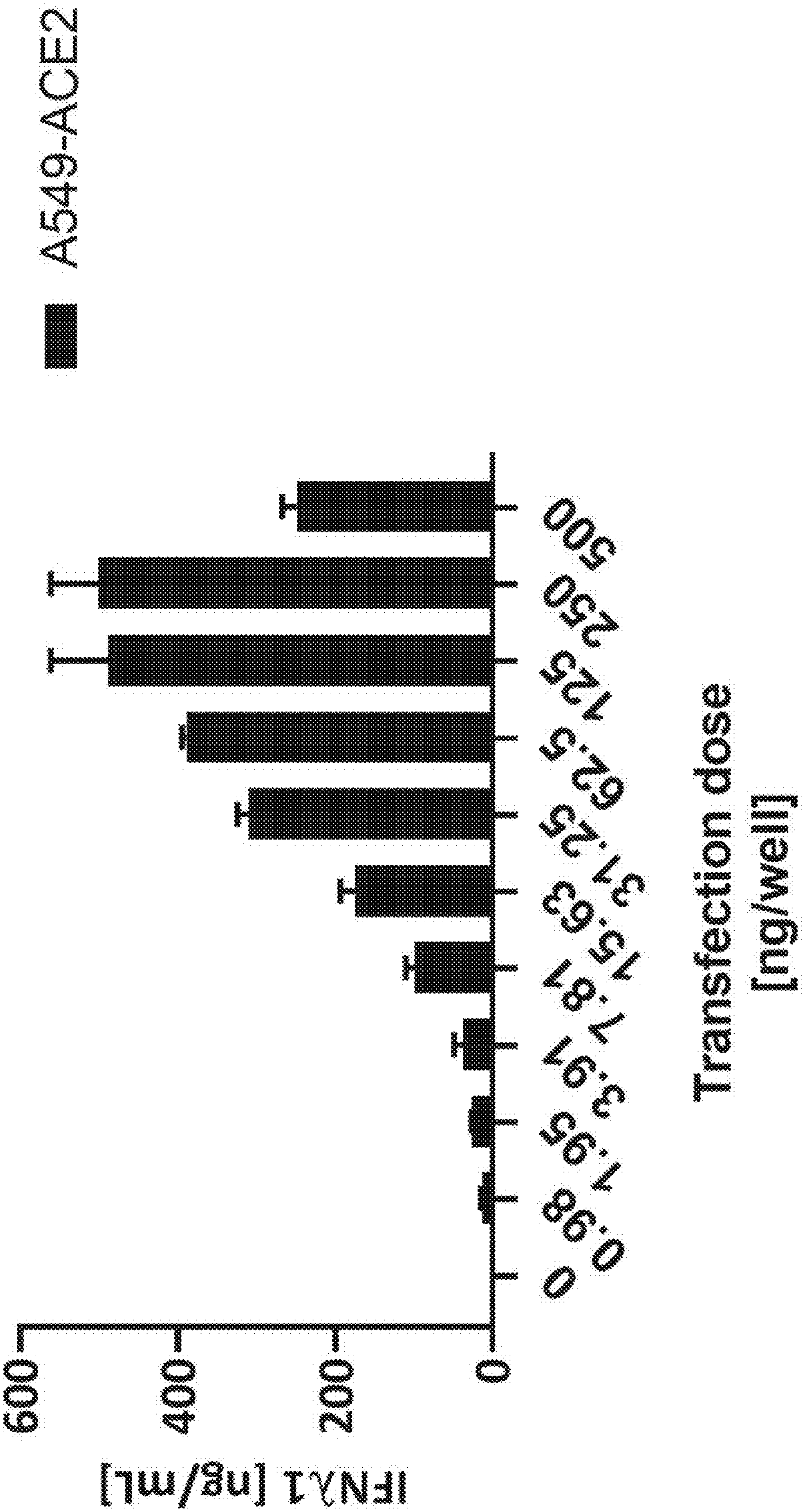

Downstream target activation 6 hours post treatment with recombinant IFNλ1 or mRNA coding for IFNλ1 was assessed via qPCR for IFIT1, IFIT3, OAS3 and ISG15. Downstream target activation is plotted against measured IFNλ1 levels. IFIT1, IFIT3 and ISG15 activation was higher at low IFNλ1 levels when provided by transfection of IFNλ1 mRNA compared to incubation with the recombinant IFNλ1 protein (see FIG. 7).

Summary of Examples 1 and 2

Upon transfection of A-549 cells with mRNA coding for IFNλ1 and medium exchange 6 h post transfection, IFNλ1 was detectable in supernatants of these cells up to 168 h with a peak at 48 h. Downstream targets were highly induced also with low doses of mRNA transfection and remained upregulated up to 120 h post mRNA transfection.

Regarding treatment with recombinant hIL-29, downstream target activation was observed at 6 h post treatment and declined rapidly after medium exchange.

For the Examples described in the Examples, the following Materials and Methods were used:

1 Methods 1.1 In Vitro 1.1.1 Cell Culture 1.1.1.1 Submersed Cells

HEK293, A-549 and 16HBE14o-cells were cultivated in MEM supplemented with 10% heat inactivated FBS and 1% P/S at 37 °C, in a humidified atmosphere with 5% $CO_2$. For 16HBE14o-cells, coated flasks were used. FreeStyle 293-F cells were cultivated in suspension in a 125 mL vented Erlenmeyer flask using FreeStyle F17 Expression Medium. 24 h prior transfection cells were seeded in 96-well plates in a total volume of 100 μL with following densities:

HEK293:25.000 c/well

FreeStyle 293-F: 25.000 c/well

16HBE14o-: 25.000 c/well

A-549: 20.000 c/well 1.1.1.2 ALI (Air-Liquid-Interface) Cultures

For 16HBE14o- and A-549 ALI cultures, $6\times10^4$ submersed cells (at 80-90% confluency) were seeded in coated 24-well inserts. For 16HBE14o-ALIs, inserts were coated with 50 μg/mL collagen type I diluted in 20 mM acetic acid. Cells were seeded in 250 μL 16HBE14o- or A-549 medium apical. For 16HBE14o-500 μL medium and for A-549 700 μL medium was added to the basolateral side. Cells were incubated for 72 h to attach to the membrane with medium on the apical and basolateral side. 24 h prior transfection, basal medium was replaced by fresh medium and the seeding medium on the apical side was carefully aspirated (air-lift). The cells were maintained as ALI cultures without liquid on the apical side.

MUCILAIR™ inserts were purchased at Epithelix and cultivated in 700 μL MUCILAIR™ culture medium at 37 °C, in a humidified atmosphere with 5% C02 as ALI (Air-Liquid-Interface) cultures. Prior transfection the cells were let rest for 2-3 days upon arrival. To maintain culture, medium was exchanged every 2-3 days.

1.1.2 Transfection 1.1.2.1 Submersed Cultures mRNA was transfected using LIPOFECTAMINE™ MESSENGERMAX™ in a RNA to LIPOFECTAMINE™ ratio of 1:1.5 (w/v). A dose titration ranging from 500 to 0.98 ng mRNA/well was performed. For lipoplex formation mRNA was diluted in $dH_2O$ and Lipofectamine® MESSENGERMAX™ was diluted in serum free medium and mixed by pipetting. After LIPOFECTAMINE™/MMax incubation of 10 min at RT, the RNA solution was added to the LIPOFECTAMINE™ MESSENGERMAX™ solution, mixed and incubated for another 5 min at RT. Afterwards, 25 μL of the Lipoplex solution for desired concentrations is added to the respective wells.

1.1.2.2 ALI Cultures

Prior transfection of Epithelix primary human ALIs a mucus wash was performed. 200 μL of PBS (w/o Mg/Ca) was added to the apical side and incubated for 20 min at 27 °C. Total time of apical washing should not exceed 30 min. To detach the mucus from the apical surface three back and forth movements were done with 100 μL from the apical liquid with a P200 pipet. PBS from the apical surface of the ALI culture was removed by gentle aspiration without damaging the epithelium. To remove traces of PBS, WFI wash using 200 μL WFI was performed. 16HBE14o- and A-549 ALIs were washed solely using WFI. Subsequently, the cells were transfected with 0.1, 0.3, 1, 3 and 6 μg mRNA in LNP/insert. Formulations were thawed at RT and kept on ice until further use. Detailed calculations are shown in Table 1.

TABLE 1

| Calculation for ALI transfection | | | | | | |
|---|---|---|---|---|---|---|
| | | 0.1 μg | 0.3 μg | 1 μg | 3 μg | 6 μg |
| Dose | μg/cm$^2$ | 0.3 | 0.9 | 3 | 9 | 18 |
| | μg/insert | 0.1 | 0.3 | 1 | 3 | 6 |
| transfection. Vol | [μl] | 25 | 25 | 25 | 25 | 25 |
| final LNP conc. in well | [ng/μL] | 4 | 12 | 40 | 120 | 240 |
| LNP conc. of stock | [μg/mL] | 500 | 500 | 500 | 500 | 500 |
| wells | | 3 | 3 | 3 | 3 | 3 |
| dilution (incl. excess) | μL LNP | 1.0 | 2.1 | 7 | 21 | 36 |
| | Vehicle | 124.0 | 85.4 | 80.5 | 66.5 | 39.0 |

6 h post transfection, LNP was aspirated.

1.1.3 Harvest 1.1.3.1 Submersed Cultures

At respective time points post transfection, supernatant of cells were collected and stored in a fresh 96-well storage plate at −80 °C until ELISA. Prior ELISA the supernatants were centrifuged at 500×g for 2 min to pellet cell debris.

For qPCR, after collecting the supernatant, submersed cells were washed with 150 μL D-PBS per well and cell pellets were frozen at −80 °C.

1.1.3.2 ALI Cultures 24 h post transfection, apical side of the inserts was washed using 200 μL PBS, which was pipetted up and down three times. Wash solution was collected in a 96-well storage plate. Also 200 μL of basal medium was collected in a storage plate. Samples were stored at −80 °C until ELISA was performed.

For qPCR, medium was removed completely from the inserts without PBS washing. 175 μL RLT buffer from RNEASY®Mini Kit (Qiagen, 74104), complemented with DTT (40 μL/mL) was added on the insert. With a mini cell scraper the cells were loosened from the insert. The RLT buffer was transferred into a QIAshredder column. To ensure all cells were transferred, the insert was washed with another 175 μL of RLT buffer. To finish the cell lysis, the columns were centrifuged for 2.5 min at max speed. Cell lysates can be frozen at −80 °C or used immediately to isolate RNA.

1.1.4 IFNλ1 ELISA

IFNλ ELISA was performed according to Kit instructions (IL-29 Human ELISA Kit, Abcam, ab100568) except that TMB was incubated for 10 instead of 30 min.

1.1.5 RNA Isolation 1.1.5.1 Submersed Cells

For submersed cells, RNA isolation was performed using SINGLESHOT™ Cell Lysis Kit (BioRad, Art.Nr.: 1725080).

Preparation of the SINGLESHOT™ cell lysis buffer was done according to Table 2. Preparation was done always fresh and on ice. The lysis buffer was mixed thoroughly, centrifuged and was used within 2 h.

TABLE 2

| Lysis Buffer | | |
|---|---|---|
| Component | Volume per well [μL] | Volume for 96-well plate [μL] (with excess) |
| SINGLESHOT ™ Cell Lysis Buffer | 48 | 4800 |
| Proteinase K Solution | 1 | 100 |
| DNase Solution | 1 | 100 |

50 μL lysis buffer for RNA isolation was added per well to frozen samples and incubated without agitation for 10 min at RT. Samples were processed within 20 min. Subsequently the cell lysate was transferred to a PCR plate. Protein and DNA was digested using the program "BioDNA" with the following conditions (see Table 3): Thermal cycler protocol for cell lysis

TABLE 3

| Thermal cycler protocol for cell lysis | |
|---|---|
| Time | Temperature |
| 5 min | 37 °C |
| 5 min | 75 °C |

The cell lysate can be stored for up to 4 h on ice, for up to 2 months at −20 °C, or for up to 12 months at −80 °C.

1.1.5.2 ALI Cultures

RNA was isolated using the RNEASY® Mini Kit (Qiagen, 74104) according to the manufacturer's protocol. Elution was done using 30 μL RNAse free water.

1.1.6 cDNA Synthesis 1.1.6.1 for Submersed Cells

ISCRIPT™ Select cDNA Synthesis Kit (BioRad, Art.Nr.: 1708897) was used. The plates with cell lysates were thawed on ice. All kit components, except ISCRIPT™ reverse transcriptase, were thawed on ice and mixed thoroughly and centrifuged briefly. cDNA synthesis was done using OligodT primers. Following components were added to a 2 mL tube, where the ISCRIPT™ reverse transcriptase was added after the other components (see Table 4).

TABLE 4

| Master Mix ISCRIPT ™ Select cDNA Synthesis | | |
|---|---|---|
| Component | Volume per well [μL] | Volume for 96-well plate [μL] |
| Nuclease free water | 9 | 900 |
| 5× ISCRIPT ™ reaction mix | 4 | 400 |
| OligodT | 2 | 200 |
| ISCRIPT ™ reverse transcriptase | 1 | 400 |
| Total | 16 | 1600 |

4 μL of the cell lysate were pipetted in a new PCR plate using a multi-channel pipet, before adding 16 μL of the master mix on top. The plate was sealed using a cover foil and mixed gently at 400 rpm before the plate was spun down briefly. cDNA synthesis was performed using a thermal cycler with following protocol ("ISCRIPT™2")

TABLE 5

| Thermal cycler protocol for cDNA synthesis | | |
|---|---|---|
| Time | Temperature | Step |
| 60 min | 42 °C | cDNA synthesis |
| 5 min | 85 °C | Heat inactivation |

cDNA can be stored at −20 °C until qPCR is performed.

1.1.6.2 ALI Cultures

For cDNA synthesis of ALI cultures Transcriptor First Strand cDNA Synthesis Kit (Roche, 4896866001) was used. In accordance to manufacturers protocol RNA was transcribed to cDNA. For a two-step cDNA synthesis 1 μg of total RNA and 1 μL Oligo(dT) Primers in a total volume of 13 μL were necessary to prepare the first step. One example for the preparation of template-primer mixture is given in Table 6:

TABLE 6

| Template-Primer-Mix | | | | |
|---|---|---|---|---|
| Name | Nucleic Acid Conc. [ng/μL] | Volume RNA [μL] | Oligo(dT) Primer [μL] | Water (RNAse free) [μL] |
| Sample No. 1 | 147.7 | 6.8 | 1.0 | 5.2 |
| | | | Total volume | 13 |

The optional denaturation step at 65 °C for 10 min was done in a thermal block cycler. Afterwards, all remaining reagents except enzymes, Reverse Transcriptase and RNAse Inhibitor, were thawed on ice and briefly centrifuged. To prepare a master-mix following components listed in Table 7 were added into a fresh tube:

TABLE 7

| Master-Mix | | |
|---|---|---|
| Name | 1× [μL] | n = 4 |
| 5× reaction buffer | 4 | 16 |
| RNAse Inhibitor | 0.5 | 2 |
| dNTPS | 2 | 8 |
| Reverse transcriptase | 0.5 | 2 |
| Total volume [μL] | 7 | 28 |

At last, enzymes were added to the reagents listed in Table 7. Volume of master-mix was adapted according to number of samples. 7 μL of master-mix were added to each tube, which contained template-primer mixture to get a final volume of 20 μL per tube, see Table 6. The tubes were mixed carefully and briefly centrifuged. Tubes were put back to a thermal block cycler and following program for reverse transcription (here step two of cDNA synthesis) was used:

TABLE 8

| Program for reverse transcription using Oligo(dT) primer | | |
|---|---|---|
| Step in thermal block cycler | Duration [min] | Temperature [°C] |
| 1 | 30 | 55 |
| 2 | 5 | 85 |

cDNA can be stored at −20 °C until qPCR is performed.

1.1.7 qPCR Using TAQMAN® Probes

The following components shown in Table 9 were combined and vortexed briefly. To bring the reaction mix to the bottom of the tube and to eliminate air bubbles the mix was briefly centrifuged. 18 μL of TAQMAN® master mix were transferred to an optical 96-well qPCR reaction plate. 2 μL cDNA template (cDNA and nuclease free water) were added as shown in Table 10 to the optical 96-well qPCR reaction plate to obtain a final volume of 20 μL. The optical 96-well qPCR reaction plate was sealed with optical adhesive film and briefly centrifuged.

TABLE 9

| Master mix qPCR TAQMAN ® | | |
|---|---|---|
| Component | Volume per well [μL] | Volume for 96-well plate [μL] |
| Nuclease free water | 7 | 700 |
| TAQMAN ® Probe | 1 | 100 |
| TAQMAN ® Fast Advanced Master Mix | 10 | 1000 |
| Total | 18 | 1800 |

TABLE 10

| cDNA template preparation | | |
|---|---|---|
| Component | Volume per well [μL] | Volume for 96-well plate [μL] |
| cDNA | 1 | 96 |
| Nuclease free water | 1 | 96 |
| Total | 2 | 192 |

TAQMAN® assay was performed using following parameters:

| Mode | Cycle | Step |
|---|---|---|
| 2 Step Amplification | 40 | 95 °C for 5 s<br>60 °C for 30 s |

| TAQMAN ®Probes | Supplier | Cat no. |
|---|---|---|
| IFIT3 | Thermo Fisher Scientific | Hs01922752_s1 |
| IFIT1 | Thermo Fisher Scientific | Hs03027069_s1 |
| OAS3 | Thermo Fisher Scientific | Hs00196324_m1 |
| ISG15 | Thermo Fisher Scientific | Hs01921425_s1 |

1.2 In Vivo 1.2.1 Animal Housing

Mice were housed under specific pathogen free conditions (facility tested negative for any FELASA listed pathogens according to the annual health and hygiene survey 2017) in individually ventilated cages under a circadian light cycle (lights on from 7 a.m. to 7 p.m.). Food and drinking water were provided ad libitum. After arrival, animals were given at least 7 days for acclimatization until they enter the study.

1.2.2 Intratracheal Application

Animals were anesthetized by the inhalation of pure oxygen containing 4% Isoflurane (Isothesia, Henry Shine, Germany). Unconscious animals were intubated using a 20 gauge catheter shortened to 37 mm. Test item in a final volume of 50 μL was applied as one drop at the proximal tip of the tubus and thereby aspirated during the physiological inspiratory movement of the animal. Finally, 150 μL of air was applied, to assure that no liquid remains within the catheter.

1.2.3 Clinical Examination

Animals were examined clinically before application of the test item and 24 hours later using a clinical mouse scoring system. Clinical examination consisted of 4 different categories which were scored separately. The scorings of each of the 4 categories were summarized to a total clinical score. A summarized score of more than 4 points or a score of more than 1 point in a single category are considered as moderate suffering and thereby as a humane endpoint.

1.2.4 Necropsy

Animals were set under full anesthesia by intraperitoneal injection of Fentanyl/Midazolam/Medetomidin (0.05/5.0/0.5 mg/kg bw). Subsequently, mice were killed by cervical dislocation.

1.2.5 BALF and Lung Withdrawal

The thoracal and abdominal cavity were opened and a 18G catheter was placed into the trachea. 0.5 mL PBS was injected and retrieved from the lungs and centrifuged at 300×g for 10 min at 4 °C. Supernatant was taken and stored at −80 °C until further processing. The cell pellet was biobanked at −80 °C. Next, the lungs were explanted and as well stored at −80 °C until further processing.

1.2.6 Lung Homogenisation

Samples were homogenized using liquid nitrogen. Therefore, the organ was put in a mortarwhich is placed in an ice box. Liquid nitrogen was added in a volume, which covers the lung completely. The lung was pulverized in the mortar using a pistle. A stapula was immersed in nitrogen and used to devide the organ powder in two halfs. Both halfs were weighed in an empty tared tube each. Mortar, pistle and stapula were cleaned using Ethanol after every sample.

For ELISA, lysis was done in 250 μL Triton X-100 lysis buffer (0.25 M Triethanolamine, 0.1% Triton X-100, pH7.7), complemented with protease inhibitor. For qPCR lysis was done in 350 μL lysis buffer per 30 mg organ. Lysis buffer RLT was provided by the kit and complemented with 40 μL/mL DTT. For qPCR, additional homogenizing in lysing tubes was performed. Therefore, volumes were applied as described above and procedure was performed for 3×20 sec in a Tissue homogenizer (MP FASTPREP™-24 Tissue and Cell Homogenizer).

Samples were incubated for 10 min on ice and centrifuged for 10 min at 4 °C in a Mikro 22R centrifuge (Hettich Zentrifugen) with maximum speed. Supernatant was transferred in fresh tubes and stored at −80 °C until further analysis.

1.2.7 Cell Lysis and cDNA Synthesis for qPCR

RNA isolation was done using the NUCLEOSPIN® RNA Kit (Macherey & Nagel, 740984.50) according to manufacturer's protocol.

cDNA synthesis was done using Transcriptor First Strand cDNA Synthesis Kit (Roche, 4896866001). In accordance to manufacturer's protocol RNA was transcribed to cDNA. For a two-step cDNA synthesis 1 μg of total RNA and 1 μL OligoDT Primers in a total volume of 13 μL were necessary to prepare the first step. One example for the preparation of template-primer mixture is given in Table 11:

TABLE 11

| Template primer mixture | | | | |
|---|---|---|---|---|
| Name | Nucleic Acid Conc. [ng/μL] | Volume mRNA [μL] | OligoDT Primer [μL] | Water (RNase free) [μL] |
| Sample No. 1 | 147.7 | 6.8 | 1 | 5.2 |
| | | | Total volume | 13 |

The denaturation step at 65 °C for 10 min was done in a thermo block cycler. Afterwards, all remaining reagents except enzymes, Reverse Transcriptase and RNAse Inhibitor were thawed on ice and briefly centrifuged. To prepare a master-mix following components listed in Table 12 are added into a fresh tube:

TABLE 12

| Master mix | |
|---|---|
| Name | 1× [μL] |
| 5× reaction buffer | 4 |
| RNAse Inhibitor | 0.5 |
| dNTPs | 2 |
| Reverse transcriptase | 0.5 |
| Total volume [μL] | 7 |

At last, enzymes were added to the reagents listed in Table 12. Volume of master mix was adapted according to number of samples. 7 μL of master mix were added to each tube, which contains template-primer mixture to get a final volume of 20 μL per tube. The tubes were mixed carefully and briefly centrifuged. Tubes were put back to a thermo block cycler and following program for reverse transcription was started:

| Step in thermo block cycler | Duration [min] | Temperature [°C] |
|---|---|---|
| Reverse transcription | 30 | 55 |
| Enzyme denaturation | 5 | 85 |

cDNA can be stored at −20 °C until qPCR is performed.

1.2.8 Real-time PCR Using TAQMAN® Probes for Downstream Targets See 1.1.7

| TAQMAN ® Probes | Supplier | Cat no. |
|---|---|---|
| IFIT3 | Thermo Fisher | Mm01704846_s1 (ifit3, |
| IFIT1 | Thermo Fisher | mM07295796_m1 |
| OAS3 | Thermo Fisher | Mm00460944_m1 |
| ISG15 | Thermo Fisher | Mm01705338_s1 |
| IFNλ | Thermo Fisher | Mm00558035_m1 |

1.2.9 qPCR Using UPL for Quantification of SNIM® RNA

For quantification of ETH061T02 SNIM RNA in mouse lungs qPCR was done. Therefore, 1 μg of IFNλ1 SNIM RNA was used for cDNA Synthesis and synthesis was done as described in section 1.1.6. cDNA of IFNλ1 mRNA was diluted in RNAse-free water in the following dilutions: $1{:}10^1$, $1{:}10^2$, $1{:}10^3$, $1{:}10^4$, $1{:}10^5$, $1{:}10^6$ resulting in a standard curve. It is important that the cDNA dilution series is prepared in a larger volume (e.g. 20 μL), to avoid inaccuracies during pipetting. 0.25 μL cDNA of mouse lung samples or the respective standard curve samples were mixed with 3.75 μL RNAse-free water and pipetted in a LIGHTCYCLER® 480 Multiwell Plate 96. Preparation of qPCR Master Mix is done according to Table 13.

TABLE 13

| UPL Master-Mix | | |
|---|---|---|
| Component | Volume per well [μL] | Volume for 96-well plate [μL] |
| Nuclease free water | 0.625 | 60 |
| Primer 1 [20 μM] | 0.150 | 14.4 |
| Primer 2 [20 μM] | 0.150 | 14.4 |
| UPL [stock] | 0.075 | 7.2 |
| Fast Start Essential DNA Probes Master | 5 | 480 |
| Total | 6 | 576 |

The master mix was added to 4 μL of diluted cDNA sample or standard in each well to LIGHTCYCLER® 480 Multiwell Plate 96 using a multi-pipette. The plate was covered with LIGHTCYCLER® 480 Sealing Foil and spun down briefly. qPCR was done using program for UniversalProbes on LIGHTCYCLER® 96 system.

Example 3: Effectiveness of IFNλ1 Encoding mRNA in A-549 Cells Expressing ACE2 in Comparison to Recombinant IFNλ1

Downstream target activation 48 hours post treatment of A549 or A549-ACE2 cells with recombinant IFNλ1 (FIG. 8 *a*) or mRNA coding for IFNλ1 (FIG. 8 *b*) was assessed via qPCR for IFIT1, IFIT3, OAS3 and ISG15. Whereas transfection with mRNA coding for IFNλ1 resulted in similar induction of IFIT1, IFIT3, OAS3 and ISG15, induction of the same downstream targets was reduced on A549-ACE2 cells compared with A459 cells after treatment with recombinant IFNλ1. Transfection of A549-ACE2 cells with mRNA coding for IFNλ1 resulted in dose-dependent production of IFNλ1 (FIG. 8 *c*).

Example 4: IFNλ1 Encoding mRNA is Translated in Various Cells Types

Figure 9:
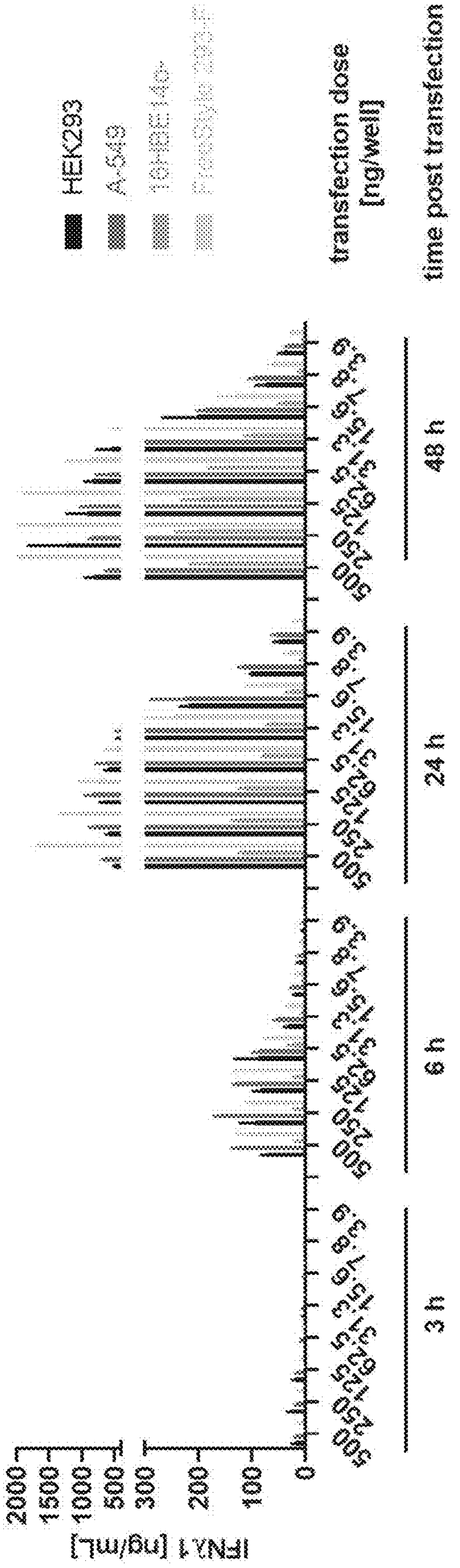
Figure 10A:
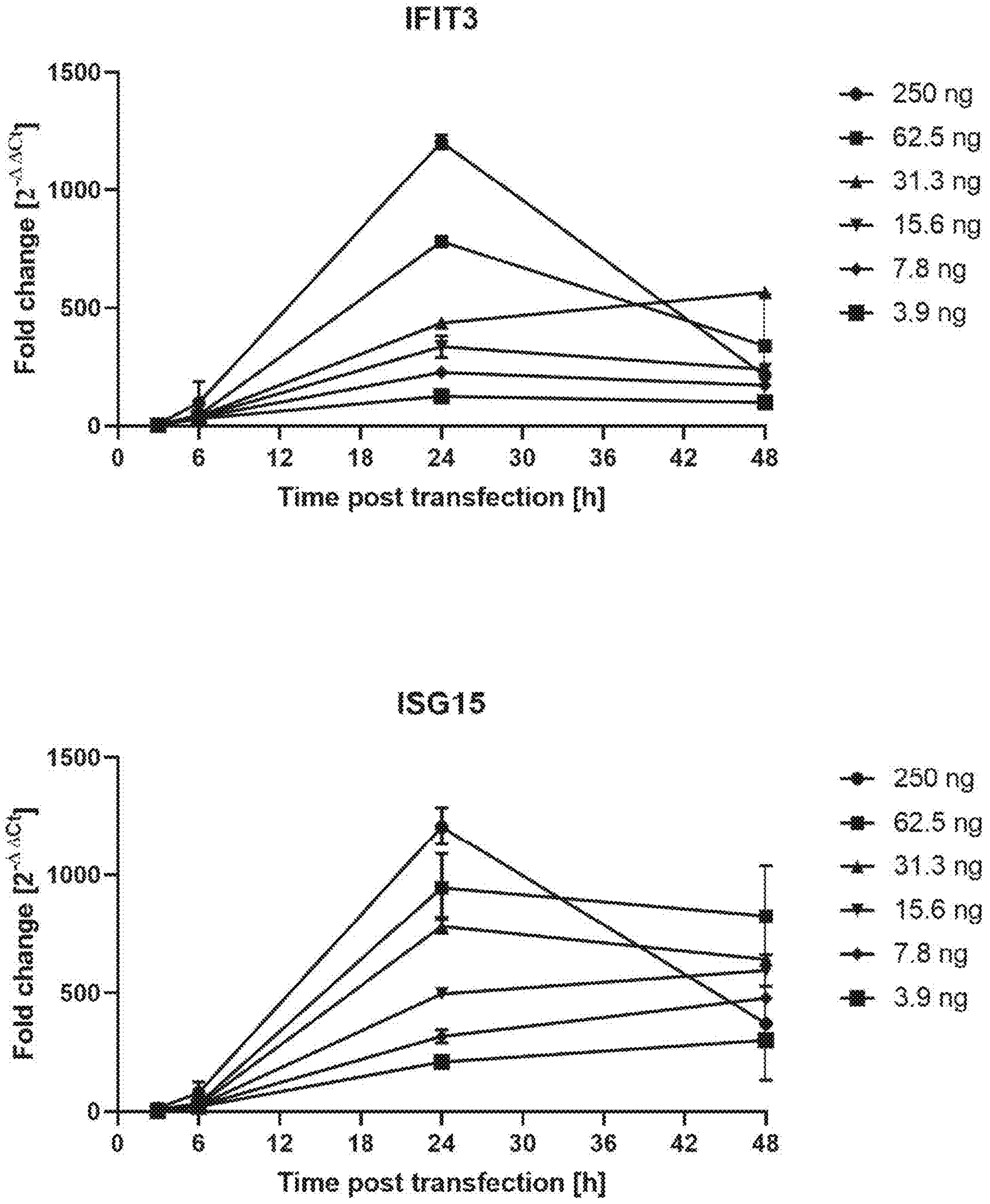
Figure 10A:
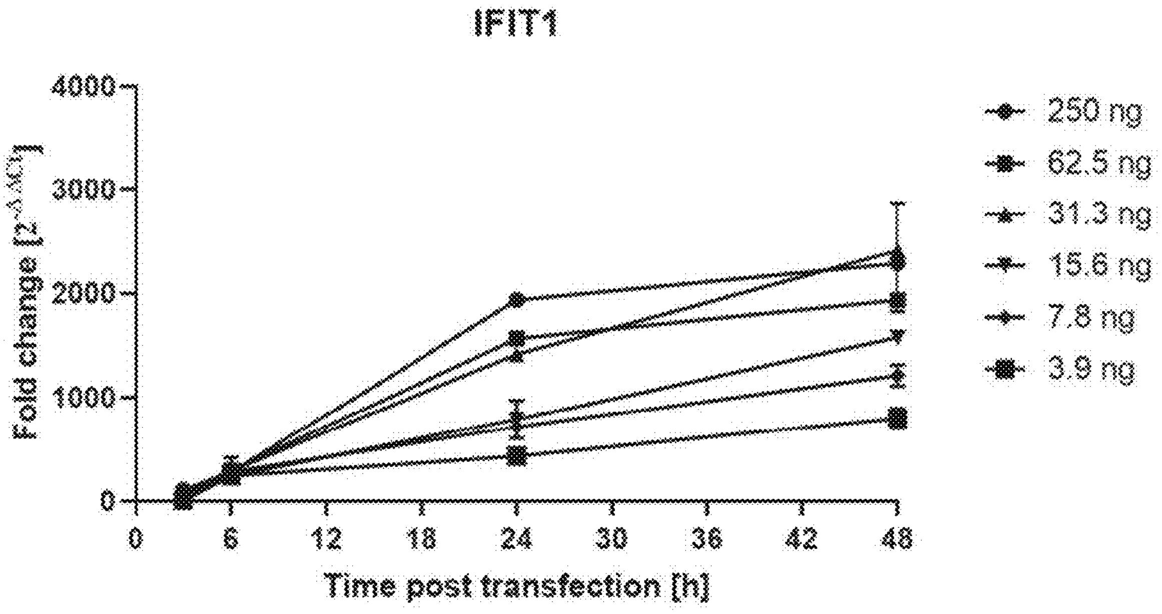
Figure 10A:
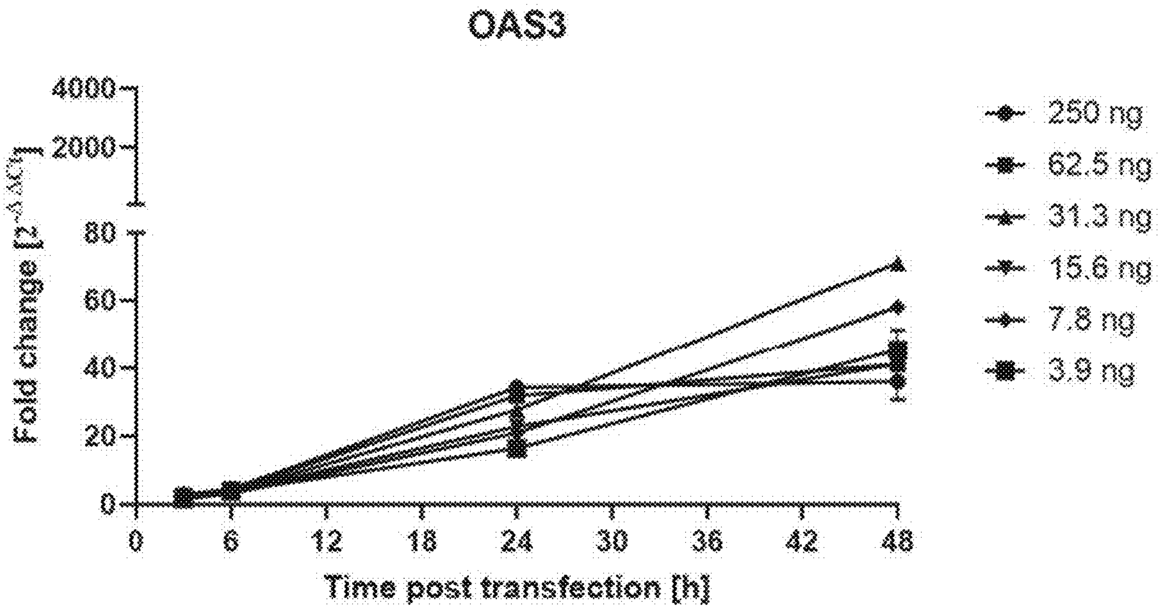
Figure 10B:
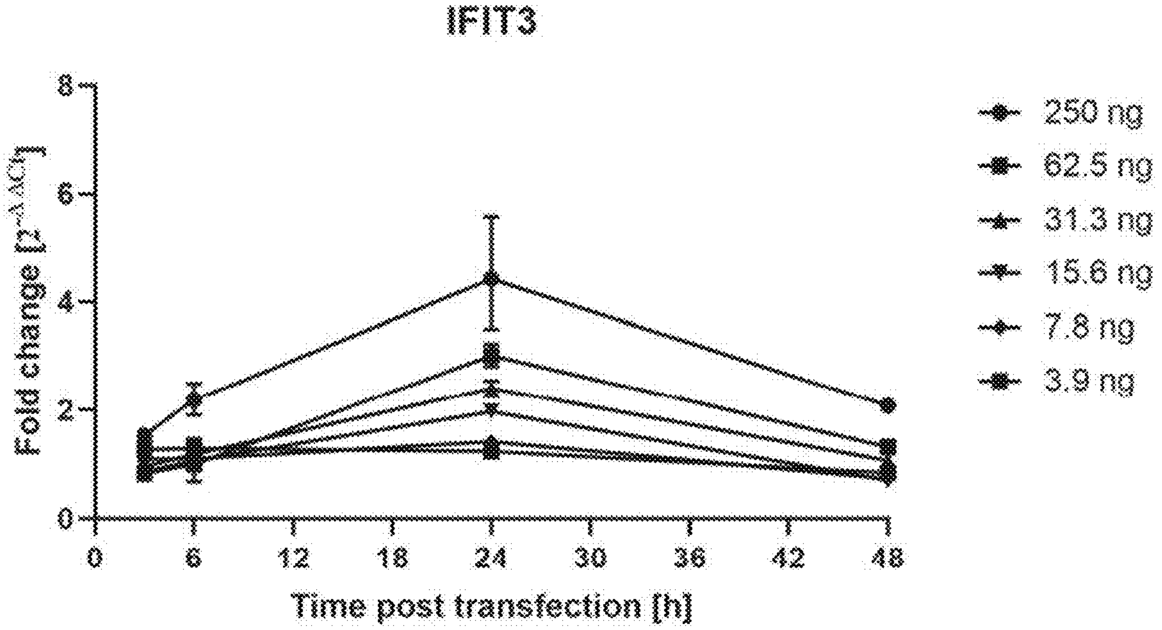
Figure 10B:
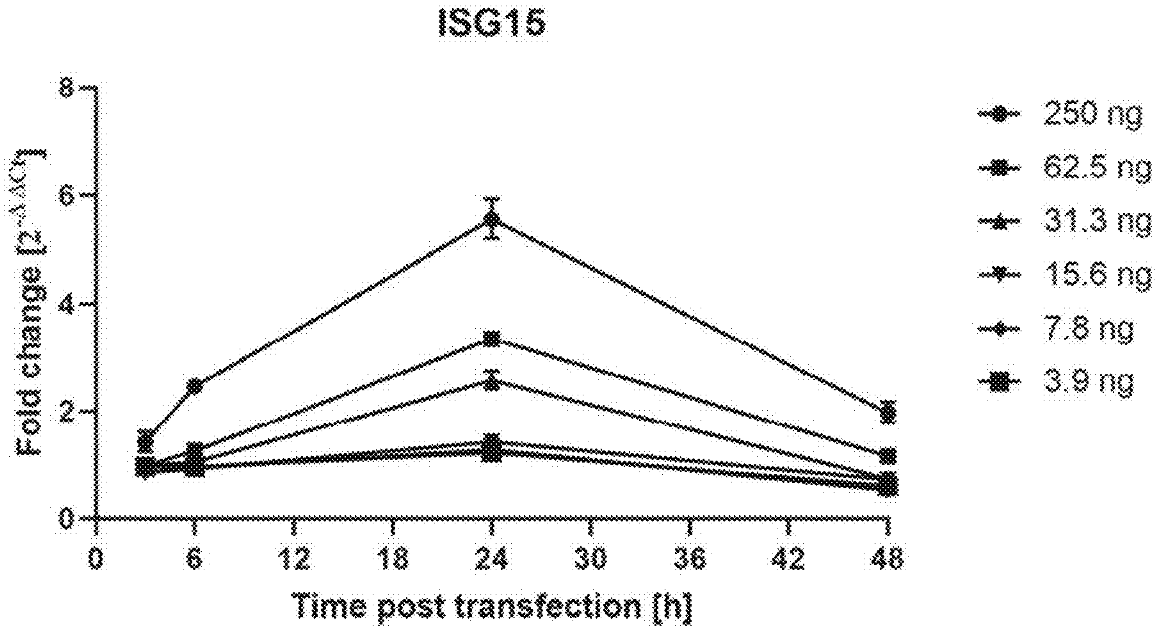
Figure 10B:
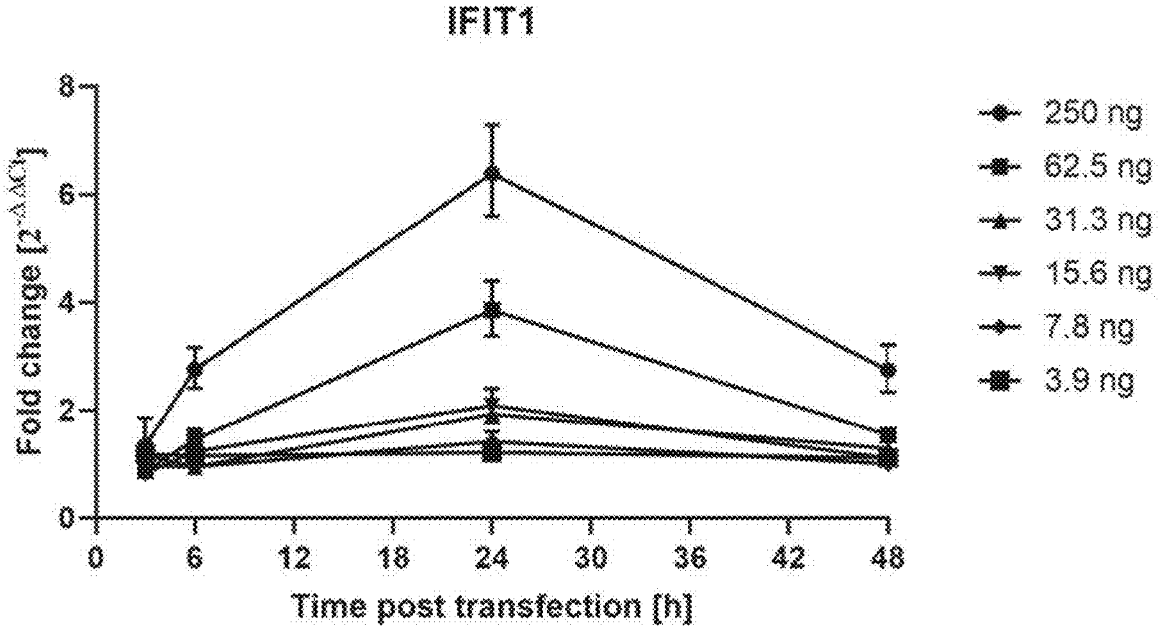
Figure 10B:
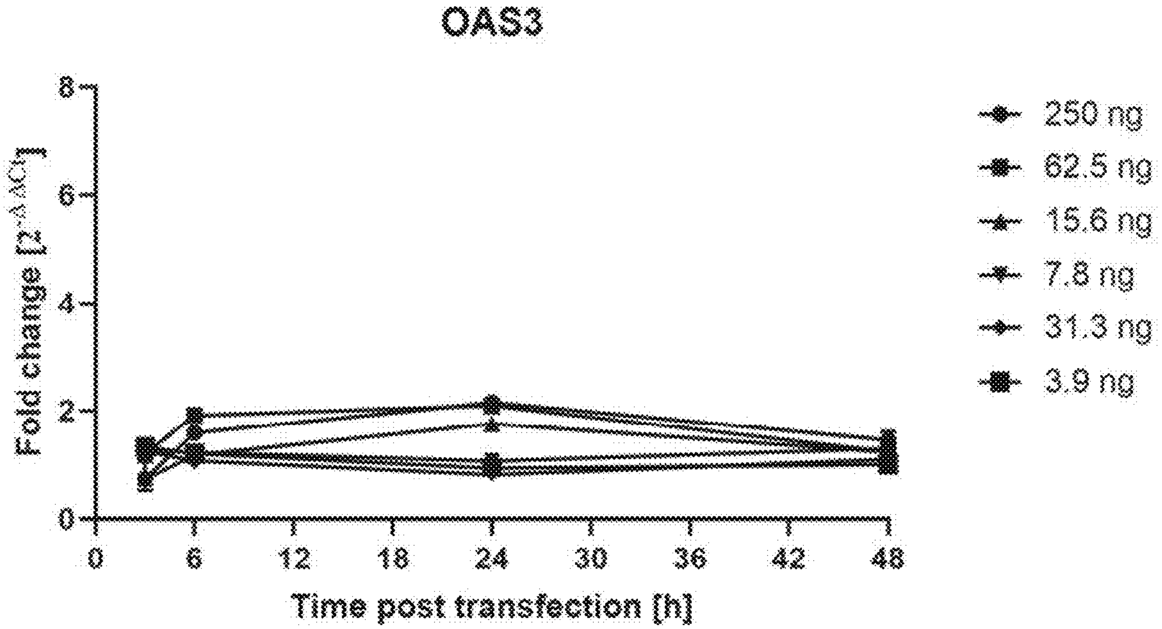
Figure 11A:
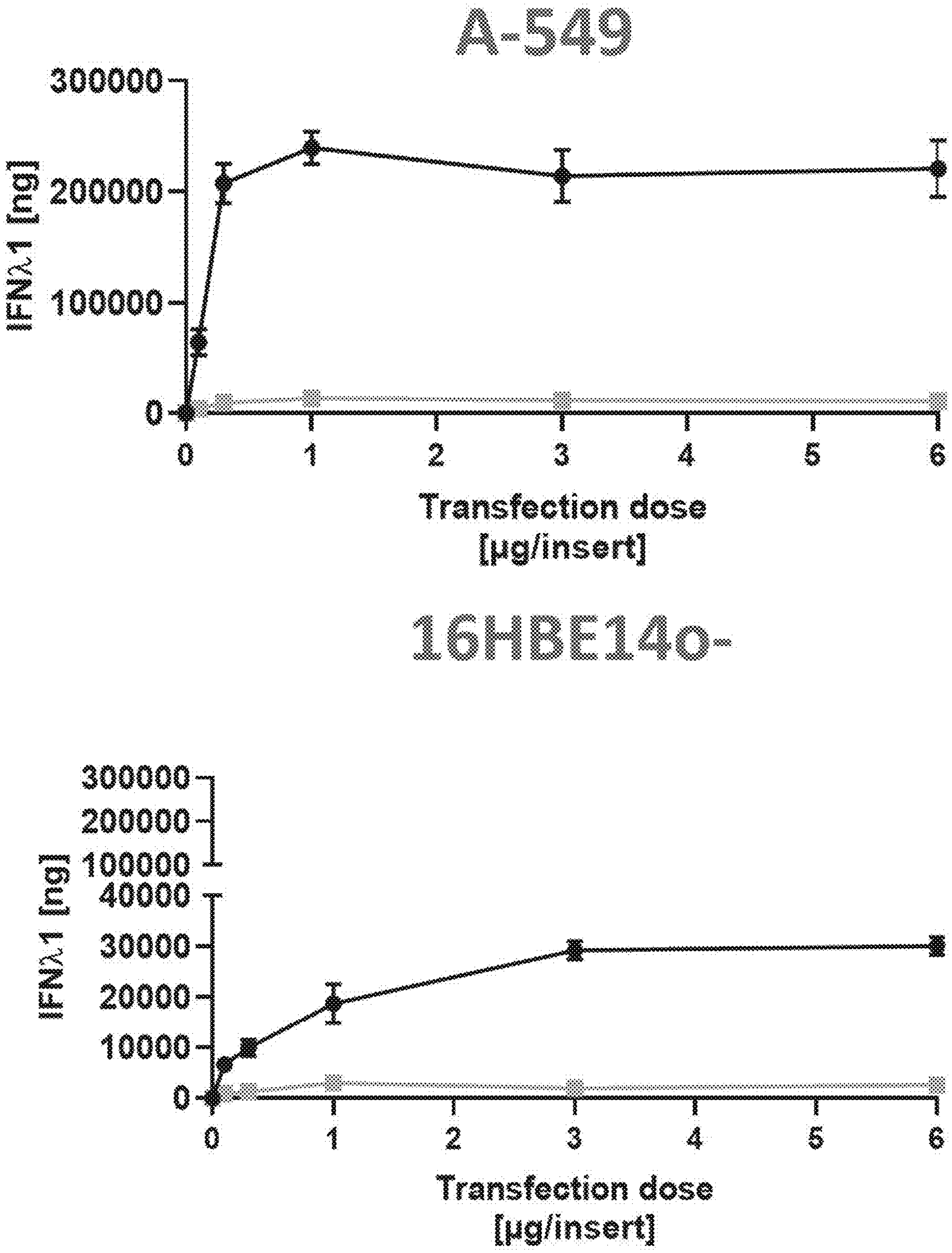
Figure 11A:
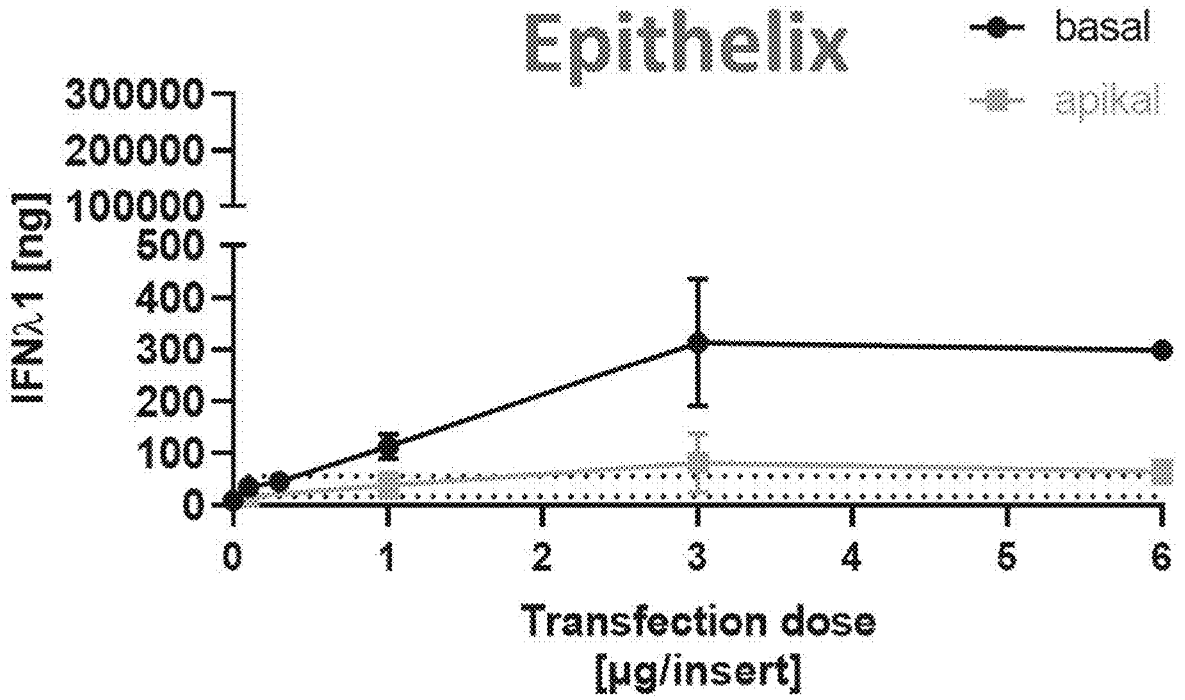
Figure 11B:
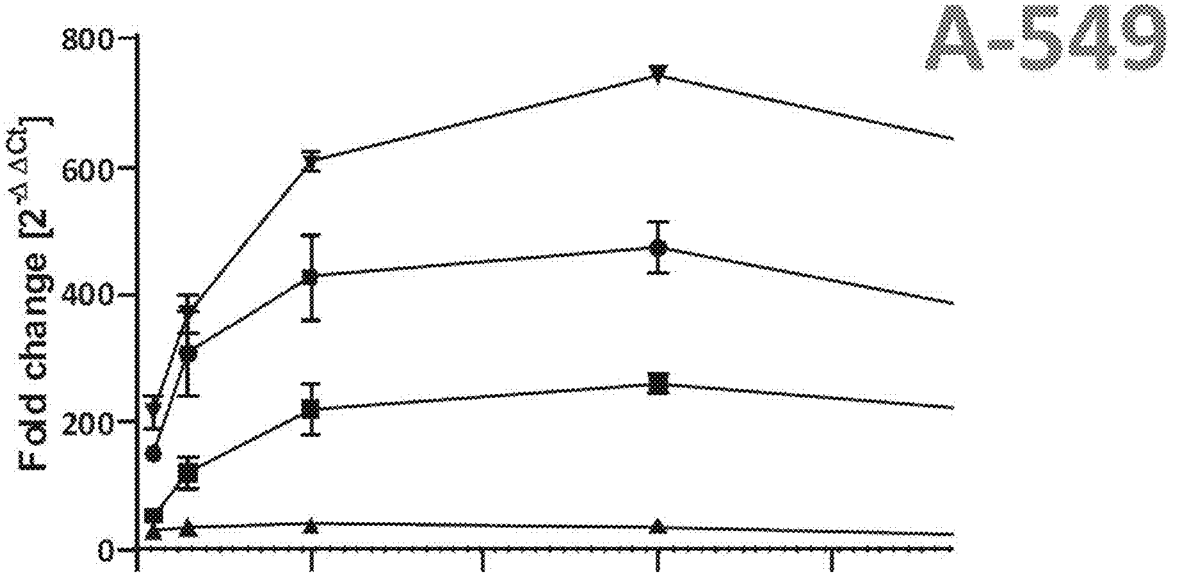
Figure 11B:
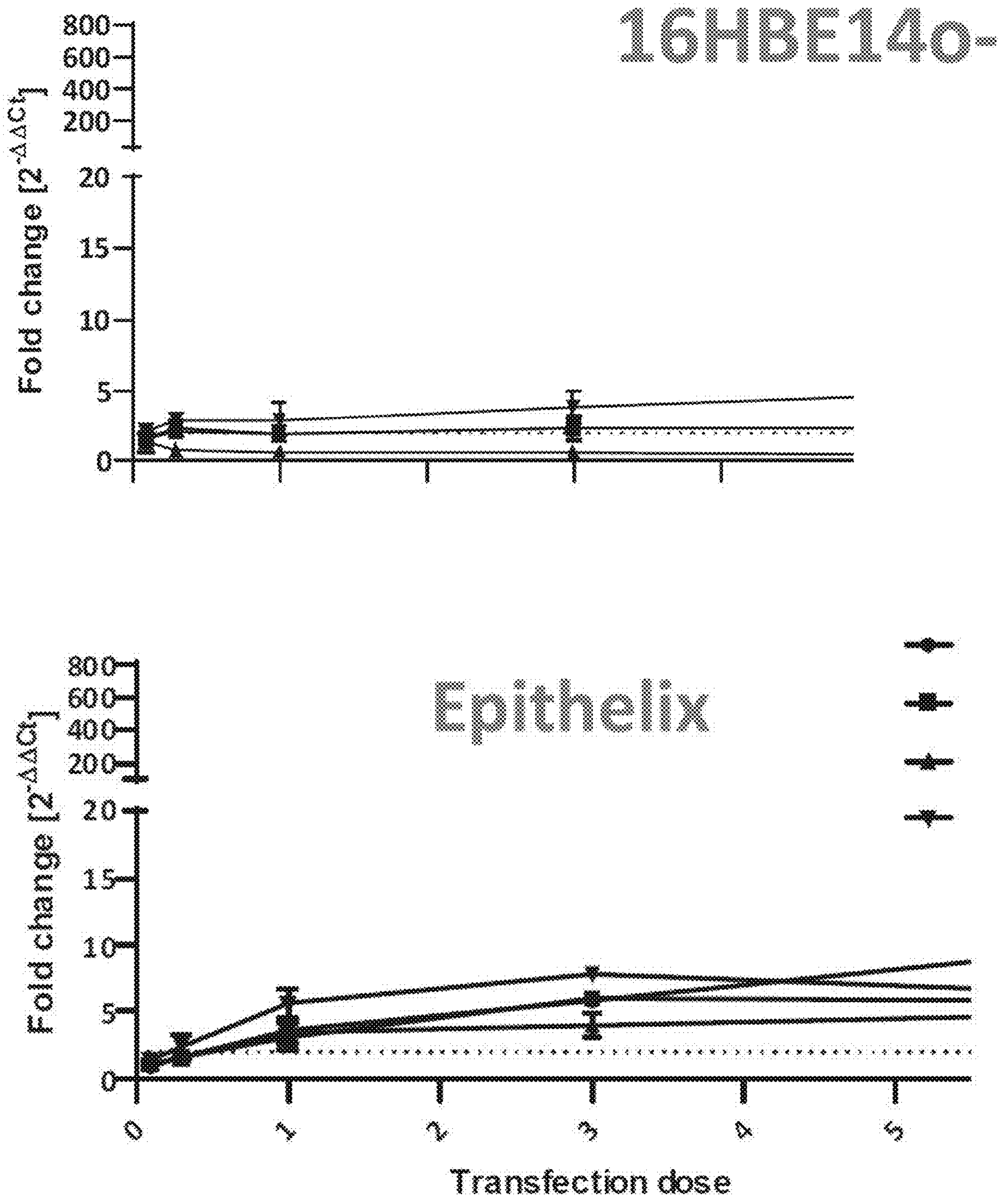
Figure 11C:
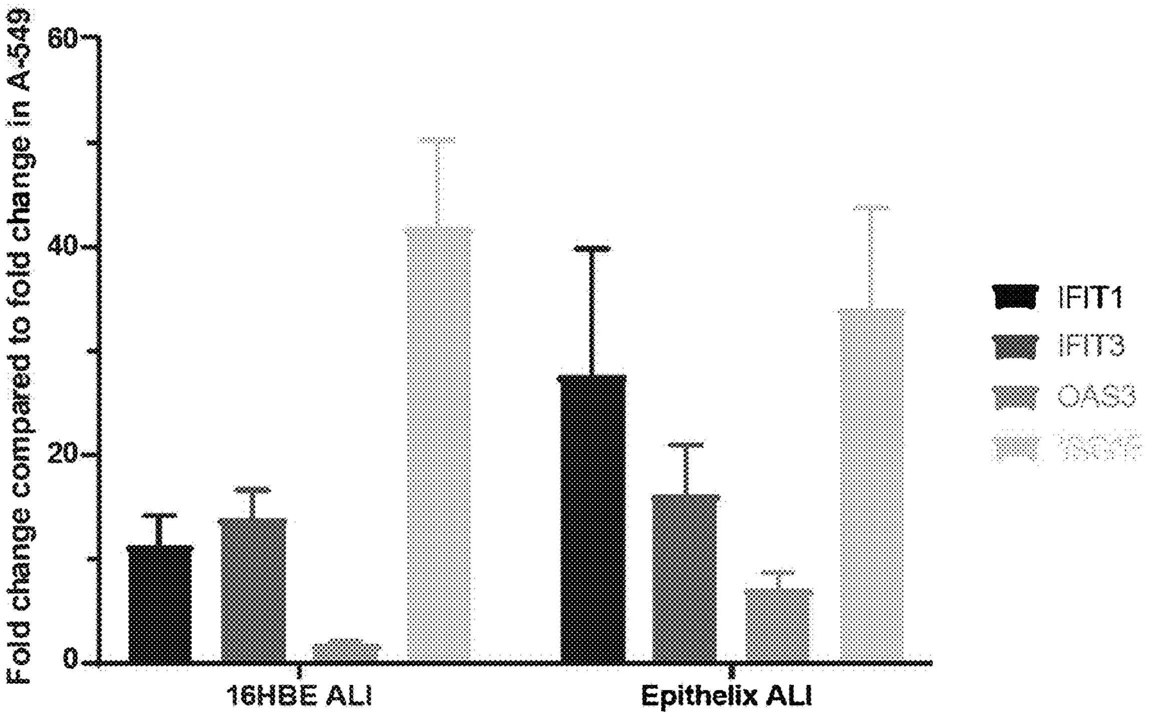
Figure 12A:
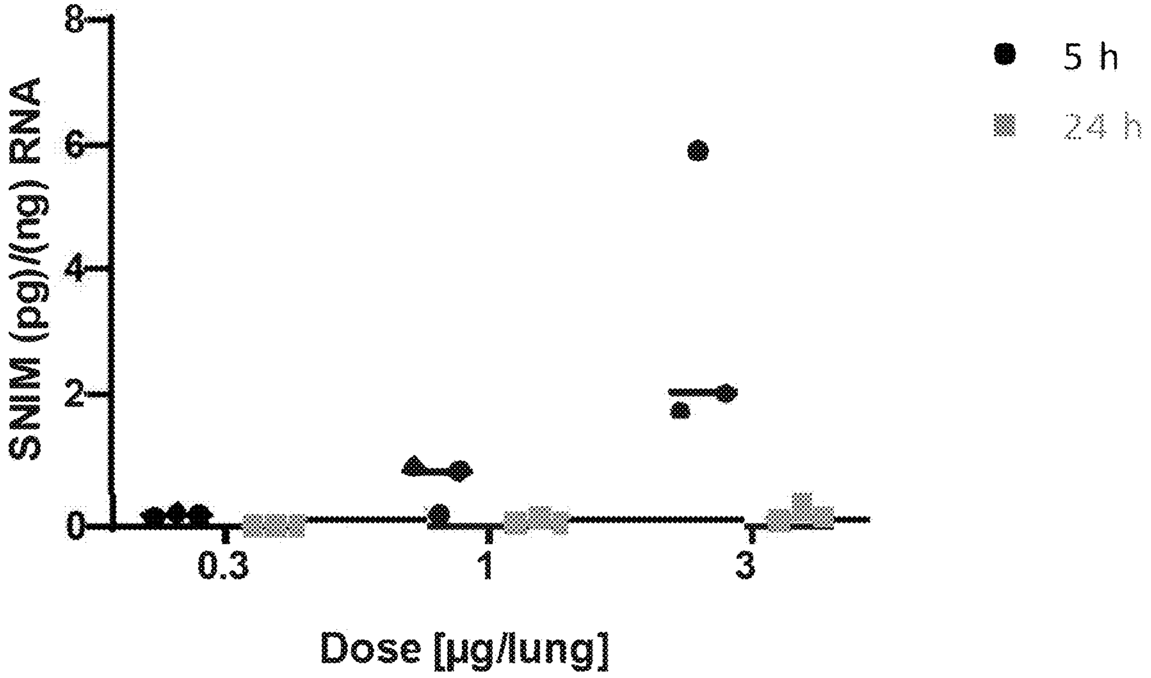
Figure 12B:
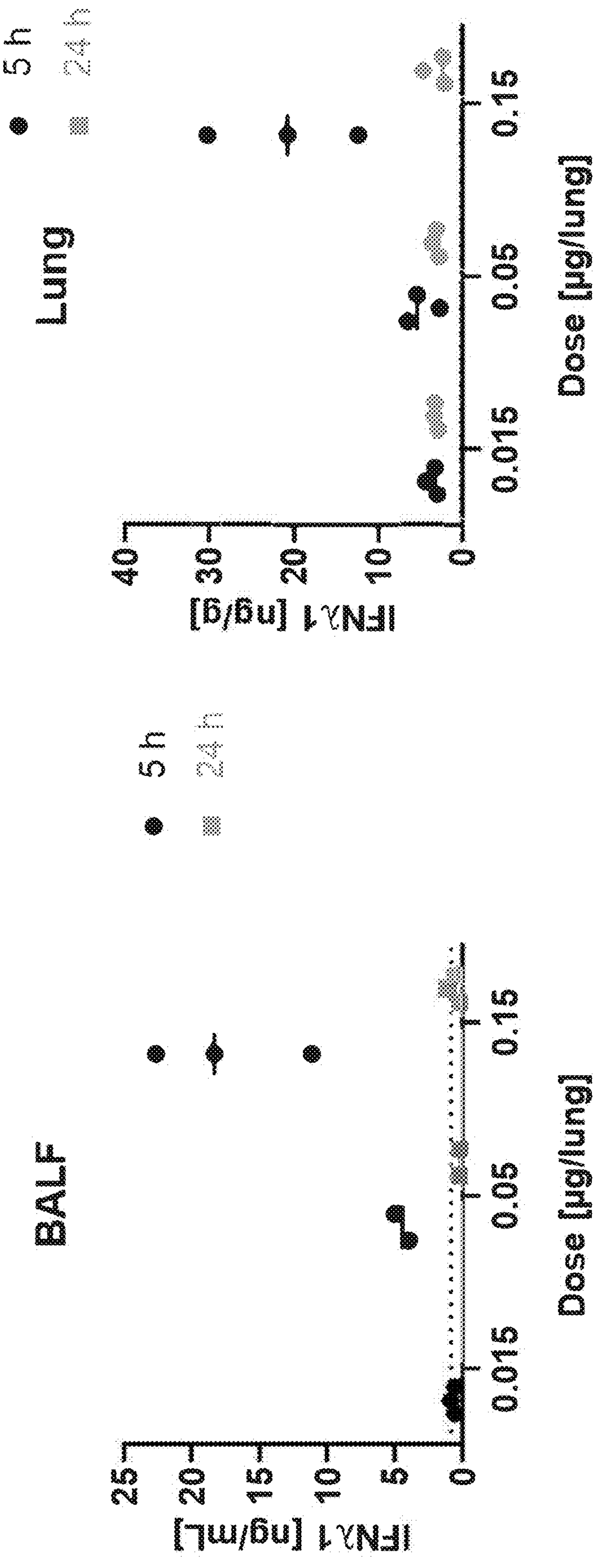
Figure 12C:
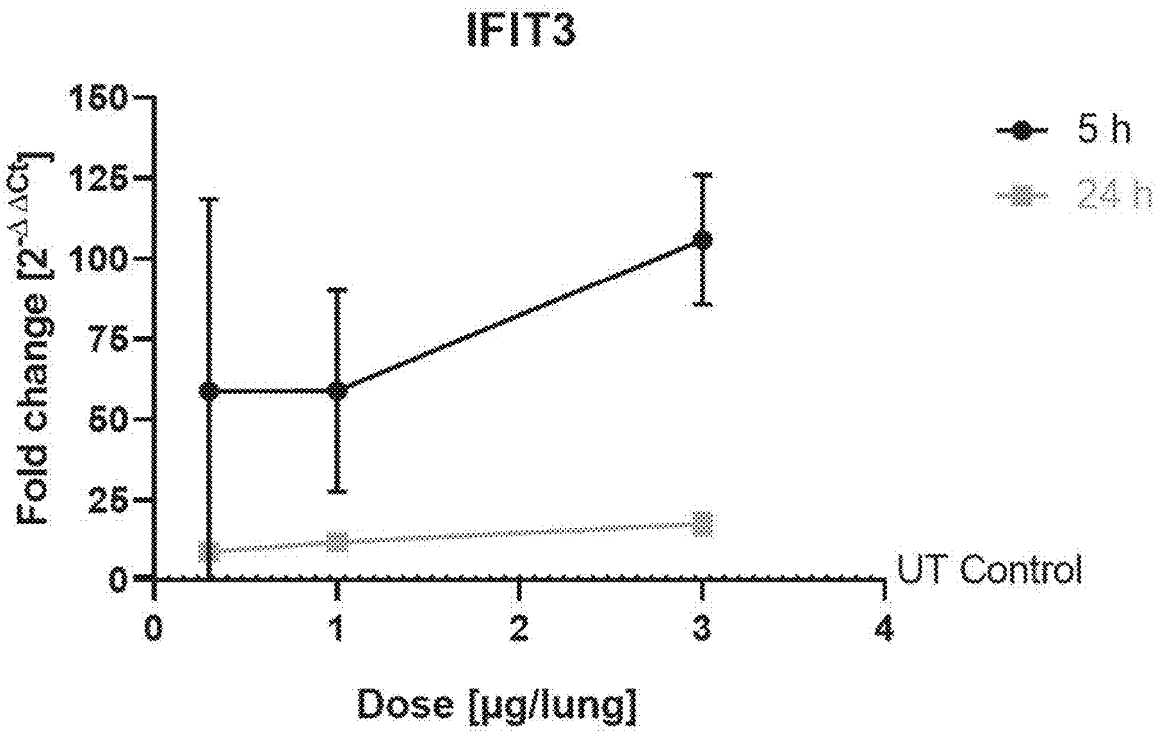
Figure 12C:
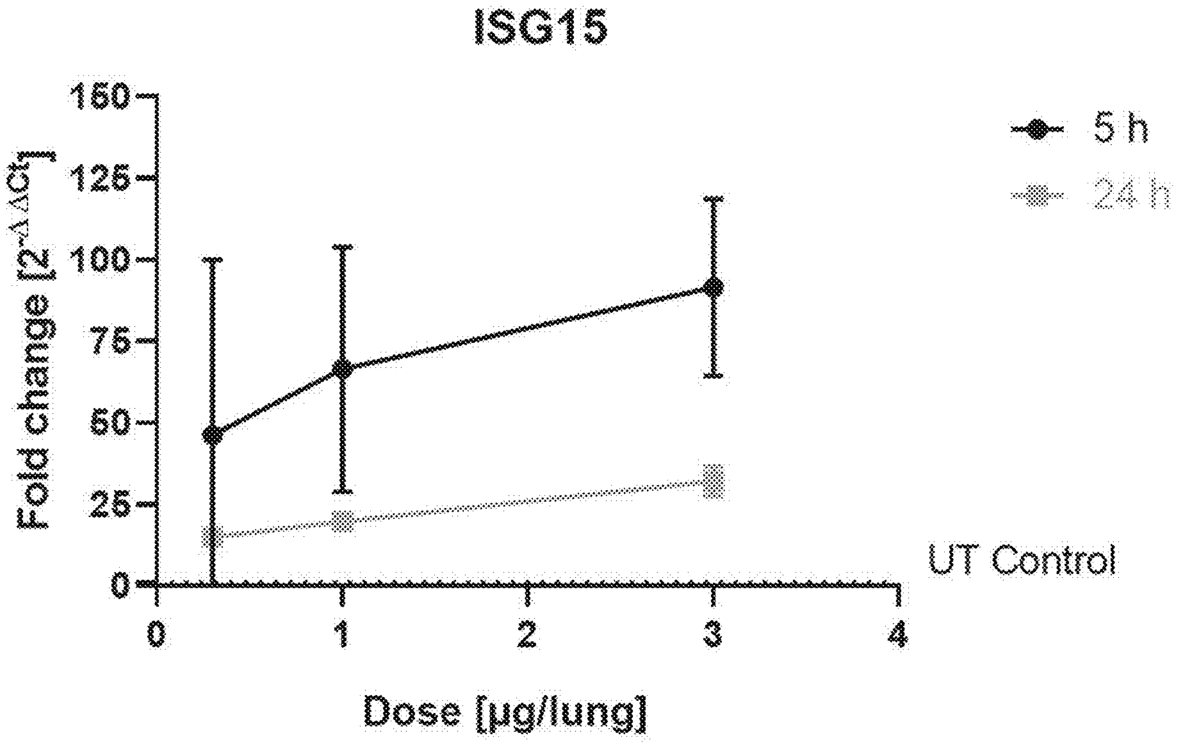
Figure 12C:
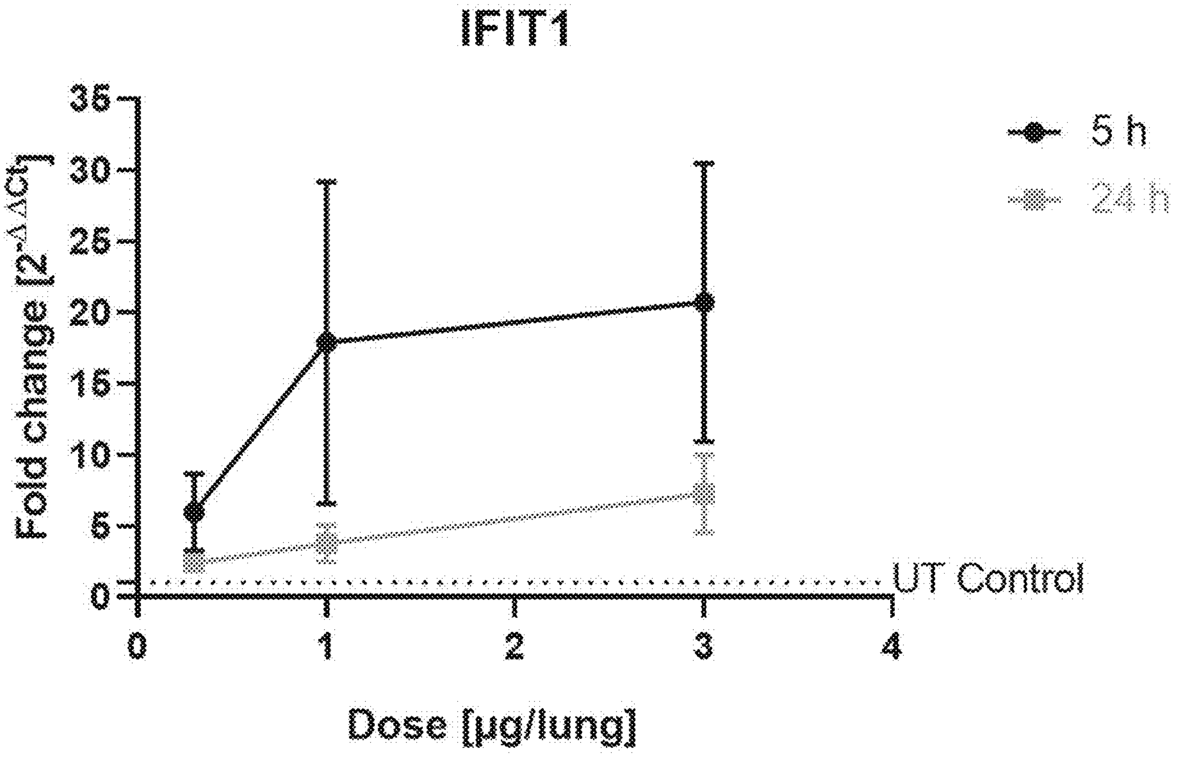
Figure 12C:
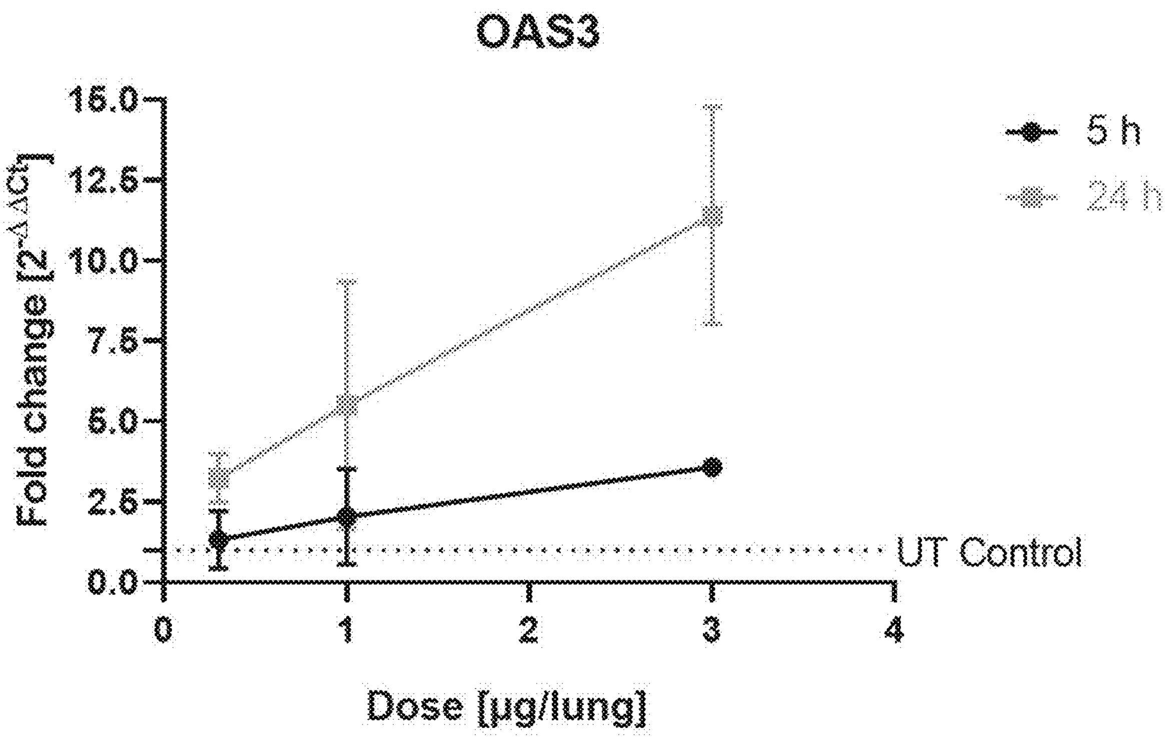

Transfection of mRNA coding for IFNλ1 leads to a time- and dose-dependent production of IFNλ1 in HEK293, A549, 16HBE14o- and FreeStyle 293-F cells as measured by IFNλ1 ELISA (FIG. 9).

Example 5: Time- and Dose-Dependent Induction of Downstream Targets in A549 and 16HBE14o-Cells in Submerse Culture after Transfection with IFNλ1 Encoding mRNA Transfection of mRNA coding for IFNλ1 leads to a time- and dose-dependent induction of IFIT1, IFIT3, OAS3 and ISG15 as assessed via qPCR (FIG. 10 *a* and *b*).

Example 6: Dose-Dependent Production of IFNλ1 and Induction of Downstream Targets In Airway Liquid Interface (ALI) Cultures Derived from A549, 16HBE14o- or Primary Human Lung Cells (Epithelix)

Transfection of mRNA coding for IFNλ1 formulated in LF92 leads to dose-dependent production of IFNλ1 (FIG. 11 *a*) and induction of IFIT1, IFIT3, OAS3 and ISG15 as assessed via qPCR 24 hours after treatment (FIG. 11 *b*). Endogenous levels of IFIT1, IFIT3, OAS3 and ISG15 are elevated in ALI cultures derived from 16HBE14o- or primary human lung cells compared with A459-derived ALI cultures (FIG. 11 *c*).

Example 7: Dose-Dependent Production of IFNλ1 and Induction of Downstream Targets in the Lungs of Mice Instilled with mRNA Coding for IFNλ1

Delivery of mRNA coding for IFNλ1 formulated in LF92 leads to dose- and time-dependent IFNλ1 mRNA lung deposition (FIG. 12 *a*), production of IFNλ1 in lung tissue and broncheoalveolar lavage fluid (BALF) (FIG. 12 *b*) and induction of IFIT1, IFIT3, OAS3 and ISG15 as assessed via qPCR 5 and 24 hours after treatment (FIG. 12 *c*).

Example 8: Comparison of hIFNλ1 mRNA Transfection with Recombinant Protein

Enhanced target gene activation following single apical transfection of primary bronchial epithelial airway liquid interface (ALI) cultures with hIFNλ1 encoding mRNA compared to apical treatment with recombinant protein. Due to basolateral receptor expression, inhaled (apical) administration of hIFNλ1 encoding mRNA and subsequently greater basal than apical secretion of type III IFN is expected to be more efficacious in humans than inhaled administration of recombinant protein.

Transfection with hIFNλ1 mRNA led to 30-40 μg total protein at apical compartment 24 h after transfection when transfection mixture was aspirated at 6 h post transfection (FIG. 13*a*). This corresponds to a concentration of 90 ng/mL in the airway surface lining fluid (ASL), assuming that the volume of the ASL in ALI cultures is 0.33 μL (0.33 $cm^2$ surface area of the insert×0.001 cm height of the cilia layer). For this reason, target gene activation post transfection was compared to treatment with 100 ng/mL of recombinant protein.

Figure 13:
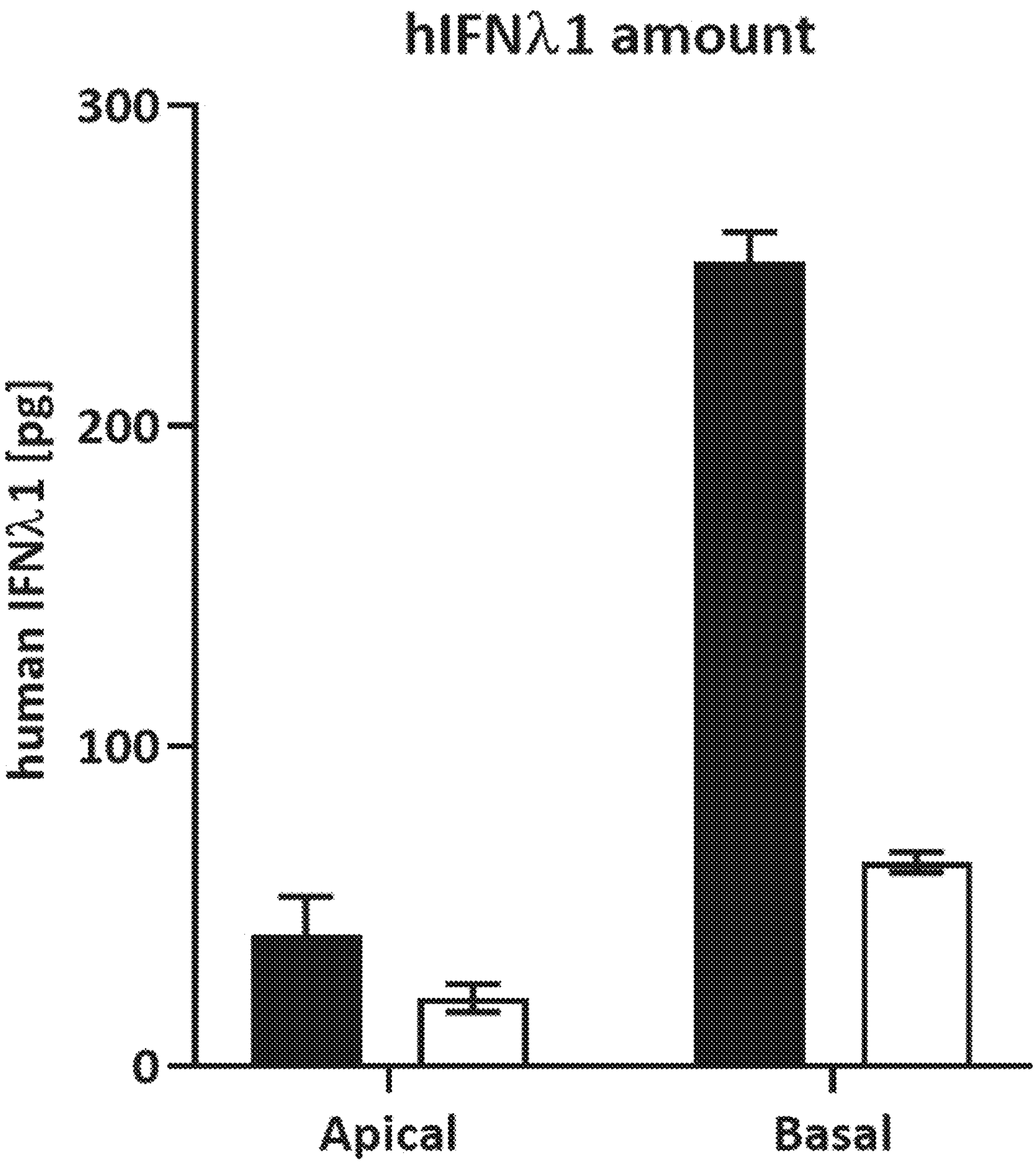
FIG. 13 shows comparison of hIFNλ1 mRNA transfection with recombinant protein (see also Example 8).
Figure 13:
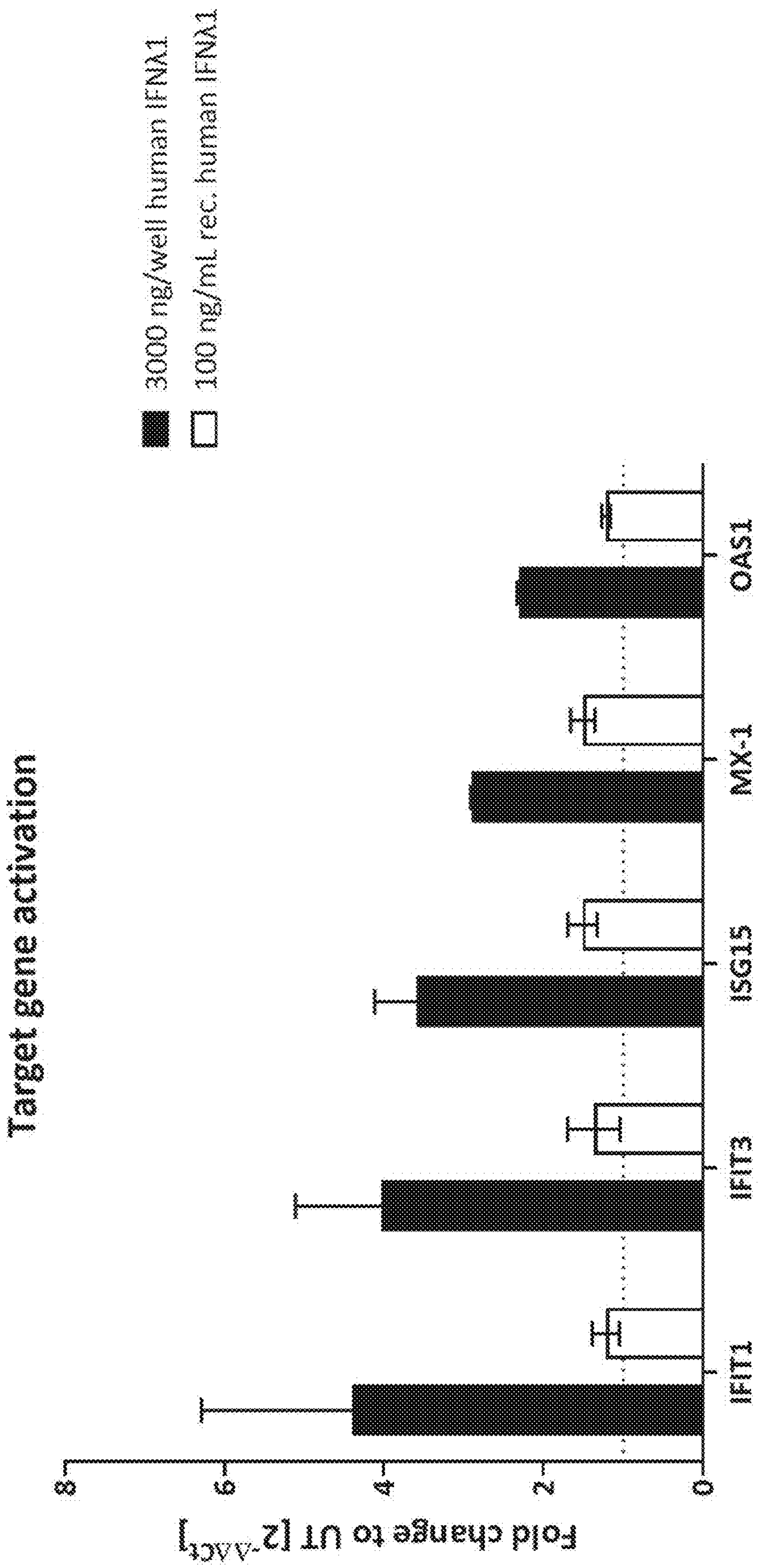

Following apical mRNA transfection, target gene expression was 4-fold higher compared to Stop mRNA control (FIG. 13*b*). In contrast, following apical administration of recombinant hIFNλ1 protein at a concentration of 100 ng/mL, target gene induction was lower compared to mRNA transfection and did not exceed a 2-fold induction relative to Stop mRNA control (FIG. 13*b*). This effect might be due to longer exposure to hIFNλ following mRNA transfection (mRNA translation continues after exchange of medium at 6 hours) and hence potential accumulation and therefore higher protein level on apical and basal compartments compared to treatment with recombinant protein. These observations highlight the potential for added PK/PD benefit of mRNA treatment over treatment with recombinant protein (FIG. 13).

Figure 14:
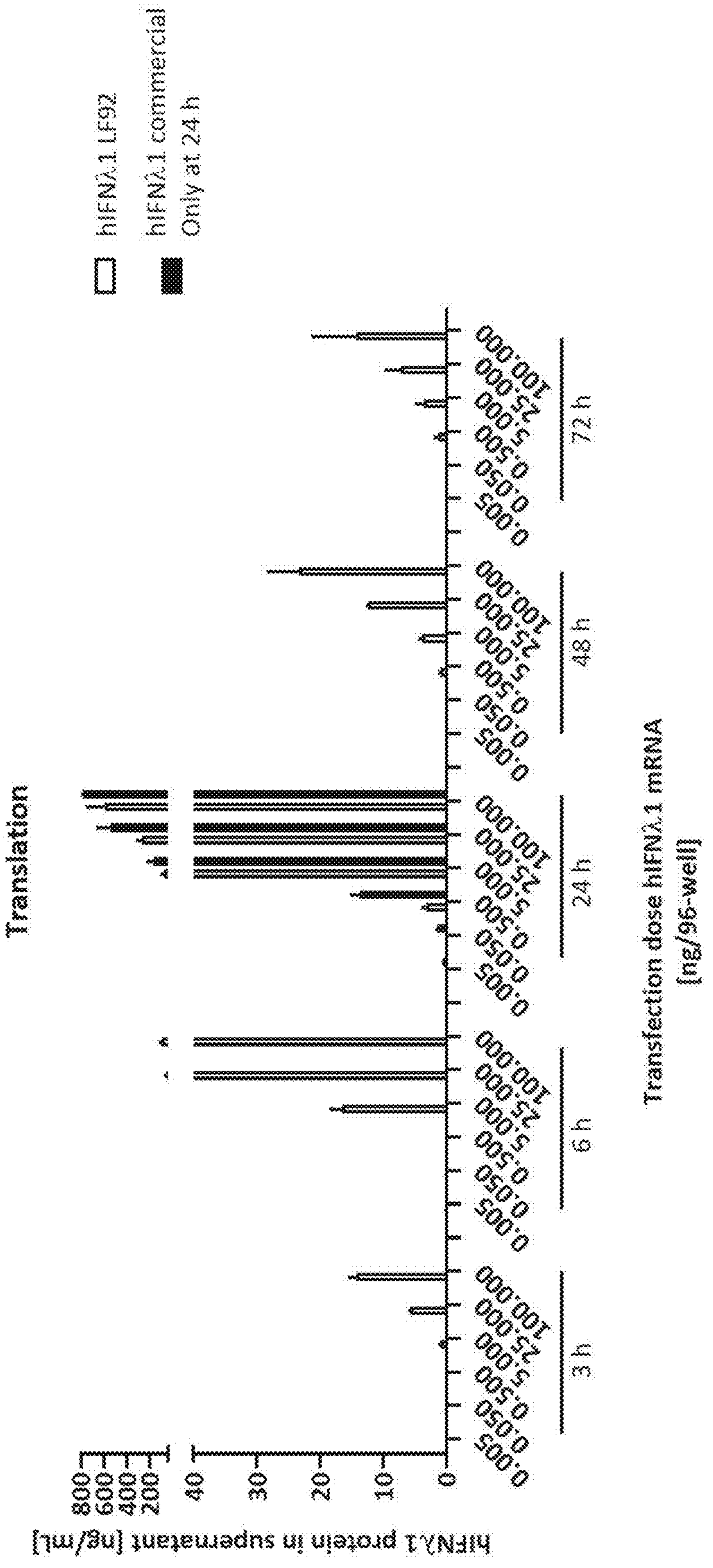
FIG. 14 shows hIFNλ ELISA from supernatants of transfected A-549 cells: LF92 vs. commercially available transfection reagent (see also Example 9).

Example 9: HIFNλ ELISA from Supernatants of Transfected A-549 Cells: LF92 vs. Commercially Available Transfection Reagent At 6 and 24 h post transfection, medium was exchanged at each plate that was not harvested at these time points. Hence, 24 h time point reflects translation between 6 and 24 h, and 48 and 72 h time points reflect translation after 24 h. Translation following mRNA transfection occurred in a dose- and time dependent manner and to a similar extent with LF92 formulated mRNA as when using a commercial transfection reagent (FIG. 14).

Example 10: Target Gene Induction by LF92 Formulated mRNA

Figure 15:
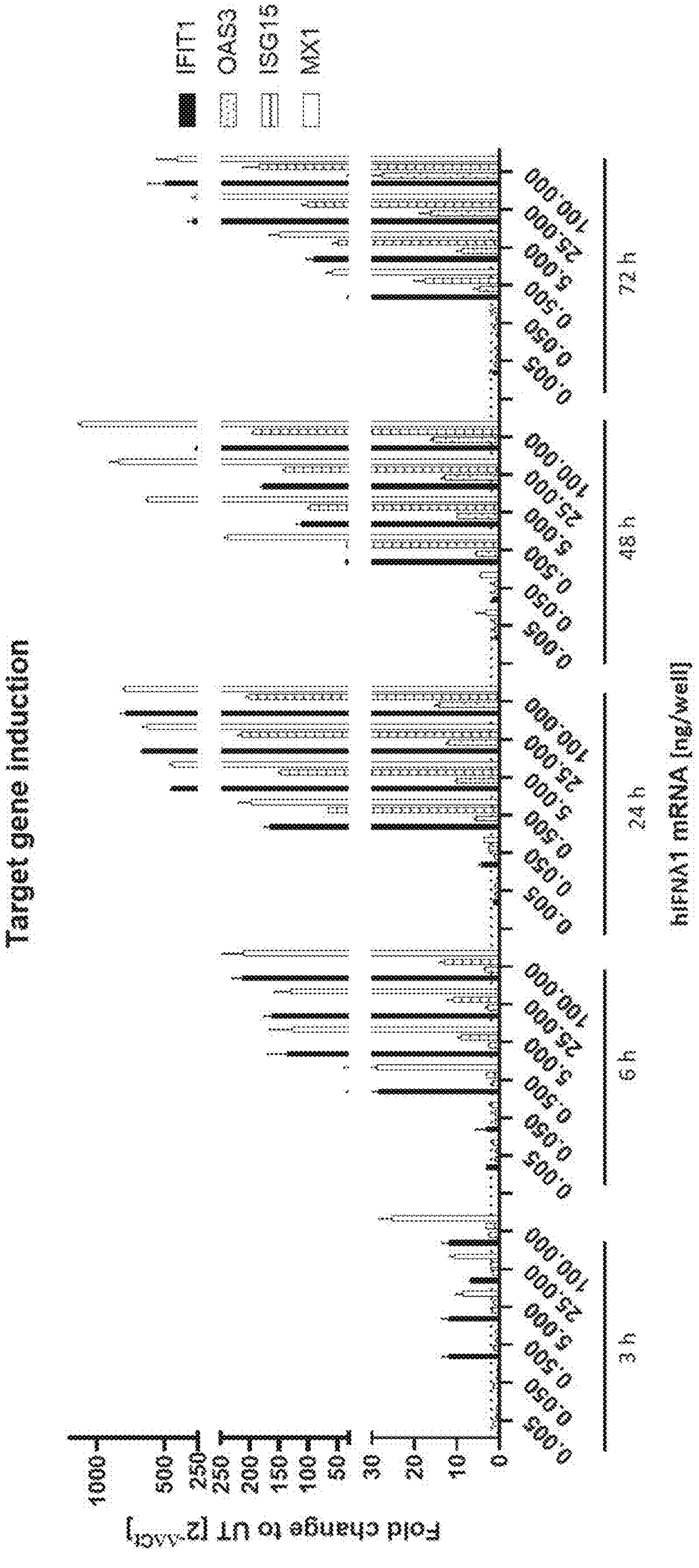
FIG. 15 shows Target gene induction by LF92 formulated mRNA (see also Example 10).

At 6 and 24 h post transfection, medium was exchanged at each plate that was not harvested at these time points. Hence, 24 h time point reflects translation between 6 and 24 h, and 48 and 72 h time points reflect translation after 24 h. Dose-dependent and sustained hIFNλ1 target gene activation following single transfection of A549 lung cells with LF92 formulated mRNA encoding hIFNλ1 was observed (FIG. 15).

Example 11: In Vitro Tolerability of LF92 Formulated mRNA Encodinq hIFNλ1

Figure 16:
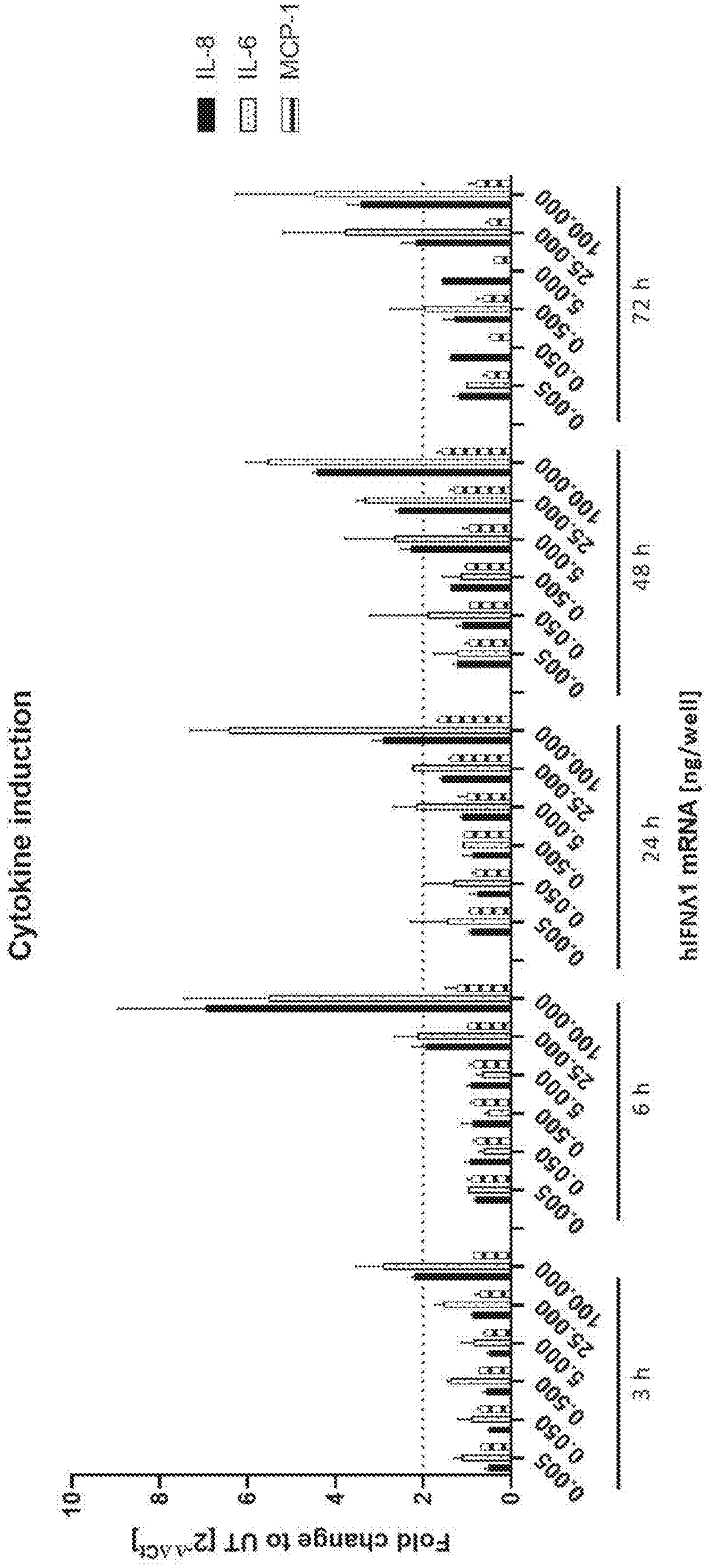
FIG. 16 shows in vitro tolerability of LF92 formulated mRNA encoding hIFNλ1 (see also Example 11).
Figure 17A:
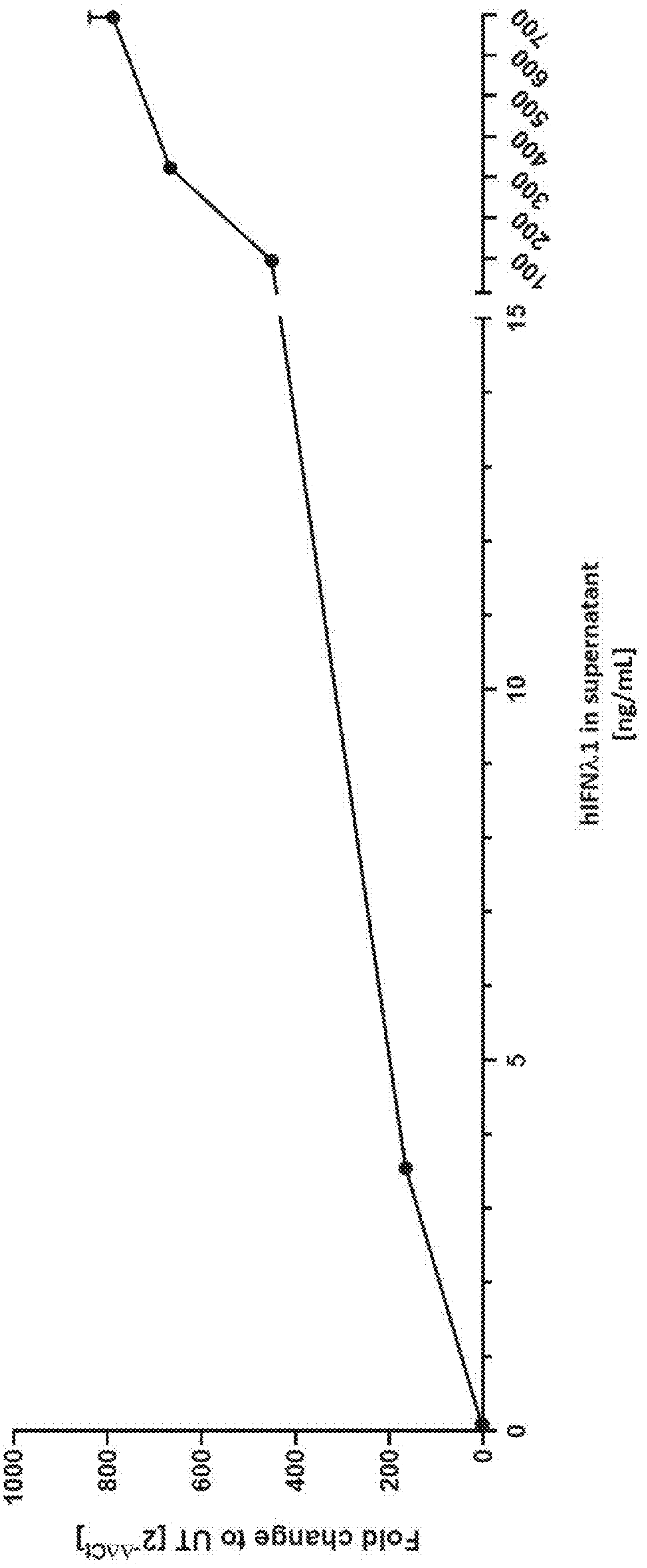
FIG. 17 shows correlation of mRNA translation and target gene induction of (a) IFIT1 (b) OAS3 (c) ISG15 and (d) MX1 (see also Example 12).
Figure 17B:
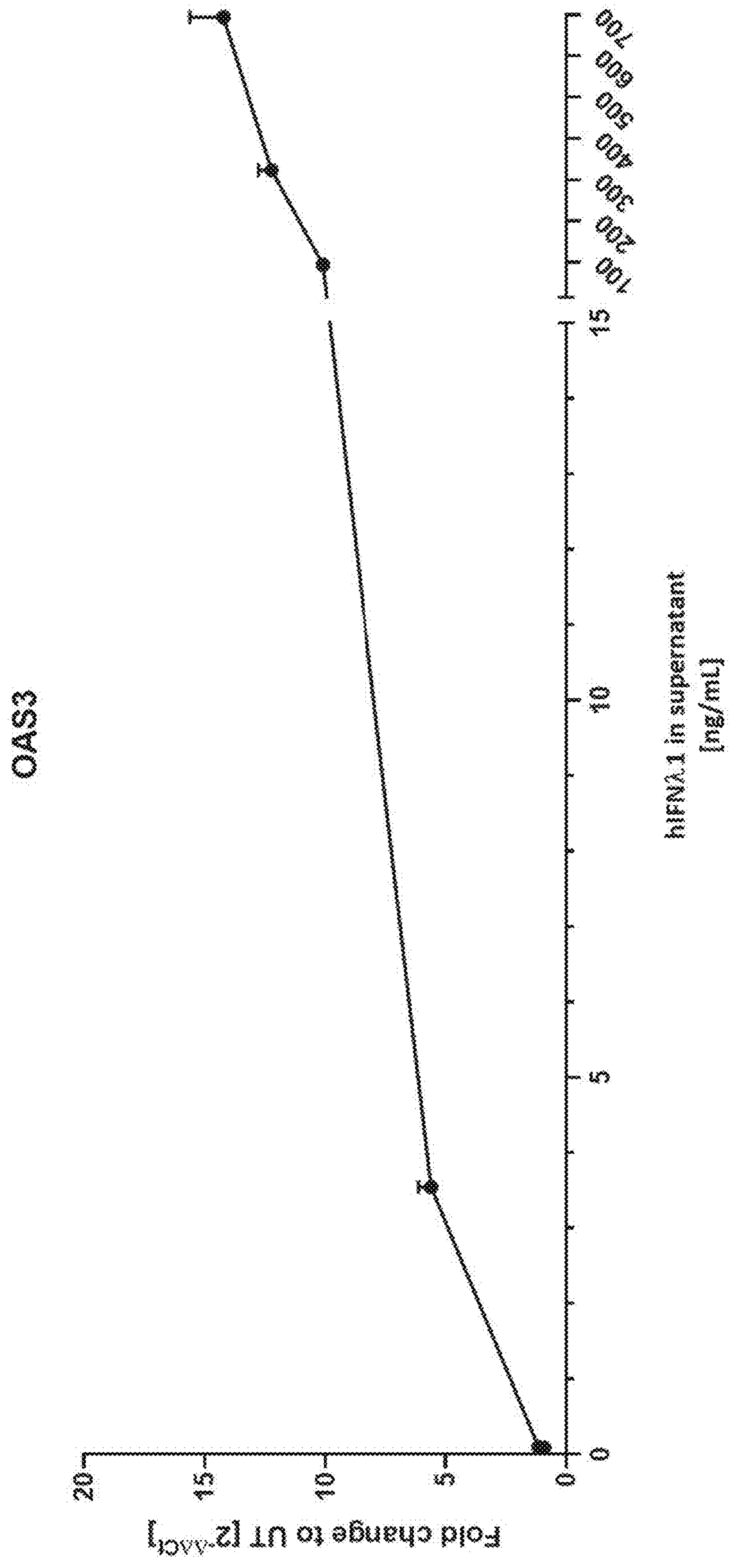
Figure 17C:
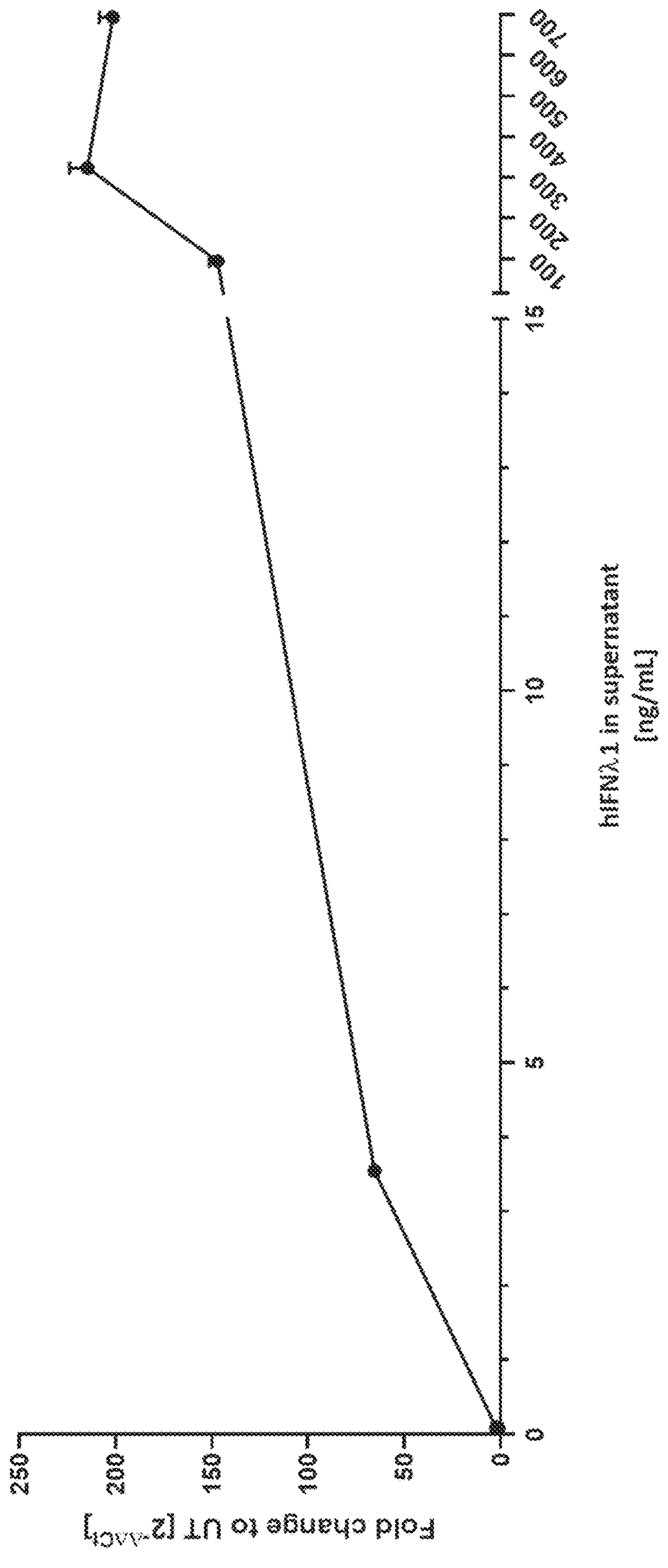
Figure 17D:
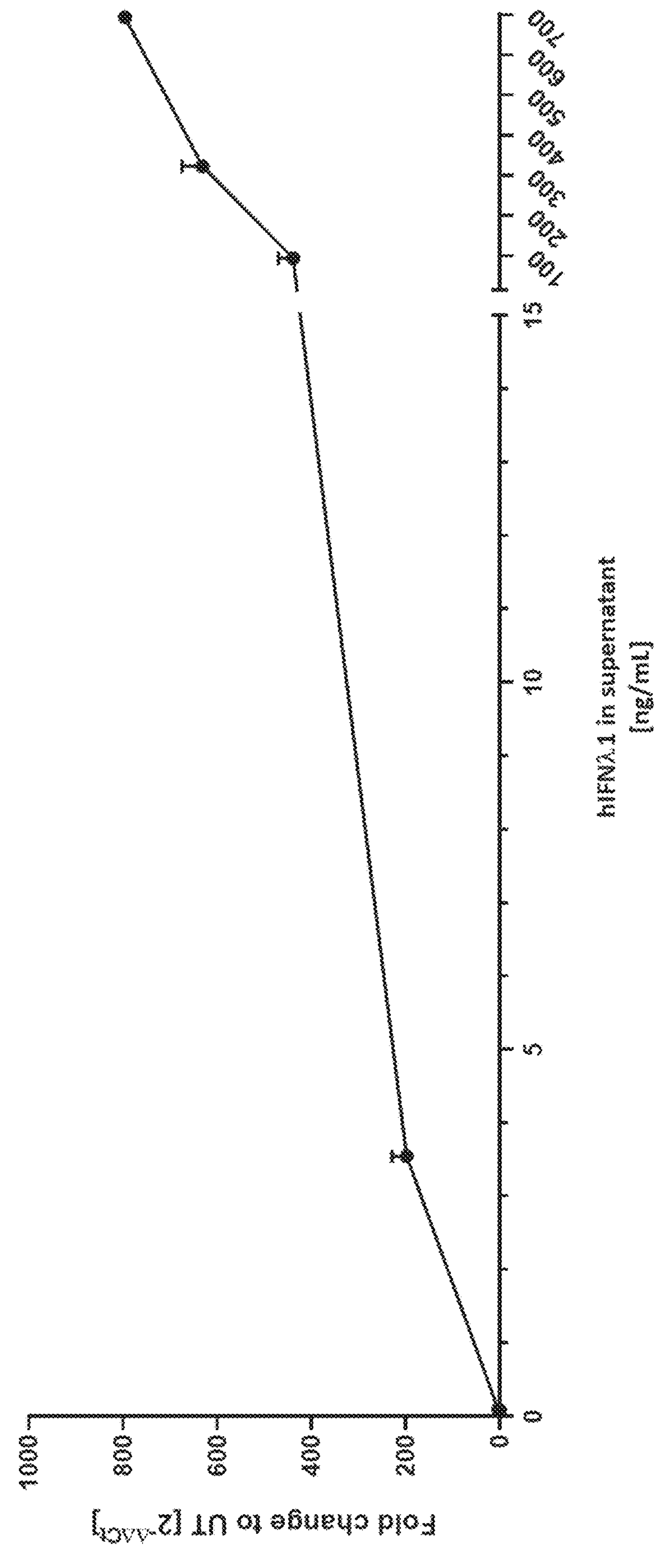

At 6 and 24 h post transfection, medium was exchanged at each plate that was not harvested at these time points. Hence, 24 h time point reflects translation between 6 and 24 h, and 48 and 72 h time points reflect translation after 24 h. Induction of cytokine mRNA expression following single transfection of A549 lung cells with LF92 formulated mRNA encoding hIFNλ1 was observed only at high doses associated with plateau of target gene induction (FIG. 16).

Example 12: Correlation of mRNA Translation and Target Gene Induction

At 6 and 24 h post transfection, medium was exchanged at each plate that was not harvested at these time points. Hence, 24 h time point reflects translation between 6 and 24 h, and 48 and 72 h time points reflect translation after 24 h. Amount of hIFNλ1 measured in supernatant correlates with extent of target gene induction (FIG. 17).

Example 13: Virus Inhibition In Vitro Assessed by gPCR

Figure 18A:
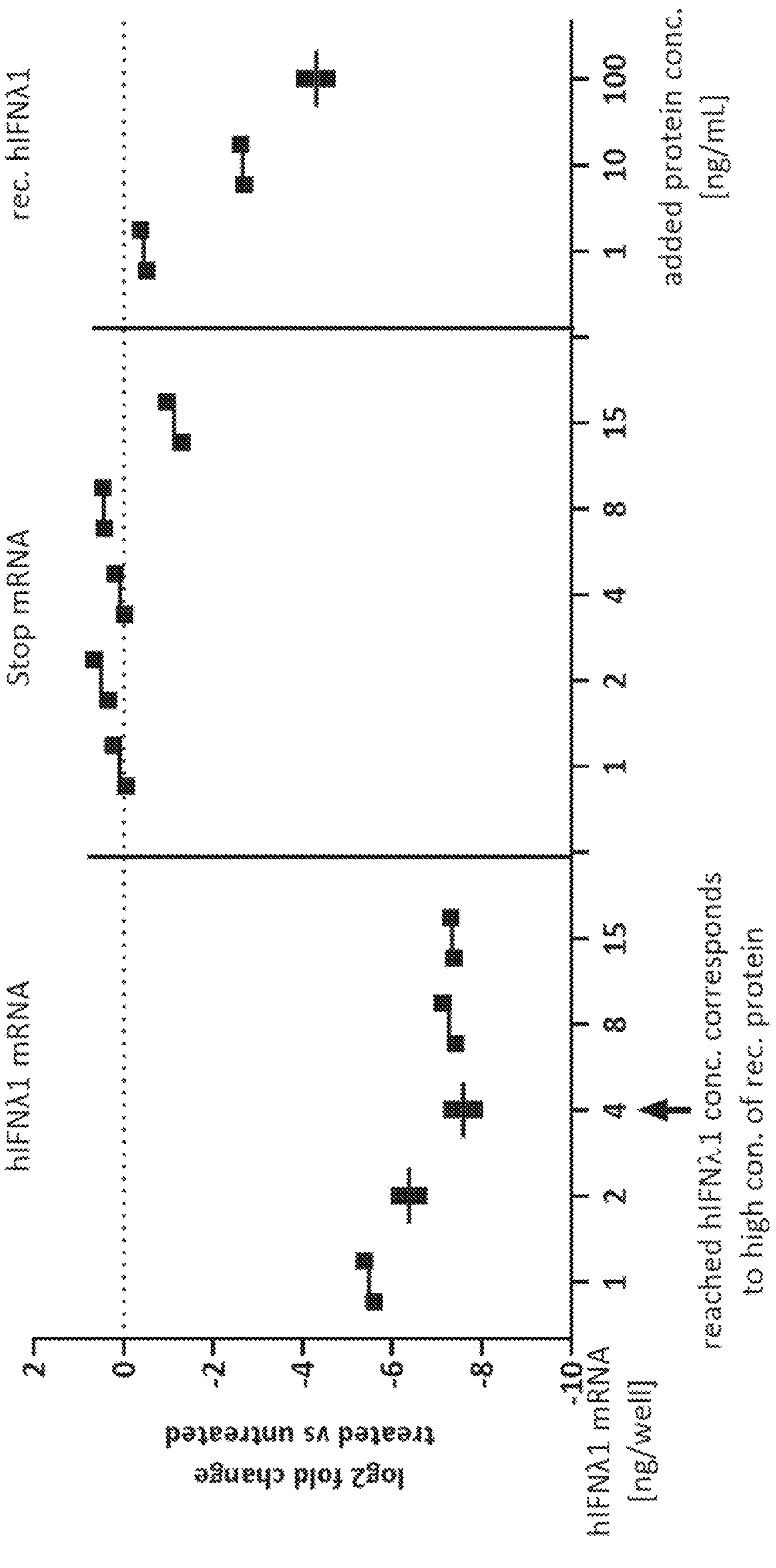
FIG. 18 shows (a) SARS-CoV-2 and (b) IAV inhibition in vitro assessed by qPCR (see also Example 13).
Figure 18B:
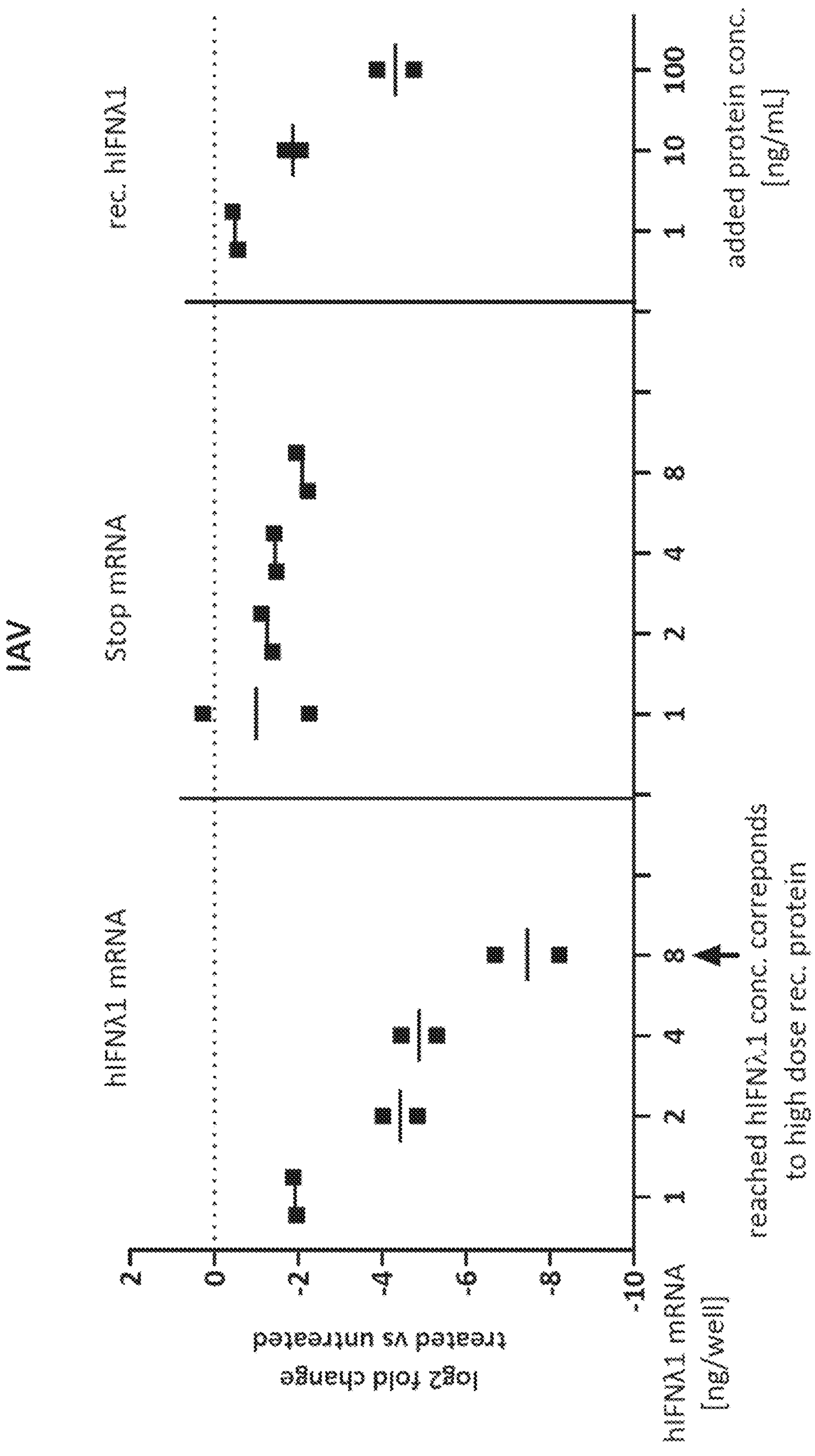

Prophylactic treatment with hIFNλ1 mRNA reduced SARS-CoV-2 and IAV virus load while Stop mRNA did not (FIG. 18). Dose dependent reduction of virus load by recombinant hIFNλ1 was observed, but was lower with recombinant protein compared to mRNA treatment (FIG. 18). Treatment was done 24 h prior infection. Samples were taken 48 h post infection.

Example 14: Detection of hIFNλ1 mRNA in Lung Homogenate

Figure 19:
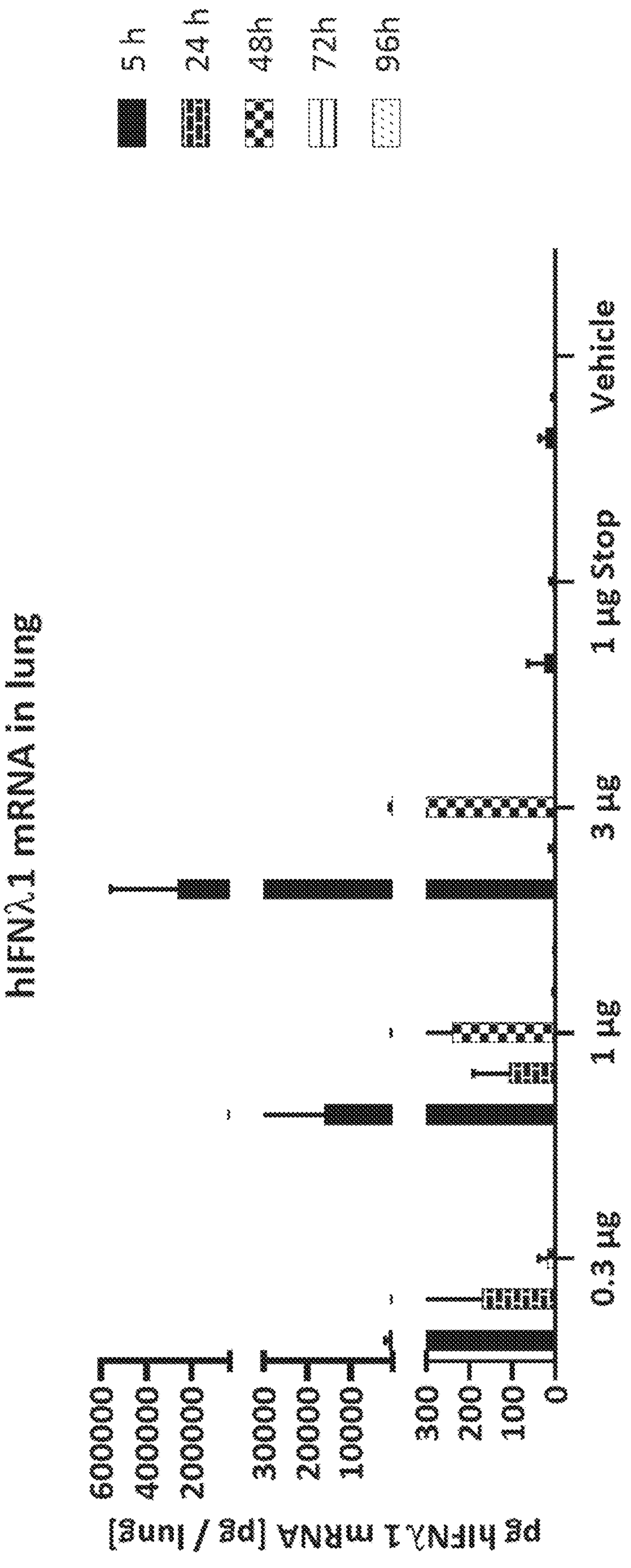
FIG. 19 shows detection of hIFNλ1 mRNA in lung homogenate (see also Example 14).

Dose-dependent deposition of mRNA encoding human IFNλ1 was observed at 5 h following single nasal administration in mice (FIG. 19). Three animals per group were assessed.

Example 15: Detection of hIFNλ1 Protein in Lung Homogenate

Figure 20:
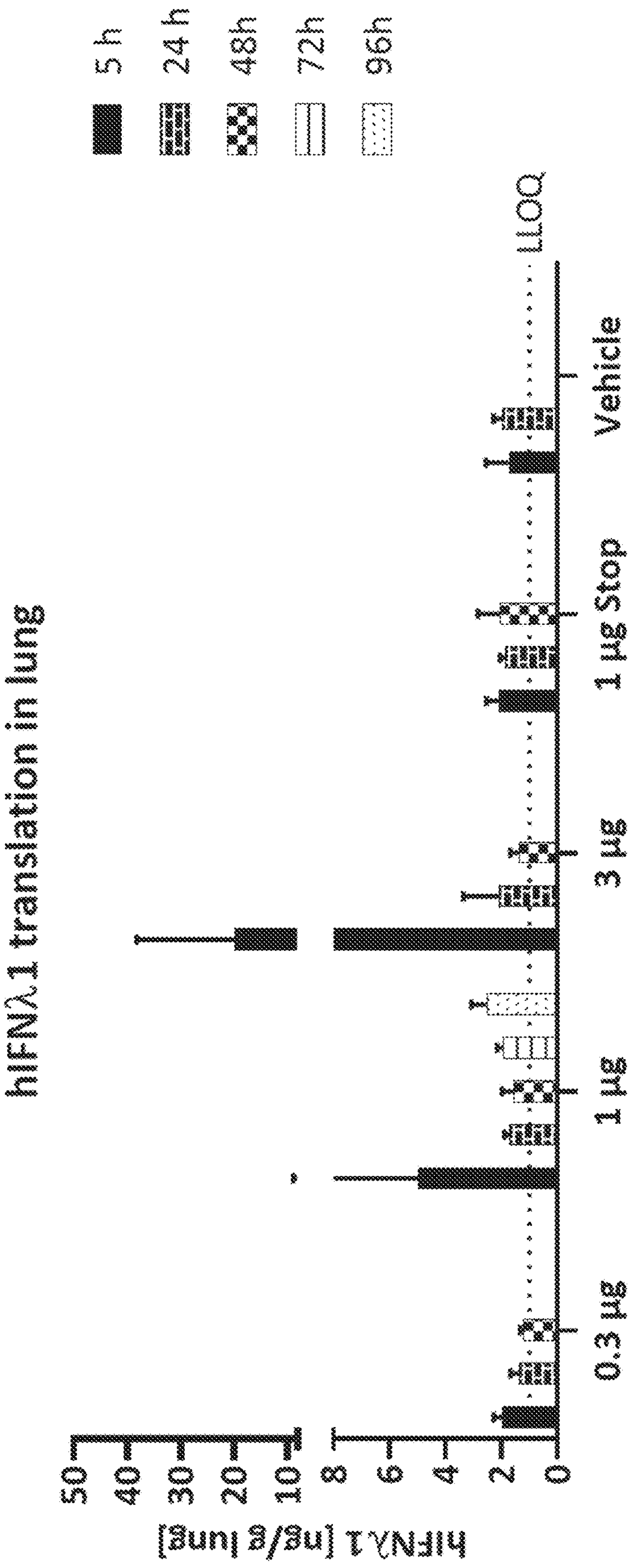
FIG. 20 shows detection of hIFNλ1 protein in lung homogenate (see also Example 15).
Figure 21A:
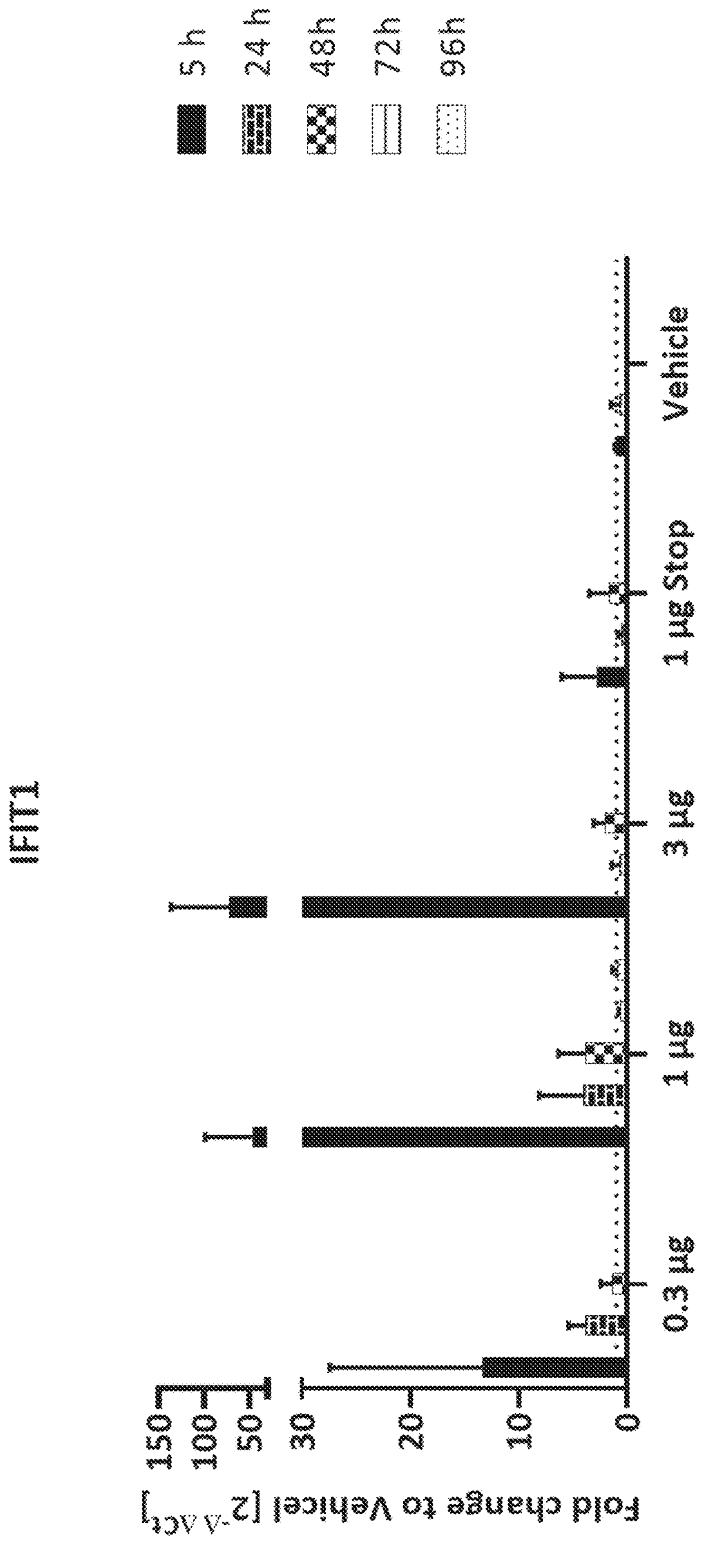
FIG. 21 shows target gene activation of (a) IFIT1 (b) IFIT3 (c) ISG15 and (d) OAS3 in lung tissue after hIFNλ1 mRNA application (see also Example 16).
Figure 21B:
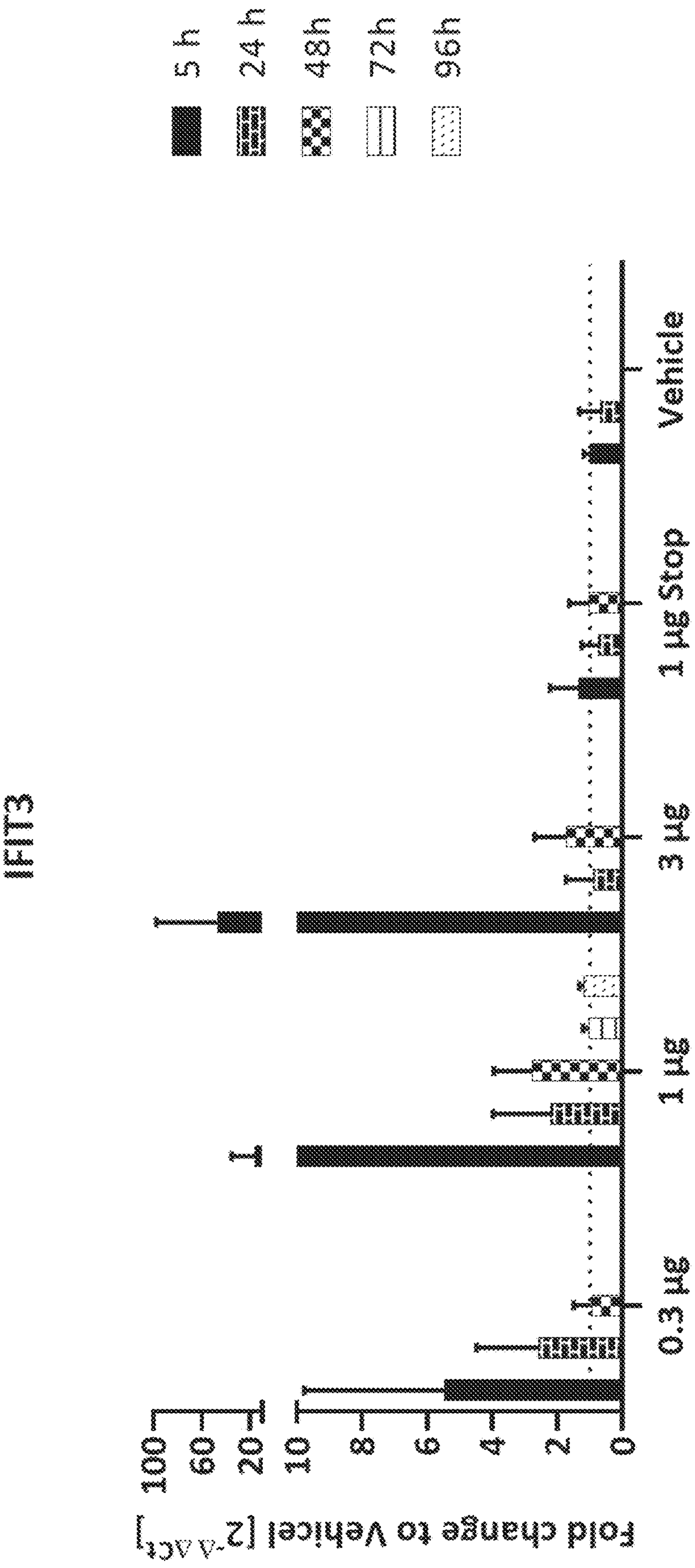
Figure 21C:
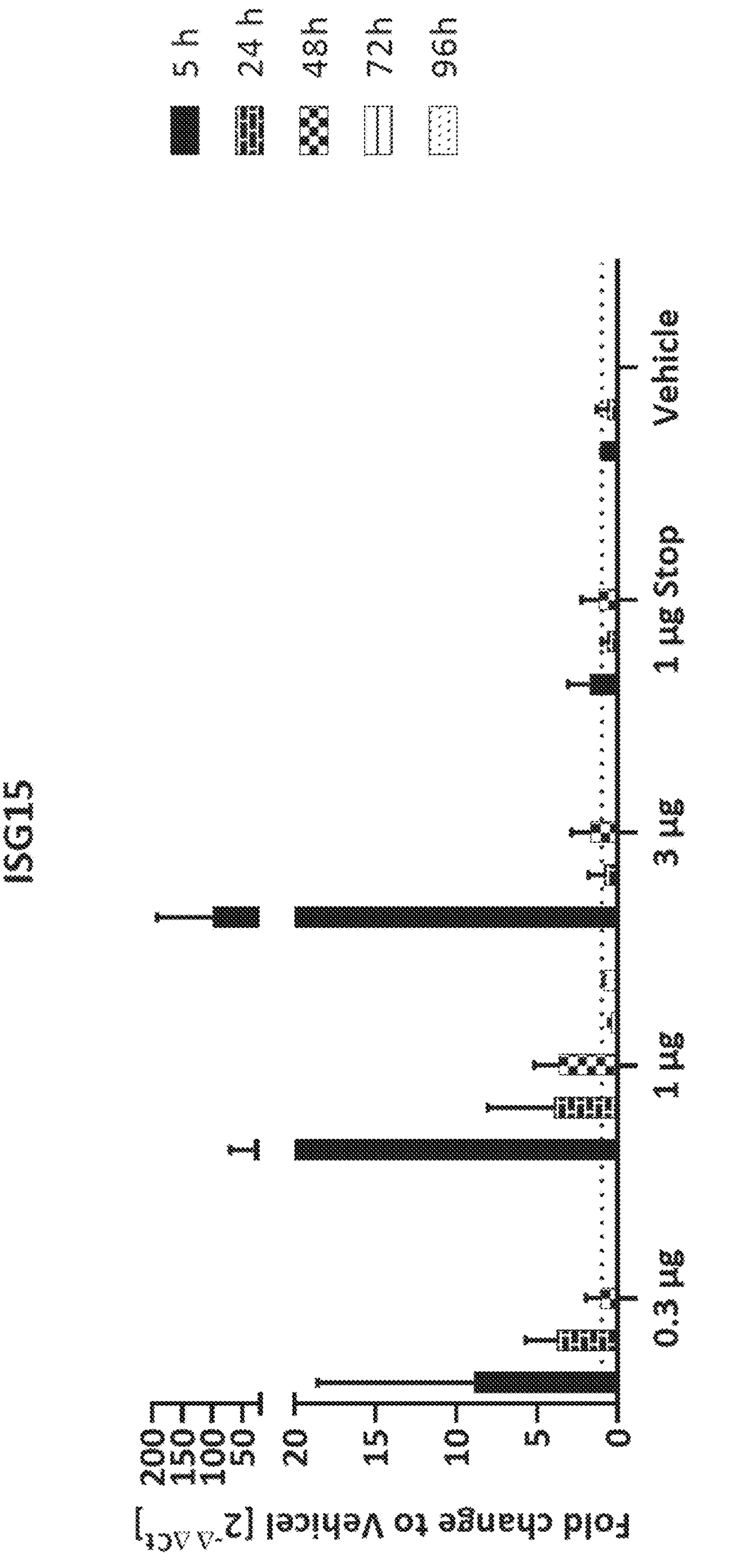
Figure 21D:
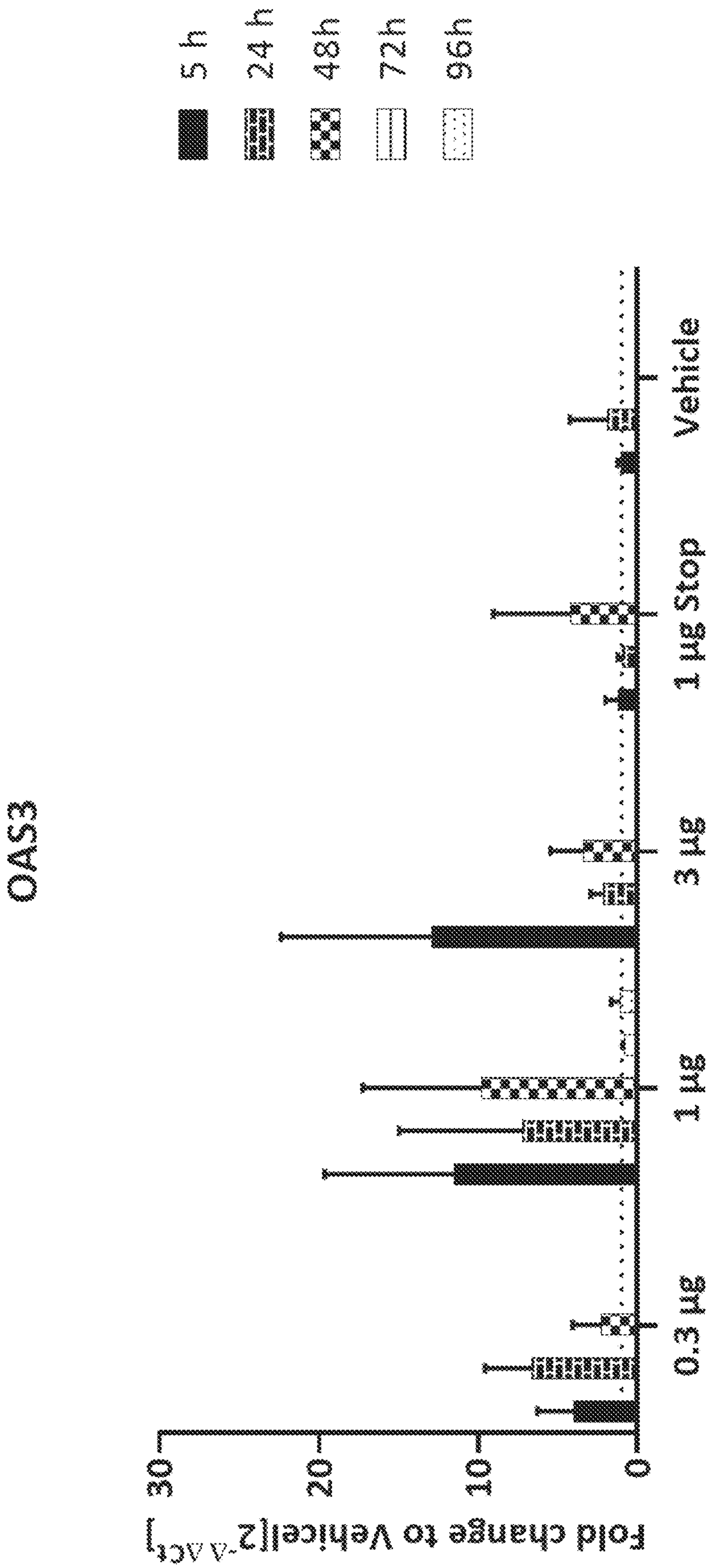

Human IFNλ1 quantification in lung homogenate revealed dose and time dependent protein translation upon single intranasal treatment with mRNA encoding human IFNλ1 protein (FIG. 20). Three animals per group were assessed.

Example 16: Target Gene Activation in Lunq Tissue after hIFNλ1 mRNA Application hIFNλ1 mRNA application was well tolerated and potently induced pulmonary target gene expression at low doses following single nasal administration in mice (FIG. 21).

The analyzed target genes OAS3, ISG15, IFIT1 and IFIT3 displayed a dose dependent activation for all dose levels at the 5 hours' time point (FIG. 21). Only OAS3 showed a dose dependent activation up to 24 h after application (FIG. 21*d*). Three animals per group were assessed.

Figure 22:
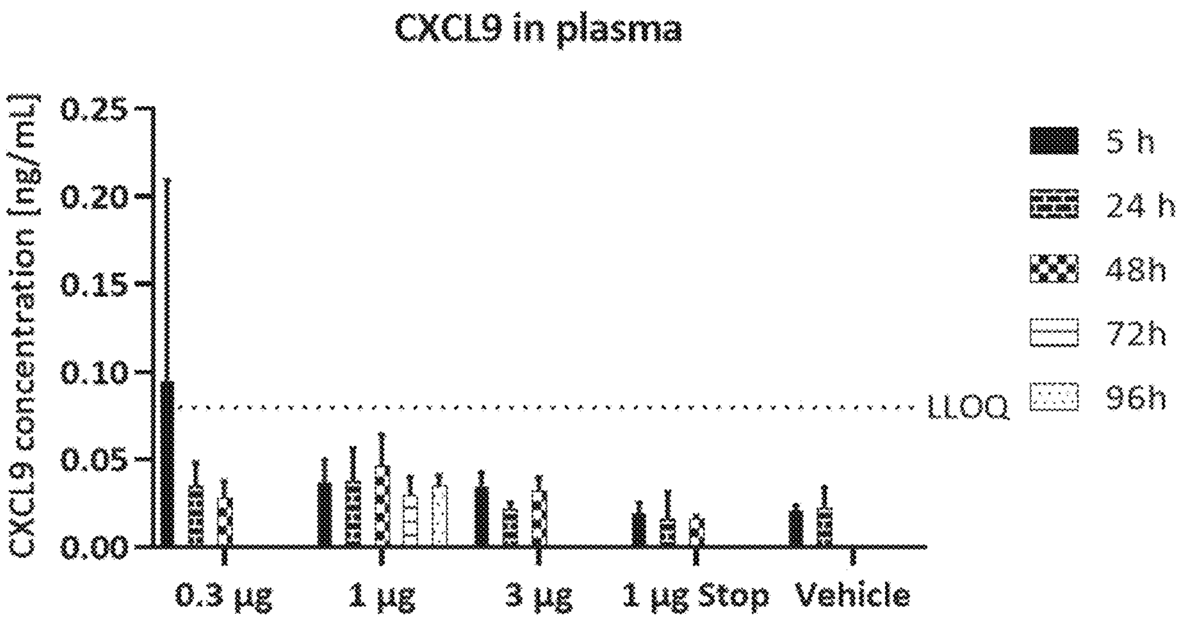
FIG. 22 shows detection of chemokines in plasma after single nasal application of hIFNλ1 mRNA (see also Example 17).
Figure 22:
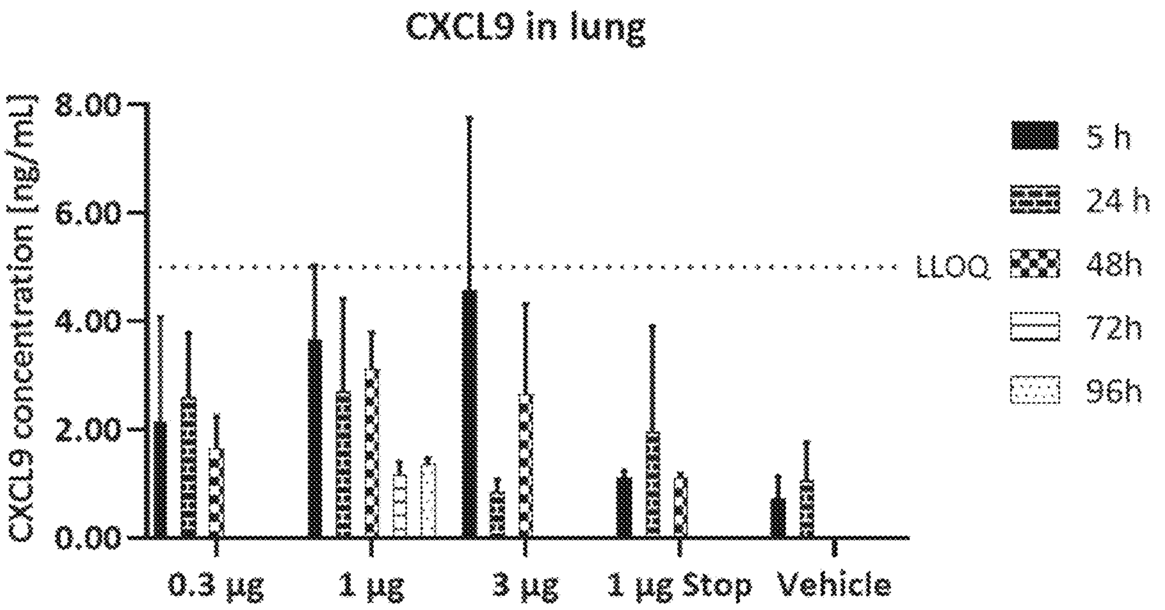
Figure 22:
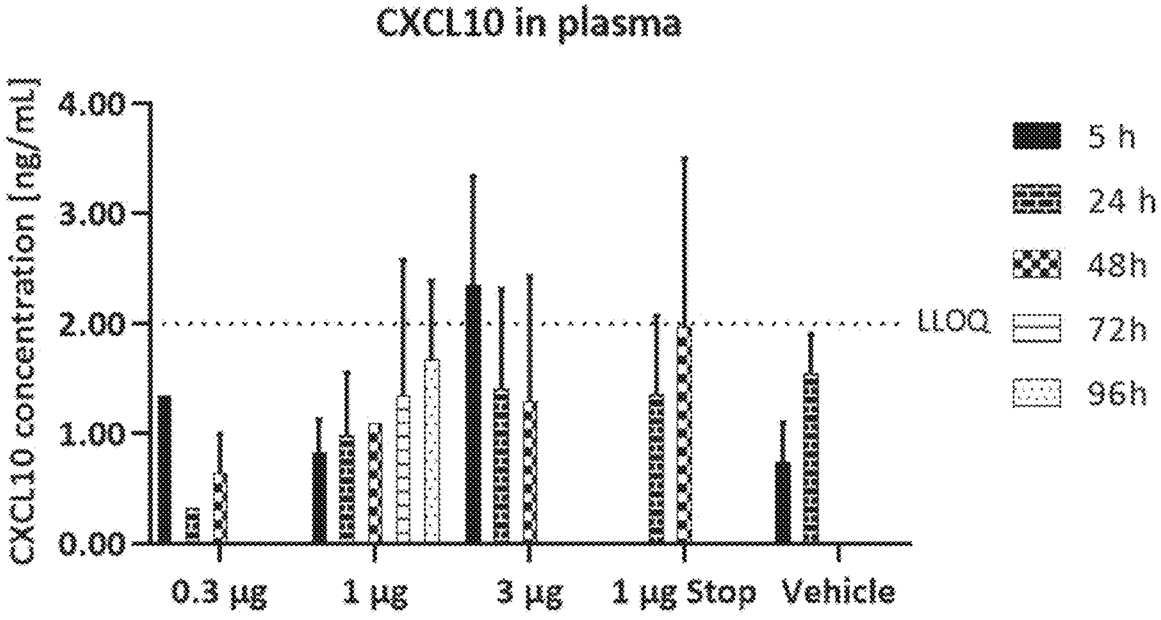
Figure 22:
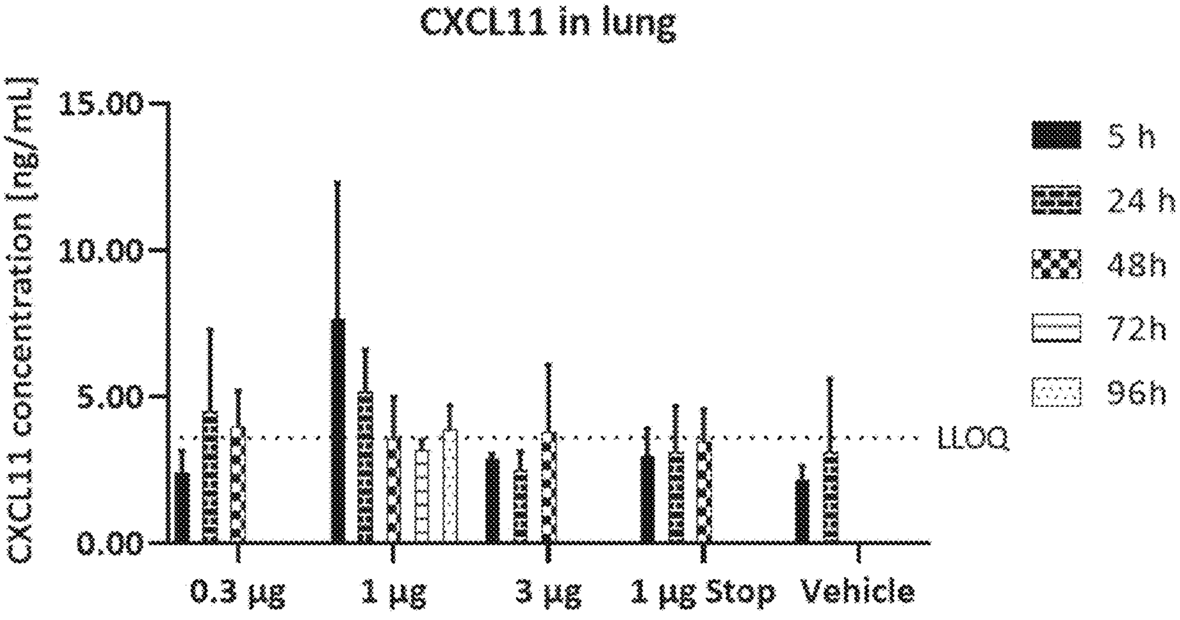
Figure 23A:
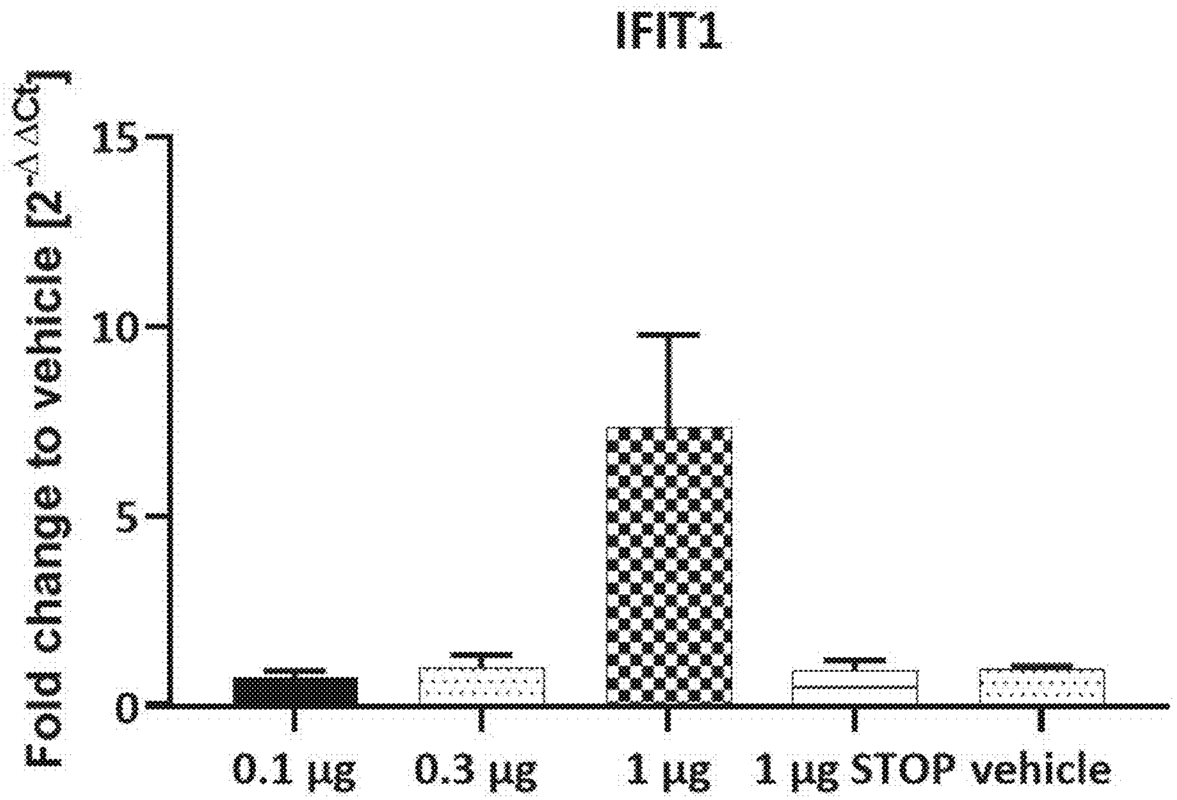
FIG. 23 shows target gene activation of (a) IFIT1 (b) IFIT3 (c) ISG15 and (d) OAS3 in lung tissue upon treatment with hIFNλ1 mRNA (see also Example 18).
Figure 23B:
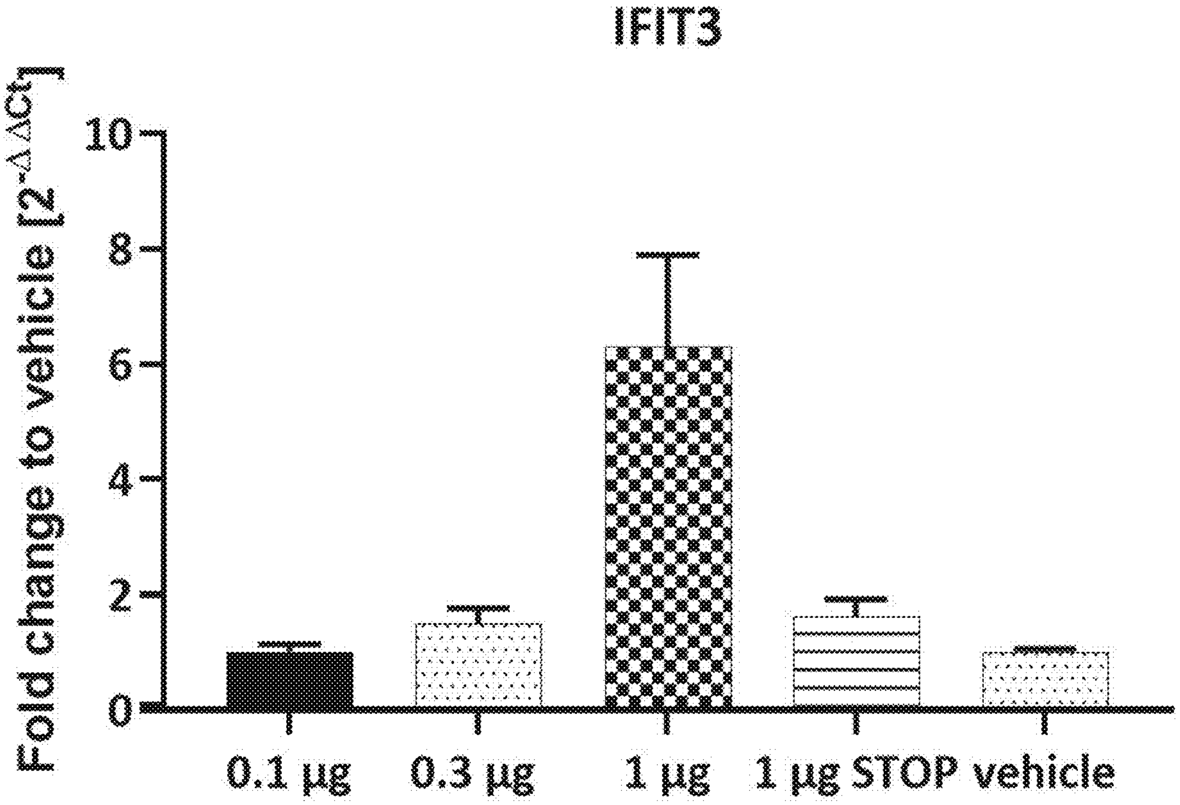
Figure 23C:
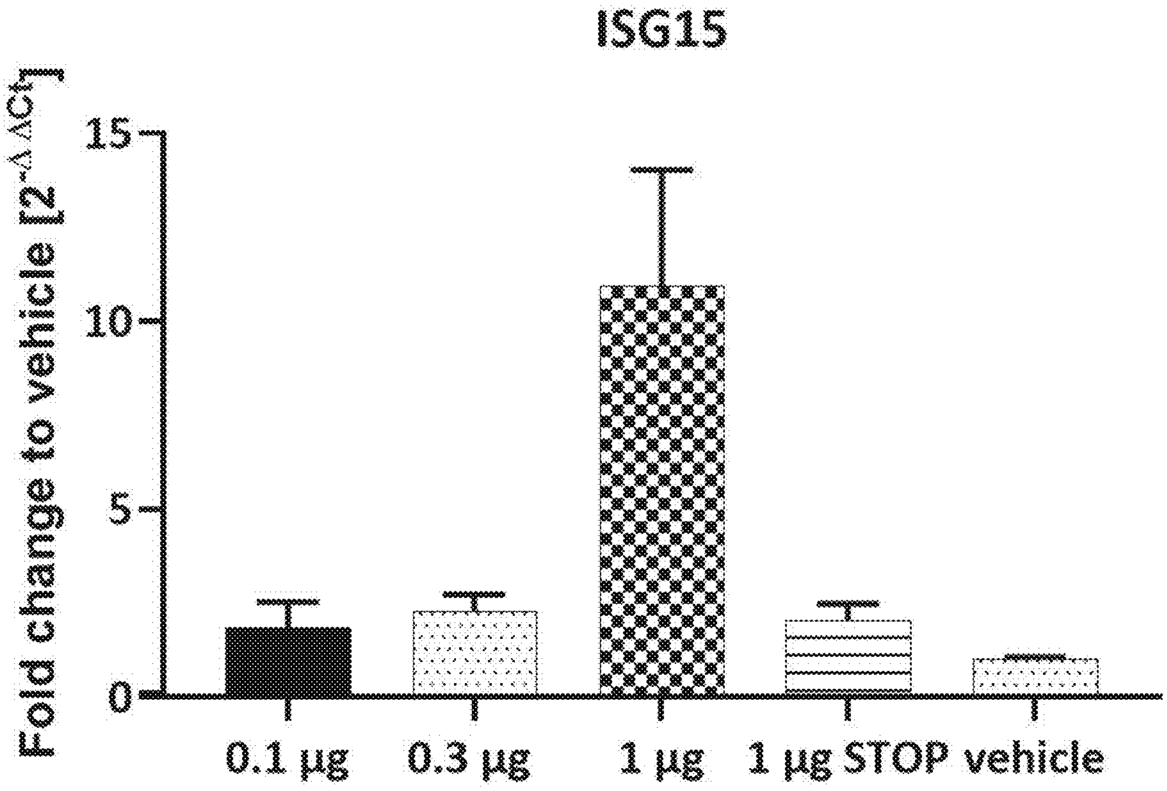
Figure 23D:
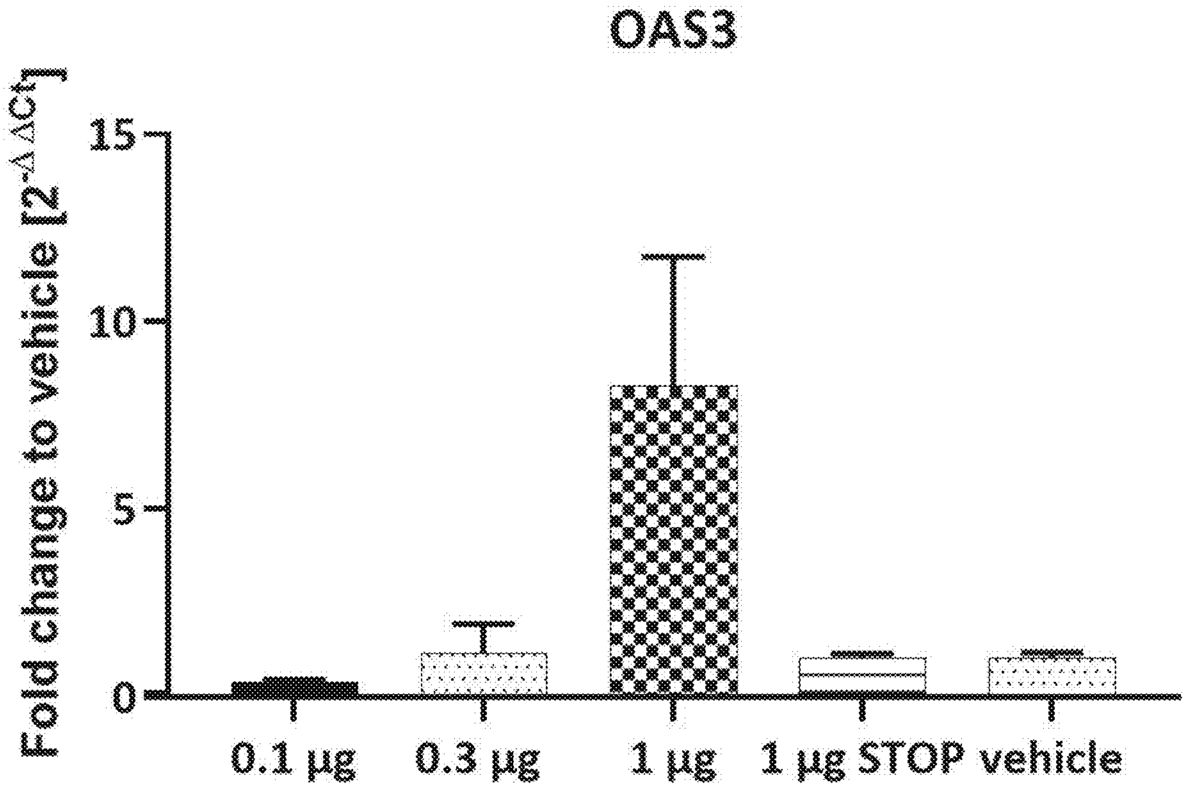

Example 17: Detection of Chemokines in Plasma after Single Nasal Application of hIFNλ1 mRNA There was no change in plasma concentrations of the measured chemokines following single nasal administration of hIFNλ1-encoding mRNA or STOP mRNA compared to vehicle at all dose levels in mice (FIG. 22). Three animals per group were assessed.

Example 18: Target Gene Activation in Lung Tissue Upon Treatment with hIFNλ1 mRNA LF92 formulated hIFNλ mRNA was well tolerated and potently induced pulmonary target gene expression at low dose following multiple nasal administrations in mice (FIG. 23). Three doses in 48 h intervals were administered and samples collected 24 h after the last application. Expression of hIFNλ target genes in lung homogenates increased in a dose-dependent manner (FIG. 23). An up to 15-fold activation of all target genes analysed was seen at a dose level 1 μg hIFNλ mRNA (FIG. 23). Lack of target gene activation in STOP and vehicle groups suggest that the observed effect is target-induced (FIG. 23). Six animals per group were assessed.

Figure 24:
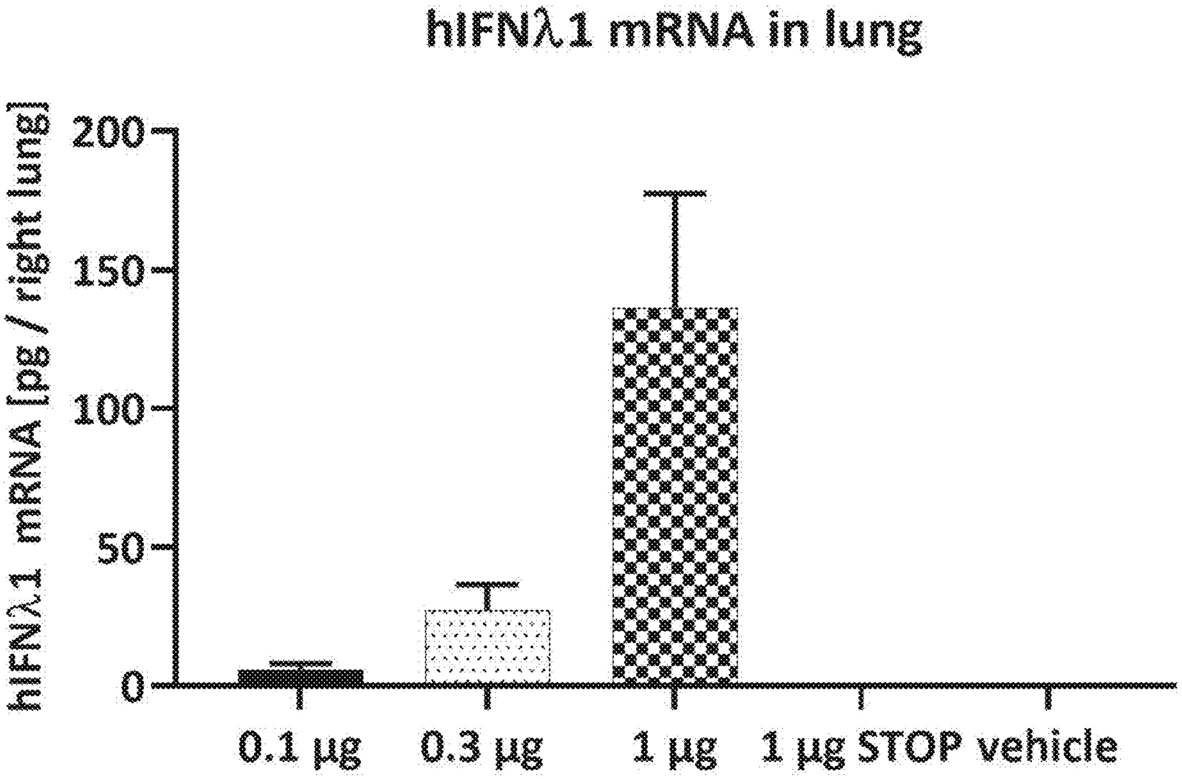
FIG. 24 shows detection of hIFNλ1 mRNA deposited in the lung after nasal application in mice (see also Example 19).

Example 19: Detection of hIFNλ1 mRNA Deposited in the Lung after Nasal Application in Mice Three doses in 48 h intervals were administered and samples collected 24 h after the last application. Dose-dependent deposition of mRNA encoding human IFNλ1 was observed (FIG. 24). Six animals per group were assessed.

Example 20: Body Weight During Repeated Administration of hIFNλ1 mRNA

Three doses in 48 h intervals were administered by nasal application in mice and body weight was measured daily. No changes in body weight were recorded (FIG. 25). Six animals per group were assessed.

Figure 26:
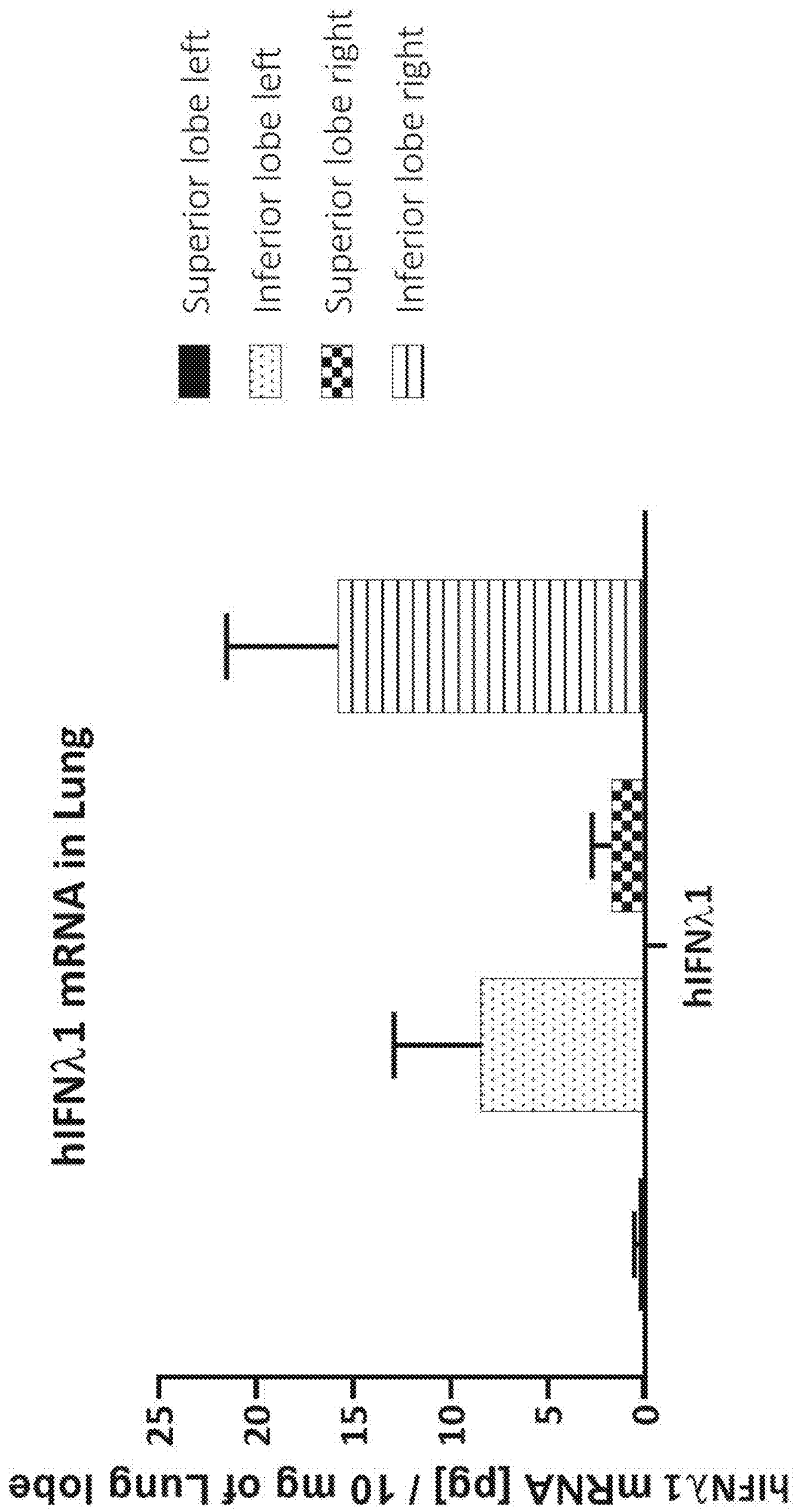
FIG. 26 shows quantification of hIFNλ1 mRNA in ferret lung homogenate (see also Example 21).

Example 21: Quantification of hIFNλ1 mRNA in Ferret Lung Homogenate hIFNλ1 mRNA was deposited in all lung lobes after single nasal administration in ferret (FIG. 26). Three animals per group were assessed.

Figure 27:
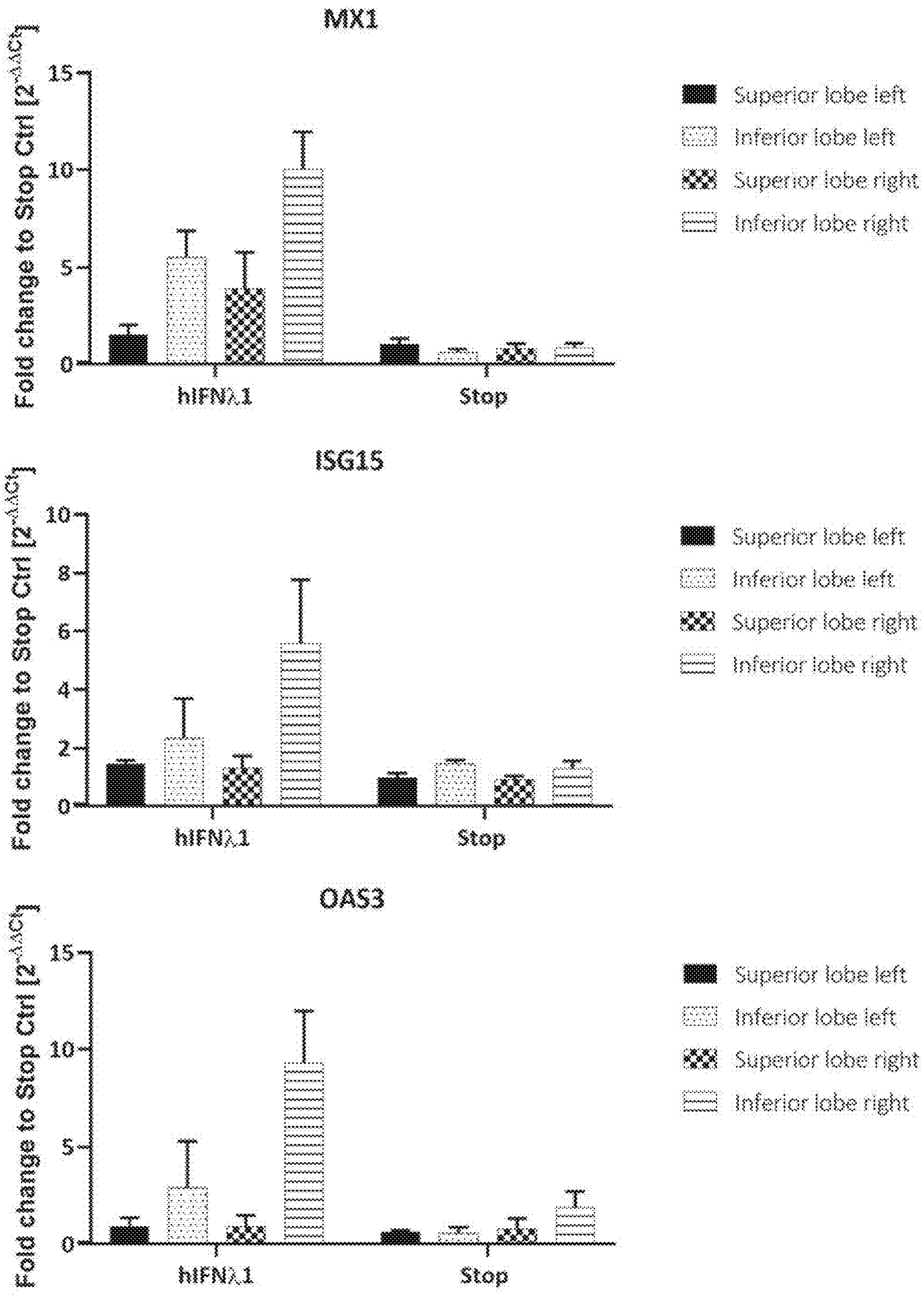
FIG. 27 shows target gene activation in ferret lung homogenate (see also Example 22).

Example 22: Target Gene Activation in Ferret Lung Homogenate hIFNλ1 treatment lead to induction of ISG15, MX1 and OAS3 after single nasal administration in ferret (FIG. 27). Three animals per group were assessed.

Figure 28:
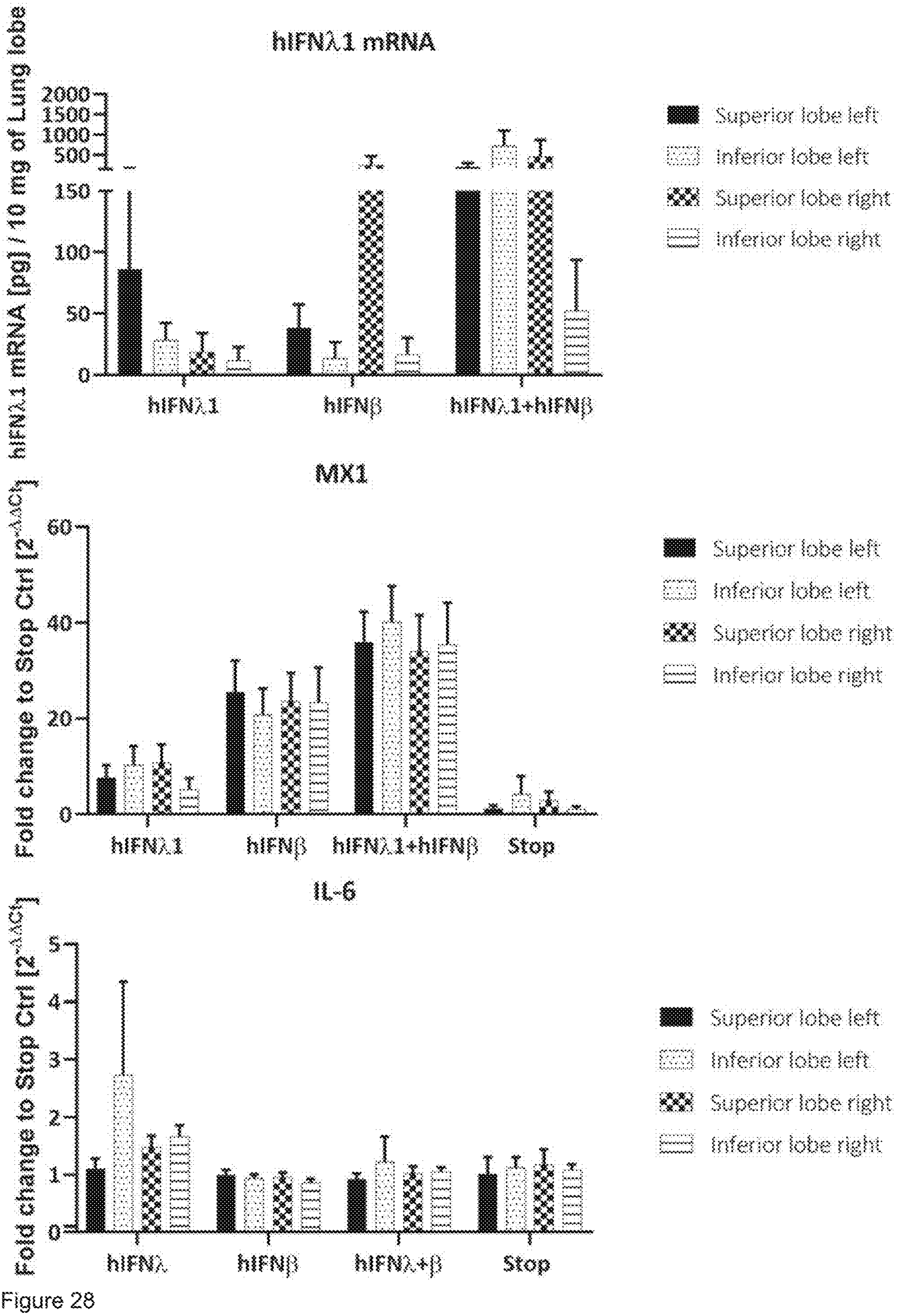
FIG. 28 shows quantification of IFN mRNA, target gene activation, and cytokine induction in ferret lung homogenate (see also Example 23).
Figure 28:
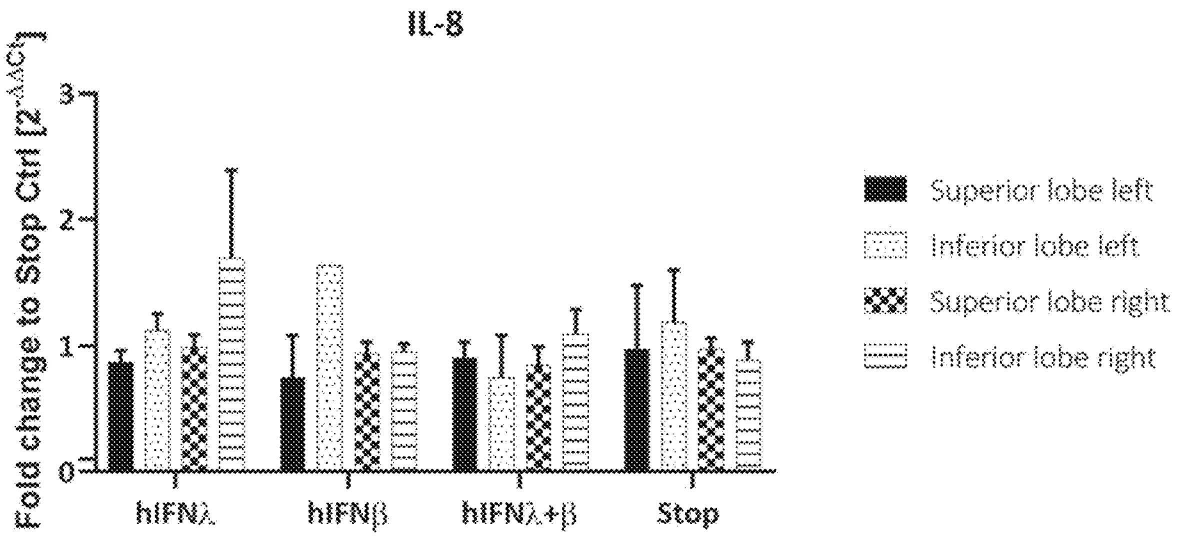
Figure 28:
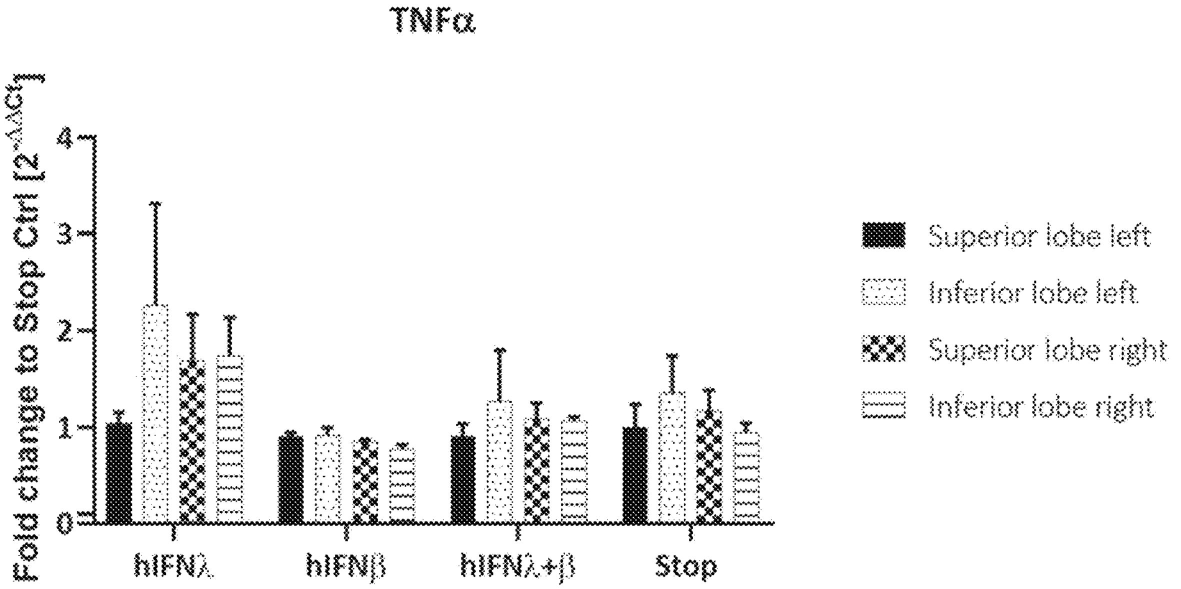
Figure 28:
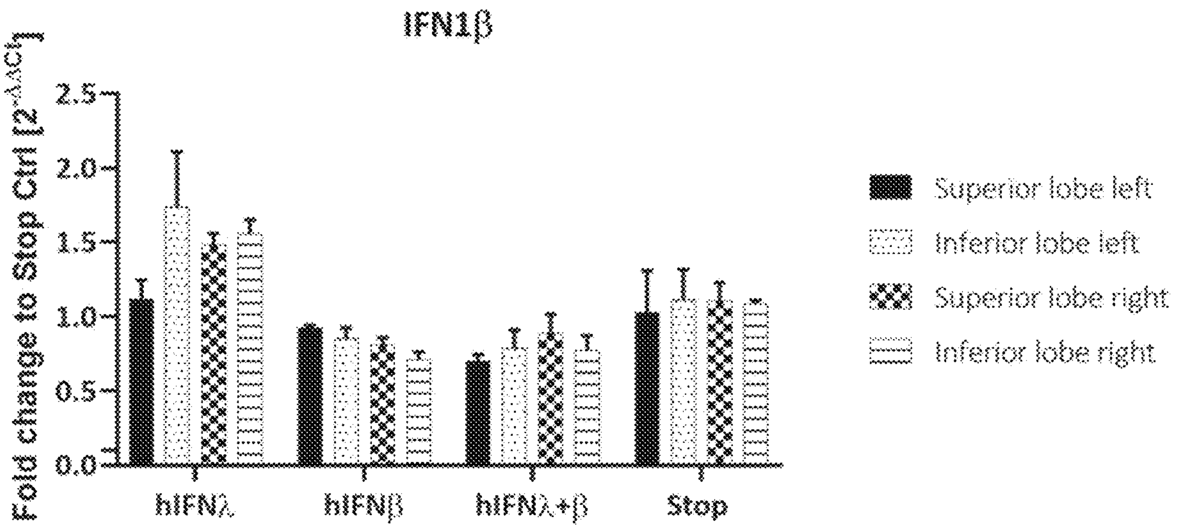
Figure 28:
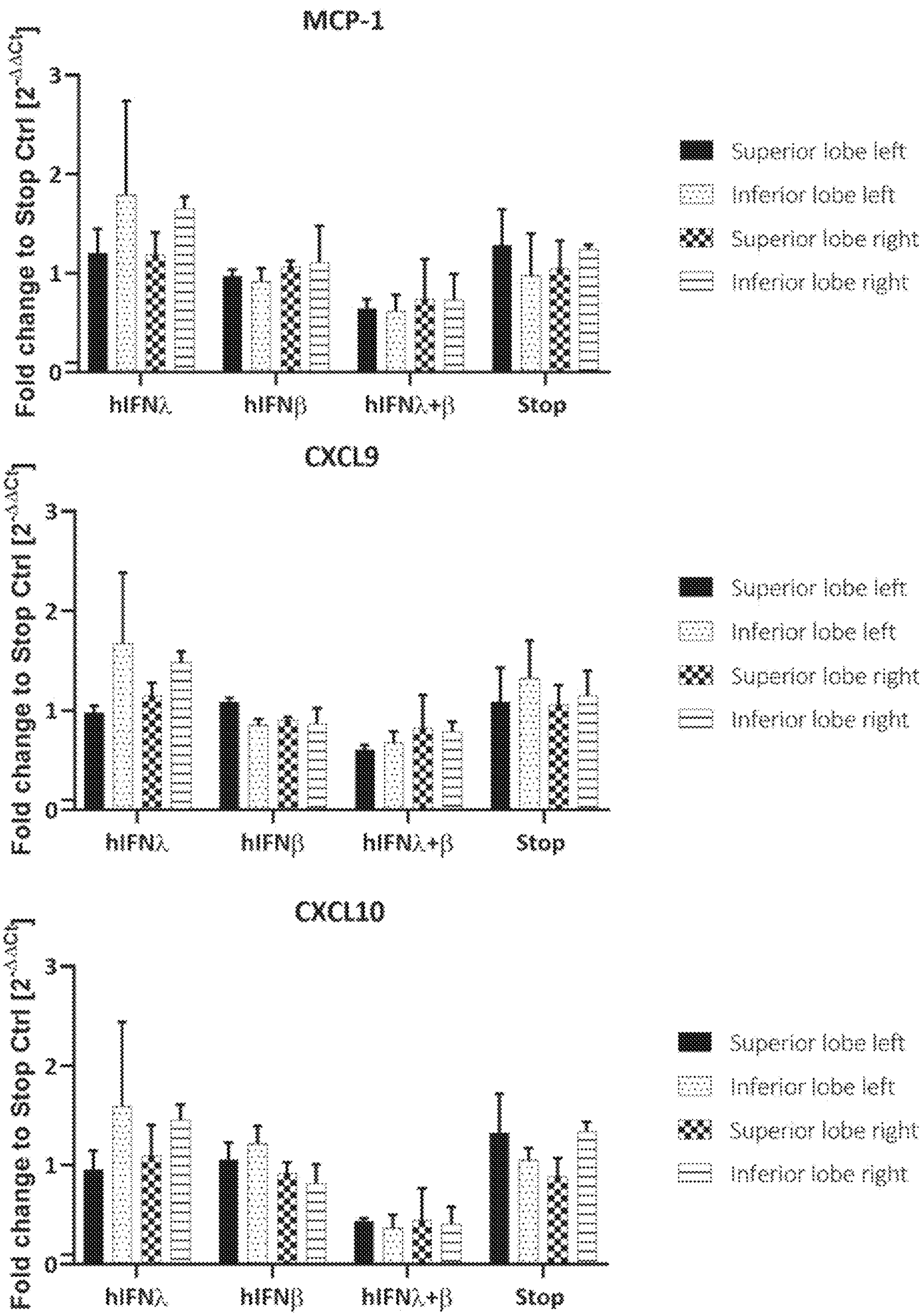
Figure 28:
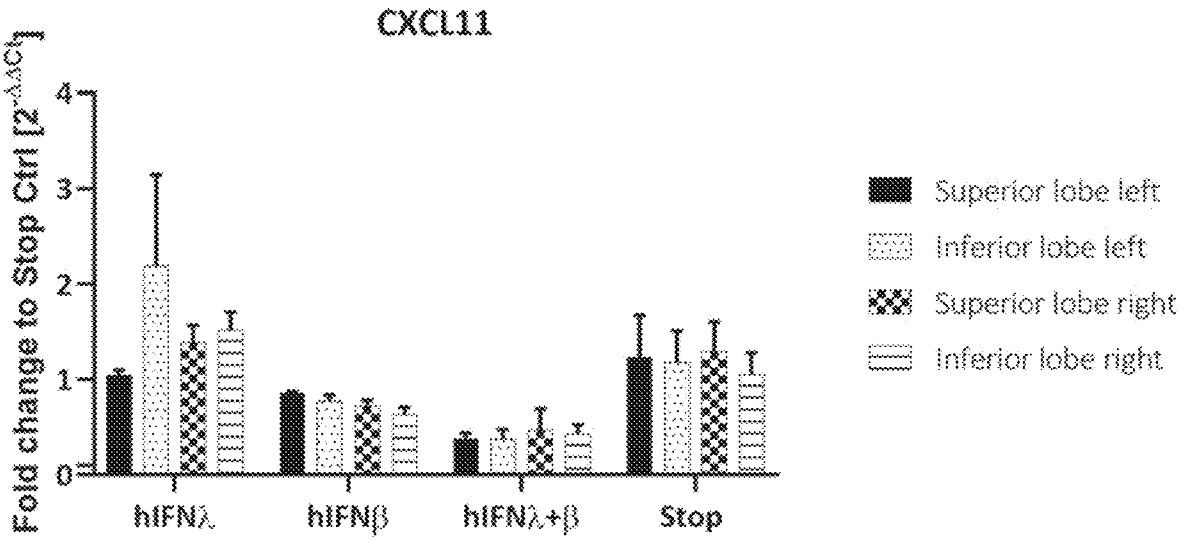

Example 23: Quantification of IFN mRNA, Target Gene Activation, and Cytokine Induction in Ferret Lung Homogenate Single nasal administration of mRNAs encoding hIFNλ1, hIFNs or both resulted in mRNA deposition in all lung lobes (FIG. 28). Mx-1 was induced by all three treatments while none of the analyzed cytokines was induced (FIG. 28). Three animals per group were assessed.

Example 24: Reduction of IAV Replication by mRNAs Encoding IFNs

Figure 29:
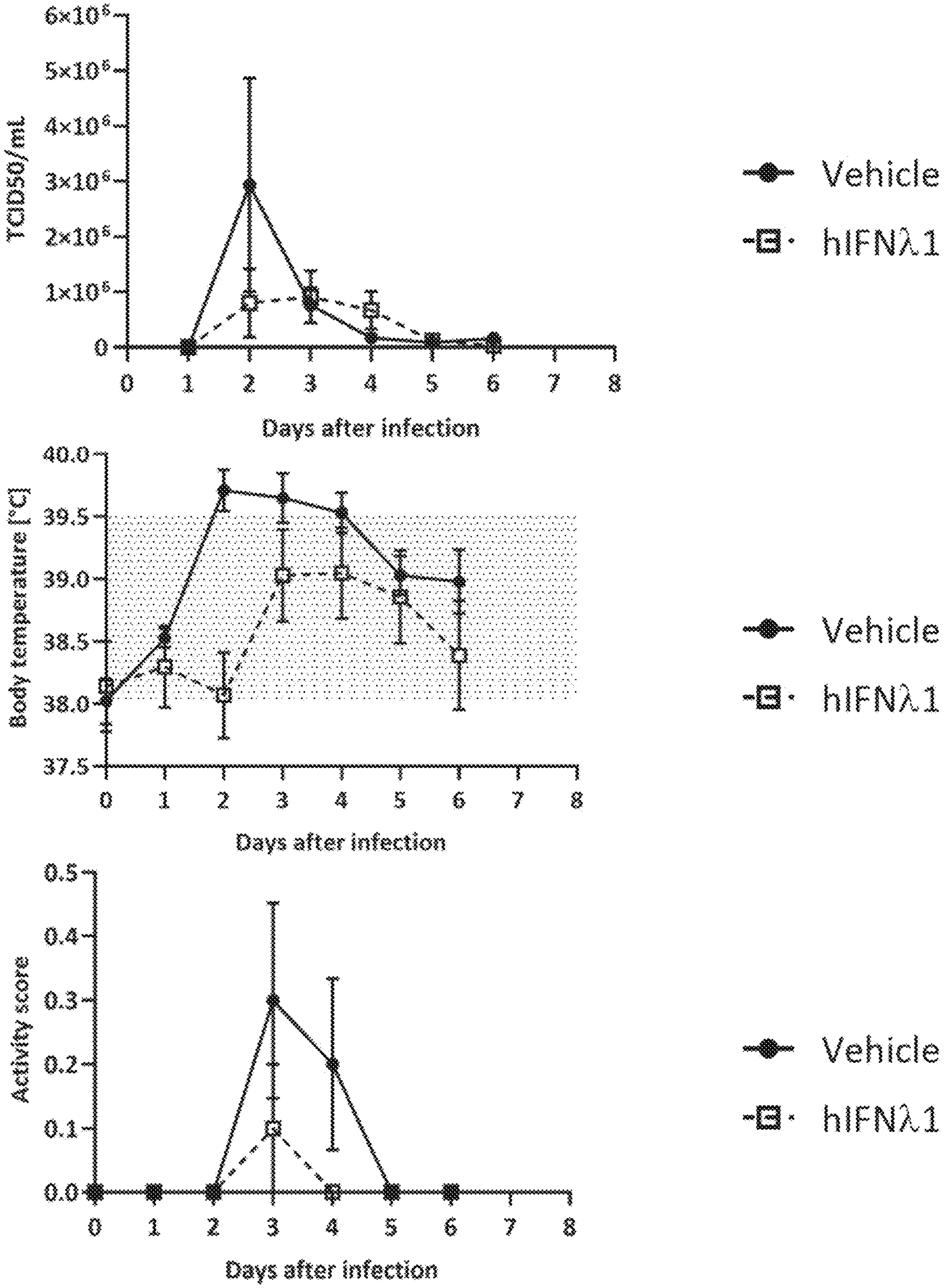
FIG. 29 shows reduction of IAV replication by mRNAs encoding IFNs (see also Example 24).
Figure 29:
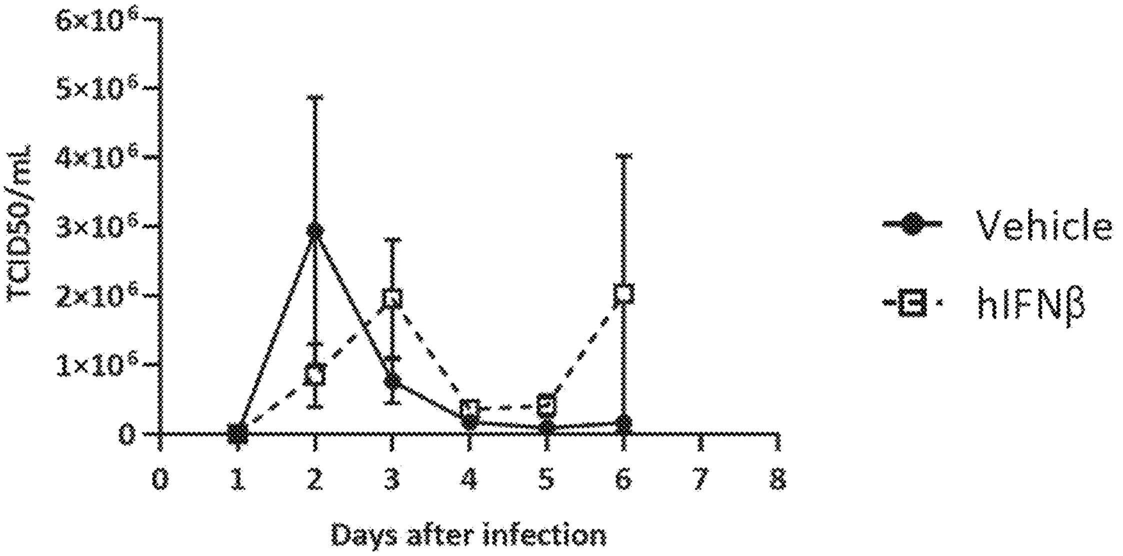
Figure 29:
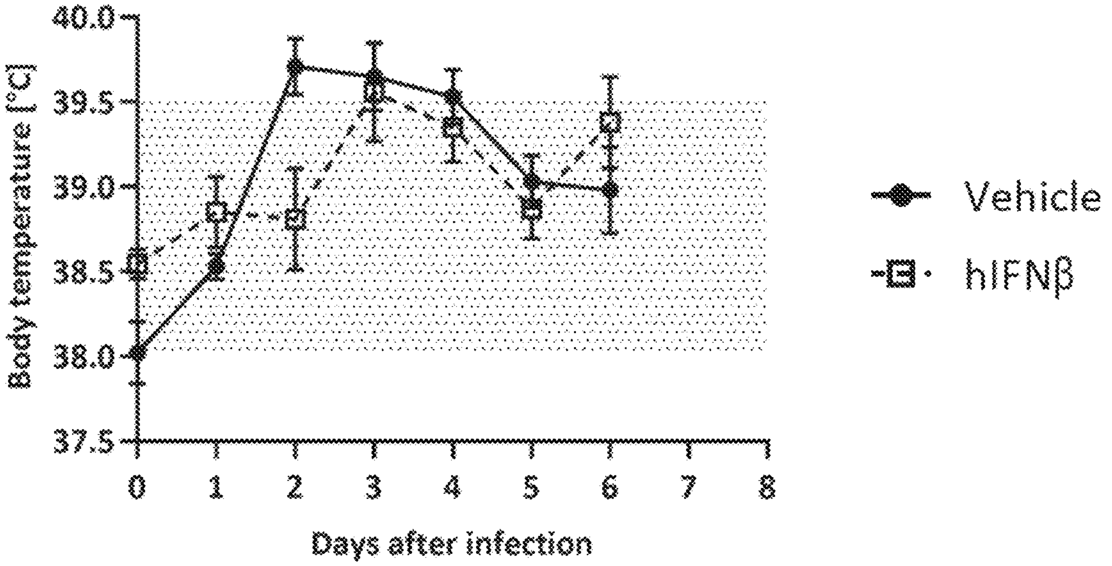
Figure 29:
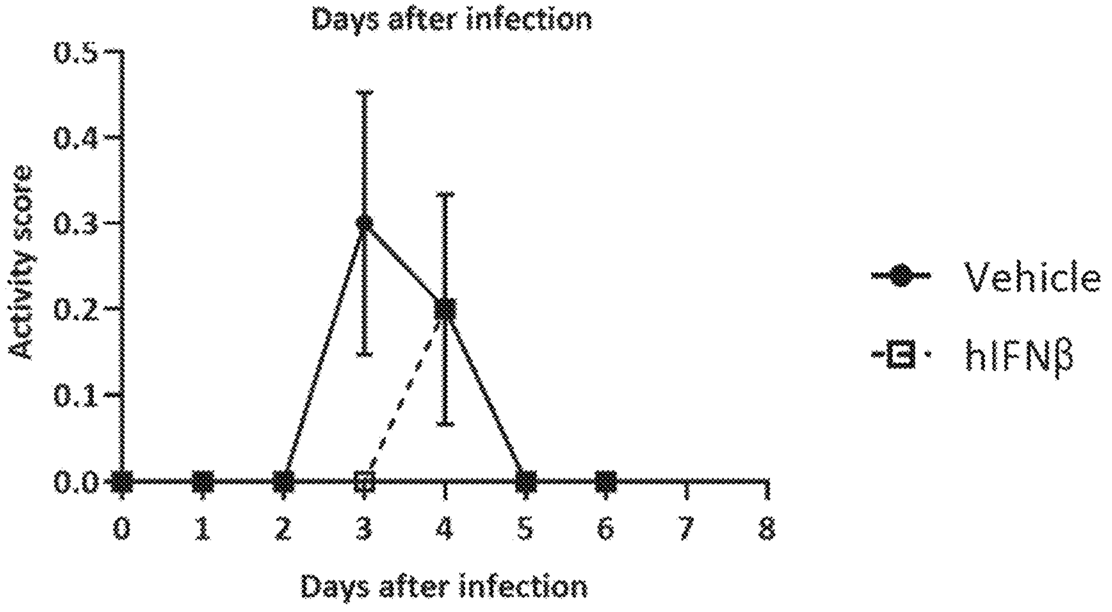
Figure 29:
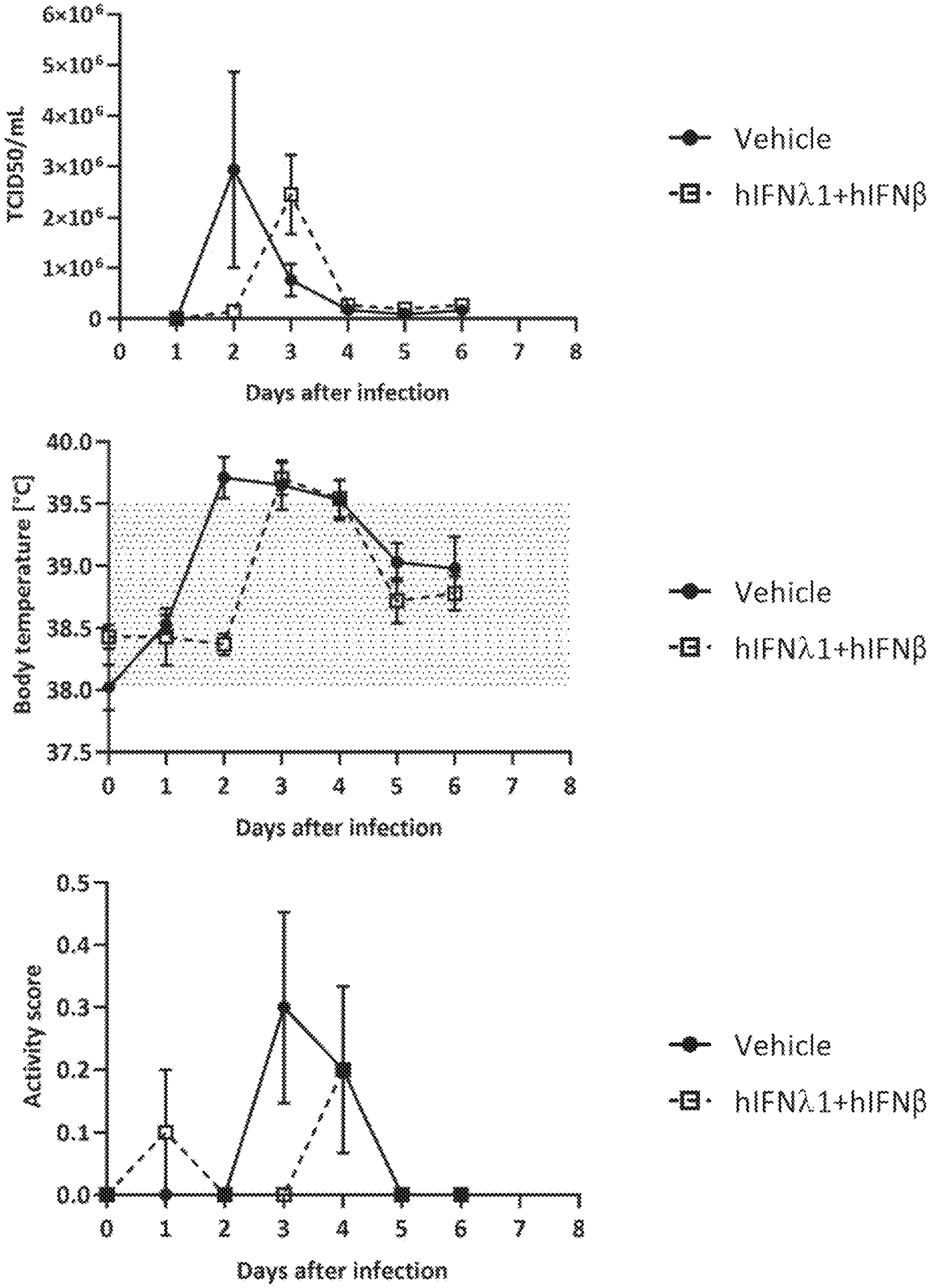

Intra-nasal administration of mRNA encoding hIFNλ1 (FIG. 29*a*), hIFNs (FIG. 29*b*) or both (FIG. 29*c*) was well tolerated and reduced early virus replication and clinical symptoms in a ferret influenza model (FIG. 29). Treatment was performed on study days −1, 1 and 3 while infection was done on day 0. Ten animals per group were assessed.

Example 25: Reduction of SARS-CoV2 Replication by mRNA Encoding hIFNλ1

Figure 30:
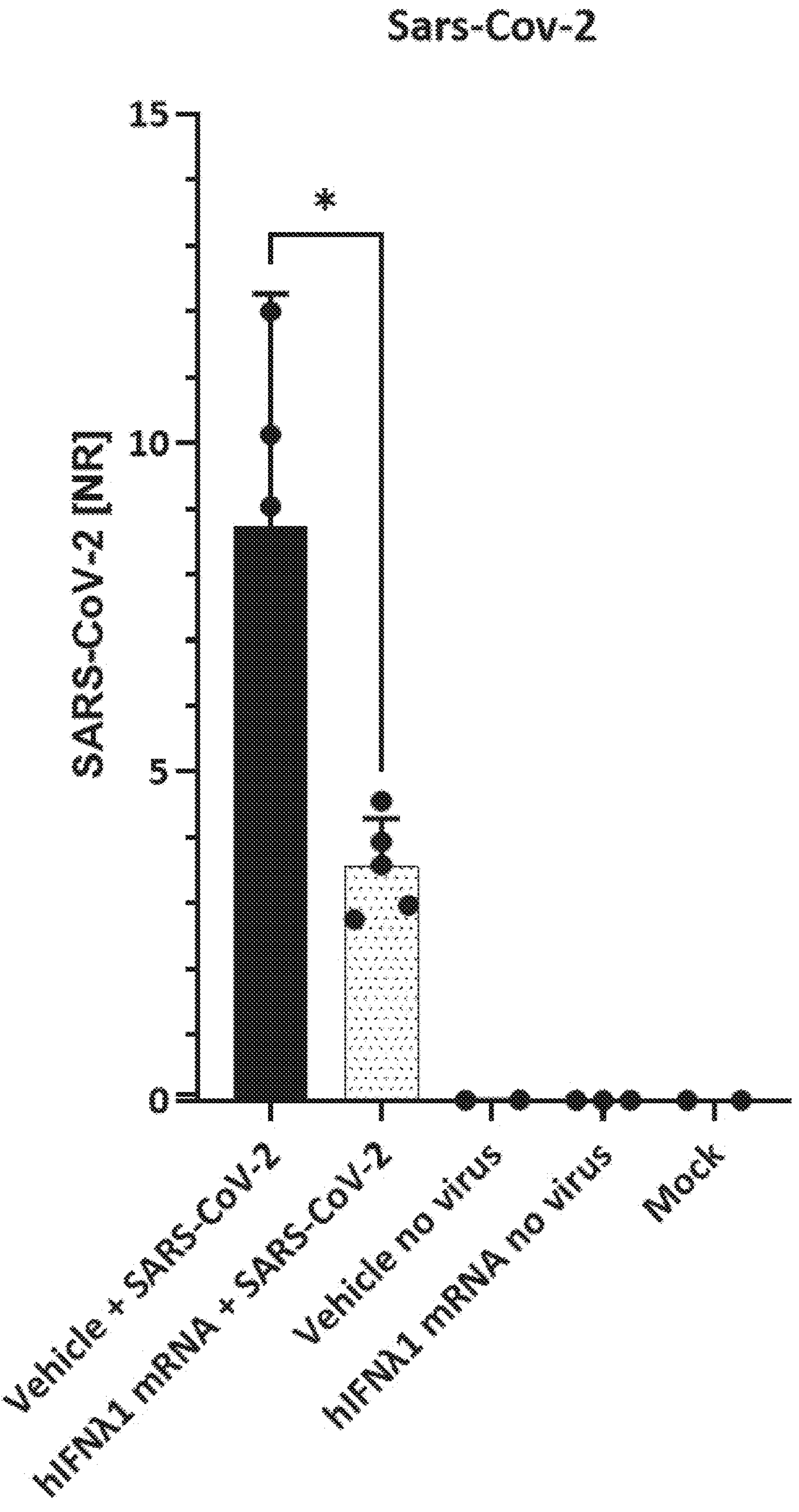
FIG. 30 shows Reduction of SARS-CoV2 replication by mRNA encoding hIFNλ1 (see also Example 25).
Figure 30:
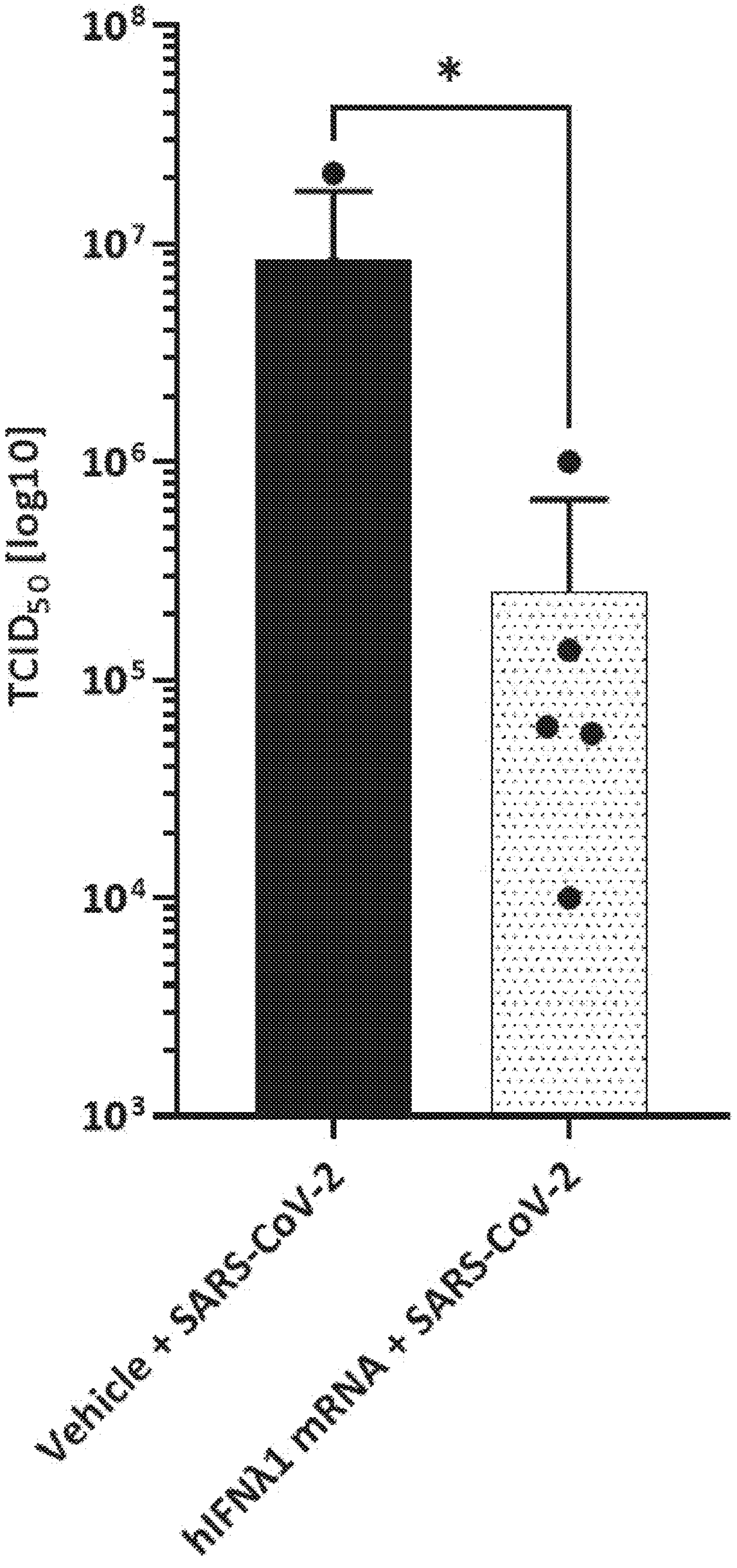
Figure 30:
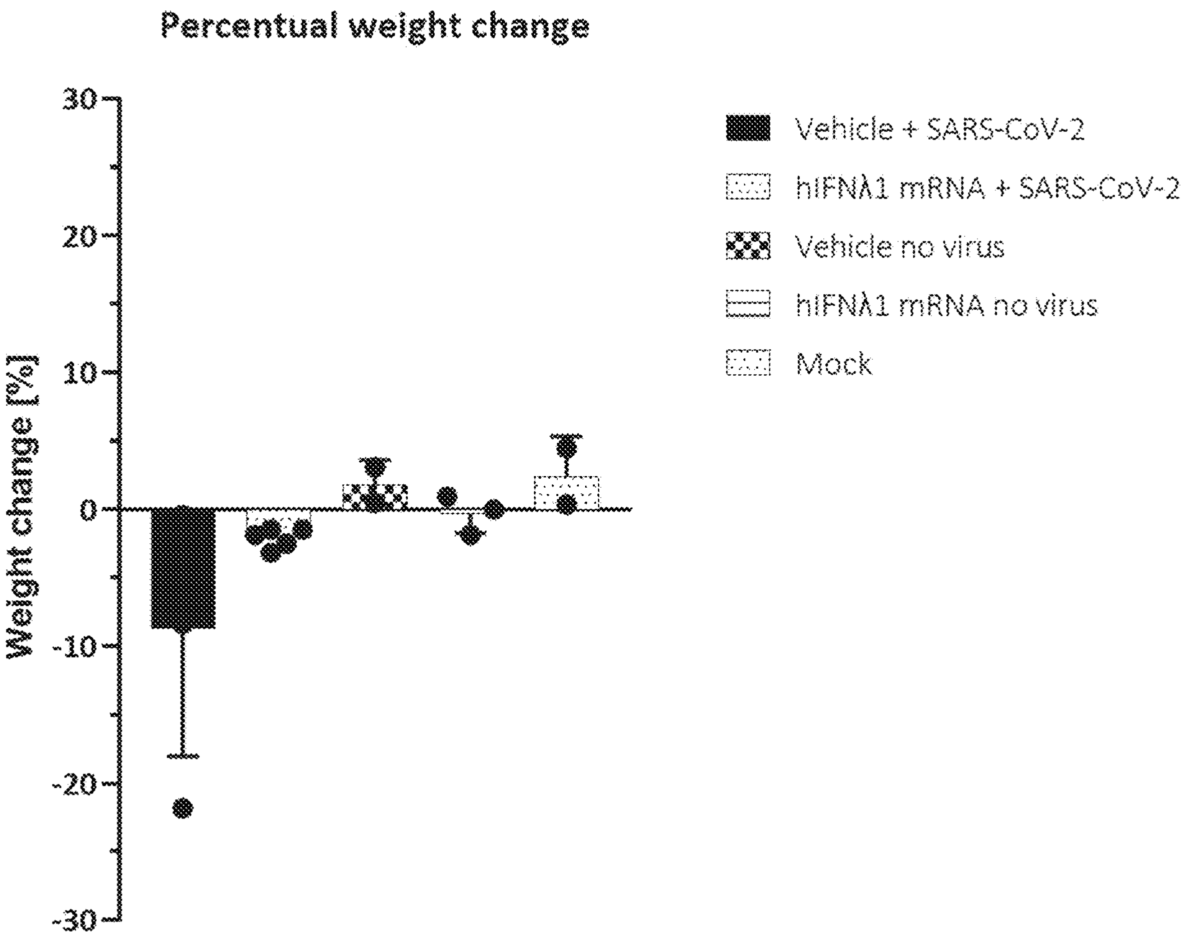

Intra-nasal administration of mRNA encoding hIFNλ1 was well tolerated and reduced virus replication and body weight reduction in a hACE2-TG mouse model challenged with SARS-CoV-2 alpha compared to vehicle treated animals (FIG. 30). Viral replication was assessed by measurement of genomic viral RNA via RT-qPCR (60% reduction compared to vehicle) (FIG. 30*a*) and by determination of infectious virus particles using the $TCID_{50}$ method (97% reduction compared to vehicle) (FIG. 30*b*). Body weight is shown as percentual weight change of day 3 after virus inoculation (FIG. 30*c*). Two to five animals per group were assessed. Following controls were employed: Mock treated, hIFNλ1 mRNA but not virus treated and vehicle but not virus treated mice.

In Examples 8 to 25 the following Materials were used.

2.1 Materials

| Material | Supplier | Cat no. |
|---|---|---|
| QIAshredder | Qiagen | 79656 |
| RNEASY ® Mini Kit | Qiagen | 74104 |
| DL-Dithiothreitol solution (DTT) | Sigma-Aldrich | 646563-10X.5ML |
| Transcriptor First Strand cDNA Synthesis Kit | Roche | 4896866001 |
| IL-29 Human ELISA Kit (IFNλ1) | Abcam | ab100568 |
| FBS, heat-inactivated | Thermo Fisher Scientific | 10500064 |
| MEM with GLUTAMAX ™ | Gibco | 41090-028 |
| LIPOFECTAMINE ™ MMax | Thermo Fisher Scientific | LMRNA008 |
| SINGLESHOT ™ cell lysis Kit | BioRad | 1725080 |
| ISCRIPT ™ Select cDNA Synthesis Kit | BioRad | 1708897 |
| DMEM | Sigma | D6429 |
| DPBS 1× without Ca and Mg | Thermo Fisher Scientific | Gibco 14190-250 |
| FBS | Sigma | F7524 |
| Penicillin-Streptomycin | Sigma | P4333 |
| Recombinant hIFNλ1 | Abcam | ab155625 |
| Carboxymethylcellulose | Sigma | SAFS21904-250G |
| Crystal violet | Carl Roth GmbH | T123.1 |
| Fast Start Essential DNA Probes Master | Roche | 06402682001 |
| Isoflurane | Isothesia, Henry Shine | 1311758 |
| LIGHTCYCLER ® 480 Multiwell Plate 96, white; VE: 50 plates with foils | Roche | 4729692001 |
| Lysing Matrix D Tubes | MP Biomedicals | 6913500 |
| TAQMAN ® Fast Advanced Master Mix | Thermo Fischer | 4444557 |
| Twin.tec PCR Plate96, unskirted, low profile, farblos VE: 20 | Omnilab | 5425895 |
| Casein | Thermo Fisher Scientific | 37528 |
| Mouse CXCL9/MIG DUOSET ™ ELISA, 15 Plate | R&D System | DY572 |
| Mouse CXCL10/IP-10/CRG-2 DUOSET ™ ELISA, 15 Plate | R&D System | DY466 |
| Mouse CXCL11/I-TAC DUOSET ™ ELISA, 15 Plate | R&D System | DY492 |
| 10× PBS | Roche | 11666789001 |
| Custom Premix Mouse Cyto/Chemokine MAG09 | Merck | MCYTOMAG-70K-09C |
| Tween-20 | Carl Roth | 9127.1 |

| Device | Supplier | Cat no. |
|---|---|---|
| 96-well cell culture plate | Corning | Costar 3599 |
| 96-well storage plate | Corning | Costar 3363 |
| Countess Cell Counter | Thermo Fisher Scientific | C10281 |
| Countess Cell Counting chamber slides | Thermo Fisher Scientific | C10283 |
| INCUCYTE ® | Sartorius | Incucyte S3 |
| LIGHT CYCLER ®96 | Roche | Light Cycler ®96 |
| Microplate reader | Tecan | Infinite M200 Pro |
| Microplate shaker | Heidolph | Titramax |
| Tissue and Cell Homogenizer | MP Biomedicals | MP FASTPREP ™-24 |
| MAGPIX ® | Luminex | MAGPX14184703 |

2.2 Methods 2.2.1 Cell Cultures 2.2.1.1 ALl Cultures

MUCILAIR™ inserts were purchased at Epithelix and cultivated in 700 μL MUCILAIR™ culture medium at 37 °C, in a humidified atmosphere with 5% C02 as Air-Liquid-Interface (ALl) cultures. Prior transfection the cells were let rest for 2-3 days upon arrival. To maintain culture, medium was exchanged every 2-3 days.

2.2.1.2 A-549 Cell Culture

A-549 cells were cultured as described in 2.1, supra.

2.2.1.3 A549-ACE2 Cell Culture

A549-ACE2 cells were cultivated in DMEM with 10% FBS and 100 μg/mL Streptomycin and 100 IU/mL Penicillin. 10,000 cells were seeded in 96-well plates in a total volume of 100 μL 24 h before treatment.

2.2.2 Transfection/Treatment

Prior transfection a mucus wash was performed. Therefore, 200 μL of PBS (w/o Mg/Ca) were added to the apical side and incubated for 20 min at 37 °C. Total time of apical washing should not exceed 30 min. To detach the mucus from the apical surface three back and forth movements were done with 100 μL from the apical liquid with a P200 pipet. PBS from the apical surface of the ALI culture was removed by gentle aspiration without damaging the epithelium. To remove traces of PBS, WFI wash using 200 μL WFI was performed.

Subsequently, the cells were transfected/treated with desired dose. Formulations were thawed at RT and kept on ice until further use. Recombinant protein was diluted in medium.

mRNA and recombinant protein was removed from the apical side 6 h post transfection. In case of recombinant protein, also the basal medium was renewed. At 24 h post transfection, apical side of the inserts was washed using 200 μL PBS, which was pipetted up and down three times. Wash solution was collected in a 96-well storage plate for ELISA analysis. Also 200 μL of basal medium was collected in a storage plate. Samples were stored at −80 °C until ELISA.

For qPCR, 175 μL RLT buffer from RNeasy RNEASY® Mini Kit, complemented with DTT (40 μL/mL), were added on the insert. With a mini cell scraper the cells were loosened from the insert. The RLT buffer was transferred into a QIAshredder column. To ensure all cells were transferred, the insert was washed with another 175 μL of RLT buffer. To finish the cell lysis, the columns were centrifuged for 2.5 min at max. speed. Column was removed and cell lysates in tube can be frozen at −80 °C or used immediately to isolate RNA.

2.2.2.1 Transfection Using LIPOFECTAMINE™ MMax in Examples 9 to 12

Transfection using LIPOFECTAMINE™ MMax was performed as described in 2.3, supra, with the exception that a dose titration ranging from 0.005 to 100 ng mRNA/well was performed and afterwards, 25 μL of the Lipoplex solution was added to the respective wells, in which medium was exchanged by 100 μL fresh complete medium.

2.2.2.2 Transfection Using LIPOFECTAMINE™ MMax in Example 13

Transfection using LIPOFECTAMINE™ MMax was performed as described in 2.3, supra, with the exception that a dose titration ranging from 15 ng/25 μL down to desired concentration was performed. Medium of the cells was exchanged by 100 μL fresh medium.

Afterwards, 25 μL of the Lipoplex solution was added to the respective wells. For treatment with recombinant protein, proteins were pre-diluted in medium and added to the cells in 25 μL with desired concentrations.

2.2.2.3 Transfection Using LF92 Formulated mRNA

LF92 formulated mRNA was diluted in Vehicle (10% (w/v) sucrose, 50 mM NaCl and a proprietary excipient) to desired concentrations. 25 μL of each dilution was added to the respective wells, in which medium was exchanged by 100 μL fresh complete medium.

2.2.3 RNA Isolation

RNA isolation was performed as described in 1.1.5.2, supra.

2.2.4 cDNA Synthesis cDNA synthesis was performed as described in 1.1.6, supra.

2.2.5 qPCR Using TAQMAN® Probes qPCR using TAQMAN® probes was performed as described in 1.1.7, supra. Analysis of qPCR results was done with the ΔΔCt method. To do so, first the ΔCt value of each sample was calculated. This was done by subtracting the average Ct value of the housekeeper (RPLPO) from the target Ct value. Then the ΔΔCt was calculated by subtracting the average ΔCt of the reference samples (vehicle control) from the target ΔCt. Finally, the fold change was calculated with the formula: $2^{-\Delta\Delta Ct}$.

2.2.6 hIFNλ1 ELISA (IL-29 ELISA)

hIFNλ1 ELISA was performed as described in 1.1.4, supra. Interpolation was done using a 4PL standard curve. Analysis was done with GraphPad Prism Software and Excel.

2.2.7 Harvest

Harvest was done at 3, 6, 24, 48 and 72 h post transfection. For each plate a medium exchange was performed at 6 and 24 h post transfection.

For ELISA, supernatant of the cells was collected in a 96-well storage plate and frozen at −80 °C. As two different ELISAs were performed, the supernatants were splitted on two plates to enable separate thawing. For qPCR, cells are washed using 150 μL $PBS^{-/-}$ and cells are frozen without liquid at −80 °C.

2.2.8 RNA Isolation Using the SINGLESHOT™ Cell Lysis Kit

RNA Isolation using the SINGLESHOT™ Cell Lysis Kit was performed as described in 2.2.5.

2.2.9 Preparation of Virus Stocks

SARS-CoV-2-MUC-IMB-1, SARS-CoV-2-GFP strains, wild type Influenza A virus (IAV-WT) (SC35M) and IAV (SC35M) NS1-GFP were produced by infecting Vero E6 cells cultured in DMEM medium (10% FCS, 100 μg/ml Streptomycin, 100 IU/ml Penicillin) for 2 days (MOI 0.01). Viral stock was harvested and spun twice (1000 g/10 min) before storage at −80 °C.

Titer of viral stock was determined by plaque assay. For this, confluent monolayers of Vero E6 cells were infected with serial five-fold dilutions of virus supernatants for 1 hour at 37 °C. The inoculum was removed and replaced with serum-free MEM containing 0.5% carboxymethylcellulose. Two days post-infection, cells were fixed for 20 minutes at room temperature with formaldehyde directly added to the medium to a final concentration of 5 Fixed cells were washed extensively with PBS before staining with $H_2O$ containing 1% crystal violet and 10% ethanol for 20 minutes. After rinsing with PBS, the number of plaques was counted, and the virus titer was calculated.

2.2.10 Virus Infection

Cells were infected 24 h after transfection with SARS-CoV-2 (MOI 3) or IAV (MOI 0.5). Virus was added in 25 μL medium directly to the cell culture. For the analysis of infection kinetics under live imaging system, the SARS-CoV-2-GFP and IAVGFP were used.

2.2.11 Cell Monitoring in the INCUCYTE®

After the infection, plates were placed in the INCUCYTE® S3 Live-Cell Analysis System where whole-well real-time images of mock (Phase channel) and infected (GFP and Phase channel) cells were captured every 4 hours for 48 hours. Cell viability (mock) and virus growth (mock and infected) were assessed as the cell confluency per well (Phase area) and integrated GFP intensity normalized on cell confluency per well (Integrated GFP intensity/Phase area) respectively using INCUCYTE® S3 Software (Essen Bioscience; version 2019B Rev2).

2.2.12 qPCR for SARS-CoV-2 and IAV mRNA

For relative transcript quantification POWERUP™ SYBR™ Green was used. All steps were performed according to manufacturer's instructions. RPLPO was employed as housekeeper.

2.2.13 Animal Housing

All animals were housed as described in 1.2.1, supra. All procedures were approved by the local animal welfare authorities (Regierung von Oberbayern) under the file number Az. 2532.Vet_03-17-114 and were conducted according to the German animal protection law (Tierschutzgesetz).

2.2.14 Nasal Application in Examples 14 to 17

Animals were anesthetized by inhalation of pure oxygen at a flow rate of 2 L/min supplemented with approximately 4% of the anesthetic gas Isoflurane in an inhalation chamber. hIFNλ1 mRNA was applied in two 25 μL boluses, by using a laboratory pipette, on both nose holes so that the liquid was actively inhaled through the nose by the animal during a physiological inspiratory movement. The animal was held in perpendicular position during this procedure and was subsequently placed in supine position until recovery from anesthesia.

2.2.15 Clinical Examination in Examples 14 to 17

Clinical examination was performed as described in 1.2.3, supra, with the exception that Animals were examined clinically before and 5 hours after treatment as well as daily until the day of necropsy. Furthermore, body weight was measured before application and daily until the final day of the experiment.

2.2.16 Necropsy

Scheduled necropsy time points were chosen 5, 24 or 48 h after application, respectively. In A01, an additional 72 h time point for necropsy was included. In A02, group 2, additional necropsies at 72 and 96 h after application of hIFNλ1 mRNA were performed. Animals were set under full anesthesia by intraperitoneal injection of Fentanyl/Midazolam/Medetomidin (0.05/5.0/0.5 mg/kg bw). Capillary blood was taken from retrobulbar venous plexus using nonheparinized 0.8 mm capillaries and collected in EDTA tubes. Blood samples were centrifuged at 2.000×g for 5 min at 4 °C. Subsequently, mice were killed by cervical dislocation.

The thoracical and abdominal cavity were opened, and the lung was explanted unflushed in toto, and snap frozen on dry ice and stored at −80 °C until further processing.

2.2.17 Lung homogenization 2.2.17.1

Samples were homogenized using liquid nitrogen. Therefore, the organ was put in a mortar which was placed in an ice box. Liquid nitrogen was added in a volume, which covered the lung completely. The lung was pulverized in the mortar using a pistle. It was always ensured that the organ was covered by liquid nitrogen. A stapula was immersed in nitrogen and used to devide the organ powder in three parts. The organ powder was put in an empty and tared Eppendorf Tube. About 5 mg of the powder was taken for bDNA assay and the remaining powder was devided in two halfs, one for ELISA, one for qPCR. Each organ weight was noted.

Mortar, pistle and stapula were cleaned using Ethanol after every sample.

2.2.17.2

For ELISA, lysis was done in Triton X-100 lysis buffer (0.25 M Triethanolamine, 0.1% Triton X-100, pH7.7). Lysis was done on ice for at least 10 min. After every $6^{th}$ sample, lysates were centrifuged at 14000 rpm for 10 min. Supernatant was collected in a fresh tube and stored at −80 °C until further processing.

2.2.17.3

For qPCR, 600 μL lysis buffer was added to the tube containing the organ powder. Lysis buffer RLT was provided by the kit and complemented with 40 μL/mL DTT. The solution was then transferred to a Lysing Matrix D tube and homogenization was done for 3×20 sec in a Tissue homogenizer. The lysate was transferred to a fresh Eppendorf tube. The volume of homogenate which refers to 10 mg lung was calculated, transferred into a fresh Eppendorf tube and mixed using lysis buffer to a final volume of 350 μL. These samples were used directly for isolation of RNA without freezing. The left-over lung homogenates were stored at −80 °C.

2.2.18 RNA Isolation and cDNA Synthesis for qPCR in Examples 14 to 17 and 18 to 20 RNA Isolation from the Lung Lysates was Done Using 10 mg of Lysed Lung Homogenate and the RNEASY® Mini Kit from Qiagen According to Manufacturer's Protocol.

cDNA synthesis was performed as described in 1.1.6.1, supra. For a two-step cDNA synthesis 1 μg of total RNA and 1 μL OligoDT Primers in a total volume of 13 μL were used to prepare the first step, here called the template primer mixture.

2.2.19 Preparation of Standard Curve for Quantification of hIFNλ1 mRNA

For the exact calculation of amount of mRNA encoding human IFNλ1 in the samples a standard curve is needed. Therefore, 1 μg of hIFNλ1 mRNA was reverse. Then a serial dilution of cDNA in nuclease free water was made in following dilutions: $1{:}10^1$, $1{:}10^2$., $1{:}10^3$, $1{:}10^4$, $1{:}10^5$, $1{:}10^6$ $1{:}10^7$. The dilutions were prepared independently. This means that e.g. the $1{:}10^2$ dilution was not made from the $1{:}10^1$ dilution used in the assay, but from a separate $1{:}10^1$ dilution. From each dilution 2 μL were added to 8 μL master mix to perform qPCR.

2.2.20 qPCR Using UPL Probe

For quantification of mRNA encoding human IFNλ1, including standard curve, an universal probe library (UPL) probe was used.

The following components shown in Table 14 were combined and vortexed briefly. To bring the reaction mix to the bottom of the tube and to eliminate air bubbles the mix was briefly centrifuged at 3200 µg for 2 min.

8 µL of TAQMAN® master mix were transferred to an optical 96-well qPCR reaction plate. 2 µL cDNA template were added to the optical 96-well qPCR reaction plate to obtain a final volume of 10 µL. The optical 96-well qPCR reaction plate was sealed with optical adhesive film and briefly centrifuged at 3200 µg for 2 min.

Run mode "new experiment based on Roche Template" was selected and "HydrolysisProbes" was chosen on LightCycler96.

TABLE 14

Master mix qPCR UPL

| Component | Volume per well [µL] |
|---|---|
| Nuclease free water | 2.625 |
| Primer 1 [20 µM] | 0.150 |
| Primer 2 [20 µM] | 0.150 |
| UPL [stock] | 0.075 |
| Fast Start Essential DNA Probes Master | 5 |
| Total | 8 |

2.2.21 Calculation of hIFNλ1 mRNA Content

The amount of mRNA encoding human IFNλ1 in the sample can be determined with the standard curve. The standard curve was made by placing the log (amount of hIFNλ1 mRNA) on the x-axis and the ct values on the y-axis from the standard curve.

Exemplary equation from the standard curve $$Y=-3,2449X+9,1445$$

From this the amount of IFNλ1 mRNA in the sample (X: log of concentration) was determined (Y: ct value of sample).

TABLE 15

Example calculation: Calculation of the total amount of IFNλ1 mRNA per lung

| Sample | Lung weight [mg] | Ct Value | Log (measured IFNλ1 mRNA [ng]) = X | Measured IFNλ1 mRNA [pg] | IFNλ1 mRNA in 30 mg lung tissue [pg] | Total amount of IFNλ1 mRNA in lung [pg] |
|---|---|---|---|---|---|---|
| Sample 1 | 360.8 | 18.25 | −2.81 | 1.56 | 78.14 | 939.77 |
| Sample 2 | 270.9 | 16.75 | −2.34 | 4.53 | 226.54 | 2045.62 |

2.2.22 CXCL9 and CXCL10 ELISA in Plasma

Plasma samples of this study were measured according to the manufacturer's instructions. Changes to the protocol can be found in Table 16.

TABLE 16

Parameters of the CXCL9 + 10 ELISA protocols in plasma not included in the manufacturer's instructions.

| Sample Type | Cytokine | Blocking solution | Diluent for antibodies and samples | Time for TMB | Sample dilution | LLOQ |
|---|---|---|---|---|---|---|
| Plasma | CXCL9 | Casein | 0.05% Tween-20 in 1x PBS | 16 min | 1:2 | 40 pg/mL |
| | CXCL10 | 1% BSA in 1x PBS | 1% BSA in 1x PBS | 25 min | 1:20 | 100 pg/mL |

2.2.23 CXCL9 and CXCL11 ELISA in Lung Homogenate

Lung homogenates of this study were measured according to the manufacturer's instructions. Changes to the protocol can be found in Table 17.

TABLE 17

Parameters of the CXCL9-11 ELISA protocols in plasma not included in the manufacturer's instructions.

| Sample Type | Cytokine | Blocking solution | Diluent for antibodies and samples | Time for TMB | Sample dilution | LLOQ |
|---|---|---|---|---|---|---|
| Lung homogenate | CXCL9 | Casein | 0.05% Tween-20 in 1x PBS | 16 min | 1:50 | 100 pg/mL |
| | CXCL11 | Casein | 0.05% Tween-20 in 1x PBS | 16 min | 1:30 | 120 pg/mL |

2.2.24 Intranasal Application in Examples 18 to 20

Animals were anesthetized by inhalation of pure oxygen at a flow rate of 2 L/min supplemented with approximately 3% of the anesthetic gas Isoflurane in an inhalation chamber. hIFNλ1 mRNA was applied at a volume of 50 μL on the nosetip as one droplet and was subsequently actively inhaled through both nostrils during the next following physiological inspiratory movement. The animal was held in the perpendicular position during this procedure and was subsequently placed in the supine position until recovery from anesthesia. Treatment was performed every other day for a total of 3 drug administrations. Necropsy was performed 24 hours after the last application.

2.2.25 Clinical Examination in Examples 18 to 20

Clinical examination was performed as described in 1.2.3, supra, with the exception that animals were examined clinically before and 3 hours after the first treatment and subsequently daily until the day of necropsy. Furthermore, body weight was measured before application and daily until the final day of the experiment.

2.2.26 Necropsy in Examples 18 to 20

Animals were set under full anesthesia by intraperitoneal injection of Fentanyl/Midazolam/Medetomidin (0.05/5.0/0.5 mg/kg bw). Capillary blood was taken from retrobulbar venous plexus using non-heparinized 0.8 mm capillaries and was collected in EDTA tubes. Subsequently, mice were killed by cervical dislocation. The thoracical and abdominal cavity were opened and the lung was explanted unflushed in toto.

The right main bronchus was ligated, the right lung explanted and snap frozen on dry ice and stored at −80 °C until further processing. The left lung was insufflated with 0.4 mL fixative (4% paraformaldehyde-solution) via the trachea. Subsequently, the left bronchus was ligated and the insufflated left lung including the trachea transferred to 4% paraformaldehyde solution for diffusion fixation for about 24 h. After completion of fixation time, the lung samples were transferred to 70% ethanol.

2.2.27 Preparation of Plasma

EDTA-blood samples were centrifuged at 2.000×g for 5 min at 4 °C. Supernatant was frozen on dry ice and subsequently stored at −80 °C until further processing.

2.2.28 Lung Homogenization in Examples 18 to 20

Lung homogenization was performed as described in 2.2.17.3, supra.

2.2.29 Test System in Examples 21 to 24

Species: *Mustela putorius* (ferret)

Strain: Sable

Source of supply: Triple F Farms (Gillett, PA)

Ferrets were between 20 and 24 weeks old at the time of LF92 formulated hIFN mRNA dosing. In Example 24, ferrets were five months old at the time of LF92 formulated hIFN mRNA dosing. Animals ranged from 0.7 kg to 1.1 kg in weight on the day before dosing (Day −1). Each animal was permanently identified by unique ear tag at NLS following animal receipt.

2.2.30 Test System Housing in Examples 21 to 24

Animals were acclimated for 10 to 12 days prior to study initiation. During the acclimation period, the health status of animals was evaluated daily by technical staff for clinical presentation and behavioral signs indicating normality or illness. Animals were housed in groups of three in stainless steel cages with wire bottoms during acclimation and throughout the in-life phase of the study.

2.2.31 Test Dosing in Examples 21 to 23

Animals were administered 1 mL of LF92 formulated hIFN mRNA by nasal instillation with a pipet (0.5 mL/nostril). LF92 formulated human IFNλ1 or Stop mRNAs were applied at a mRNA concentration of 0.07 mg/mL. In Example 23 a mRNA concentration of 1.25 mg/mL was applied leading to a total mRNA concentration of 2.5 mg/mL in case of the combination of human IFNλ1 and human IFNβ.

2.2.32 Test Dosing in Example 24

On study Day −1, 1 and 3, animals were administered LF92 formulated hIFN mRNA by nasal instillation with a pipet (0.5 mL/nostril of 0.125 or 0.25 mg/mL solution). LF92 formulated mRNA encoding human IFNλ1, human IFNs or a combination of both was applied at a mRNA concentration of 1.25 mg/mL, leading to a total mRNA concentration of 2.5 mg/mL in case of the combination. Vehicle was applied as control.

On study day 0 animals of all groups were challenged by nasal instillation with 1 ml of freshly diluted H1 N1 A/California/04/09 virus until $2\times10^2$ $TCID_{50}$/ml titer. The viral titer was confirmed the same day additionally (back titration).

2.2.33 Necropsy in Examples 21 to 23

All animals were humanely euthanized while under a heavy plane of sedation at 6 hours post dosing. Lung tissue specimens were collected from the upper, middle, and lower regions of the upper left (left cranial), upper right (right cranial), lower left (left caudal), and lower right (right caudal) lobes of the lungs. Tissue specimens were weighed, cut into 3 pieces and placed into cryovial tubes containing 1 mL RNALATER® and stored at 4 °C overnight to allow RNALATER® to penetrate tissue. RNALATER® solution was removed from the tubes and the tissues were snap frozen and stored at −80 °C until shipped to ethris.

2.2.34 Lung Homogenization in Examples 21 to 23

600 μL lysis buffer was added to Lysing D tubes and stored at ice. Lysis buffer RLT was provided by the kit and complemented with 40 μL/mL DTT. The frozen organ was weighed and depending on weight transferred to one lysing tube or cut into pieces and transferred to several lysing tubes. 300-350 mg in 600 μL lysis buffer was determined to be the maximum amount of tissue and volume of lysis buffer for one lysing tube. While processing further samples, organs in lysis buffer were stored on ice. Homogenization was done for 3×20 sec in a tissue homogenizer. Lysates were then centrifuged for 3 min at maximum speed (14000 rpm). The supernatant was transferred to a fresh Eppendorf tube. The volume of homogenate which referred to 10 mg lung was transferred into an additional fresh Eppendorf tube. To this tube, lysis buffer was added to a final volume of 600 μL. These samples as well as residual lysates were frozen at −80 °C before isolation of RNA.

2.2.35 Clinical Observations in Example 24

Ferrets were observed twice daily and scored for clinical signs of illness, including sneezing, nasal discharge, and activity. A score of 0 or 1 was assigned for the absence or presence of sneezing or nasal discharge. Activity was scored as 0=normal activity, 1=reduced activity, and 2=inactive. Daily scores were reported for each individual ferret displaying the specific clinical sign on a given day. Scores were also reported as the number of ferrets within the groups displaying one or more signs of infection on a given day.

2.2.36 Body Weights and Body Temperatures in Example 24

Body weights were measured at the time of receipt, prior to first administration of the LF92 formulated hIFN mRNA and on each following day of the study.

Body temperatures were measured daily using transponders implanted subdermally into the ferrets on Day −1.

2.2.37 Viral Titers in Nasal Washes

Nasal washes were collected on Days 1, 2, 3, 4, 5, and 6 post-viral challenge by flushing the nasal cavities with 2 mL of sterile PBS containing 0.5% bovine serum albumin (BSA), penicillin, streptomycin, and amphotericin B. Washes on Days 1 and 3 were collected prior to LF92 formulated hIFN mRNA administration. Nasal washes were collected and aliquoted into sterile 1.5-ml Eppendorf tubes and immediately frozen on dry ice then stored at −80 °C until used for determination of viral titer by $TCID_{50}$.

Serial ½-$log_{10}$ dilutions of nasal washes from $10^{-1}$ to $10^{-10}$ were prepared in viral growth medium (DMEM supplemented with 0.3% BSA) without TPCK-trypsin. Twenty-five microliters (25 μl) of ½-$log_{10}$ dilutions of each nasal wash were added (four (4) replicates for each dilution) to MDCK cells in a 96-well microplate and incubated at 37 °C, 5% $CO_2$ for 60 min. One hundred seventy-five microliter (175 μl) of viral growth medium (DMEM supplemented with 0.3% BSA with 1 μg/ml TPCK-trypsin) was added to each well following the 60-minute incubation. The cells were then incubated 48 h at 37 °C, 5% $CO_2$. The content of each well was tested for hemagglutination by incubating 50 μl of tissue culture supernatant with 50 μl of 0.5% turkey red blood cells in 1×PBS for 30 min at room temperature. The $TCID_{50}$ was calculated by the Reed and Muench method. Briefly, the presence of influenza virus will agglutinate red blood cells. The number of positives (wells with hemagglutination) and negatives wells at each dilution was determined. The 'cumulative positive', 'cumulative negative", ratio and % of positives were calculated. Then the 'proportional distance' between dilution showing >50% positives and the dilutions to the dilution showing <50% positives was calculated using next equation: Proportional distance=((% positive value above 50%) 50)/(% positive value above 50%-% positive value below 50%)×0.5 (correction factor for % log dilution). The viral $TCID_{50}$ for each specimen was calculated by adding the proportional distance to the dilution showing >50% positive.

2.2.38 Necropsy in Example 24

Animals were humanely euthanized on Day 6 and lung tissue was harvested from all four lung lobes. Lungs were photographed, and individually weighed. Three portions of each lobe were collected. Two of the portions were placed into pre-weighed tubes containing RNALATER® (or equivalent) and weighed, the third lung portion was placed into 10% buffered formalin.

2.2.39 Quantification of Viral RNA in Lung

Quantification of influenza virus in ferret lung tissues was determined by one-step RT-qPCR in an Applied Biosystems QuantStudio 6-flex thermal cycler (Applied Biosystems, Foster City, CA, USA). Viral RNA was extracted from lung tissue specimens harvested from the upper left lobe using Zymo Research Quick-RNA Miniprep Plus Kit (Santa Ana, CA) obtaining 60 μL of eluted viral RNA which was aliquoted and stored at −80 °C until used for quantification. Five microliters (5 μL) of extracted RNA was used to program 20 μL one-step RT-qPCR reactions containing qScript XLT One-Step RT-qPCR TOUGHMIX™ plus Rox (QuantBio) and 0.2 μM of primers M+24 F (5'-AGA TGA GTC TTC TAA CCG AGG TCG-3' (SEQ ID NO: 28)) and Rev-mod (5'-TGC AAA GAC ACT TTC CAG TCT CTG-3' (SEQ ID NO: 29)) and TAQMAN® probe M+64 (5'6-FAM/TC AGG CCC C/ZEN/C TCA AAG CCG A-3'BkFQ (SEQ ID NO: 30)) for amplification of sequences on viral gene segment 7 encoding the viral Matrix protein. Amplification was performed in a 96-well plate with a single cycle of 50 °C for 10 minutes for reverse transcription followed by 3 minutes at 95 °C and 45 cycles of 95 °C for 10 seconds, 60 °C for 30 seconds for DNA amplification. The quantity of viral RNA in each sample was interpolated from a standard curve generated by amplification of serial dilutions of viral RNA extracted from cell culture stock ($8\times10^6$ pfu/mL) of Influenza A/California/04/2009 pdmH1 N1. The total viral RNA in each sample was normalized to the relative quantity of ferret GAPDH RNA in one milligram of total RNA. Three microliters (3 μL) of extracted RNA was used to program 20 μL one-step RT-qPCR reactions containing qScript XLT One-Step RT-qPCR TOUGHMIX™ plus Rox (QuantBio) and 0.2 μM of primers Fer_GAPDH FWD (5'-CAA CGG ATT TGG CCG TAT TG-3' (SEQ ID NO: 31)) and Fer_GAPDH REV (5'-CTG GAA CAT GTA GAC CAT GTA GT-3' (SEQ ID NO: 32)) and TAQMAN® probe Fer_GAPDH PRB (5Cy5/AGGGTCATT/TAO/GATGGCGACAATATCCAC/3IAbRQSp/(SEQ ID NO: 33)) for amplification of GAPDH sequences. Amplification was performed with a single cycle of 50 °C for 10 minutes for reverse transcription followed by 3 minutes at 95 °C and 45 cycles of 95 °C for 10 seconds, 60 °C for 30 seconds for DNA amplification. The quantity of GAPDH in the samples was interpolated from a standard curve generated by amplification of serial dilutions of pooled extracted ferret lung RNA (250 ng/μL). Results were processed by 21 CFR Part 11 Software Module for QUANTSTUDIO™ 6 and 7 Systems and data from RT-qPCR analysis were imported into GraphPad Prism for analysis.

2.2.40 Quantification of Viral Reproduction in Example 25

2.2.40.1 Study Approval

All experiments involving animals were approved in advance by the Animal Ethics Committee at the Danish Veterinary and Food Administration (Stationsparken 31-33, 2600 Glostrup, Denmark) and were carried out in accordance with the Danish Animal Welfare Act for the Care and Use of Animals for Scientific Purposes.

2.2.40.2 Biosafety

All aspects of this study were approved by the office of Danish Working Environment Authority, Landskronagade 33, 2100 Copenhagen 0, before initiation of this study. Work with SARS-CoV-2 was performed in a biosafety level 2+laboratory by personnel equipped with powered air-purifying respirators.

2.2.40.3 SARS-CoV-2 Propagation

B.1.1.7 SARS-CoV2 (Kent, UK, isolate) was provided under MTA by Professor Arvind Patel, University of Glasgow. The viruses used are clinical isolates. The B.1.1.7 variant is in the database as MZ314997. The viruses were propagated in VeroE6 cells expressing human TMPRSS2 (VeroE6-hTMPRSS2) (kindly provided by Professor Stefan Pohlmann, University of Gottingen) (Hoffmann et al., 2020). Briefly, VeroE6-hTMPRSS2 cells were infected with a multiplicity of infection (MOI) of 0.05, in DMEM (Gibco)+2% FCS (Sigma-aldrich)+1% Pen/Strep (Gibco)+L-Glutamine (Sigma-Aldrich) (From here, complete medium). 72 h post infection supernatant, containing new virus progeny, was harvested, and concentrated on 100 kDa AMICON® ultrafiltration columns (Merck) by centrifugation at 4000×g for 30 minutes. Virus titer was determined by TCID50% assay and calculated by Reed-Muench method. To convert to the mean number of plaque forming units (pfu)/mL, the TCID50/mL was multiplied by factor 0.7 (ATCC—Converting TCID[50] to plaque forming units (PFU)).

2.2.40.4 Animal Housing

K18-hACE c57BL/6J mice (strain: 2B6.Cg-Tg(K18-ACE2)2Prlmn/J) were obtained from The Jackson Laboratory. Hemizygote offspring were used for experiment. Age matched male and female mice and fed standard chow diets groups and fed standard chow diets and were housed in in pathogen free facility. Mice were weighed every day at the same time of the day until day 3 of post infection (post infection, and the animals were killed at 20% weight loss or when they reached humane endpoint.

2.2.40.5 Treatment of Mice

Mice were treated intranasally under Isoflurane anesthesia with an 15 μL inoculum of formulated human IFNλ1 mRNA (7.5 μg mRNA, corresponds to 3 μg deposited in the lung) one day before and one day following infection.

2.2.40.6 Infection of Mice

Inoculation of SARS-CoV-2 was performed in the same way as the application of mRNA (intranasal application of a 15 μL aliquot under Isoflurane inhalation anaesthesia).

2.2.40.7 RNA Isolation, Real-Time qPCR

Lunges were homogenized with steel beads (Qiagen) in a Tissuelyser (II) (Qiagen) in PBS and immediately used for RNA isolation. RNA was isolated using the High Pure RNA Isolation Kit (Roche) and equal amount of RNA was used for standard One-Step RT-PCR (Applied Biosystems TAQMAN® RNA to CT One Step Kit). For the SARS-CoV-2 N gene qPCR primers AAATTTTGGGGACCAG-GAAC (SEQ ID NO:34) and TGGCACCTGTGTAGGT-CAAC (SEQ ID NO:35) and probe FAM-ATGTCGCGCATTGGCATGGA-BHQ (SEQ ID NO:36) were used. For the IFN-β, Mx1 and β-Actin the TAQMAN® Gene Expression Assays were used (Applied Biosystems). RNA levels of SARS-CoV-2 N gene, IFNβ, or Mx1 were normalized to the mouse housekeeping gene β-Actin using the formula 2^(Ct(18S-rRNA)-Ct(Sars-CoV-2 RNA)).

2.2.40.8 TCID50 Assay

To determine the amount of infectious virus in cell culture supernatant or generated virus stocks, a limiting dilution assay was performed. $2\times10^4$ VeroE6-TMPRRS2 cells were seeded in 90 μL DMEM5 in a 96 well plate. The next day, samples were thawed and 10× diluted, followed by 10-fold serial dilution using DMEM, and 10 μL of each dilution was added to the cells in eight replicates. The cells were incubated 72 h in a humidified C02 incubator at 37 °C, 5% C02. Cytopathic effect (CPE) was scored after fixing with 5% formalin (Sigma-Aldrich) and crystal violet stain (Sigma-Aldrich), using a light microscope (Leica DMi1), and the tissue culture infectious dose 50 (TCID50/mL) was calculated using the Reed and Muench method.

The invention claimed is:

1. A method of treating or inhibiting a viral-induced respiratory disorder comprising administering to a subject an effective amount of a pharmaceutical composition comprising an mRNA molecule, wherein the mRNA molecule comprises a cap, a 5' untranslated region (UTR), a coding region that encodes an interferon (IFN)-λ1, and a poly A tail, wherein the IFN-λ1 comprises the amino acid sequence of SEQ ID NO:2, and wherein the mRNA molecule comprises a combination of modified nucleotides and unmodified nucleotides, thereby treating or inhibiting the viral-induced disorder, wherein said viral-induced respiratory disorder is induced by a respiratory virus.

2. The method of claim 1, wherein said viral-induced respiratory disorder is caused by a respiratory virus belonging to the family of Pneumoviridae.

3. The method of claim 1, wherein the respirator virus respiratory syncytial virus.

4. The method of claim 2, wherein the virus is a virus which enters cells via the ACE2 receptor.

5. The method of claim 1, wherein said respiratory virus is influenza, SARS-CoV-2, respiratory syncytial virus, or rhinovirus.

6. The method of claim 1, comprising administering the mRNA molecule by delivery into the respiratory system of the subject.

7. The method of claim 6, wherein said delivery into the respiratory system is via inhalation or instillation.

8. The method of claim 7, wherein said inhalation is inhalation of an aerosol comprising said mRNA molecule.

9. The method of claim 1, wherein the mRNA molecule comprises a combination of unmodified and modified nucleotides, wherein 5 to 50% of uridine nucleotides in the mRNA molecule and 5 to 50% of cytidine nucleotides in the mRNA molecule are modified uridine nucleotides and modified cytidine nucleotides, respectively.

10. The method of claim 1, wherein the coding region that encode the IFN-λ1 comprises SEQ ID NO. 1.

11. The method of claim 1, wherein the mRNA molecule comprises SEQ ID NO. 13.

12. The method of claim 1, further comprising administering to the subject an effective amount of an mRNA encoding a type I interferon and/or an mRNA encoding a type II interferon.

13. The method of claim 12, wherein the type I interferon is selected from the group consisting of IFN-α, and IFN-β, and wherein the type II interferon is IFN-γ.

14. The method of claim 9, wherein the modified uridine nucleotides are 2-thiouridine and the modified cytidine nucleotides are 5-methylcytidine.

15. The method of claim 13, wherein IFN-α is IFN-α16.

16. A method of treating or inhibiting a virus-induced exacerbation of a lung disease in a subject, comprising administering to the subject an effective amount of a pharmaceutical composition comprising an mRNA molecule, wherein the mRNA molecule comprises a cap, a 5' untranslated region (UTR), a coding region that encodes an interferon (IFN)-λ1, and a poly A tail, wherein the IFN-λ1 comprises the amino acid sequence of SEQ ID NO: 2, and wherein the mRNA molecule comprises a combination of modified nucleotides and unmodified nucleotides, thereby treating or inhibiting the viral-induced exacerbation of the ling disease in the subject, wherein said viral-induced exacerbation of the ling disease is caused by a respiratory virus.

17. The method of claim 16, wherein the lung disease is asthma or chronic obstructive pulmonary disease.

18. An mRNA molecule, wherein the mRNA molecule comprises a cap, a 5' untranslated region (UTR), a coding region that encodes an interferon (IFN)-λ1, and a poly A tail, wherein the IFN-λ1 comprises the amino acid sequence of SEQ ID NO: 2, and wherein the mRNA molecule comprises a combination of modified nucleotides and unmodified nucleotides.

19. A pharmaceutical composition comprising an effective amount of the mRNA molecule of claim 18.

20. The mRNA molecule of claim 18, wherein the coding region is codon optimized.

21. The mRNA molecule of claim 20, wherein the coding region comprises SEQ ID NO: 1.

22. The method of claim 16, wherein the respiratory virus belongs to the family of Pneumoviridae.

23. The method of claim 16, wherein the respiratory virus causing the virus-induced disorder is respiratory syncytial virus.

24. The method of claim 1, wherein the mRNA molecule comprises 2.5% to 100% modified nucleotides.

25. The method of claim 1, wherein the mRNA comprises 2.5% to 100% modified uridine (U) nucleotide, 2.5% to 100% modified cytidine (C) nucleotide, 2.5% to 100% modified guanosine (G) nucleotide or 2.5% to 100% modified adenosine (A) nucleotide.

26. The method of claim 7, wherein said delivery is nasal delivery or lung delivery.

27. The method of claim 16, comprising administering the mRNA molecule by delivery into the respiratory system of the subject.

28. The method of claim 27, wherein said delivery into the respiratory system is via inhalation or instillation.

29. The method of claim 28, wherein said inhalation is inhalation of an aerosol comprising said mRNA.

30. The method of claim 16, wherein the mRNA molecule comprises a combination of unmodified and modified nucleotides, wherein 5 to 50% of uridine nucleotides in the mRNA and 5 to 50% of cytidine nucleotides in the mRNA are modified uridine nucleotides and modified cytidine nucleotides, respectively.

31. The method of claim 16, wherein the coding region that encodes the IFN-λ1 comprises SEQ ID NO: 1.

32. The method of claim 1, comprising administering the pharmaceutical composition as:

(i) one dose once;

(ii) one dose every two days over a period of 2, 4, 6, 8, 10 or 14 days;

(iii) one dose daily over a period of time of 2, 3, 4, 5, 6, 7, 8, 9, or 10 days; or (iv) two doses daily over a period of time of 2, 3, 4, 5, 6, 7, 8, 9, or 10 days.

33. The method of claim 16, comprising administering the pharmaceutical composition as one dose per week.

34. The method of claim 33, wherein the composition is to be administered for up to 7 months.

* * * * *